US012364765B2

(12) United States Patent
Bublil et al.

(10) Patent No.: US 12,364,765 B2
(45) Date of Patent: Jul. 22, 2025

(54) PEGYLATED CYSTATHIONINE BETA SYNTHASE FOR ENZYME THERAPY FOR TREATMENT OF HOMOCYSTINURIA

(71) Applicants: TRAVERE THERAPEUTICS SWITZERLAND GMBH, Rapperswil-Jona (CH); THE REGENTS OF THE UNIVERSITY OF COLORADO, A BODY CORPORATE, Denver, CO (US)

(72) Inventors: Erez Bublil, Ets Efraim (IL); Frank Glavin, Belmont, MA (US); Marcia Sellos-Moura, West Newbury, MA (US); Jan P. Kraus, Denver, CO (US); Tomas Majtan, Aurora, CO (US); Randy Wanner, Martinsried (DE); Orhan Causevic, Martinsried (DE)

(73) Assignees: The Regents of the University of Colorado, A Body Corporate, Denver, CO (US); Travere Therapeutics Switzerland GmbH (CH)

( * ) Notice: Subject to any disclaimer, the term of this patent is extended or adjusted under 35 U.S.C. 154(b) by 647 days.

(21) Appl. No.: 17/622,112

(22) PCT Filed: Jun. 26, 2020

(86) PCT No.: PCT/US2020/039870
§ 371 (c)(1),
(2) Date: Dec. 22, 2021

(87) PCT Pub. No.: WO2020/264333
PCT Pub. Date: Dec. 30, 2020

(65) Prior Publication Data
US 2022/0265835 A1    Aug. 25, 2022

Related U.S. Application Data

(60) Provisional application No. 62/866,810, filed on Jun. 26, 2019, provisional application No. 62/983,860, filed on Mar. 2, 2020.

(51) Int. Cl.
*A61K 47/60* (2017.01)
*A61K 9/19* (2006.01)
*A61K 47/02* (2006.01)
*A61K 47/26* (2006.01)
*A61P 43/00* (2006.01)

(52) U.S. Cl.
CPC .......... *A61K 47/60* (2017.08); *A61K 9/19* (2013.01); *A61K 47/02* (2013.01); *A61K 47/26* (2013.01); *A61P 43/00* (2018.01)

(58) Field of Classification Search
CPC .......... A61K 47/60; A61K 9/19; A61K 47/02; A61K 47/26; A61K 38/51; A61K 45/06; A61P 43/00; A61P 1/08; A61P 3/00; A61P 9/00; A61P 27/02; C12Y 402/01022
See application file for complete search history.

(56) References Cited

U.S. PATENT DOCUMENTS

| | | |
|---|---|---|
| 5,523,225 A | 6/1996 | Kraus |
| 5,635,375 A | 6/1997 | Kraus et al. |
| 5,643,575 A | 7/1997 | Martinez et al. |
| 5,656,425 A | 8/1997 | Kraus |
| 7,485,307 B2 | 2/2009 | Kraus et al. |
| 8,007,787 B2 | 8/2011 | Kraus |
| 8,398,989 B2 | 3/2013 | Kraus et al. |
| 9,011,844 B2 | 4/2015 | Kraus |
| 9,034,318 B2 | 5/2015 | Kraus et al. |
| 9,243,239 B2 | 1/2016 | Carrillo et al. |
| 9,284,546 B2 | 3/2016 | Kraus |
| 9,447,406 B2 | 9/2016 | Kraus et al. |
| 9,631,188 B2 | 4/2017 | Kraus |
| 9,675,678 B2 | 6/2017 | Kraus et al. |
| 10,046,036 B2 | 8/2018 | Kraus et al. |
| 10,160,962 B2 | 12/2018 | Carrillo et al. |
| 10,265,387 B2 | 4/2019 | Kraus et al. |
| 10,280,415 B2 | 5/2019 | Kraus |
| 10,624,959 B2 | 4/2020 | Kraus et al. |
| 10,653,755 B2 | 5/2020 | Kraus et al. |
| 10,729,753 B2 | 8/2020 | Kraus et al. |

(Continued)

FOREIGN PATENT DOCUMENTS

| | | |
|---|---|---|
| CA | 2898772 A1 | 8/2014 |
| EP | 1396537 A1 | 3/2004 |

(Continued)

OTHER PUBLICATIONS

Connolly et al., Protein Aggregation in Frozen Trehalose Formulations: Effects of Composition, Cooling Rate, and Storage. Temperature J. Pharma. Sci., 2015, vol. 104: 4170-4184. (Year: 2015).*
Morris et al., Guidelines for the diagnosis and management of cystathionine beta-synthase deficiency. J Inherit Metab Dis., 2017, vol. 40: 49-74. (Year: 2017).*
Reslan et al., Lack of a synergistic effect of arginine-glutamic acid on the physical stability of spray-dried bovine serum albumin. Pharma. Develop. Technol., 2017, vol. 22(6); 785-791. (Year: 2017).*
Barber et al., "The successful treatment of homocystinuria with pyridoxine." *J. Pediatr.* 75(3):463-78, Sep. 1969.

(Continued)

*Primary Examiner* — Ganapathirama Raghu
(74) *Attorney, Agent, or Firm* — Seed IP Law Group

(57) ABSTRACT

The present disclosure provides formulations for a drug product comprising a PEGylated CBS protein having the amino acid sequence of SEQ ID NO: 1. Dosages and dosing regimens are provided for treatment of homocystinuria in a subject in need thereof. Additionally, the dosages and dosing regimens are also provided to reduce the level of homocysteine (Hcy) or increase the levels of cysteine (Cys) and/or cystathionine (Cth) in a subject in need thereof.

22 Claims, 3 Drawing Sheets

Specification includes a Sequence Listing.

(56) References Cited

U.S. PATENT DOCUMENTS

| | | | |
|---|---|---|---|
| 10,941,392 | B2 | 3/2021 | Carrillo et al. |
| 11,077,175 | B2 | 8/2021 | Kraus et al. |
| 11,324,811 | B2 | 5/2022 | Majtan et al. |
| 11,400,143 | B2 | 8/2022 | Kraus et al. |
| 11,771,745 | B2 | 10/2023 | Kraus et al. |
| 2005/0036981 | A1 | 2/2005 | Yagi et al. |
| 2007/0010492 | A1 | 1/2007 | Generale |
| 2018/0187154 | A1 | 7/2018 | Kahvejian et al. |
| 2022/0290116 | A1 | 9/2022 | Sellos-Moura et al. |
| 2023/0039591 | A1 | 2/2023 | Majtan et al. |
| 2023/0042914 | A1 | 2/2023 | Kraus et al. |

FOREIGN PATENT DOCUMENTS

| | | | |
|---|---|---|---|
| WO | WO 9507714 | A1 | 3/1995 |
| WO | WO 0209515 | A1 | 2/2002 |
| WO | WO 03106971 | A2 | 12/2003 |
| WO | WO 2011025964 | A2 | 3/2011 |
| WO | WO 2012001336 | A1 | 1/2012 |
| WO | WO 2013148580 | A1 | 10/2013 |
| WO | WO 2014120770 | A1 | 8/2014 |
| WO | WO 2015033279 | A1 | 3/2015 |
| WO | WO 2017083327 | A1 | 5/2017 |
| WO | WO 2018195006 | A1 | 10/2018 |
| WO | WO 2020264333 | A1 | 12/2020 |

OTHER PUBLICATIONS

Bublil et al., "Classical homocystinuria: From cystathionine beta-synthase deficiency to novel enzyme therapies," *Biochemie* 173:48-56, 2020.

Bublil et al., "Enzyme replacement with PEGylated cystathionine β-synthase ameliorates homocystinuria in murine model," *J Clin Invest.* 126(6):2372-2384, 2016.

ClinicalTrials.gov, "OT-58 as an Enzyme Replacement Therapy for Patients With Cystathionine Beta-Synthase Deficient Homocystinuria (CBSDH)," *U.S. National Library of Medicine*, NCT03406611, first posted Janaury 15, 2018, retrieved Oct. 26, 2022, 9 pages.

ClinicalTrials.gov, "OT-58 as an Enzyme Therapy for Patients with Cystathionine Beta-Synthase Deficient Homocystinuria (CBSDH)," *U.S. National Library of Medicine*, NCT03406611, first posted Dec. 4, 2019, accessed Oct. 26, 2022, 10 pages.

Dong et al., "Secondary Structure of Recombinant Human Cystathionine β-Synthase in Aqueous Solution: Effect of Ligand Binding and Proteolytic Truncation," *Archives of Biochemistry and Biophysics* 344(1):125-132, Aug. 1, 1997.

Frank et al., "Purification and characterization of the wild type and truncated human cystathionine β-synthase enzymes expressed in *E. coli*," *Archives of Biochemistry and Biophysics* 470(1):64-72, 2008.

Frank et al., "Solvent-Accessible Cysteines in Human Cystathionine β-Synthase: Crucial Role of Cysteine 431 in S-Adenosyl-L-methionine Binding," *Biochemistry* 45:11021-11029, 2006.

Gupta et al., "Betaine supplementation is less effective than methionine restriction in correcting phenotypes of CBS deficient mice," *J. Inherit. Metab. Dis.* 39:39-46, 2016.

Gupta et al., "Cysthathionine beta-synthase-deficient mice thrive on a low-methionine diet," *FASEB J.* 28(2):781-90, Feb. 2014.

Gupta et al., "Mouse models of cystathionine beta-synthase deficiency reveal significant threshold effects of hyperhomocysteinemia." *FASEB J.* 23(3):883-893, Mar. 2009.

Harris et al., "Effect of pegylation on pharmaceuticals," *Nature Reviews Drug Discovery* 2(3):214-221, Mar. 2003.

Komrower et al., "Dietary Treatment of Homocystinuria." *Arch. Dis. Child* 41(220):666-671, Dec. 1966.

Kraus et al., "Cystathionine β-Synthase and Its Deficiency." In Carmel et al. (eds.), *Homocysteine in Health and Disease*, Cambridge University Press, Cambridge, United Kingdom, pp. 223-243, 2001.

Kraus et al., "Cystathionine β-synthase from Human Liver: Improved Purification Scheme and Additional Characterization of the Enzyme in Crude and Pure Form," *Arch. Biochem. Biophys.* 222(1):44-52, Apr. 1983.

Kraus et al., "Human cystathionine β-synthase cDNA: sequence, alternative splicing and expression in cultured cells," *Human Molecular Genetics* 2(10):1633-1638, 1993.

Kraus et al., "Purification and Properties of Cystathionine β-Synthase from Human Liver," *J. Biol. Chem.* 253(18):6523-6528, 1978.

Kraus, "Cystathionine β-synthase (human)," *Methods Enzymol.* 143:388-394, 1987.

Levy, "Physician's Guide to The Homocystinurias," *National Organization for Rare Disorders (NORD)*, Jan. 2010, Retrieved from Internet: URL:http://www.rarediseases.org/docs/Homocystinuria_11_29b.pdf (8 pages).

Majtan et al., "Behavior, body composition, and vascular phenotype of homocystinuric mice on methionine-restricted diet or enzyme replacement therapy," *FASEB J.* 33:12477-12486, Nov. 2019.

Majtan et al., "Engineering and Characterization of an Enzyme Replacement Therapy for Classical Homocystinuria," *Biomacromolecules* 18:1747-1761, Apr. 21, 2017.

Majtan et al., "Enzyme replacement prevents neonatal death, liver damage, and osteoporosis in murine homocystinuria," *FASEB J.* 31:5495-5506, Dec. 2017.

Majtan et al., "Enzyme Replacement Therapy Ameliorates Multiple Symptoms of Murine Homocystinuria," *Molecular Therapy* 26(3):834-844, Mar. 2018.

Majtan et al., "Folding and activity of mutant cystathionine β-synthase depends on the position and nature of the purification tag: characterization of the R266K CBS mutant." *Protein Expr Purif.* 82(2):317-324, 2012 (NIH Public Access Author Manuscript, available in PMC Apr. 1, 2013) (21 pages).

Majtan et al., "Interplay of enzyme replacement therapy, diet and betaine in murine cystathionine beta-synthase-deficient homo cystinuria," *J Inherit Metab Dis* 41(Suppl 1):S56, 2018. (2 pages).

Majtan et al., "Pharmacokinetics and pharmacodynamics of PEGylated truncated human cystathionine beta-synthase for treatment of homocystinuria," *Life Sciences* 200:15-25, 2018.

Majtan et al., "Purification and characterization of cystathionine β-synthase bearing a cobalt protoporphyrin," *Archives of Biochemistry and Biophysics* 508:25-30, 2011.

Majtan et al., "Rescue of Cystathionine β-Synthase (CBS) Mutants with Chemical Chaperones: Purification and Characterization of Eight CBS Mutant Enzymes." *J Biol Chem.* 285(21):15866-15873, May 21, 2010.

Sacharow et al., "Homocystinuria Caused by Cystathionine Beta-Synthase Deficiency," *GeneReviews*:1-21, Jan. 15, 2004.

Schiff et al., "Treatment of Inherited Homocystinurias," *Neuropediatrics* 43:295-304, 2012 (10 Pages).

Van Guldener et al., "Homocysteine-lowering treatment: an overview," *Expert Opin Pharmacother.* 2(9): 1449-1460, 2001.

Van Guldener, "Why is homocysteine elevated in renal failure and what can be expected from homocysteine-lowering?" *Nephrol Dial Transplant* 21:1161-1166, 2006.

Walter et al., "Strategies for the treatment of cystathionine β-synthase deficiency: the experience of the Willink Biochemical Genetics Unit over the past 30 years," *Eur. J. Pediatr.* 157(Suppl 2):S71-6, Apr. 1998.

Watanabe et al., "Mice deficient in cysthathionine β-synthase: animal models for mild and severe homocyst(e)inemia," *Proc. Natl. Acad. Sci. U.S.A.* 92(5):1585-1589, Feb. 1995.

Wilcken et al., "Homocystinuria-the effects of betaine in the treatment of patients not responsive to pyridoxine," *N. Engl. J. Med.* 309(8):448-453, 1983.

Yap et al., "Vascular outcome in patients with homocystinuria due to cystathionine beta-synthase deficiency treated chronically: a Multicenter observational study," *Arterioscler. Thromb. Vasc. Biol.* 21(12):2080-2085, Dec. 2001.

Yap, "Classical homocystinuria: Vascular risk and its prevention," *J. Inherit. Metab. Dis.* 26:259-265, 2003.

Yap, "Homocystinuria due to cystathionine β-synthase deficiency," *Orphanet Encyclopedia*, Feb. 2005, Retrieved from Internet: URL: http://www.orpha.net/data/patho/GB/uk-CbS.pdf (13 Pages).

(56) References Cited

OTHER PUBLICATIONS

Baranov et al., "Homocystinuria in children," *Issues of modern pediatrics* 16(6): 457-467, 2017.

Izutsu et al., "Characterization of Frozen Aqueous Solution for Formulation and Process Design of Freeze-dried Pharmaceuticals," *Netsu Sokutei* 36(2):112-120, 2009 (with English abstract). (9 pages).

Izutsu et al., "Freeze-drying of protein pharmaceuticals," *Pharmacology* 72(6):353-358, 2012 (with Machine Translation). (12 pages).

James et al., "Metabolic biomarkers of increased oxidative stress and impaired methylation capacity in children with autism," *Am J Clin Nutr* 80:1611-1617, Dec. 2004. (7 pages).

* cited by examiner

PEGYLATED CYSTATHIONINE BETA SYNTHASE FOR ENZYME THERAPY FOR TREATMENT OF HOMOCYSTINURIA

CROSS REFERENCE TO RELATED APPLICATIONS

This application is a 371 National Stage filing of International Application No. PCT/US2020/039870, filed on Jun. 26, 2020, which claims priority to U.S. Provisional Patent Application Nos. 62/866,810 filed on Jun. 26, 2019, and 62/983,860 filed on Mar. 2, 2020, the contents of each of which are herein incorporated by reference in their entirety.

REFERENCE TO THE SEQUENCE LISTING

The Sequence Listing associated with this application is provided in text format in lieu of a paper copy, and is hereby incorporated by reference into the specification. The name of the text file containing the Sequence Listing is 790116_433USPC_SEQUENCE LISTING. The text file is 17.9 KB, was created on Dec. 22, 2021, and is being submitted electronically via EFS-Web.

FIELD OF THE DISCLOSURE

The disclosure relates to compositions and methods for enzyme therapy for treatment of homocystinuria using the drug product described herein.

BACKGROUND OF THE DISCLOSURE

Cystathionine β-synthase deficient homocystinuria (CBSDH), also known as classical homocystinuria (HCU) or HCU Type 1, is an orphan disease affecting both children and adults. CBSDH is a rare autosomal-recessive metabolic condition characterized by an excess of the compound homocysteine (Hcy) in the urine, tissues, and plasma, due to reduced or absence of activity of the cystathionine β-synthase (CBS) enzyme (see Kraus et al., In: Carmel R, Jacobsen D W, eds. Homocysteine in Health and Disease. Cambridge, United Kingdom: Cambridge University Press; 2001:223-243; Sacharow et al., Homocystinuria Caused by Cystathionine Beta-Synthase Deficiency. In: Adam M P, Ardinger H H, Pagon R A, Wallace S E, Bean L J H, Mefford H C, et al, eds. GeneReviews™ [Internet]. Seattle (Wash.): University of Washington, Seattle, 2017; each of which is incorporated by reference herein in its entirety).

The diagnosis of CBSDH may be confirmed by molecular genetic testing of the CBS gene as described in Sacharow et al. CBS is an enzyme in the metabolism of the sulfur amino acid methionine (Met), which is present in proteins in the diet (see Maclean et al. J Biol Chem. 2012; 287(38):31994-32005, which is hereby incorporated by reference in its entirety). Therefore, CBSDH may also be diagnosed by the measurement of markedly increased concentrations of total methionine in plasma. These elevated amino acid findings may be substantiated by the detection of reduced CBS enzyme activity or by the detection of biallelic pathogenic variants in the gene encoding cystathionine β-synthase (see Picker et al., Homocystinuria Caused by Cystathionine Beta-Synthase Deficiency. 2004 Jan. 15 [Updated 2014 Nov. 13]. In: Pagon R A, Adam M P, Ardinger H H, et al., eds. GeneReviews™ [Internet]. Seattle (Wash.): University of Washington, Seattle; 1993-2016, available from: ncbi.nlm.nih.gov, which is hereby incorporated by reference in its entirety). CBS deficiency also leads to reduced levels of cystathionine (Cth) and cysteine (Cys) (see Veeranki et al. Int J Mol Sci. 2013 Jul. 18; 14(7):15074-91, which is hereby incorporated by reference in its entirety).

CBSDH may be suspected based on the following (Picker et al. 2014): 1) clinical findings including ectopia lentis (dislodgment of the lens in eye) and/or severe myopia, asthenic habitus (tall and slender), skeletal abnormalities, early onset osteoporosis, and/or thromboembolic events, unexplained developmental delay/intellectual disability; 2) newborn screening for hypermethioninaemia or specifically a positive family history for CBS deficiency may lead to pre-symptomatic patient identification (see Yap et al. J Inherit Metab Dis 1998; 21:738-47, which is hereby incorporated by reference in its entirety); and 3) family history. There is considerable variability in all of these clinical signs and the age of symptom onset among patients. The current screening approaches usually fail to detect newborns with less severe CBS deficiency and only detect a minority of patients with more severe CBSDH (see, Huemer et al. J Inherit Metab Dis. 2015 November; 38(6):1007-19; Yap, Orphanet Encyclopedia [online serial]. 2005, pages 1-13; Schiff et al. Neuropediatrics. 2012 December; 43(6):295-304; each of which is hereby incorporated by reference in its entirety). It is the most common genetic disorder of sulphur metabolism, with an estimated prevalence of 1:200,000 to 1:335,000 worldwide. In the sulphur metabolism pathway, the essential amino acid L-methionine is metabolized to Hcy, followed by a two-step trans-sulphuration first to Cth and finally Cys. CBS is found primarily in the liver and kidney, which catalyzes Hcy to Cth. Excess Hcy can be re-methylated to methionine by betaine-Hcy 5-methyl transferase, raising levels of plasma Met as well.

Although some patients are diagnosed with the disease shortly after birth, often the diagnosis of CBSDH occurs later in life after classic clinical symptoms have developed (see Huemer et al. J Inherit Metab Dis. 2015 November, 38(6):1007-19; Yap, Orphanet Encyclopedia [online serial]. 2005, pages 1-13; which are both incorporated by reference herein in their entireties). CBSDH is characterized by developmental delay/intellectual disability, ectopia lentis and/or severe myopia, skeletal abnormalities (excessive height and length of the limbs), and thromboembolism. There is considerable variability in all of these clinical signs among patients.

Normal total homocysteine (tHcy) levels vary with age, sex, and nutritional status, but typically range between 4.5 and 11 μmol/L (see Quest Diagnostics Reference Range; questdiagnostics.com, which is hereby incorporated by reference in its entirety). Men tend to have slightly (by 1 to 2 μmol/L) higher tHcy levels than women, and an approximate doubling of mean values is observed as patients aged from childhood to 80 years (see Refsum et al. Clin Chem 2004; 50:3-32, which is hereby incorporated by reference in its entirety). In folate-supplemented populations, the upper limit (97.5%) of tHcy levels is approximately 12 μmol/L in adults <65 years old and 16 μmol/L in adults greater than 65 years. Many CBSDH patients present with severe hyperhomocysteinemia with total tHcy levels greater than 100 μmol/L, while others exhibit elevations ranging from mild to several times normal (see Morris et al. J Inherit Metab Dis 2017; 40:49-74, which is hereby incorporated by reference in its entirety). tHcy levels have been observed to be highly correlated with the severity of the disease (see Yap et al. J Inherit Metab Dis 1998; 21:738-747, which is hereby incorporated by reference in its entirety).

CBSDH is characterized by conditions of the eye (ectopia lentis and/or severe myopia), skeletal system (excessive height, long limbs, scoliosis, and pectus excavatum), vascular system (thromboembolism), and central nervous system (CNS) (developmental delay/intellectual disability). There is variable expression of these clinical signs in patients, where there may be involvement of all systems or as few as one. Some patients have a severe childhood-onset multisystem disease, whereas those with a less severe disease presentation may remain asymptomatic into adulthood. Without treatment, life expectancy is markedly reduced in the more severe patients (see Morris et al. J Inherit Metab Dis 2017; 40:49-74, which is hereby incorporated by reference in its entirety).

Studies have shown that a reduction of Hcy levels in CBSDH patients is correlated with less severe manifestations of the clinical symptoms (see Yap et al. J Inherit Metab Dis 1998; 21:738-747, which is hereby incorporated by reference in its entirety). The pathways through which Hcy levels cause damage to these systems have been widely described (e.g., Ajith et al. Clin Chim Acta 2015; 450:316-321; Sato et al. Bone 2005; 36:721-726; Behera et al. J Cell Physiol 2016, each of which is hereby incorporated by reference in its entirety) and have led to studies to also investigate the role of Hcy in the general population.

Currently, few therapies are available for the management of CBSDH. Current therapies target the sulphur metabolism pathway through a combination of one or more of the following: 1) dietary modification to reduce protein and/or Met intake; 2) supplementation with some or all of the following: folate, vitamin B12, vitamin B6; and 3) supplementation with the methyl donor betaine to enhance enzymatic re-methylation of accumulated Hcy to Met. Although no studies have been published on the Quality of Life (QoL) of CBSDH patients, patients and their caregivers have been observed to suffer from the psychosocial effects of following and managing a highly restricted and socially isolating diet and are extremely anxious about the long-term medical consequences of the disease. Many patients report yearning for the ability to relax their diets without compromising their long-term prospects.

Therefore, there is a long felt need in the art for a method of treating CBSDH having greater efficacy and fewer negative effects on patients than the present therapies.

SUMMARY OF THE DISCLOSURE

Various embodiments of the disclosure provide a drug substance comprising: (a) an isolated cystathionine β-synthase (CBS) protein comprising SEQ ID NO: 1; and (b) a PEG molecule covalently bound to the CBS protein. In certain embodiments of the drug substance described herein, the PEG molecule is ME-200GS.

Various embodiments of the disclosure provide a pharmaceutical composition comprising the drug substance and a pharmaceutically acceptable adjuvant, diluent, or carrier.

In certain embodiments, the formulation is lyophilized. Various embodiments of the disclosure provide a lyophilized formulation, which, upon reconstitution, the reconstituted liquid formulation comprises a ready-to-use drug product in a concentration of between about 20-30 mg/ml, or about 25 mg/ml, in phosphate buffered saline (PBS); about 11.4 mM of di-sodium hydrogen phosphate; about 137 mM of sodium chloride; about 2.70 mM potassium chloride; and about 1.98 mM potassium di-hydrogen phosphate. A ready-to-use drug product herein is a liquid pharmaceutical formulation comprising a therapeutically effective amount of the drug product, e.g., a unit dose of a pharmaceutical composition including the drug substance of a PEGylated human truncated CBS protein with an amino acid sequence of SEQ ID NO: 1 (e.g., 20NHS PEG-CBS). The ready-to-use drug product can be provided in a vial or similar container for facilitating administration to a subject.

Various embodiments of the disclosure provide a lyophilized formulation, which, upon reconstitution, the reconstituted liquid formulation comprises 20-30 mg, or about 25 mg, of the drug substance; 1 mL of water; 2 mg of di-sodium hydrogen phosphate (dihydrate); 8 mg of sodium chloride; 0.2 mg of potassium chloride; and 0.3 mg of potassium di-hydrogen phosphate. Alternatively, a lyophilized formulation can be reconstituted to comprise the drug substance, a buffer, and an excipient. In certain embodiments, the buffer is 15 mM potassium phosphate. In certain embodiments, the excipient is 8% (w/v) trehalose.

Various embodiments of the disclosure provide a method of treating homocystinuria in a subject, the method comprising: administering to the subject a therapeutically effective amount of the formulation of the pharmaceutical composition described herein.

In certain embodiments, the therapeutically effective amount is a dosage selected from the range of about 0.25 mg/kg to about 10 mg/kg. For example, the dosage is about 0.33 mg/kg, about 0.66 mg/kg, about 1.0 mg/kg, or about 1.5 mg/kg. Alternatively, the dose is about 2 mg/kg, about 7 mg/kg, and about 10 mg/kg. For example, the dose may be about 0.5 mg/kg. Alternatively, the therapeutically effective amount is a dosage selected from the range of about 5.0 mg/kg to about 50 mg/kg, and about 10.0 mg/kg to about 25 mg/kg. For example, the dosage is selected from the group consisting of: about 0.25 mg/kg, about 0.33 mg/kg, about 0.66 mg/kg, about 1.00 mg/kg, about 1.50 mg/kg, about 2.00 mg/kg, about 3.00 mg/kg, about 4.00 mg/kg, about 5.00 mg/kg, about 6.00 mg/kg, about 7.00 mg/kg, about 8.00 mg/kg, about 9.00 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, about 21.0 mg/kg, about 22.0 mg/kg, about 23.0 mg/kg, about 24.0 mg/kg, about 25.0 mg/kg, about 26.0 mg/kg, about 27.0 mg/kg, about 28.0 mg/kg, about 29.0 mg/kg, about 30.0 mg/kg, about 31.0 mg/kg, about 32.0 mg/kg, about 33.0 mg/kg, about 34.0 mg/kg, about 35.0 mg/kg, about 36.0 mg/kg, about 37.0 mg/kg, about 38.0 mg/kg, about 39.0 mg/kg, about 40.0 mg/kg, about 41.0 mg/kg, about 42.0 mg/kg, about 43.0 mg/kg, about 44.0 mg/kg, about 45.0 mg/kg, about 46.0 mg/kg, about 47.0 mg/kg, about 48.0 mg/kg, about 49.0 mg/kg, and about 50.0 mg/kg.

In certain embodiments, the method further comprises administering at least one selected from the group consisting of: pyridoxine, vitamin B6, and betaine, to the subject. In certain embodiments, the subject is on a methionine (Met)-restricted diet. In certain embodiments, the method further comprises administering an anti-platelet agent. In certain embodiments, the anti-platelet agent is a warfarin blood thinner or an anti-coagulation agent. In certain embodiments, the administering step occurs about once every 3 days. In certain embodiments, the administering step occurs about once per day. In certain embodiments, the administering step occurs about once per week. In certain embodiments, the administering step is repeated for about 6 weeks. In certain embodiments, the administering step is repeated for about 3 months. In certain embodiments, the administering step is repeated for about 6 months. In certain embodiments, the administering step is repeated for longer than 6 months. In certain embodiments, the administering step is repeated for the remaining life span of the subject.

Various embodiments of the disclosure provide a method of decreasing the level of homocysteine (Hcy) in a subject, the method comprising: administering to the subject a therapeutically effective amount of the formulation of the pharmaceutical composition described herein.

In certain embodiments, the level of Hcy is less than about 80 µM following the administering step. In certain embodiments, the level of Hcy is reduced by up to 10% following the administering step. In certain embodiments, the level of Hcy is reduced by up to 20% following the administering step. In certain embodiments, the level of Hcy is reduced by up to 30% following the administering step. In certain embodiments, the level of Hcy is reduced by up to 40% following the administering step. In certain embodiments, the level of Hcy is reduced by up to 50% following the administering step. In certain embodiments, the level of Hcy is reduced by up to 60% following the administering step. In certain embodiments, the level of Hcy is reduced by up to 70% following the administering step. In certain embodiments, the level of Hcy is reduced by up to 80% following the administering step. In certain embodiments, the level of Hcy is reduced by up to 90% following the administering step. In certain embodiments, the level of Hcy is within the range of about 10 µM to about 20 µM following the administering step. In certain embodiments, the level of Hcy is less than 10 µM following the administering step. In certain embodiments, the level of Hcy is about 55 µM following the administering step.

In certain embodiments, the therapeutically effective amount is a dosage selected from the range of about 0.25 mg/kg to about 10 mg/kg. For example, the dosage may be about 0.33 mg/kg, about 0.66 mg/kg, about 1.0 mg/kg, about 1.50 mg/kg, about 2.0 mg/kg, about 7.0 mg/kg, or about 10 mg/kg. In certain embodiments, the dosage is less than 10 mg/kg.

In certain embodiments, the method further comprises administering at least one selected from the group consisting of: pyridoxine, vitamin B6, and betaine, to the subject. In certain embodiments, the subject is on a methionine (Met)-restricted diet. In certain embodiments, the method further comprises administering an anti-platelet agent. In certain embodiments, the anti-platelet agent is a warfarin blood thinner or an anti-coagulation agent. In certain embodiments, the administering step occurs about once every 3 days. In certain embodiments, the administering step occurs about once per day. In certain embodiments, the administering step occurs about once per week. In certain embodiments, the administering step is repeated for about 6 weeks. In certain embodiments, the administering step is repeated for about 3 months. In certain embodiments, the administering step is repeated for about 6 months. In certain embodiments, the administering step is repeated for longer than 6 months. In some embodiments, the administering step is repeated for the remaining life span of the subject.

Various embodiments of the disclosure provide a method of increasing the level of cysteine (Cys) in a subject, the method comprising: administering to the subject a therapeutically effective amount of the formulation of the pharmaceutical composition described herein.

Various embodiments of the disclosure provide a method of increasing the level of cystathionine (Cth) in a subject, the method comprising: administering to the subject a therapeutically effective amount of the formulation of the pharmaceutical composition described herein.

Various embodiments of the disclosure provide a method of treating, alleviating, or preventing negative clinical outcomes associate with the ocular system, skeletal system, vascular system, and/or central nervous system of a subject, the method comprising: administering to the subject a therapeutically effective amount of the formulation of the pharmaceutical composition described herein.

BRIEF DESCRIPTION OF THE DRAWINGS

The foregoing and other objects, features and advantages will be apparent from the following description of particular embodiments of the disclosure, as illustrated in the accompanying drawings. The drawings are not necessarily to scale; emphasis instead being placed upon illustrating the principles of various embodiments of the disclosure.

DETAILED DESCRIPTION

I. Introduction

Figure 1:
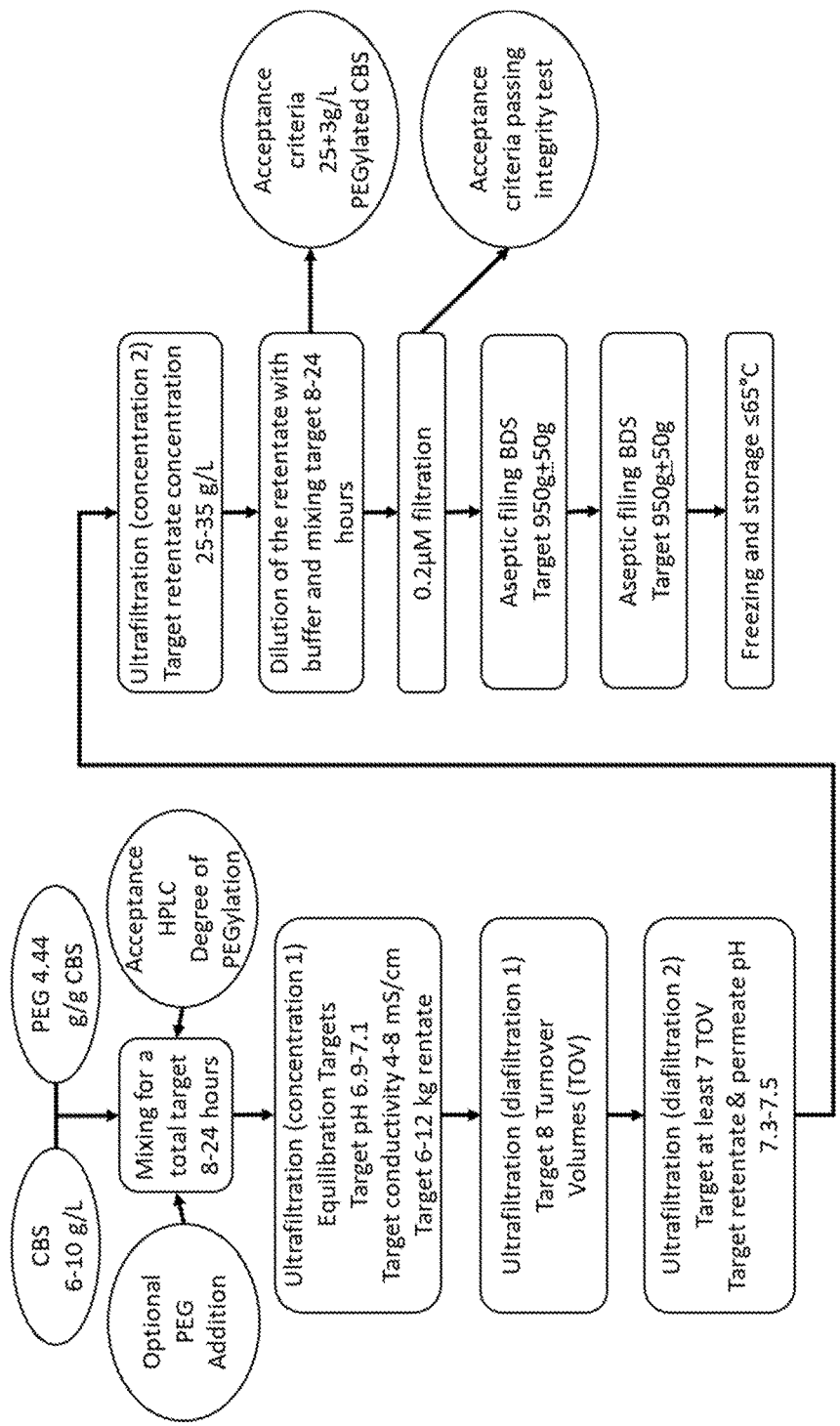
FIG. 1 provides a flow diagram of the PEGylation process utilized in certain embodiments described herein.

Cystathionine beta synthase deficient homocystinuria (CBSDH) is characterized by increased levels of plasma homocysteine (Hcy), together with high levels of Met and decreased concentrations of cysteine (Cys) (see Yap S. Homocystinuria due to cystathionine beta-synthase deficiency. Orphanet Encyclopaedia [serial online] 2005; Morris et al. J Inherit Metab Dis 2017; 40:49-74; NORD, Kraus J P. Homocystinuria due to cystathionine beta-synthase deficiency. NORD [serial online] 2017; each of which is hereby incorporated by reference in its entirety). To date, more than 180 different mutations of the CBS gene associated with CBSDH have been identified (see Human Genome Mutation Database. 2017. Ref Type: Online Source. Available at hgmd.cfac.uk/ac/index.php, which is hereby incorporated by reference in its entirety). Homocysteine (Hcy) is a naturally occurring amino acid which, together with serine, serves as a substrate for the CBS enzyme. CBS governs the unidirectional flow of sulphur from methionine (Met) to cysteine (Cys) by operating at the intersection of the transmethylation, transsulfuration, and remethylation pathways (see Maclean et al. J Biol Chem. 2012; 287(38):31994-32005, which is hereby incorporated by reference in its entirety). Native CBS is activated by the binding of the allosteric activator S-adenosylmethionine (SAM) and catalyzes a β-replacement reaction in which serine condenses with Hcy in a pyridoxal-5'-phosphate (pyridoxine, or vitamin B6)-dependent manner to form cystathionine (Cth). Cystathionine γ-lyase (CGL), operating downstream of CBS, uses Cth as a substrate to generate Cys. Thus, proper function of CBS is important for the regulation of the metabolism of Hcy, Met, and Cys.

The severity and presentation of CBSDH signs and symptoms vary widely among patients (see Karaca et al. Gene 2014; 534:197-203; Trondle et al. Acta Med Austriaca 2001; 28:145-151; Kluijtmans et al. Am J Hum Genet 1999;

65:59-67; each of which is hereby incorporated by reference in its entirety). Many patients present with severe hyper homocysteinemia with total homocysteine (tHcy) levels greater than 100 µmol/L, while others exhibit tHcy elevations ranging from mild to several times normal (see Morris et al. J Inherit Metab Dis 2017; 40:49-74, which is hereby incorporated by reference in its entirety). Significantly elevated tHcy levels generally correlate with a more severe presentation, while lower levels typically correlate with a milder form of the disease. Normal tHcy levels vary with age and nutritional status, but typically range between 10 and 15 µmol/L.

CBSDH is commonly classified according to whether the affected individual responds to total homocysteine (tHcy)-lowering treatment with pyridoxine (vitamin B6), a CBS enzyme cofactor required for normal CBS function (see Mudd et al. Am J Hum Genet 1985; 37: 1-31; Abbott et al. Am J Med Genet 1987; 26:959-969; which are hereby incorporated by reference in their entireties). In general, patients who are responsive to pyridoxine have lower tHcy levels, resulting in a milder form of the disorder. These patients may present later in life with only one or a few CBSDH symptoms, and many remain undiagnosed. Consequently, patients who are highly responsive to pyridoxine are believed to be under-represented in most studies.

Retrospective studies show that patients with the highest tHcy levels (treated or untreated) present with more severe symptoms and earlier in life (see Yap et al. J Inherit Metab Dis 1998; 21:738-747; Mudd et al. Am J Hum Genet 1985; 37:1-31, both of which are hereby incorporated by reference in its entirety). Untreated individuals with elevated tHcy levels typically present with failure to thrive, thromboembolism, severe myopia with subsequent dislocation of the optic lens, osteoporosis-type fractures, a Marfanoid habitus (in particular elongation of the long bones) and psychiatric abnormalities, including learning difficulties (see Yap S. Homocystinuria due to cystathionine beta-synthase deficiency. Orphanet Encyclopaedia [serial online] 2005; Morris et al. J Inherit Metab Dis 2017; 40:49-74; NORD, Kraus J P. Homocystinuria due to cystathionine beta-synthase deficiency. NORD [serial online] 2017, each of which is hereby incorporated by reference in its entirety). Some patients with elevated tHcy levels have a severe childhood-onset multi-system disease. Without treatment, life expectancy is markedly reduced in the more severe patients (see Morris et al. J Inherit Metab Dis 2017; 40:49-74, which is hereby incorporated by reference in its entirety).

Normal human plasma contains less than 16 mM of Hcy-derived compounds, measured as tHcy and consisting of free-thiol homocysteine (Hcy-SH or fHcy), disulfides (such as homocysteine-cysteine and homocysteine) and protein bound homocysteine (see Ueland; Nord Med 1989; 104:293-298; Mudd et al. N Engl J Med 1995; 333:325; Mudd et al. Arterioscler Thromb Vasc Biol 2000; 20:1704-1706; each of which is hereby incorporated by reference in its entirety). The distinction between the sulfhydryl form (homocysteine; Hcy) and the disulfide form (homocysteine) (see Yap S. Homocystinuria due to cystathionine beta-synthase deficiency. Orphanet Encyclopaedia [serial online] 2005, which is hereby incorporated by reference in its entirety) is important because many of the pathophysiological effects depend on the presence of the sulfhydryl group in Hcy (see Yap S. Homocystinuria due to cystathionine beta-synthase deficiency. Orphanet Encyclopaedia [serial online] 2005; Ueland et al. Nord Med 1989; 104:293-298; Mudd et al. N Engl J Med 1995; 333:325; each of which is hereby incorporated by reference in its entirety).

CBS is mainly expressed in liver, pancreas, kidney and brain (see Morris et al. J Inherit Metab Dis 2017; 40:49-74, which is hereby incorporated by reference in its entirety). The catalytic domain binds pyridoxal 5'-phosphate (the cofactor also known as pyridoxine or vitamin B6) and the regulatory domain binds SAM (an allosteric activator).

Insufficient levels of CBS enzymatic activity block the transsulfuration pathway at the first step, resulting in Hcy accumulation, elevated SAH and Met levels and decreased Cth and Cys levels. As the clinical evidence of these dysregulated Met metabolites reviewed herein demonstrates elevated Hcy (most often measured clinically as plasma tHcy) is most strongly implicated in the pathophysiology of CBSDH.

Higher than normal Hcy levels modify sulfhydryl groups on proteins, preventing correct protein crosslinking and leading to structural abnormalities across multiple body systems. Elevated Hcy levels also impair intracellular signaling, resulting in endothelial dysfunction and, ultimately, thromboembolism and vascular disease. In CBSDH, accumulation of Hcy, leads to ocular, skeletal, vascular, and psychological manifestations.

The diagnosis of CBSDH is sometimes confirmed by molecular genetic testing of the CBS gene (see Sacharow et al. Homocystinuria Caused by Cystathionine Beta-Synthase Deficiency. In: Adam M P, Ardinger H H, Pagon R A, Wallace S E, Bean L J H, Mefford H C, et al, editors. GeneReviews™ [Internet]. Seattle (Wash.): University of Washington, Seattle; 1993-2017, which is hereby incorporated by reference in its entirety). The current screening approaches usually fail to detect newborns with less severe CBS deficiency and only detect a minority of patients with more severe CBSDH (see Huemer et al. J Inherit Metab Dis. 2015 November; 38(6):1007-19; Yap, Orphanet Encyclopedia [online serial]. 2005, pages 1-13; Schiff et al. Neuropediatrics. 2012 December; 43(6):295-304).

The measurement of choice to determine Hcy levels in clinical samples is tHcy which includes free Hcy as well as Hcy bound to protein or in the form of disulfides. Normal tHcy levels vary with age, sex, and nutritional status, but typically range between 4.5 and 11 µM (QUEST DIAGNOSTICS™ reference range). Many CBSDH patients present with severe hyper-homocystinuria with total tHcy levels greater than 100 µM, while others exhibit elevations ranging from mild to several times normal (see Morris et al. J Inherit Metab Dis. 2017 January; 40(1):49-74, which is hereby incorporated by reference in its entirety). tHcy levels are highly correlated with the severity of the disease (see Yap et al. J Inherit Metab Dis 1998; 21: 738-47).

Studies have shown that a reduction of Hcy levels in CBSDH patients is correlated with less severe manifestations of the clinical symptoms (see Yap et al. J Inherit Metab Dis 1998; 21: 738-47; Yap et al. Arterioscler Thromb Vasc Biol. 2001 December; 21(12):2080-5; which are both hereby incorporated by reference herein). The pathways through which homocysteine levels cause damage to these systems have been widely described (see Ajith et al. Clin Chim Acta 2015; 450:316-321; Behera et al. J Cell Physiol 99999:1-6, 2016; Saha et al. FASEB J 2016; 30:441-456; which are hereby incorporated by reference in their entireties) and have led to studies investigating the role of Hcy in the general population, which have exposed the significant pathogenic role of Hcy in disease.

One goal of treatment with the drug product described herein is to increase CBS enzyme activity in circulation, resulting in improved metabolic control, thereby ameliorating the clinical manifestations of the disease and slowing or preventing further deterioration. High molecular-weight compounds, such as enzymes, have limited tissue penetration capability and are thus mainly present in the plasma. These proteins are typically maintained in the circulation for a short period of time, as they are removed from the bloodstream by several mechanisms (see Vugmeyster et al. World J Biol Chem. 2012; 3(4):73-92, which is hereby incorporated by reference in its entirety). Ideally, administered CBS would maintain high activity in plasma for sufficient time to have a steady effect on sulfur amino acid metabolism. This goal may be achieved by PEGylation, the addition of PEG moieties onto the surface of the protein. PEGylation of proteins is a strategy that has become widely accepted and has been shown to minimize proteolysis, immune response, and antigenicity, while increasing protein stability and size and reducing renal excretion (see Kang et al. 2009; 14(2):363-380, which is hereby incorporated by reference in its entirety). The drug product described herein is a PEGylated htCBS C15S enzyme formulated for administration to a subject and designed for prolonged systemic exposure.

A. Clinical Manifestation of Homocystinuria

There is significant evidence indicating the causal effect of elevated tHcy levels and negative clinical outcomes in the four systems commonly affected in CBSDH patients (ocular, skeletal, cardiovascular, and neurologic). These data are further supplemented by studies in the general population demonstrating a strong relationship between mildly elevated levels of tHcy and negative outcomes.

1. Eyes

Abnormalities affecting the eyes may be an early clinical sign of CBSDH. Many individuals develop displacement of the lenses of the eyes away from the center of the eyeball (ectopia lentis). Affected individuals also usually develop severe myopia (short or near sightedness) and iridodonesis (quivering of the colored portion of the eye). Ectopia lentis and myopia usually develop after the first year of life and, in untreated individuals, before ten years of age (see Mudd et al. Am J Hum Genet 1985; 37: 1-31, which is hereby incorporated by reference in its entirety). Other eye abnormalities that occur less frequently include cataracts, degeneration of the optic nerve and glaucoma. Some individuals may have retinal detachment, which can cause blurred vision or the appearance of "floaters" in the field of vision (see Burke et al. Br J Ophthalmol, 1989; 73(6): 427-31, which is hereby incorporated by reference in its entirety).

Elevated Hcy levels are a strong and independent risk factor for ocular complications, in particular lens dislocation, in patients with CBSDH and in the general population (see Mudd et al. Am J Hum Genet 1985; 37: 1-31; Ajith et al. Clin Chim Acta 2015; 450:316-321; Mulvihill et al. J AAPOS 2001; 5:311-315; which are hereby incorporated by reference in their entireties). Even with prescribed pharmacologic and dietary interventions, the majority of CBSDH patients eventually present with ocular complications. Lowering Hcy levels has been observed to delay and perhaps prevent lens dislocation in CBSDH patients (see Yap et al. J Inherit Metab Dis 1998; 21: 738-47, which is hereby incorporated by reference in its entirety).

2. Central Nervous System

Developmental delay and learning problems, such as mental retardation, may also be early signs of CBSDH occurring at one to three years of age (see Screening, Technology and Research in Genetics (STAR-G) Project. 2016. Homocystinuria. Available at newbornscreening.info; National Institutes of Health (NIH), US National Library of Medicine, Genetics Home Reference. Homocystinuria. 2016. ghr.nlm.nih.gov; which are hereby incorporated by reference in their entireties). Intelligence quotient (IQ) in individuals with CBSDH has been reported to range from 10 to 138. Patients with the highest tHcy levels are more likely to have lower IQs (with a mean IQ of 57 if untreated) compared to less severely affected patients (with a mean IQ of 79) (see Sacharow et al., Homocystinuria Caused by Cystathionine Beta-Synthase Deficiency. In: Adam M P, Ardinger H H, Pagon R A, Wallace S E, Bean L J H, Mefford H C, et al, editors. GeneReviews™ [Internet]. Seattle (Wash.): University of Washington, Seattle; 1993-2017, which is hereby incorporated by reference in its entirety).

Seizures occur in approximately 20% of untreated individuals with CBSDH (see Mudd et al. Am J Hum Genet 1985; 37: 1-31, which is hereby incorporated by reference in its entirety). Many individuals have psychiatric problems including personality disorder, anxiety, depression, obsessive compulsive behavior, and psychotic episodes (see Sacharow et al. 2017). Extrapyramidal signs such as dystonia may occur as well (see Screening, Technology and Research in Genetics (STAR-G) Project. 2016. Homocystinuria. Available at newbornscreening.info, which is hereby incorporated by reference in its entirety).

Studies have shown that early decreases in Hcy levels, induced by a low Met diet, folic acid/B vitamin supplementation and/or pyridoxine and betaine therapy can delay and sometimes prevent or reverse progression of various neurological disorders and allow normal IQ development in patients with CBSDH (see El Bashir et al. JIMD Rep 2015; 21:89-95; Yap et al. J Inherit Metab Dis 2001; 24:437-447; which are hereby incorporated by reference in their entireties). Associations between elevated levels of Hcy and central nervous system (CNS) symptoms, including mental retardation, neurodegenerative diseases, seizures, dystonia, psychosis, cognitive impairment, dementia and depression, are well documented in CBSDH patients and in the general population (see Abbott et al. Am J Med Genet 1987; 26:959-969; Schimke et al. JAMA 1965; 193:711-719; Herrmann et al. Clin Chem Lab Med 2011; 49:435-441; which are hereby incorporated by reference in their entireties).

3. Skeletal System

Individuals with CBSDH frequently develop a variety of skeletal abnormalities. Affected individuals are often tall and slender with "marfanoid" habitus, which includes thinning and lengthening of the long bones (dolichostenomelia), knees that are bent inward so that they touch when the legs are straight ("knock knees" or genu valgum), a highly arched foot (pes cavus), abnormal sideways curvature of the spine (scoliosis), an abnormally protruding chest (pectus carinatum) or an abnormally sunken chest (pectus excavatum). By the teenage years, 50% of individuals show signs of osteoporosis (see Screening, Technology and Research in Genetics (STAR-G) Project. 2016. Homocystinuria. Available at newbornscreening.info, which is hereby incorporated by reference in its entirety). CBSDH is associated with an increased risk of osteoporotic fractures that partly can be attributed to low bone mineral density (see Mudd et al. Am J Hum Genet 1985; 37: 1-31; Weber et al. Mol Genet Metab 2016; 117:351-354; which are hereby incorporated by reference in their entireties).

In a study of 25 Irish patients with CBSDH followed over 25 years found that the risk of skeletal abnormalities was considerably lower in patients with good compliance with Hcy-lowering treatment compared with non-compliant patients (see Yap et al. J Inherit Metab Dis 1998; 21: 738-47, which is hereby incorporated by reference in its entirety).

4. Cardiovascular System

The relationship between CBSDH and vascular disease was first demonstrated in 1985 in an epidemiological study in patients with moderate to severely elevated Hcy levels due to homozygous CBSDH (see Mudd et al. Am J Hum Genet 1985; 37: 1-31, which is hereby incorporated by reference in its entirety). Thromboembolism is the most serious, often life threatening, complication of CBSDH, and can affect any vessel. It is the major cause of morbidity and early death in patients with CBSDH (see Yap et al. Arterioscler Thromb Vasc Biol. 2001 December; 21(12):2080-5, which is hereby incorporated by reference in its entirety).

The risk of thromboembolic events was approximately 25% by age 16 years and 50% by age 29 years. Several reports described how treatments decreasing tHcy levels significantly reduced the incidence of vascular events, the main cause of morbidity, in CBSDH patients (see Wilcken et al. J Inherit Metab Dis 1997; 20:295-300; Yap et al. Arterioscler Thromb Vasc Biol. 2001 December; 21(12): 2080-5, which are hereby incorporated by reference in their entireties). Since then, a number of other studies demonstrated an increased risk of vascular events, in particular venous thrombosis, in CBSDH patients (see Kelly et al. Neurology 2003; 60:275-279; Magner et al. J Inherit Metab Dis 2011; 34:33-37; which are hereby incorporated by reference in their entireties).

5. Additional Manifestations

Although less common, several additional findings have been reported in patients with CBSDH including extremely fine, fragile skin, brittle hair, discoloration of the skin (hypopigmentation) and rashes on the cheeks (malar flushing). Some individuals may develop fatty changes in the liver, protrusion of part of the intestines through a tear in the abdominal wall (inguinal hernia) or inflammation of the pancreas. Abnormal front-to-back curvature of the spine (kyphosis) and a collapsed lung (spontaneous pneumothorax) have also been reported in individuals with CBSDH (see Yap; Orphanet Encyclopedia [online serial]. 2005, pages 1-13, which is hereby incorporated by reference in its entirety).

To summarize, the MRD alone is effective in correcting multiple symptoms of HCU in spite of failing to reduce plasma Hcy concentration below the recommended level and leading to increased anxiety and reduced bone mineralization. On other hand, enzyme therapy with 20NHS PEG-CBS, as described herein, decreased plasma Hcy concentrations below the suggested threshold of 100 μM and corrected all the monitored symptoms of HCU. Furthermore, 20NHS PEG-CBS retains its efficacy under Met restriction yielding fully normalized plasma biochemical profile. By extrapolating these data to human patients, our results establish 20NHS PEG-CBS as a single life-long therapy could be efficacious in prevention and correction of clinical symptoms of HCU. In addition, treatment with 20NHS PEG-CBS should allow for elimination of Met/diet restriction, and thus, in turn, substantially improve quality of life of HCU patients and their families.

II. Compositions

A. Native Human CBS Enzyme

The CBS full native enzyme is a tetramer with four identical monomers, in which each monomer (63 kDa is size) is organized into three functional domains. The first is a N-terminal region of about 70 amino acids that binds heme and is thought to function in redox sensing and/or enzyme folding. The second is a central domain that contains the catalytic core and shows the fold of the type II family PLP (pyridoxal-5'-phosphate)-dependent enzymes. The coenzyme PLP is deeply buried in a cleft between the N- and C-terminal domains. The third region is the C-terminal regulatory domain, that consists of a tandem pair of CBS motifs that upon binding to S-adenosylmethionine (SAM) activates the enzyme. Removal of the regulatory region generates an enzyme which is constitutively active (see Miles et al. J Biol Chem. 2004 Jul. 16; 279(29):29871-4, which is hereby incorporated by reference in its entirety).

The pyridoxal-5'-phospahte (PLP)-dependent enzyme fold contains a heme group. It catalyzes the PLP-dependent beta-replacement reaction in which it condenses L-homocysteine with L-serine to form L-cystathionine. It is allosterically regulated by binding of S-adenosyl-L-methionine (Ado-Met) to the C-terminal regulatory domains, resulting in a conformational rearrangement of these domains and a release of an autoinhibitory block. CBS activation can also be achieved by totally removing the C-terminal regulatory domains, generating a dimeric form of the enzyme which is constitutively active (see Miles et al. J Biol Chem. 2004 Jul. 16; 279(29):29871-4; Ereno-Orbea et al. Proc Natl Acad Sci USA 111(37), E3845-3852 (2014); each of which is hereby incorporated by reference in its entirety).

The active substance in the drug product described herein is a recombinant human truncated CBS protein with a cysteine to serine substitution at amino acid position 15 of the protein (htCBS C15S) compared to the amino acid sequence of SEQ ID NO: 2 in the present sequence listing and SEQ ID NO: 2 of WO 2017/083327 (which is hereby incorporated by reference in its entirety), which represents a native CBS protein, that has been modified by the addition of polyethylene glycol (PEG). The enzyme is also known as htCBS C15S. In certain embodiments, the drug substance htCBS C15S has the amino acid sequence of SEQ ID NO: 1.

This form of the enzyme has a high tendency toward aggregation, which poses a major constraint on manufacturing and production of human CBS (hCBS). PEGylated htCBS C15S (including "20NHS PEG-CBS" as defined herein) has been engineered to form dimers rather than tetramers, which are less susceptible to aggregation. High molecular-weight compounds, such as enzymes, are removed from circulation by degradation by proteolysis and various clearance mechanisms (see Vugmeyster et al. World J Biol Chem. 2012; 3(4):73-92, which is hereby incorporated by reference in its entirety). PEGylation is known to minimize proteolysis and immunogenicity, while increasing protein stability and reducing renal excretion (see Kang et al. 2009; 14(2):363-380, which is hereby incorporated by reference in its entirety). These structural modifications make the drug product described herein comprising PEGylated htCBS C15S a more suitable candidate than native hCBS as an enzyme therapy (ET) for CBSDH.

Native CBS is an intracellular enzyme, and no mechanism is known to exist for the uptake of the enzyme from the extracellular environment to its primary intracellular site of action, while PEGylated htCBS C15S acts extracellularly. Unlike native endogenous CBS, PEGylated htCBS C15S corrects the metabolic abnormalities by operating directly in circulation and indirectly in tissues and does so without requiring SAM for activation. The native hCBS enzyme is activated in cells upon binding of S-adenosyl methionine (SAM) to its C-terminal regulatory domain. However, SAM levels in circulation in both patients and healthy individuals are far below the levels required for CBS activation (see Stabler et al. Metabolism, 2002. 51(8): p. 981-8, which is hereby incorporated by reference in its entirety). Therefore, administration of native CBS into the circulation would be ineffective, as CBS would not become activated. PEGylated htCBS C15S, although it remains in circulation and does not enter cells, has been engineered to bypass the need for SAM activation by the removal of the CBS C-terminal regulatory domain rendering the enzyme constitutively active.

B. Enzyme Therapy (ET)

PEGylated htCBS C15S is a PEGylated, truncated hCBS with a cysteine to serine substitution at position 15 for ET for the treatment of CBSDH. This modification optimizes the enzyme to form dimers rather than tetramers and is constitutively active.

PEGylated htCBS C15S supplements deficient CBS activity, thereby reducing plasma, urine, and tissue levels of homocysteine (Hcy) and methionine (Met), increasing cystathionine (Cth) levels, and normalizing cysteine (Cys) levels in patients with CBSDH. Reduction of total Hcy (tHcy) levels is the current treatment target (see, Morris et al. J Inherit Metab Dis. 2017 January; 40(1):49-74, which is hereby incorporated by reference in its entirety) and is strongly correlated with amelioration of clinical (ocular, skeletal, vascular, and neurological) outcomes (Yap; Orphanet Encyclopedia [online serial]. 2005, pages 1-13, which is hereby incorporated by reference in its entirety).

PEGylated htCBS C15S is a recombinant form of the native human CBS enzyme, which is produced in *E. coli* bacteria. The DNA sequence of native human CBS (SEQ ID NO: 3 in the present sequence listing and SEQ ID NO: 1 of WO 2017/083327, which is hereby incorporated by reference in its entirety) was genetically modified to remove the C-terminal regulatory region (amino acids 414-551) (SEQ ID NO: 4 in the present sequence listing and SEQ ID NO: 3 of WO 2017/083327), forming the human truncated CBS. The DNA sequence of the human truncated CBS was further modified to introduce a point mutation of T→A at position 43 of the DNA coding region, resulting in a cysteine to serine substitution at position 15 of the translated protein, generating the human truncated CBS C15S (htCBS C15S) (SEQ ID NO: 5 in the present sequence listing and SEQ ID NO: 13 of WO 2017/083327). This change reduces aggregation and allows for batch to batch consistency compared to the native hCBS.

The enzyme is further modified in the *E. coli* bacteria during expression, resulting in a removal of the first Met from the protein as shown in SEQ ID NO: 1. After its purification, the htCBS C15S enzyme is further modified by PEGylation with N-hydroxylsuccinimide ester functionalized 20 kDa PEG moieties, which react with primary amines on the surface of the protein. An approximate average of 5.1 PEG molecules are attached to each monomeric unit of the enzyme yielding a heterogeneous dimeric product of mean molecular weight of 290 kDa.

C. PEGylation of htCBS C15S to Produce 20NHS PEG-CBS

ME-200GS (also referred to as methoxy-PEG-CO(CH$_2$)$_3$COO—NHS) is used herein to PEGylate htCBS C15S:

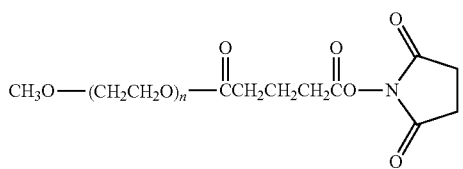

ME-200GS has a molecular weight of 20 kDa and a chemical name of α-Succinimidyloxyglutaryl-ω-methoxy, polyoxyethylene. ME-200GS targets free amines on the surface of htCBS C15S. An amide bond is formed between the PEG and the lysine residue on htCBS C15S. The resulting molecule is referred to throughout the disclosure as "20NHS PEG-CBS," and is a PEGylated human cystathionine beta-synthase molecule that is truncated and that has a C15S mutation, as provided in SEQ ID NO: 1.

A tangential flow filtration (TFF) with a molecular weight cut-off of 100 kDa and 15 volume exchanges is used to deplete free PEG and other PEGylation impurities and is subsequently used for formulation against PBS buffer. All process-related substances including ammonium ions and others, imidazole, Triton X-100, and NHS groups released from PEG during PEGylation are expected to be at trace levels following the 2 cycles of large cutoff TFF diafiltration step.

The PEG ME-200GS is manufactured by NOF Corporation under cGMP conditions according to the process flow diagram provided in FIG. 1. All raw materials used in the manufacture of the ME-200GS product are of synthetic or inorganic nature. The impurities that could be potentially present in the PEG ME-200GS raw material are small molecules.

D. Post-Translational Modifications

Post-translational modifications can require additional bioprocess steps to separate modified and unmodified polypeptides, increasing costs and reducing efficiency of biologics production. Accordingly, in some embodiments, production of a polypeptide agent in a cell is enhanced by modulating the expression of a target gene encoding a protein that affects post-translational modification. In additional embodiments, biologics production is enhanced by modulating the expression of a first target gene encoding a protein that affects a first post-translational modification and modulating the expression of a second target gene encoding a protein that affects a second post-translational modification.

Additionally, proteins expressed in prokaryotic or eukaryotic cells can undergo several post-translational modifications that can impair production and/or the structure, biological activity, stability, homogeneity, and/or other properties of the biological product. Many of these modifications occur spontaneously during cell growth and polypeptide expression and can occur at several sites, including the peptide backbone, the amino acid side-chains, and the amino and/or carboxyl termini of a given polypeptide. In addition, a given polypeptide can comprise several different types of modifications. For example, proteins expressed in bacterial cells, such as *E. coli*, can be subject to acetylation, histone clipping, carboxylation, and/or deamidation (see Yang et al., PNAS 111 (52) E5633-E5642 (2014), which is hereby incorporated by reference in its entirety). For example, proteins expressed in avian and mammalian cells, such as Chinese hamster ovary (CHO) cells, can be subject to acetylation, carboxylation, gamma-carboxylation, histone clipping, deamidation, N-terminal glutamine cyclization and deamidation, and asparagine deamidation.

In some embodiments, protein production is enhanced by modulating expression of a target gene which encodes a protein involved in protein deamidation. Proteins can be deamidated via several pathways, including the cyclization and deamidation of N-terminal glutamine and deamidation of asparagine. Thus, in one embodiment, the protein involved in protein deamidation is N-terminal asparagine amidohydrolase. Protein deamidation can lead to altered structural properties, reduced potency, reduced biological activity, reduced efficacy, increased immunogenicity, and/or other undesirable properties and can be measured by several methods, including but not limited to, separations of proteins based on charge by, e.g., ion exchange chromatography, HPLC, isoelectric focusing, capillary electrophoresis, native gel electrophoresis, reversed-phase chromatography, hydrophobic interaction chromatography, affinity chromatography, mass spectrometry, or the use of L-isoaspartyl methyltransferase.

In some embodiments, the protein that affects protein secretion is a molecular chaperone selected from the group consisting of: Hsp40, HSP47 (also referred to as serpin peptidase inhibitor, clade H; heat shock protein 47), HSP60, Hsp70, HSP90, HSP100, protein disulfide isomerase, peptidyl prolyl isomerase, calnexin, Erp57 (protein disulfide isomerase family A, member 3), and BAG 1. In some embodiments, the protein that affects protein secretion is selected from the group consisting of γ-secretase, p115, a signal recognition particle (SRP) protein, secretin, and a kinase (e.g., MEK).

It is contemplated that further optimization could be achieved by systematically either adding or removing nucleotides to generate longer or shorter sequences and testing those sequences generated by walking a window of the longer or shorter size up or down the target RNA from that point. Coupling this approach to generating new candidate targets with testing for effectiveness of RNA effector molecules based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

E. Stability

The drug substance or the drug product is stable at a variety of temperatures and storage conditions. In some embodiments, the drug substance or the drug product is stable when stored at −65° C. and −20° C. Alternatively, the drug substance or the drug product may be stable when stored at a temperature in a range of about 2° C. to about 8° C. Alternatively, the drug substance or the drug product may be stable when stored at a temperature in a range of 25° C.±2° C. For example, the drug substance or the drug product remains stable between 20° C. and 25° C. In certain embodiments, the drug substance or the drug product is stable under reducing conditions. In certain embodiments, the drug substance or the drug product is stable under non-reducing conditions. In some embodiments, the drug substance or the drug product remains stable for at least 2 days, at least 7 days, at least 1 month, at least 2 months, at least 3 months, at least 6 months, or at least 12 months. For example, the drug substance or the drug product remains stable during storage for about 2 days. For example, the drug substance or the drug product remains stable during storage for about 7 days. For example, the drug substance or the drug product remains stable during storage for about 1 month. For example, the drug substance or the drug product remains stable during storage for about 2 months. For example, the drug substance or the drug product remains stable during storage for about 3 months. For example, the drug substance or the drug product remains stable during storage for about 6 months. For example, the drug substance or the drug product remains stable during storage for about 12 months. For example, the drug substance or the drug product remains stable during storage for about 18 months.

In some embodiments, the drug substance or the drug product remains stable for storage at −65° C. for up to 18 months. In some embodiments, the drug substance or the drug product remains stable for storage between about 2° C. and about 8° C. for up to 3 months. In some embodiments, the drug substance or the drug product remains stable for storage at 25° C.±2° C. for up to 1 month.

In some embodiments, the drug substance or the drug product remains stable for at least 3 freeze and thaw cycles. In some embodiments, the drug substance or the drug product remains stable for up to 6 freeze and thaw cycles. For example, the drug substance or the drug product remains stable for 5 freeze and thaw cycles. In certain embodiments, the drug product is stable following ejection from a syringe.

III. Pharmaceutical Compositions

The drug product described herein comprising PEGylated htCBS C15S is intended to restore metabolic control and ameliorate the clinical manifestations of the disease by reducing homocysteine levels, and normalizing cysteine levels in patients with CBSDH. htCBS C15S is manufactured by recombinant technology using *E. coli* BL21 (DE3) and is formulated as a sterile drug product in phosphate buffered saline. The drug product is intended for administration by subcutaneous (SC) injection.

PEGylated htCBS C15S activity in circulation improved or even entirely normalized the metabolite profiles in tissues as well (see WO 2017/083327, which is hereby incorporated by reference in its entirety). Therefore, the drug product does not necessarily need to be delivered into its native intracellular milieu.

The drug product reduces the accumulation of toxic Hcy in circulation, urine, and tissues of patients of CBSDH; normalizes Cys levels in circulation and tissues; increases the levels of Cth in circulation and tissues; and/or prevents, delays, and/or reverses the onset of CBSDH manifestations. The drug product achieves at least one of these benefits while allowing the patients to enjoy normal diet. In fact, increased Cth activity even with a regular diet (e.g. 4.0 g/kg of MET) has been observed to be evidence of increased activity of the drug product and/or decreased renal elimination.

20NHS PEG-CBS drug substance was formulated at a concentration of between 20-30 mg/mL, or about 25 mg/mL, in phosphate buffered saline (PBS) containing di-sodium hydrogen phosphate (Dihydrate) (11.4 mM), sodium chloride (137 mM), potassium chloride (2.7 mM) and potassium di-hydrogen phosphate (1.98 mM), prepared with water for injection (WFI). The drug substance was freely soluble in aqueous solution.

The molecular weight of the drug substance calculated from isotopically averaged molecular weight from SEC/UV/MS is 45.290 kDa for the monomer and 90.58 kDa for the dimer.

All batches were a clear liquid that was practically free from visible particles and dark red in color. Additionally, SDS-PAGE performed in both reducing and non-reducing conditions and a Western blot provided results were consistent with each other for each batch. A distinctive, uniform, and constant pattern of the PEGylation variant was demonstrated using each of these methods. Concomitant medications, including anticoagulants, vitamin and mineral supplementation, betaine, antidepressants, may also be combined with the drug product described herein to enhance the efficacy of the pharmaceutical composition.

IV. Formulations

For the above-mentioned therapeutic uses, the dosage administered will vary with the compound employed, the mode of administration, the treatment desired and the disorder indicated. For example, the daily dosage of the compound of the disclosure, if inhaled, may be in the range from 0.05 micrograms per kilogram body weight (μg/kg) to 100 micrograms per kilogram body weight (μg/kg). Alternatively, if the compound is administered orally, then the daily dosage of the compound of the disclosure may be in the range from 0.01 micrograms per kilogram body weight (μg/kg) to 100 milligrams per kilogram body weight (mg/kg).

The protein having an amino acid sequence SEQ ID NO: 1, which is PEGylated to form the drug substance described herein, may be used on its own but will generally be administered in the form of a pharmaceutical composition in association with a pharmaceutically acceptable adjuvant, diluent, or carrier. Therefore, the present disclosure further provides a pharmaceutical composition comprising the drug substance described herein in association with a pharmaceutically acceptable adjuvant, diluent or carrier.

Pharmaceutically acceptable adjuvants, diluents or carriers that may be used in the pharmaceutical compositions of the disclosure are those conventionally employed in the field of pharmaceutical formulation, and include, but are not limited to, sugars, sugar alcohols, starches, ion exchangers, alumina, aluminum stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat (lanolin).

The pharmaceutical compositions of the present disclosure may be administered orally, parenterally, by inhalation spray, rectally, nasally, buccally, vaginally or via an implanted reservoir. In one embodiment, the pharmaceutical composition may be administered orally. In one embodiment, the pharmaceutical composition may be administered subcutaneously. The pharmaceutical compositions of the disclosure may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable adjuvant, diluent, or carrier, for example, as a solution in 1,3-butanediol. Among the acceptable adjuvants, diluents, and carriers that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this disclosure may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of the disclosure may also be formulated in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions herein may be in a form to be administered through the circulatory system as shown in WO 2015/153102, WO 2016/183482, and WO 2018/009838, which are each hereby incorporated by reference in its entirety. The CBS protein may be encoded by a recombinant nucleic acid expressed by enucleated hematopoietic cells (EHCs), including erythroid or thromboid cells. For example, the erythroid cells are red blood cells, erythrocytes, or reticulocytes. For example, the thromboid cells are platelets. In certain embodiments, the encoded CBS protein is fused to a translated membrane-anchored polypeptide. In certain embodiments, the CBS protein is localized on the surface of the EHC. The CBS protein may be cleaved for activation of the enzyme in the extracellular space. Alternatively, the internally localized CBS protein may be released into the extracellular space by lysis of the EHC. Alternatively, the enzymatic target of the CBS protein may enter the EHC and then exits through the membrane after alteration. In certain embodiments, the CBS protein has an amino acid sequence of SEQ ID NO: 1, SEQ ID NO: 2, SEQ ID NO: 4 or SEQ ID NO: 5 in the present sequence listing or SEQ ID NOs: 2, 3, or 13 of WO 2017/083327 (which is hereby incorporated by reference in its entirety).

Depending on the mode of administration, the pharmaceutical composition will comprise from 0.05 to 99% w (percent by weight), more specifically from 0.05 to 80% w, still more specifically from 0.10 to 70% w, and even more specifically from 0.10 to 50% w, of active ingredient, all percentages by weight being based on total composition.

Conventional procedures for the selection and preparation of suitable pharmaceutical formulations are described in, for example, "Pharmaceutics—The Science of Dosage Form Design", M. E. Aulton, Churchill Livingstone, 1988, which is herein incorporated by reference in its entirety.

The buffer solution of di-sodium hydrogen phosphate (Dihydrate), sodium chloride, potassium chloride, and potassium di-hydrogen phosphate are introduced to the drug substance through diafiltration.

The drug product is formulated at a target concentration of 20-30 mg/mL, or about 25 mg/mL, in PBS (pH=7.4±0.2). The PBS buffer contains di-sodium hydrogen phosphate (Dihydrate) (11.4 mM), sodium chloride (137 mM), potassium chloride (2.7 mM), and potassium di-hydrogen phosphate (1.98 mM). Table 1 provides the formulation details.

TABLE 1

Formulation of drug product

| Component | Amount (g) per Batch |
|---|---|
| Drug Substance | 25 mg/mL (range 20-30 mg/mL) |
| Water for injection (WFI) | Quantity sufficient to volume |
| di-Sodium hydrogen phosphate (Dihydrate) | 11.4 mM |
| Sodium chloride | 137 mM |
| Potassium chloride | 2.7 mM |
| Potassium di-hydrogen phosphate | 1.98 mM |

Table 2 provides an example unit dose composition of the drug product described herein.

TABLE 2

Unit dose of drug product

| Component | Single Dose Quantity (1 mL/vial) | Function |
|---|---|---|
| Drug substance | 25 mg | Active Ingredient; Enzyme |
| Water for injection (WFI) | 1 mL | Solvent |
| di-Sodium hydrogen phosphate (Dihydrate) | 2.0 mg | Buffer component |
| Sodium chloride | 8.0 mg | Excipient |
| Potassium chloride | 0.2 mg | Excipient |
| Potassium di-hydrogen phosphate | 0.3 mg | Buffer component |

In certain embodiments, the drug product is formulated for exposure of about 50 mU/μL in a subject. A lyophilized formulation may be used for administration to humans upon reconstitution.

A. Lyophilization

The pharmaceutical compositions may be in a lyophilized formulation. In some embodiments, the lyophilized formulation comprises the drug substance, a buffer, and an excipient. In certain embodiments, upon reconstitution of the lyophilized formulation in a suitable reconstitution buffer, water or any other pharmaceutically acceptable adjuvant, diluent or carrier, the concentration of the drug substance is between about 20-30 mg/ml. In some embodiments, the concentration of the drug substance is about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, or about 30 mg/ml. In some embodiments, the concentration of the drug substance is about 25.4 mg/ml. In certain embodiments, upon reconstitution of the lyophilized formulation in a suitable reconstitution buffer, water or any other pharmaceutically acceptable adjuvant, diluent or carrier, the buffer is potassium phosphate at a concentration of 15 mM. In certain embodiments, the excipient is trehalose at a concentration of 8% (w/v). In some embodiments, the formulation comprises sucrose such that, upon reconstitution of the lyophilized formulation in a suitable reconstitution buffer, water, or pharmaceutically acceptable adjuvant, diluent or carrier, the concentration of sucrose is 5%. In some embodiments, the collapse onset temperature (Tc,on) determined by freeze drying microscopy is −21° C. In some embodiments, the formulation has a pH of 7.5.

In some embodiments, the lyophilization process may be performed in 48 hours or less without the melting of the crystalline cake structure. The lyophilization process may be optimized to tune one or more of the following parameters or properties such as, but not limited to, (i) reduced reconstitution time of the lyophilized formulation (e.g. less than 1 minute), (ii) reduced viscosity to allow a more concentrated drug product, (iii) incorporation of an isotonic buffer to minimize pain to patients, and/or (iv) reduced de-PEGylation.

The lyophilized formulation may be prepared using the following protocol. Three days prior to the formulation preparation, the drug substance (stored at −80° C.) at 20-30 mg/ml or about 25 mg/ml is thawed for 72 hours at 2-8° C. in a refrigerator. After thawing, the drug substance is homogenized by gentle swirling. Dialysis is performed under controlled conditions at 2-8° C. for 24 hours. Dialysis cassettes with a 20-kDa cut-off are used and buffer is exchanged three times at a volume ratio of greater than or equal to 1:50 each time. The buffer is exchanged after 3 and 6 hours of total dialysis time. The last dialysis step is performed overnight. After dialysis, the formulation is recovered from the dialysis cassettes and filtered by using a 0.22-μm polyvinylidene difluoride (PVDF) filter. After filtration, vials are filled with a filling volume of 1.0 ml under laminar air-flow conditions.

Lyophilization is performed in an Epsilon 2-12D pilot scale freeze dryer (Martin Christ, Osterode, Germany). The chamber pressure is controlled by a capacitance gauge and regulated by a vacuum pump and a controlled nitrogen dosage.

After equilibration of the vials to 5° C., the vials are frozen to −45° C. and equilibrated for further 5 hours at −45° C. Shelf temperature is set to −15° C. for 31 hours in primary drying. Secondary drying is performed at a shelf temperature of 40° C. for 2.5 hours. At the end of the lyophilization process, the chamber is aerated with nitrogen to 800 mbar and the vials are stoppered by lifting the shelves. After stoppering, the chamber is aerated to atmospheric pressure with nitrogen. Table 3 shows the lyophilization process parameters after optimization of the cycle.

TABLE 3

Lyophilization process parameters

| # | Step | Time [hh:mm:ss] | Temperature [° C.] | Pressure [mbar] | Total time [h] | Ramp [° C./min] |
|---|---|---|---|---|---|---|
| 1 | Loading | 0:00:00 | 5 | 1,000 | 0.0 | |
| 2 | Equilibration to 5° C. | 1:00:00 | 5 | 1,000 | 1.0 | |
| 3 | Freezing | 1:40:00 | −45 | 1,000 | 2.7 | 0.50 |
| 4 | Freezing | 5:00:00 | −45 | 1,000 | 6.7 | |
| 5 | Primary drying | 0:30:00 | −45 | 0.1 | 7.2 | |
| 6 | Primary drying | 1:00:00 | −15 | 0.1 | 8.2 | 0.50 |
| 7 | Primary drying | 31:00:00 | −15 | 0.1 | 39.2 | |
| 8 | Secondary drying | 3:00:00 | 40 | 0.1 | 42.2 | 0.31 |
| 9 | Secondary drying | 2:30:00 | 40 | 0.1 | 44.7 | |
| 10 | Aeration | 0:30:00 | 40 | 800 | 45.2 | |
| 11 | Stoppering | 0:01:00 | 40 | 800 | 45.2 | |
| 12 | Storage | 0:30:00 | 5 | 1,000 | 45.7 | |

During the freeze-drying process, product temperature, shelf temperature, condenser temperature and chamber pressure (capacitance and Pirani gauge) are monitored. The product temperature is monitored by Pt100 sensors (OMEGA™).

V. Treatments of Diseases, Disorders, or Conditions

Individuals with CBSDH are typically asymptomatic at birth and, unless they are treated, symptoms appear in these individuals over time, some as early as infancy, many in childhood, and, as this is a spectrum disease, in some patients symptoms appear only in adulthood (see Yap, 2005; Mudd et al. Am J Hum Genet 1985; 37:1-31; Morris et al. Guidelines for the diagnosis and management of cystathionine beta-synthase deficiency. J Inherit Metab Dis 2017; 40:49-74; Mudd et al. In: Scriver C L, Beaudet A L, Sly W S, Valle D, eds. The Metabolic and Molecular Basis of Inherited Diseases. 7 ed. New York: McGraw Hill; 2001; 1279-1327, each of which is hereby incorporated by reference in its entirety). Four main organ systems are typically involved, ocular, skeletal and vascular systems, as well as the CNS. Other organs, such as liver, pancreas, gastrointestinal tract and skin, including hair follicles, may also be involved (see Mudd et al. Am J Hum Genet 1985; 37:1-31; Morris et al. J Inherit Metab Dis 2017; 40:49-74; Muacevic-Katanec et al. Coll Antropol 2011; 35:181-185; Suri et al. J Neurol Sci 2014; 347:305-309, each of which is hereby incorporated by reference in its entirety).

The accumulated data show that the reduction of Hcy levels can serve as an indicator for the successful application of enzyme therapy (ET) in CBSDH. It is consistent with the definition by the NIH-FDA Biomarker Working Group (see FDA-NIH Biomarker Working Group. BEST (Biomarkers, EndpointS, and other Tools) Resource [Internet]. Silver Spring (Md.): Food and Drug Administration (US); 2016-. Reasonably Likely Surrogate Endpoint. 2017 Sep. 25. Co-published by National Institutes of Health (US), Bethesda (Md.). ncbi.nlm.nih.gov/books/NBK326791/, which is hereby incorporated by reference in its entirety) of a "pharmacodynamic/response biomarker, whose level changes in response to exposure to a medical product . . ." and, even further, of a marker closely linked, in the case of an ET for CBSDH, to the drug mechanism of action. Therefore, blood or plasma Hcy is not only a useful marker for pharmacodynamic studies but has also been previously recognized as a "reasonably likely surrogate endpoint" for homocystinuria (HCU).

In infants and children with CBSDH, the priority is to prevent complications associated with CBSDH and to ensure proper growth and development of normal intelligence (see Morris et al. J Inherit Metab Dis 2017; 40:49-74, which is hereby incorporated by reference in its entirety). In patients diagnosed later in life, the aims of treatment should be to prevent life-threatening thromboembolism and to minimize progression of already established complications. To address these goals, the biochemical abnormalities associated with CBSDH must be improved and, if possible, normalized (see Morris et al. J Inherit Metab Dis 2017; 40:49-74, which is hereby incorporated by reference in its entirety).

According to the 2016 Guidelines for the Diagnosis and Management of CBSDH, Hcy levels should be maintained as close to normal as possible (at or below 10 to 15 µmol/L). This is not typically possible in patients with CBSDH given available treatments and so aspirational targets are suggested, below 50 µmol/L in patients with pyridoxine-responsive CBSDH and below 100 µmol/L in non-pyridoxine responsive patients (see Morris et al. J Inherit Metab Dis 2017; 40:49-74, which is hereby incorporated by reference in its entirety). As noted earlier, non-pyridoxine responsive patients tend to have higher Hcy levels than pyridoxine responsive ones. Although two goals are recommended for patients with the same disease, these goals were designed to be achievable, rather than optimized, in order to minimize complications.

Overall, the effectiveness of long-term treatments required for managing CBSDH, especially because they most frequently depend upon dietary restrictions and supplementation, are subject to poor or inconsistent lifelong compliance. An ET for CBSDH would avoid many of these pitfalls. By compensating for the metabolic defect in CBSDH through a mechanism that should not require severe Met restriction or Cys supplementation, an ET would be expected to achieve more consistent Hcy lowering, while not dangerously elevating Met levels, and also allowing for liberalization or normalization of the diet.

There is presently no cure for CBSDH that corrects the underlying genetic causes of the condition, but the generally accepted therapeutic goal is to reduce tHcy levels as much as possible (see Morris et al. J Inherit Metab Dis. 2017 January; 40(1):49-74, which is hereby incorporated by reference in its entirety). Consequently, current therapy is directed at correcting the biochemical abnormalities thereby reducing the risk of adverse clinical manifestations of the disease. Hcy levels are seldom fully normalized by treatments currently available for patients with CBSDH.

A combination of strategies is required to achieve treatment targets in most patients. These treatment strategies include: 1) increasing residual CBS activity by administering pharmacologic doses of pyridoxine (vitamin B6, a cofactor for CBS, along with folic acid) to pyridoxine sensitive patients (see Yap et al. Arterioscler Thromb Vasc Biol. 2001 December; 21(12):2080-5, which is hereby incorporated by reference in its entirety); 2) decreasing the methionine load through severe dietary/protein restriction, while supplementing the diet with products beyond the metabolic block, and 3) enhancing alternative metabolic pathways to counter the effects of the CBS deficiency, e.g., administer betaine (a methyl donor) to enhance remethylation of Hcy to Met. In certain embodiments, folate supplementation and (if needed) vitamin B12 supplements are provided (see Morris et al. J Inherit Metab Dis. 2017 January; 40(1):49-74, which is hereby incorporated by reference in its entirety).

A. Current Therapies for CBSDH

In some embodiments, patients with CBSDH should receive adequate folate supplementation and (if needed) vitamin B12 supplements (see Morris et al. J Inherit Metab Dis 2017; 40:49-74, which is hereby incorporated by reference in its entirety). In addition, patients should be treated with pyridoxine therapy (if responsive), a Met-restricted, Cys-supplemented diet and/or betaine therapy. A combination of strategies is required to achieve treatment targets in most patients.

The most common prescribed treatment was a combination of diet and betaine, followed by betaine alone and diet alone (see Adam et al. Mol Genet Metab 2013; 110:454-459, which is hereby incorporated by reference in its entirety). As patients become older than 16, they are most often prescribed betaine only without diet, in recognition of the poor compliance of adult patients with the Met-restricted diet. However, compliance with betaine in adults is also poor. The median protein intake varied widely among patients and increased dramatically with age.

Consistent with these findings, a recent report stated that only four adult patients among 24 patients prescribed a low protein diet with specific CBSDH-appropriate amino acid supplementation followed this treatment (see Lorenzini et al. J Inherit Metab Dis. 2017 Oct. 4, which is hereby incorporated by reference in its entirety). Multiple CBSDH experts have described similarly wide variability in the United States (Orphan Technology Scientific Advice Board comprised of physicians who are US CBSDH experts). A study comparing tHcy values from untreated versus treated patients (25 and 93 patients, respectively) concluded that there were no significant differences between these two groups (tHcy ranges 15.7 to 281.4 and 4.8 to 312 µmol/L, respectively; median values 125.0 and 119.0 µmon, respectively) although the study provided no details about the patients' treatment regimens (see Stabler et al. JIMD Rep 2013; 11:149-163, which is hereby incorporated by reference in its entirety). These results suggest all or a combination of the following conclusions: that patients either had a heterogeneous presentation of the disease, that standard treatments were ineffective, and/or that compliance with treatment was poor.

1. Pyridoxine

Upon diagnosis, patients are tested for responsiveness to pyridoxine, a co-factor of CBS. Administration of pyridoxine (Vitamin B6) at pharmacologic doses increases the residual activity of CBS in individuals who have been shown to be pyridoxine responsive. The definition of pyridoxine responsiveness varies widely from site to site, though the 2016 guideline, written as part of the European network and registry for homocystinuria and methylation defects (EHOD), defined pyridoxine responsiveness as a 20% reduction in tHcy levels within 6 weeks of pyridoxine exposure. Patients with severely elevated tHcy levels and patients with mildly or moderately elevated tHcy levels can both be defined as responsive despite presenting with very different tHcy levels. Furthermore, different treatment centers define pyridoxine responsiveness differently, and therefore classification of patients by tHcy levels, rather than by their pyridoxine responsiveness, is more appropriate and rigorous. In general, patients who are responsive to pyridoxine have some residual CBS activity and therefore lower tHcy levels resulting in less severe presentation.

Pyridoxine is generally considered to be safe in patients with CBSDH (see Yap; Orphanet Encyclopedia [online serial]. 2005, pages 1-13, which is hereby incorporated by reference in its entirety). Its most commonly reported adverse effects include peripheral neuropathy in patients treated with high doses defined as greater than 900 mg/day (see Schaumburg et al. N Engl J Med 1983; 309:445-448; Ludolph et al. Eur J Pediatr 1993; 152:271; which are hereby incorporated by reference in their entireties), apnea and unresponsiveness in neonates receiving pyridoxine at 500 mg/day (Mudd et al. Am J Hum Genet 1985; 37: 1-31, which is hereby incorporated by reference in its entirety), and rhabdomyolysis (see Shoji et al. J Inherit Metab Dis 1998; 21:439-440, which is hereby incorporated by reference in its entirety).

While pyridoxine treatment is widely used, it provides a modest decrease in tHcy levels, and most patients who are defined as responsive are not able to significantly reduce, let alone normalize, tHcy levels on pyridoxine alone, as their starting levels are many fold above normal (see Morris et al. J Inherit Metab Dis. 2017 January; 40(1):49-74, which is hereby incorporated by reference in its entirety). Besides long-term pyridoxine treatment, it is recommended that pyridoxine responsive patients CBSDH patients also receive folate and as required, vitamin B12 supplementation.

2. Dietary Restriction

Lifelong dietary restrictions have been recommended previously for all patients with CBSDH (see Morris et al. J Inherit Metab Dis. 2017 January; 40(1):49-74; Walter et al. Eur J Pediatr. 1998 April; 157 Suppl 2:S71-6; which are hereby incorporated by reference in their entireties). The recommended diet is extremely limited and is aimed at reducing Met intake by restriction of protein content.

The mainstay of the present therapy for CBSDH patients is a lifelong low protein diet including as little as 5 g of natural protein per day (www.hcunetworkamerica.org) supplemented with Met-free-L-amino acids and, in many cases, additional Cys (Yap et al. J Inherit Metab Dis 1998; 21: 738-47; Morris et al. J Inherit Metab Dis. 2017 January; 40(1):49-74; which are hereby incorporated by reference in their entireties) is given to supplement the diet. The severely restricted diet consists of low-methionine cereal-based foods, low-methionine fruits and vegetables, low-methionine medical foods, oils, and sugar. Foods such as meat, chicken, fish, eggs, milk, yogurt, cheese, soy products, nuts, legumes and many fruits and vegetables that contain moderate amounts of Met should be avoided. Since native CBS is a key enzyme in Met metabolism, the ingestion of Met, an essential amino acid found in many foods, results in elevated plasma concentrations of tHcy and reduced concentrations of the downstream metabolites Cth and Cys.

Prepared foods, baked goods, and packaged foods must be highly restricted, as they often contain milk, eggs or flour.

The amount of protein needed and tolerated by each CBSDH patient is different and is likely to vary with time. This amount is adjusted according to tHcy levels which are monitored in frequent blood tests (ASIEM Low Protein Handbook for Homocystinuria). The majority of patients on dietary treatment also requires a daily consumption of a poorly palatable, Met-free synthetic amino acid formula to prevent secondary malnutrition and for proper growth in children, and in adults for proper nutrition (see Morris et al. J Inherit Metab Dis. 2017 January; 40(1):49-74; which is hereby incorporated by reference in its entirety).

Though dietary modifications with combination of vitamin supplementation can decrease tHcy levels to some extent in individuals fully compliant with the highly restrictive diet, the tHcy levels of most CBSDH patients remain several-fold to orders of magnitude above normal. For most individuals, it is highly challenging to achieve full lifelong compliance with dietary modifications and the resulting periods of poor metabolic control have cumulative deleterious effects (see Morris et al. J Inherit Metab Dis. 2017 January; 40(1):49-74; which is hereby incorporated by reference in its entirety). Compliance with diet is often poor and generally deteriorates further during adolescence and adulthood (see Walter et al. Eur J Pediatr. 1998 April; 157 Suppl 2:S71-6; Schiff et al. Neuropediatrics. 2012 December; 43(6):295-304; Garland et al. Paediatr Child Health. 1999 November; 4(8):557-62; which are hereby incorporated by reference in their entireties). Moreover, eating high Met foods does not elicit an immediate negative physical reaction, further compounding the difficulty with diet compliance (www.hcunetworkamerica.org). Met restriction is even more challenging in children because of the need to ensure sufficient Met to facilitate growth and development. The majority of patients on dietary treatment also requires a Cys-enriched, Met-free L-amino acid supplement for proper growth in children, and in adults for proper nutrition (see Morris et al. J Inherit Metab Dis 2017; 40:49-74; which is hereby incorporated by reference in its entirety).

A recent report stated that only four adult patients among 24 patients prescribed a low protein diet with specific CBSDH-appropriate amino acid supplementation followed this treatment (see Lorenzini et al. J Inherit Metab Dis. (2018) 41:109-115, which is hereby incorporated by reference in its entirety). Multiple CBSDH experts have described similarly wide variability in the United States.

3. Betaine Supplementation

The problems associated with therapies based largely on diet have necessitated other approaches for Hcy lowering, most notably supplementation with betaine (N,N,N-trimethylglycine, marketed as CYSTADANE™) administered at least twice per day. Betaine is seldom effective as a monotherapy (Sakamoto et al. Pediatr Int 2003; 45:333-338, which is hereby incorporated by reference in its entirety), and is normally used as an adjunct to pyridoxine and/or a Met-restricted diet (see Morris et al. J Inherit Metab Dis. 2017 January; 40(1):49-74; which is hereby incorporated by reference in its entirety).

Betaine does not address the underlying CBS deficiency but rather induces an alternate pathway, resulting in remethylation of Hcy back to Met and by correcting the partial misfolding of CBS mutants (see Kopecka et al. J Inherit Metab Dis 2011; 34:39-48, which is hereby incorporated by reference in its entirety). In the presence of betaine, the enzyme betaine homocysteine methyltransferase (BHMT) remethylates Hcy to Met (Singh et al. Genet Med 2004; 6:90-95, which is hereby incorporated by reference in its entirety), thus partially reducing Hcy levels while increasing already highly elevated Met levels. Metabolites downstream of CBS are not ameliorated by betaine administration and Cys supplementation may be necessary. Moreover, betaine treatment has been associated with cerebral white matter abnormalities—a sign of vascular damage in the brain (Prins et al. Nat Rev Neurol 2015; 11:157-165, which is hereby incorporated by reference in its entirety)—in patients with (Devlin et al. J Pediatr 2004, 144:545-548; Yaghmai et al. Am J Med Genet 2002; 108:57-63; which are hereby incorporated by reference in their entireties) and without (Vatanavicharn et al. J Inherit Metab Dis 2008; 31 Suppl 3:477-481; Brenton et al. J Child Neurol 2014; 29:88-92; Sasai et al. Tohoku J Exp Med 2015; 237:323-327; which are hereby incorporated by reference in their entireties) acute cerebral edema.

Betaine may be unpalatable (Walter et al. Eur J Pediatr. 1998 April; 157 Suppl 2:S71-6, which is hereby incorporated by reference in its entirety) and result in unpleasant fishy body odor and/or breath (see Manning et al. JIMD Rep 2012; 5:71-75, which is hereby incorporated by reference in its entirety). Both effects potentially exacerbated by the requirement for high doses (greater than 6 g/day in adult and pediatric patients). Consequently, compliance is generally poor (see Adam et al. Mol Genet Metab. 2013 December; 110(4):454-9; Walter et al. Eur J Pediatr. 1998 April; 157 Suppl 2:S71-6; Sakamoto et al. Pediatr Int 2003; 45:333-338; which are hereby incorporated by reference in their entireties).

The pharmaceutical formulation of betaine, CYSTADANE™, was approved by the FDA in 2006 and is indicated to decrease elevated blood Hcy in homocystinuria disorders including CBS deficiency, 5,10-methylenetetrahydrofolate reductase (MTHFR) deficiency, and cobalamin cofactor metabolism (61) defects (see Recordati. CYSTADANE™ Product Information (PI). 2017. Ref Type: Online Source, which is hereby incorporated by reference in its entirety).

The largest survey to date on dietary practices among CBSDH pyridoxine non-responsive patients indicated that betaine was a common treatment choice, particularly in late diagnosed patients, adolescents and adults. The use of betaine as the primary therapy in 34% of patients without diet is believed to be due to lack of compliance with the diet, since there are no controlled studies examining betaine's long-term effectiveness when given without diet (see Adam et al. Mol Genet Metab 2013; 110:454-459, which is hereby incorporated by reference in its entirety). Indeed, a study in an CBSDH mouse model found that the ability of betaine treatment to significantly lower tHcy was decreased over time (see Maclean K N. Betaine treatment of cystathionine b-synthase-deficient homocystinuria; does it work and can it be improved? Dove press 2012; 2:23-33, which is hereby incorporated by reference in its entirety)

4. Anti-Platelet Therapies

In addition to Hcy-lowering therapies, patients with poorly controlled Hcy levels and/or those who have additional risk factors for thrombosis (e.g. Factor V Leiden, previous thrombosis and pregnancy), may benefit from treatment with anti-platelet agents (e.g. aspirin, dipyridamole or clopidogrel) (see Morris et al. J Inherit Metab Dis. 2017 January; 40(1):49-74; which is hereby incorporated by reference in its entirety). COUMADIN' blood thinners may also be used in patients with previous venous thrombosis. However, anticoagulation agents are associated with an increased risk of cerebral hemorrhage and their use should be determined on an individual patient basis (see Morris et al. J Inherit Metab Dis. 2017 January; 40(1):49-74; which is hereby incorporated by reference in its entirety).

5. Clinical Outcomes with Current Therapies

The manifestations of CBSDH continue to progress with the classic clinical symptoms reaching varying degrees of disability and impact on the quality of life of affected individuals. Regardless of the individual's age of onset, the loss of biochemical control at any age is associated with the development of serious complications that can be life-threatening (see Walter et al. Eur J Pediatr. 1998 April; 157 Suppl 2:S71-6, which is hereby incorporated by reference in its entirety).

Treatment must be continued throughout life, as periods of poor metabolic control have cumulative deleterious effects that can lead to severe complications and premature death (see Morris et al. J Inherit Metab Dis. 2017 January; 40(1):49-74, which is hereby incorporated by reference in its entirety).

Without treatment, the prognosis of pyridoxine-unresponsive CBSDH is poor and patients' life expectancy is markedly reduced. No randomized controlled trials of dietary or other therapy of CBSDH have been conducted since the disease was first described in 1962 (see Carson et al. Arch Dis Child. 1969 June; 44(235):387-92; Gerritsen et al. Biochem Biophys Res Commun. 1962 Dec. 19; 9:493-6; which are hereby incorporated by reference in their entireties). However, several observational studies have been published.

An international study that documented the natural history of 629 untreated CBS patients showed that the risk of complications increases with age (see Mudd et al. Am J Hum Genet 1985; 37: 1-31, which is hereby incorporated by reference in its entirety). Treatment (pyridoxine, Met restricted diet) was observed to lower plasma tHcy levels and markedly reduced the risk of thromboembolic events and lens dislocation, although compliance with the restricted diet was observed to be poor.

Yap et al. (Arterioscler Thromb Vasc Biol. 2001 December; 21(12):2080-5) conducted an international multicenter study in 158 treated patients. The incidence of cardiovascular events was reduced markedly in this treated group when compared to the historical control data from Mudd et al. (Am J Hum Genet 1985; 37: 1-31, which is hereby incorporated by reference in its entirety). This apparent benefit was correlated with lower (but not normalized) tHcy plasma levels in the treated patients. It was noted that consistent compliance with the required regimen was very difficult.

Overall, while several CBSDH treatment strategies are available, they are unable to restore most patients to near normal tHcy levels. Moreover, their long-term effectiveness, are subject to poor or inconsistent lifelong compliance. Thus, consistent Hcy lowering is difficult to maintain in CBSDH patients. Treatment with the drug product described herein aims to avoid many of these pitfalls. By compensating for the metabolic defect in CBSDH through a mechanism that should not require severe Met restriction or Cys supplementation, enzyme therapy (ET) therapy is expected to achieve more consistent Hcy lowering, while not dangerously elevating Met levels.

VI. Dosing and Administration

In certain embodiments, the drug product may be administered to a subject by subcutaneous (SC), intravenous (IV) or intraperitoneal (IP) injection. In one embodiment, the drug product may be administered to a subject 1, 2, 3, 4, 5, 6, 7, 8, 9, 10, 11, 12, 13, 14, 15, 16, 17, 18, 19, or 20 time(s). In another embodiment, the drug product is administered more than 20 times. In another embodiment, the drug product is administered more than 100 times. Alternatively, the drug product may be administered for the remaining life span of the subject.

In certain embodiments, the administration of the drug product may be repeated every 12 hours, 13 hours, 14 hours, 15 hours, 16 hours, 17 hours, 18 hours, 19 hours, 20 hours, 21 hours, 22 hours, 23 hours, daily, 2 days, 3 days, 4 days, 5 days, 6 days, week, 2 weeks, 3 weeks, and month. In certain embodiments, administration of the drug product is performed once every 3 days, once every 2 days, or once per day.

In certain embodiments, the administration of the drug product may be a series of doses which are minutes, hours, days or weeks apart. For example, the number of doses in a series may be 1, 2, 3, 4, 5, or 6. As a non-limiting example, a subject is administered 3 doses 24 hours apart. As another non-limiting example, a subject is administered 5 doses 12 hours apart. The subject may be a human.

In certain embodiments, the administration of the drug product may follow a dosing schedule of a series of doses that has a gap between the first series and the second series of doses. The gap between the doses may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, a week, 2 weeks, 3 weeks, monthly, 2 months, 3 months, 4 months, 5 months, 6 months, 7 months, 8 months, 9 months, 10 months, 11 months, 12 months, 13 months, 14 months, 15 months, 16 months, 17 months, or 18 months. The number of doses in a series may be 2, 3, 4, 5 or 6. As a non-limiting example, a subject may be administered a first series of 5 doses 12 hours apart and then 14 days after the first dose a subject is administered a second series of 5 doses 12 hours apart. As another non-limiting example, a subject is administered two series of doses over a period of 8 weeks where the first series is one dose twice a week for two weeks and the second series of doses is three times a week for 6 weeks.

In certain embodiments, the drug product may be administered at least once after a subject has been administered Betaine. The time between the Betaine administration the drug product administration may be 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the drug product may be administered 14 days after the subject was administered Betaine. As another non-limiting example, a subject may be administered the drug product two doses after the subject was administered Betaine. As another non-limiting example, the drug product may be administered 14 or 15 days after Betaine administration.

In certain embodiments, the drug product may be administered in combination with Betaine to a subject. The combination may be administered at least 1, 2, 3, 4, 5, 6, 7, 8, 9, 10, 11, 12, 13, 14, and 15. In certain embodiments, the drug product may be administered in combination with Betaine more than 15 times. Additional combination therapies that may be administered to a patient include the drug product and at least one treatment to lower tHcy levels, such as very low protein/Met diet and/or vitamins/supplements.

In one embodiment, the dose of the drug product administered to a subject may be between about 0.25 mg/kg and about 10 mg/kg. For example, the dose is one of about 0.33 mg/kg, about 0.66 mg/kg, 1.0 mg/kg, or 1.5 mg/kg. Alternatively, the dose is about 2 mg/kg, about 7 mg/kg, and about 10 mg/kg. For example, the dose may be about 0.5 mg/kg. Alternatively, the therapeutically effective amount is a dosage selected from the range of about 5.0 mg/kg to about 50 mg/kg, and about 10.0 mg/kg to about 25 mg/kg. For example, the dosage is selected from the group consisting of: about 0.25 mg/kg, about 0.33 mg/kg, about 0.66 mg/kg, about 1.00 mg/kg, about 1.10 mg/kg, about 1.20 mg/kg, about 1.30 mg/kg, about 1.40 mg/kg, about 1.50 mg/kg, about 1.60 mg/kg, about 1.70 mg/kg, about 1.80 mg/kg, about 1.90 mg/kg, about 2.00 mg/kg, about 3.00 mg/kg, about 4.00 mg/kg, about 5.00 mg/kg, about 6.00 mg/kg, about 7.00 mg/kg, about 8.00 mg/kg, about 9.00 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, about 21.0 mg/kg, about 22.0 mg/kg, about 23.0 mg/kg, about 24.0 mg/kg, about 25.0 mg/kg, about 26.0 mg/kg, about 27.0 mg/kg, about 28.0 mg/kg, about 29.0 mg/kg, about 30.0 mg/kg, about 31.0 mg/kg, about 32.0 mg/kg, about 33.0 mg/kg, about 34.0 mg/kg, about 35.0 mg/kg, about 36.0 mg/kg, about 37.0 mg/kg, about 38.0 mg/kg, about 39.0 mg/kg, about 40.0 mg/kg, about 41.0 mg/kg, about 42.0 mg/kg, about 43.0 mg/kg, about 44.0 mg/kg, about 45.0 mg/kg, about 46.0 mg/kg, about 47.0 mg/kg, about 48.0 mg/kg, about 49.0 mg/kg, and about 50.0 mg/kg.

In certain embodiments, the drug product is administered to a subject on a methionine-restricted diet. Alternatively, the drug product is administered to a subject that is not on a methionine-restricted diet.

In certain embodiments, the drug product may be co-administered with another therapeutic for treating CBSDH. As used herein, "co-administered" means the administration of two or more components. These components for co-administration include but are not limited to betaine or Vitamin B6. Co-administration refers to the administration of two or more components simultaneously or with a time lapse between administration such as 1 second, 5 seconds, 10 seconds, 15 seconds, 30 seconds, 45 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 1 hour, 1.5 hours, 2 hours, 2.5 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 1.5 days, 2 days, or 3 days. In certain embodiments, the time lapse between administration of two or more components is greater than 3 days.

In certain embodiments, the drug product may be used as a parenteral agent, to be administered to patients chronically via subcutaneous (SC) injection in an initial dosing interval once per week. For example, weekly drug dosing for 6 doses. In certain embodiments, the subject may be within an age range of 18 to 65 years old. In certain embodiments, a subject as young as 16 years of age may be similarly treated.

In certain embodiments, administration occurs over the course of 1 day, 2 days, 3 days, 4 days, 5 days, or 6 days. In certain embodiments, administration occurs over the course of 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks.

In certain embodiments, drug product is administered as a combination therapy with pyridoxine (also referred to as vitamin B6) and/or an anti-platelet therapy.

VII. Patient Stratification

In certain embodiments, individuals eligible for effective enzyme therapy using the drug product described herein include patients having a diagnosis of CBSDH, based on confirmation of genetic CBS deficient homocystinuria by mutation analysis of CBS gene and a plasma level of tHcy greater than or equal to 80 µM.

A. Clinical Presentation

According to the Guidelines for the Diagnosis and Management of CBSDH, the disease should be suspected in children presenting with severe or rapidly progressing myopathy, lens dislocation and/or developmental delays (see Morris et al. Guidelines for the diagnosis and management of cystathionine beta-synthase deficiency. J Inherit Metab Dis 2017; 40:49-74, which is hereby incorporated by reference in its entirety). Tests are also warranted in adults presenting with thromboembolism and/or lens dislocation but no other symptoms and in those with multi-system disease, including ocular, connective tissue, neuro-psychiatric and vascular complications (see Mudd et al. Am J Hum Genet 1985; 37:1-31; Morris et al. Guidelines for the diagnosis and management of cystathionine beta-synthase deficiency. J Inherit Metab Dis 2017; 40:49-74; Kelly et al. Neurology 2003; 60:275-279, each of which is hereby incorporated by reference in its entirety).

B. Biochemical Analysis

Levels of plasma tHcy are determined using the sum of all free and bound homocysteine species after treating the plasma with a reducing agent. In healthy individuals with stable dietary habits, tHcy levels remain relatively constant over time (see Refsum et al. Clin Chem 2004; 50:3-32; McKinley et al. Clin Chem 2001; 47:1430-1436; each of which is hereby incorporated by reference in its entirety). However, consumption of a protein-rich meal can increase tHcy levels by approximately 10% over a period of several hours (see Verhoef et al. Am J Clin Nutr 2005; 82:553-558, which is hereby incorporated by reference in its entirety). A study in individuals with hyperhomocysteinemia (tHcy>40 µmol/L) found that intra-individual tHcy levels varied up to 25% over a period of 4 to 8 months. However, no information was provided on the variability of the diets, assay methods, and times of sampling, hindering the ability to interpret the data (see Refsum H, Smith A D, Ueland P M et al. Facts and recommendations about total homocysteine determinations: an expert opinion. Clin Chem 2004; 50:3-32, which is hereby incorporated by reference in its entirety).

In populations without folate supplementation, corresponding upper reference limits are approximately 15 and 20 µmol/L, respectively. To support a diagnosis of CBS in a neonate, tHcy in plasma is expected to be between 50 to greater than 100 µmol/L and Met in plasma is expected to be between 200 to 1500 µmol/L (i.e., 3-23 mg/dL) (see Sacharow et al. Homocystinuria Caused by Cystathionine Beta-Synthase Deficiency. GeneReviews 2017, which is hereby incorporated by reference in its entirety). To support a diagnosis of CBS in an untreated older individual, tHcy in plasma is expected to be greater than 100 µmol/L and Met in plasma is expected to be greater than 50 µmol/L (i.e., greater than 0.7 mg/dL). A control neonate or older individual would be expected to have tHcy in plasma less than 15 µmol/L and Met between 10 to 40 µmol/L (0.2-0.6 mg/dL).

High to high-normal Met levels (reference ranges are typically 40 to 45 and 12 to 15 µmol/L, respectively) in combination with low to low-normal Cth levels (reference ranges 0.05 to 0.08 and 0.35 to 0.5 µmol/L, respectively) may be useful for distinguishing CBSDH from HCU caused by genetic and nutritional disorders of Hcy remethylation (see Morris et al. J Inherit Metab Dis 2017; 40:49-74; Stabler et al. JIMD Rep 2013; 11:149-163; Bartl et al. Clin Chim Acta 2014; 437:211-217, each of which is hereby incorporated by reference in its entirety). Another useful test determines Cth production from Hcy and serine in cultured fibroblasts, using radioactive or deuterium labeled substrates (see Morris et al. J Inherit Metab Dis 2017; 40:49-74; Kraus J P. Methods Enzymol 1987; 143:388-394; Smith et al. J Chromatogr B Analyt Technol Biomed Life Sci 2012; 911: 186-191, each of which is hereby incorporated by reference in its entirety). However, enzyme analysis cannot always distinguish between pyridoxine responsive and non-responsive individuals and the enzymatic activity may be normal in mild cases (see Alcaide et al. Clin Chim Acta 2015; 438: 261-265, which is hereby incorporated by reference in its entirety). More recently, rapid stable isotope assays measuring activity of CBS released from organs into plasma showed 100% sensitivity in pyridoxine non-responsive patients, but only 86% sensitivity in pyridoxine responders (see Alcaide et al. Clin Chim Acta 2015; 438:261-265; Krijt et al. J Inherit Metab Dis 2011; 34:49-55, both of which are hereby incorporated by reference in their entirety).

C. Molecular Diagnosis

Molecular genetic testing—the gold-standard diagnostic test for CBSDH—can be performed by either single-gene testing or using a multi-gene panel (see Yap S. Homocystinuria due to cystathionine beta-synthase deficiency. Orphanet Encyclopaedia [serial online] 2005; Sacharow S J, Picker J D, Levy H L. Homocystinuria Caused by Cystathionine Beta-Synthase Deficiency. GeneReviews 2017; Morris et al. J Inherit Metab Dis 2017; 40:49-74; Katsanis et al. Nat Rev Genet 2013; 14:415-426; each of which is hereby incorporated by reference in its entirety). Individuals with high risk of having a particular CBS mutation should be screened using targeted single-gene testing. However, this is only useful in select populations with a common CBS mutation, (e.g. 93% of individuals with CBSDH from Qatar carry the p.Arg336Cys; c.1006C>T mutation) and in individuals from families with a known pathogenic variant. In other patients, the CBS gene can be sequenced, and gene-targeted deletion/duplication analysis performed only if one or no pathogenic variant is found. Alternatively, simultaneous molecular testing of multiple genes can be performed using a multiple gene panel. Methods used may include sequence analysis, deletion/duplication analysis and other non-sequencing-based tests (see Morris et al. J Inherit Metab Dis 2017; 40:49-74, which is hereby incorporated by reference in its entirety). Generally, molecular genetic testing is reserved for high-risk populations with a limited number of prevalent mutations (see Morris et al. J Inherit Metab Dis 2017; 40:49-74; Huemer et al. J Inherit Metab Dis 2015; 38:1007-101, each of which is hereby incorporated by reference in its entirety).

D. Pyridoxine Responsiveness Tests

Pyridoxine-responsiveness tests are used in the clinic to determine whether pyridoxine supplementation should be prescribed for patients with CBSDH. Because different treatment centers have defined pyridoxine responsiveness differently (see Morris et al. J Inherit Metab Dis 2017; 40:49-74, which is hereby incorporated by reference in its entirety), classification of patients by tHcy levels, rather than by their pyridoxine responsiveness, is more rigorous. Pyridoxine-responsiveness is not a measure of metabolic control but rather an indication that there remains some residual CBS activity.

E. Newborn Screening (NBS)

In general, NBS tests for CBSDH deficiency are carried out by analyzing dried blood spots to determine Met levels. Alternately, assessment of tHcy levels rather than Met in dried blood spots for NBS is available in a few centers worldwide. It is employed as a second-tier test to reduce the false-positive rates of NBS in individuals with high Met levels (see Turgeon et al. Clin Chem 2010; 56:1686-1695, which is hereby incorporated by reference in its entirety) and is not used to improve sensitivity or reduce false-negative rates.

VIII. Phenotypic Outcomes

Retrospective studies show a proportional relationship between tHcy levels and outcomes. Patients with the highest tHcy levels (treated or untreated) present with more severe symptoms earlier in life, whereas patients with lower tHcy levels present with fewer symptoms and progress less rapidly (see Yap S. Homocystinuria due to cystathionine beta-synthase deficiency. Orphanet Encyclopaedia [serial online] 2005; Mudd et al. Am J Hum Genet 1985; 37:1-31, each of which is hereby incorporated by reference in its entirety). Individuals with elevated tHcy levels typically present with failure to thrive, thromboembolism, severe myopia with subsequent dislocation of the optic lens, osteoporosis-type fractures, a Marfanoid habitus (in particular elongation of the long bones) and/or psychiatric abnormalities such as learning difficulties (see Yap S. Homocystinuria due to cystathionine beta-synthase deficiency. Orphanet Encyclopaedia [serial online] 2005; Morris et al. J Inherit Metab Dis 2017; 40:49-74; NORD, Kraus J P. Homocystinuria due to cystathionine beta-synthase deficiency. NORD [serial online] 2017, each of which are hereby incorporated by reference in its entirety). Reflecting the spectrum of CBS deficiency, some patients have a severe childhood-onset multisystemic disease, whereas those with less severely elevated Hcy may remain undiagnosed into adulthood (see Morris et al. J Inherit Metab Dis 2017; 40:49-74, which is hereby incorporated by reference in its entirety). Life expectancy is markedly reduced in patients with severely elevated Hcy levels, though even patients with moderately elevated tHcy levels suffer from multiple negative clinical outcomes.

Significant evidence has been observed to indicate the causal effect of elevated tHcy levels and negative clinical outcomes in the four systems commonly affected in CBSDH patients (ocular, skeletal, cardiovascular, and neurologic). In the ocular system, frequently observed phenotypic outcomes include: ectopia lentis, iridodonesis, myopia, and less frequently observed phenotypic outcomes include: glaucoma, optic atrophy, retinal degeneration, retinal detachment, cataracts, and corneal abnormalities. In the skeletal system, frequently observed phenotypic outcomes include: osteoporosis, biconcave vertebrae, scoliosis, Increased length of long bones, Irregular widened metaphysis, metaphyseal spicules, abnormal size/shape of epiphyses, growth arrest lines, pes cavus, and high-arched palate, and less frequently observed phenotypic outcomes include: arachnodactyly, enlarged carpal bones, abnormal bone age, pectus carinatum/excavatum, genu valgum, kyphosis, and short fourth metacarpal. In the vascular system, frequently observed phenotypic outcomes include: vascular occlusions, malar flush, and livedo reticularis. In the central nervous system, frequently observed phenotypic outcomes include: mental retardation, psychiatric disturbances, and extrapyramidal signs, and less frequently observed phenotypic outcomes include: seizures and abnormal electroencephalogram. In additional body systems, the following phenotypic outcomes are frequently observed fair, brittle hair, thin skin, fatty changes in liver, inguinal hernia, myopathy, endocrine abnormalities, reduced clotting factors, and spontaneous bowel perforation.

A strong relationship has been observed between mildly elevated levels of tHcy and negative outcomes, but data has also indicated that lowering tHcy levels positively impacts clinical manifestations. The literature on CBSDH suffers from the rarity of the disease and subsequent smaller studies but benefits from the magnification of clinical outcomes in a population with severely elevated Hcy levels. Conversely, studies in the broader population benefit from large sample sizes but smaller elevations in tHcy levels. Taken together these studies consistently demonstrate that elevated tHcy levels are strongly predictive of negative clinical outcomes and that pharmacological intervention to reduce those levels is beneficial.

A potential outcome from treatment of CBSDH with the drug product described herein is to lower the plasma tHcy concentration to the lowest possible levels while maintaining a more relaxed diet, including higher concentrations of Met than provided in other therapies for CBSDH and other essential amino acids. In infants and children with CBSDH, the priority is to prevent complications associated with CBSDH and to ensure proper growth and development of normal intelligence (see Morris et al. J Inherit Metab Dis. 2017 January; 40(1):49-74, which is hereby incorporated by reference in its entirety). In patients diagnosed later in life, the priority may be to prevent life-threatening thromboembolism and to minimize progression of already established complications. To address these goals, the biochemical abnormalities associated with CBSDH may be improved and, if possible, normalized (see Morris et al. J Inherit Metab Dis. 2017 January; 40(1):49-74, which is hereby incorporated by reference in its entirety). A survey comparing dietetic management practices for patients with CBSDH across 29 centers in 8 European countries, found that there was little consensus in treatment centers about target ranges for plasma tHcy levels, with the median recommended target of less than 55 µM and within a range of less than 20 to 100 µM among the 29 centers (see Adam et al. Mol Genet Metab. 2013 December; 110(4):454-9, which is hereby incorporated by reference in its entirety).

The cut-off value of greater than or equal to 80 µM for tHcy levels for eligibility for treatment was chosen herein to avoid excluding patients with prior plasma tHcy levels of about 100 µM given a within-person variability of 25% in plasma tHcy levels tested several months apart (see Refsum et al. Clin Chem 2004; 50:3-32; Guttormsen et al., J Clin Invest. 1996, 98(9):2174-83; each of which is hereby incorporated by reference in its entirety) to provide levels high enough to detect clinically significant reductions in a small number of patients. The within-person variability of 25% in plasma tHcy levels tested several months apart (see Refsum et al. Clin Chem 2004; 50:3-32; Guttormsen et al., J Clin Invest. 1996, 98(9):2174-83; each of which is hereby incorporated by reference in its entirety) may be partially due to changes in diet, medications, or supplements in CBSDH patients over time.

If untreated, the prognosis for patients with pyridoxine-unresponsive CBSDH is bleak (see Morris et al. J Inherit Metab Dis 2017; 40:49-74, which is hereby incorporated by reference in its entirety). In 1985, an international retrospective study documenting the natural history of CBSDH in 629 patients, by time-to-event analyses before treatment, showed that 70% of patients experienced lens dislocation by the age of 10 years, with 85% developing symptoms by 12 years (see Mudd et al. Am J Hum Genet 1985; 37:1-31; Mudd et al., Skovby F. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327, both of which are hereby incorporated by reference in its entirety). Overall, 50% of affected individuals had radiographically detected spinal osteoporosis by the age of 15 years and 23% of pyridoxine non-responsive patients (4% of responsive patients) died by the age of 30 years (see Mudd et al. Am J Hum Genet 1985; 37:1-31, which is hereby incorporated by reference in its entirety).

Taken in its entirety, the available evidence indicates that the current approaches to treatment of CBSDH, including restrictive diet and use of dietary supplements, are ineffective in halting progression of the disease progression in most patients. Consequently, there is a substantial unmet medical need to identify well tolerated therapies that will improve or normalize the metabolic abnormalities of CBSDH and slow or halt progression of the clinical manifestations of the disease.

A causal effect between increased Hcy levels and key clinical outcomes associated with CBSDH, including ocular complications (in particular, lens dislocation), skeletal outcomes (in particular, osteoporosis), vascular events (in particular, stroke and small vessel disease) and various CNS outcomes (in particular, cognitive function), has been observed. The relationship between elevated tHcy levels and negative clinical outcomes and conversely, by reduced Hcy levels and improved clinical outcomes, is further strengthened by multiple studies in the general population. Overall, these clinical findings highlight the need for early CBSDH diagnosis and prompt treatment to decrease Hcy levels to as close as possible to normal.

Although no studies have been published on the Quality of Life (QoL) of CBSDH patients, unpublished reports indicate that patients and their caregivers suffer from the psychosocial effects of following and managing a highly restricted and socially isolating diet and are extremely anxious about the long-term medical consequences of the disease. Not surprisingly, patients yearn for the ability to relax their diets without compromising their long-term prospects.

The strong relationship between tHcy levels and key clinical outcomes in patients with CBSDH shows that the change in tHcy levels is a reliable surrogate marker for a combination of clinical endpoints in CBSDH. Changes in tHcy levels are therefore useful for (i) monitoring patient progress in the clinic and (ii) predicting the clinical benefits of new treatments in a clinical trial and (ii) predicting the efficacy of a therapy.

For example, the drug product normalizes or increases femoral artery flexibility in a subject compared to before administration of the drug product to the subject. For example, I278T mice have significantly lower femoral artery flexibility compared to wildtype mice. A Met-restricted diet may, in fact, result in a smaller femoral artery diameter in I278T mice compared to a regular diet in both mice treated with the drug products and those that are not.

Studies previously conducted in 3 murine models of the disease have demonstrated that htCBS C15S is effective after systemic administration as described in WO 2017/083327, which hereby incorporated by reference in its entirety. These studies showed an up to 90% decrease in extracellular Hcy plasma and intracellular Hcy levels in tissue, such as brain. Administration of the drug product was observed to result in a concentration gradient, with flux of Hcy from higher concentrations in the intracellular space to the lower concentrations in the extracellular space where the drug product can further process it. The extracellular PEGylated htCBS C15S serves as a Hcy "sink." In summary, drug product restored control of the Met metabolism pathway in animal models of CBSDH.

These studies have shown also that SC dosing of PEGylated htCBS C15S in murine models of CBSDH corrected metabolite levels, including elevation in Cth levels and normalization of Cys levels. In addition, PEGylated htCBS C15S positively affected the phenotypic expression of the disease in mice, including facial alopecia, liver histology, osteoporosis, body composition, diabetic retinopathy (possibly secondary to renal disease) and macular and optic atrophy due to retinal vascular occlusion or non-arteritic ischemic optic neuropathy, cytokines, and lipid levels. PEGylated htCBS C15S also rescued CBS knockout (KO) mice from early death (see Looker et al. Diabetologia 2003; 46:766-772; Pusparajah et al. Front Physiol 2016; 7:200; Gerth et al. J AAPOS 2008; 12:591-596; Stanger et al. Clin Chem Lab Med 2005; 43:1020-1025; Cahill et al. Am J Ophthalmol 2003; 136:1136-1150; Minniti et al. Eur J Ophthalmol 2014; 24:735-743; each of which is hereby incorporated by reference in its entirety). PEGylated htCBS C15S was also observed to be well tolerated with no toxicological effects noted with chronic dosing in animal models of the disease.

PEGylated htCBS C15S acts in the extracellular space and is anticipated to lower tHcy plasma concentrations regardless of the patients' genetics, concurrent therapy, or baseline tHcy level. Thus, the eligible population for the study should include both pyridoxine responsive and non-responsive patients.

In healthy individuals, tHcy levels are in the range of approximately 5 to 15 µM (OECD Environmental Health and Safety Publications. Series on Principles of Good Laboratory Practice and Compliance Monitoring. No. 1 ENV/MC/CHEM(98)17 "Principles of Good Laboratory Practice (as revised in 1997), which is hereby incorporated by reference in its entirety), 98% of which is in the form of disulfides or is protein bound. Only 2% of the tHcy exists as a non-bound, free, reduced aminothiol that can serve as a substrate for the enzyme (see EMA: Guideline on bioanalytical method validation, EMEA/CHMP/EWP/192217/2009, ev. 1, 21 Jul. 2011; ATL-15-1419 Atlanbio Study Report "LC-MS/MS determination of cystathionine-D4 as product of the cystathionine β-synthase activity in monkey plasma samples collected during the study 529736"; which are both hereby incorporated by reference in their entireties). CBSDH patients on the other hand, not only present with plasma levels that may reach 400 µM and more, but also present with a dramatically altered balance, with free homocysteine reaching 10-25% of the tHcy values.

In mouse models, administration of PEGylated htCBS C15S resulted in up to 90% reduction in tHcy levels. Thus, the initial levels of free homocysteine available for the enzyme (10%-25% of the total) cannot solely account for the significant decrease in tHcy levels that were recorded, and additional pools must become available to the enzyme. For example, as free Hcy becomes scarce as a result of PEG htCBS activity, the balance between free Hcy and Hcy adducts (in the form of protein-bound Hcy or disulfides) in plasma, changes to favor the generation of free Hcy, which can further be processed by the enzyme.

A. Ocular Complications

Elevated Hcy levels are a strong and independent risk factor for ocular complications, in particular lens dislocation, in patients with CBSDH and in the general population. Even with prescribed pharmacologic and dietary interventions, the majority of CBSDH patients eventually present with ocular complications. Lowering Hcy levels has been shown to delay and perhaps prevent lens dislocation in CBSDH patients (see Yap S. Homocystinuria due to cystathionine beta-synthase deficiency. Orphanet Encyclopaedia [serial online] 2005; Mudd et al. Am J Hum Genet 1985; 37:1-31; Martinez-Gutierrez et al. Int Ophthalmol (2011) 31:227-232; Ajith et al. Clin Chim Acta 2015; 450:316-321; Mulvihill et al. J AAPOS 2001; 5:311-315; Marti-Carvajal et al. Cochrane Database Syst Rev 2015; 1:CD006612; Sweetser et al. N Engl J Med 2016, 375:1879-1890; Sadiq et al. Semin Ophthalmol 2013; 28:313-320; Wright et al. Homocysteine, folates, and the eye. Eye (Lond) 2008; 22:989-993; Lieberman et al. Am J Ophthalmol 1966, 61:252-255; Harrison et al. Ophthalmology 1998, 105:1886-1890; Ramsey et al. Am J Ophthalmol 1972; 74:377-385; Couser et al. Ophthalmic Genet 2017, 38:91-94; Ghorbanihaghjo et al. Mol Vis 2008, 14:1692-1697; Javadzadeh et al. Mol Vis 2010; 16:2578-2584; Seddon et al. Am J Ophthalmol 2006; 141:201-203; Coral et al. Eye (Lond) 2006; 20:203-207; Axer-Siegel et al. Am J Ophthalmol 2004, 137:84-89; Heuberger et al. Am J Clin Nutr 2002; 76:897-902; Huang et al. Sci Rep 2015; 5:10585; Sen et al. Indian J Clin Biochem 2008; 23:255-257; Yousefi et al. Protein Pept Lett 2013; 20:932-941; Gerth et al. J AAPOS 2008; 12:591-596; Stanger et al. Clin Chem Lab Med 2005, 43:1020-1025; Cahill et al. Am J Ophthalmol 2003, 136:1136-1150; Minniti et al. Eur J Ophthalmol 2014, 24:735-743; Turkcu et al. Medicina (Kaunas) 2013, 49:214-218; Vessani et al. Am J Ophthalmol 2003; 136:41-46; Leibovitch et al. J Glaucoma 2003, 12:36-39; Leibovitzh et al. Medicine (Baltimore) 2016; 95:e4858; Micheal et al. Mol Vis 2009; 15:2268-2278; Clement et al. J Glaucoma 2009; 18:73-78; Cumurcu et al. BMC Ophthalmol 2006; 6:6; Bleich et al. J Neural Transm (Vienna) 2002; 109:1499-1504; Lee et al. Curr Eye Res 2017; 1-6; Wang et al. Am J Ophthalmol 2004; 137:401-406; Ganapathy et al. Invest Ophthalmol Vis Sci 2009; 50:4460-4470, each of which is hereby incorporated by reference in its entirety). Even with prescribed phaiinacologic and dietary interventions, the majority of CBSDH patients eventually present with ocular complications. Lowering Hcy levels has been shown to delay and perhaps prevent lens dislocation in CBSDH patients (see Yap et al. J Inherit Metab Dis 1998; 21:738-747, which is hereby incorporated by reference in its entirety).

One of the most consistently present and earliest manifestations of CBSDH is ectopia lentis (lens dislocation) (see Mulvihill et al. J AAPOS 2001; 5:311-315, which is hereby incorporated by reference in its entirety). This usually occurs after the age of two years and is present in approximately 50% of untreated, pyridoxine non-responsive patients by the age of six years and in 50% of untreated pyridoxine-responsive patients by the age of 10 years (see Mudd et al. Am J Hum Genet 1985; 37:1-31, which is hereby incorporated by reference in its entirety). Dislocation may be partial (subluxation) or complete and, although it may occur inferiorly or nasally, it is usually bilateral (see Mulvihill et al. J AAPOS 2001; 5:311-315; Sweetser et al. N Engl J Med 2016; 375:1879-1890, both of which are hereby incorporated by reference in its entirety).

Lens dislocation often follows a period of rapidly progressing myopia, which can lead to marked astigmatism, monocular diplopia and decreased best-corrected acuity (see Sadiq et al. Semin Ophthalmol 2013; 28:313-320, which is hereby incorporated by reference in its entirety). Overall, myopia (greater than 1 diopter [D]) is believed to affect approximately 85% of CBSDH patients, with very high myopia (greater than 5D) affecting 50 to 76% of patients. Iridodonesis (quivering of the iris after moving the eyeball) affects approximately 56% of patients and spherophakia (a small, spherical lens that is prone to subluxation) affects 50% of patients (see Yap S. Homocystinuria due to cystathionine beta-synthase deficiency. Orphanet Encyclopaedia [serial online] 2005; Mulvihill et al. J AAPOS 2001; 5:311-315, each of which is hereby incorporated by reference in its entirety). Additional complications associated with CBSDH include cataract formation, chronic vitritis (inflammation of the vitreous humor) and chorioretinal inflammation, pupillary block with acute and/or chronic angle closure glaucoma and (in children), amblyopia (lazy eye) (see Sadiq et al. Semin Ophthalmol 2013; 28:313-320, which is hereby incorporated by reference in its entirety).

Evidence from a long-term, retrospective study in 25 patients under the age of 24 with CBSDH suggests that lens dislocation can be prevented, or at least significantly reduced and delayed, in patients whose tHcy levels are consistently lowered from an early age (see Yap et al. J Inherit Metab Dis 1998; 21:738-747, which is hereby incorporated by reference in its entirety). Early Hcy-lowering treatment was also associated with a reduced risk of overall ocular complications, including worsening myopia. Supportive evidence derives from a case-control study in 32 patients with CBSDH and 25 sibling controls, in which early Hcy-lowering treatment was associated with a significant reduction in ocular complications compared with patients who were treated later in life or were not fully compliant with treatment (see El Bashir et al. JIMD Rep 2015; 21:89-95, which is hereby incorporated by reference in its entirety)

The largest and longest longitudinal study to date of the ocular outcomes of 25 patients with cobalamin C deficiency, which is similarly characterized by elevated tHcy levels, found that macular degeneration, optic nerve pallor, nystagmus, strabismus, and vascular changes were all present in the majority of patients.

Numerous studies in CBSDH patients and in the general population demonstrated relationships between elevated Hcy levels and a variety of ocular disorders (see Mudd et al. Am J Hum Genet 1985; 37:1-31; Ajith, Clin Chim Acta 2015; 450:316-321; Mulvihill et al. J AAPOS 2001; 5:311-315; Wright et al. Eye (Lond) 2008; 22:989-993, each of which is hereby incorporated by reference in its entirety), including myopia and lens dislocation (see Yap S. Homocystinuria due to cystathionine beta-synthase deficiency. Orphanet Encyclopaedia [serial online] 2005; Mudd et al. Am J Hum Genet 1985; 37:1-31; Martinez-Gutierrez et al. Int Ophthalmol 2011; 31:227-232; Suri et al. J Neurol Sci 2014; 347:305-309; Mulvihill et al. J AAPOS 2001; 5:311-315; Lieberman et al. Am J Ophthalmol 1966; 61:252-255; Harrison et al. Ophthalmology 1998; 105:1886-1890; Ramsey et al. Am J Ophthalmol 1972; 74:377-385; Couser et al. Ophthalmic Genet 2017; 38:91-94; each of which is hereby incorporated by reference in its entirety), iridodonesis (see Mulvihill et al. J AAPOS 2001; 5:311-315, which is hereby incorporated by reference in its entirety), retinal arteriosclerosis (see Ghorbanihaghjo et al. Mol Vis 2008; 14:1692-1697, which is hereby incorporated by reference in its entirety), age-related macular degeneration (see Javadzadeh et al. Mol Vis 2010; 16:2578-2584; Seddon et al. Am J Ophthalmol 2006; 141:201-203; Coral et al. Eye (Lond) 2006; 20:203-207; Axer-Siegel et al. Am J Ophthalmol 2004; 137:84-89, each of which is hereby incorporated by reference in its entirety), age-related maculopathy (AMD) (see Heuberger et al. Am J Clin Nutr 2002; 76:897-902; Huang et al. Sci Rep 2015; 5:10585, both of which are hereby incorporated by reference in its entirety), cataracts (see Sen et al. Indian J Clin Biochem 2008; 23:255-257; Yousefi et al. Protein Pept Lett 2013; 20:932-941, both of which are hereby incorporated by reference in its entirety), diabetic retinopathy (possibly secondary to renal disease) (see Looker et al. Diabetologia 2003; 46:766-772; Pusparajah et al. Front Physiol 2016; 7:200, both of which are hereby incorporated by reference in its entirety) and macular and optic atrophy due to retinal vascular occlusion or non-arteritic ischemic optic neuropathy (see Gerth et al. J AAPOS 2008; 12:591-596; Stanger et al. Clin Chem Lab Med 2005; 43:1020-1025; Cahill et al. Am J Ophthalmol 2003; 136:1136-1150; Minniti et al. Eur J Ophthalmol 2014; 24:735-743; each of which is hereby incorporated by reference in its entirety).

A retrospective study of 629 patients with CBSDH found that lens dislocation usually occurs after the age of two years, and is present in approximately 50% of untreated, pyridoxine non-responsive patients by the age of six years and in 50% of untreated pyridoxine-responsive patients by the age of 10 years (see Mudd et al. Am J Hum Genet 1985; 37:1-31, which is hereby incorporated by reference in its entirety). The largest and longest longitudinal study to date of the ocular outcomes of 25 patients with cobalamin C deficiency, which is similarly characterized by elevated tHcy levels, found that macular degeneration, optic nerve pallor, nystagmus, strabismus, and vascular changes were all present in the majority of patients (see Brooks et al. Ophthalmology. 2016 March; 123(3):571-82, which is hereby incorporated by reference in its entirety).

Numerous studies in both CBSDH patients and the general population have demonstrated relationships between elevated Hcy levels and a variety of ocular disorders (see Mudd et al. Am J Hum Genet 1985; 37:1-31; Ajith T A, Ranimenon. Clin Chim Acta 2015; 450:316-321; Mulvihill et al. J AAPOS 2001; 5:311-315; Wright et al. Eye (Lond) 2008; 22:989-993; each of which is hereby incorporated by reference in its entirety), including myopia and lens dislocation (see Yap S. Homocystinuria due to cystathionine beta-synthase deficiency. Orphanet Encyclopaedia [serial online] 2005; Mudd et al. Am J Hum Genet 1985; 37:1-31; Martinez-Gutierrez et al. Int Ophthalmol 2011; 31:227-232; Mulvihill et al. J AAPOS 2001; 5:311-315; Sadiq et al. Semin Ophthalmol 2013; 28:313-320; Lieberman et al. Am J Ophthalmol 1966; 61:252-255; Harrison et al. Ophthalmology 1998; 105:1886-1890; Ramsey et al. Am J Ophthalmol 1972; 74:377-385; Couser et al. Ophthalmic Genet 2017; 38:91-94, each of which is hereby incorporated by reference in its entirety), iridodonesis (see Mulvihill et al. J AAPOS 2001; 5:311-315, which is hereby incorporated by reference in its entirety), retinal arteriosclerosis (see Ghorbanihaghjo et al. Mol Vis 2008; 14:1692-1697, which is hereby incorporated by reference in its entirety), age-related macular degeneration (see Javadzadeh et al. Mol Vis 2010; 16:2578-2584; Seddon et al. Am J Ophthalmol 2006; 141: 201-203; Coral et al. Eye (Lond) 2006; 20:203-207; Axer-Siegel et al. Am J Ophthalmol 2004; 137:84-89; each of which is hereby incorporated by reference in its entirety), age-related maculopathy (AMD) (see Heuberger et al. Am J Clin Nutr 2002; 76:897-902; Huang et al. Sci Rep 2015; 5:10585, both of which are hereby incorporated by reference in its entirety), cataracts (see Sen et al. Indian J Clin Biochem 2008; 23:255-257; Yousefi et al. Protein Pept Lett 2013; 20:932-941, both of which are hereby incorporated by reference in its entirety), diabetic retinopathy (possibly secondary to renal disease) (see Looker et al. Diabetologia 2003; 46:766-772; Pusparajah et al. Front Physiol 2016; 7:200, both of which are hereby incorporated by reference in its entirety) and macular and optic atrophy due to retinal vascular occlusion or non-arteritic ischemic optic neuropathy (see Gerth et al. J AAPOS 2008; 12:591-596; Stanger et al. Clin Chem Lab Med 2005; 43:1020-1025; Cahill et al. Am J Ophthalmol 2003; 136:1136-1150; Minniti et al. Eur J Ophthalmol 2014; 24:735-743; each of which is hereby incorporated by reference in its entirety).

Studies investigating associations between Hcy levels and glaucoma provided inconsistent results. Some showed a positive relationship between Hcy levels and normal tension glaucoma, pseudoexfoliative glaucoma (PEXG) and primary open-angle glaucoma (POAG), while others did not (see Lieberman et al. Am J Ophthalmol 1966; 61:252-255; Turkcu et al. Medicina (Kaunas) 2013; 49:214-218; Vessani et al. Am J Ophthalmol 2003; 136:41-46; Leibovitch et al. J Glaucoma 2003; 12:36-39; Leibovitzh et al. Relationship between homocysteine and intraocular pressure in men and women: A population-based study. Medicine (Baltimore) 2016; 95:e4858; Micheal et al. Mol Vis 2009; 15:2268-2278; Clement et al. J Glaucoma 2009; 18:73-78; Cumurcu et al. BMC Ophthalmol 2006; 6:6; Bleich et al. J Neural Transm (Vienna) 2002; 109:1499-1504; Lee et al. Curr Eye Res 2017; 1-6; Wang et al. Am J Ophthalmol 2004; 137:401-406; each of which is hereby incorporated by reference in its entirety). However, loss of retinal ganglion cells (RGC)—a common observation in individuals with glaucoma—was demonstrated in mice with endogenously elevated Hcy levels caused by CBS gene deletion, suggesting a likely link between glaucoma and elevated tHcy levels in patients with CBSDH (see Ganapathy et al. Invest Ophthalmol Vis Sci 2009; 50:4460-4470, which is hereby incorporated by reference in its entirety).

1. Mechanism

A number of mechanisms have been proposed to explain effects of elevated Hcy levels on ocular health (see Ajith T A, Ranimenon; Clin Chim Acta 2015; 450:316-321, which is hereby incorporated by reference in its entirety). Mechanisms explaining the effects of elevated tHcy include impaired vascular endothelial function, apoptosis of retinal ganglion cells, extracellular matrix alterations, decreased lysyl oxidase activity and oxidative stress, as well as the direct cytotoxic and pro-inflammatory effects of Hcy, that appear to contribute to lens opacification and optic nerve damage.

Potential mechanisms also include activation of the N-methyl-D-aspartate (NMDA) receptor, leading to a cellular influx of calcium and increased reactive oxygen species (ROS) production, both of which contribute to cataract formation. These changes, along with the direct cytotoxic effects of Hcy, may cause endothelial injury, which initiates thrombogenesis and apoptosis of RGC, leading to retinopathy and glaucoma. Elevated Hcy levels have also been shown to increase levels of asymmetric dimethylarginine (AMDA) and block nitric oxide synthase (NOS) activity, thereby causing vasoconstriction and optic nerve atrophy by decreasing nitric oxide (NO) levels. Finally, an accumulation of homocysteinylated proteins on the vascular wall can trigger anti-Hcy antibody production and inflammatory responses, leading to phagocytosis, oxidative stress, apoptosis of RGCs and extracellular matrix (ECM) alterations. Together, such changes damage the vasculature, lens proteins and optic nerve, ultimately causing visual dysfunction.

In CBSDH patients, lens dislocation is regarded as being primarily caused by degenerative changes in zonular fibers, in particular Cys-rich, multidomain ECM proteins such as fibrillin-1 (see Sadiq et al. Semin Ophthalmol 2013; 28:313-320; Hubmacher et al. Biochemistry 2011; 50:5322-5332; Hubmacher et al. J Biol Chem 2005; 280:34946-34955; Hubmacher et al. J Biol Chem 2010; 285:1188-1198; each of which is hereby incorporated by reference in its entirety).

In healthy individuals, formation of numerous intra-domain disulfide bonds within fibrillin-1 enables precise protein folding, essential for structural integrity and function. Fibrillin-1 strands can then form inter-strand disulfide bonds, leading to assembly of high molecular weight multiprotein assemblies known as microfibrils (see Kinsey et al. J Cell Sci 2008; 121:2696-2704; Hubmacher et al. Proc Natl Acad Sci USA 2008; 105:6548-6553, both of which are hereby incorporated by reference in its entirety).

This process is highly dependent on interactions between fibrillin-1 and fibronectin (see Hubmacher et al. Biochemistry 2011; 50:5322-5332, which is hereby incorporated by reference in its entirety). Microfibrils form a scaffold for deposition of tropoelastin, an essential step in formation of elastic fibers such as those found in skin, lung, blood vessels/arteries, ligaments and the eye (see Hubmacher et al. J Biol Chem 2010; 285:1188-1198, which is hereby incorporated by reference in its entirety). The importance of fibrillin-1 is illustrated by patients with Marfan syndrome—a condition caused by mutation(s) in the fibrillin-1 gene—in which connective tissue dysfunction is associated with symptoms such as lens dislocation, organ prolapse, osteoporosis and joint hypermobility (see Suk et al. J Biol Chem 2004; 279:51258-51265; Collod-Beroud et al. Hum Mutat 2003; 22:199-208, both of which are hereby incorporated by reference in their entirety).

In vitro studies showed that addition of Hcy to fibrillin-1 disrupted disulfide bond formation, which in turn led to abnormal protein folding, increased susceptibility to proteolytic degradation and abnormal formation of ECM and elastic fibers (see Hubmacher et al. J Biol Chem 2010; 285:1188-1198; Whiteman et al. Antioxid Redox Signal 2006; 8:338-346, both of which are hereby incorporated by reference in their entirety). Addition of Hcy to human dermal fibroblasts was also associated with reduced forms of fibronectin that bound to fibrillin-1 suboptimally, thereby preventing microfibril formation (see Hubmacher et al. Biochemistry 2011; 50:5322-5332; Hubmacher et al. J Biol Chem 2010; 285:1188-1198, both of which are hereby incorporated by reference in their entirety).

In addition to lens dislocation, degeneration of the zonular fibers in patients with CBSDH can lead to increased lens curvature, lenticular myopia, astigmatism, retinal detachment, strabismus, cataracts and iridodonesis (see Sadiq et al. Semin Ophthalmol 2013; 28:313-320, which is hereby incorporated by reference in its entirety). If untreated, anterior dislocation of the lens can cause acute pupillary block glaucoma. In extreme cases, complete lens dislocation is associated with increased ocular axial length, possibly a compensatory reaction to blurred vision (see Mulvihill et al. J AAPOS 2001; 5:311-315, which is hereby incorporated by reference in its entirety).

A retrospective study was performed on 25 CBSDH cases detected in Ireland between 1971 and 1996, either by the national NBS program or by clinical presentation, to examine the effects of Hcy-lowering therapies on clinical outcomes (see Yap et al. J Inherit Metab Dis 1998; 21:738-747, which is hereby incorporated by reference in its entirety). The majority of the cases (24/25) were pyridoxine non-responsive. Consequently, treatment of most patients consisted of a Met-free, Cys-supplemented diet, with vitamin B12 and folate supplements, if required. Treatment was started before 6 weeks of age for patients and compared to a different group where treatment began upon diagnosis and one control patient who was never treated. The mean period of follow-up was 14.3 years (range 2.5 to 23.4) in groups treated before 6 weeks of age and 14.7 years (range 11.7 to 18.8) for the other patients, resulting in a total of 365.7 patient-years of treatment. Of the 21 patients detected by NBS, 18 remained free from complications during treatment. Of these individuals, 15/18 had 20:20 vision and 3/18 had had increasing myopia during the previous two years.

Consistent with the findings of Mudd et al. (see Mudd et al. Am J Hum Genet 1985; 37:1-31, which is hereby incorporated by reference in its entirety), lens dislocation in late-diagnosed individuals occurred at around two years of age. Lens dislocation was not reported in any of the early-treated individuals who had good compliance with therapy. Three of the 'early-treated patients' (those with the highest levels of fHcy) had worsening myopia without lens dislocation, which was most likely because of the relatively high fHcy levels in this small group of patients. This led the authors to suggest that progressive myopia might be the first sign, prior to lens dislocation, of poor dietary compliance, despite patient insistence to the contrary. The worsening myopia in these patients highlights how tenuous the balance is between neutral and negative clinical outcomes for these patients. Late detected patients all developed ectopia lentis. This suggests that treatment might delay the onset of lens dislocation, rather than prevent it.

Lifetime median plasma fHcy levels were higher in patients with myopia than in those without (18, 18 and 48 µmol/L vs 11 µmol/L, respectively). Of the three patients identified by NBS that developed complications in the group where treatment began upon diagnosis, all were non-compliant with their diets. Overall, 6/24 patients had lens dislocation; of these, two had an early diagnosis but were non-compliant with their diets and four had a late diagnosis, including the one patient that was never treated. Consistent with the findings of Mudd et al. (see Mudd et al. Am J Hum Genet 1985; 37:1-31, which is hereby incorporated by reference in its entirety), lens dislocation in late-diagnosed individuals (i.e. patients presenting with complications after age 2) occurred at approximately two years of age. At the time the study was published, lens dislocation had not been reported by any of the early-treated individuals with good compliance to therapy.

The compliant patients maintained their fHcy levels to tHcy equivalent levels largely below 120 µmon. However, all patients were under 24 years at the time of publication and many were still pediatric patients. Compliance with the protein restricted diet has been shown to rapidly decrease from adolescence through adulthood. The delicate balance described above suggests that the modest reduction of tHcy levels that was achieved by these patients may delay the onset of symptoms rather than prevent them as these patients age.

These results (see Yap et al. J Inherit Metab Dis 1998; 21:738-747; Mudd et al. Am J Hum Genet 1985; 37:1-31; each of which is hereby incorporated by reference in its entirety) were supported by those from a similar case-control study, conducted in Qatar, reporting on outcomes, including vision disturbances, in 32 cases of CBSDH and 25 sibling controls (see El Bashir et al. JIMD Rep 2015; 21:89-95, which is hereby incorporated by reference in its entirety). The mean age of the subjects was 11.2 years (range 0.6 to 29) and 56% were male. Overall, 9/32 cases (28%) were diagnosed by NBS and treated in the first month of life. The rest were diagnosed between 14 and 240 months of age. tHcy and Met levels were significantly lower among those diagnosed through NBS compared with those diagnosed clinically. This was possibly attributable to better compliance with diet and medications early in life. None of the 9 cases identified by NBS had vision problems at the time the study was published, compared with 18 (78%) in the late diagnosed group (p<0.001 between groups). However, similarly to the Irish study of 25 patients described above, patients in this study ranged from 0.6 to 29 years of age, and the long-term complications cannot be known yet.

A comparison of data from Yap and Naughten (see Yap et al. J Inherit Metab Dis 1998; 21:738-747, which is hereby incorporated by reference in its entirety) with the Kaplan-Meier curves produced by Mudd et al. showed that the proportion of treatment-compliant 'early-treated' patients with lens dislocation and osteoporosis was significantly lower than that expected for untreated patients with CBSDH (p<0.001).

Therefore, an increased Hcy level is considered to be a strong and independent risk factor for ocular complications, in particular lens dislocation, in patients with CBSDH and in the general population (for example, as shown in Yap et al. and Mudd et al.). This highlights the need for early CBSDH diagnosis and treatment, as well as treatment compliance by the patient.

B. Skeletal Complications

CBSDH is associated with an increased risk of osteoporotic fractures that can be attributed partly to low bone mineral density (see Mudd et al. and Weber et al. Mol Genet Metab 2016; 117:351-354; each of which is hereby incorporated by reference in its entirety).

A retrospective chart review of data from 19 CBSDH patients over 8 years found that low bone mineral density (BMD) was common among both pediatric and adult CBSDH patients (see Weber et al.). This study suggested that accrual of bone mass during childhood and adolescence, a critical period for skeletal growth, is deficient in CBSDH and may negatively impact attainment of peak bone mass.

This study also highlighted how even diet compliant patients with moderately elevated tHcy levels of only 5-fold above the normal range already suffer from poor skeletal clinical outcomes in childhood.

According to Mudd et al., 80% of patients with CBSDH develop osteoporosis before the age of 30 years. Moreover, elevated Hcy levels are associated with an increased risk of osteoporotic fractures, even in patients that do not have CBSDH (see Sato et al. Bone 2005, 36:721-726; van Meurs et al. N Engl J Med 2004; 350:2033-2041; McLean et al. N Engl J Med 2004; 350:2042-2049; each of which is hereby incorporated by reference in its entirety).

A retrospective chart review of data from 19 subjects (9 males aged 3.5 to 49.2 years) undergoing clinical DXA bone densitometry between 2002 and 2010 found that low BMD was common among both pediatric and adult CBSDH patients (see Weber et al. Mol Genet Metab 2016; 117:351-354, which is hereby incorporated by reference in its entirety). At the time of the first DXA scan, the mean lumbar spine (LS) BMD Z-score was $-1.2\pm1.3$, and total hip BMD Z-score was $-0.89\pm0.4$; both were significantly lower than 0 (the expected mean Z-score in the general population) with p=0.002 and 0.02, respectively. The LS BMD Z-score at diagnosis was $-1.26\pm1.4$ in patients aged <21 years and $-1.06\pm1.1$ in adults. Overall, 38% of patients had low BMD for age (as defined by a Z-score$\leq-2$). Both tHcy and Met levels were positively associated with LS BMD Z-score in multiple linear regression models (see Weber et al. Mol Genet Metab 2016; 117:351-354, which is hereby incorporated by reference in its entirety). The mean tHcy levels for these 19 individuals was only 59.2 μmol/L, and the majority of the 19 patients were pediatric. This study suggests that accrual of bone mass during childhood and adolescence, a critical period for skeletal growth, is deficient in CBSDH and may negatively impact attainment of peak bone mass. This study also highlights how diet compliant patients with moderately elevated tHcy levels of only 5-fold above the normal range already suffer from poor skeletal clinical outcomes in childhood.

Previous studies have demonstrated clear relationships between Hcy levels and risk of fractures in elderly populations (see Sato et al. Bone 2005, 36:721-726; van Meurs et al. N Engl J Med 2004; 350:2033-2041; McLean et al. N Engl J Med 2004; 350:2042-2049; each of which is hereby incorporated by reference in its entirety). Results from two prospective, population-based studies, including 2406 subjects aged ≥55 years, showed that the age- and sex-adjusted risks of fracture were increased by 30% for each one SD increase in tHcy level (see van Meurs et al. N Engl J Med 2004; 350:2033-2041; which is hereby incorporated by reference in its entirety). A homocysteine level in the highest age-specific quartile was associated with an increase by a factor of 1.9 in the risk of fracture. The associations between homocysteine levels and the risk of fracture appeared to be independent of bone mineral density and other potential risk factors for fracture. An increased homocysteine level was a strong and independent risk factor for osteoporotic fractures in older men and women in the general population, similar in magnitude to that of established risk factors for fractures and for cardiovascular disease (see van Meurs et al. N Engl J Med 2004; 350:2033-2041; which is hereby incorporated by reference in its entirety). Furthermore, a US prospective study of 825 men and 1174 women (HOPE-2 trial sub-study) found that a serum tHcy level in the highest quartile was associated with a 1.9-fold increased risk of hip fractures among women and a four-fold increased risk among men, compared with serum tHcy levels in the lowest quartile (see Sawka et al. Arch Intern Med. 2007 Oct. 22; 167(19):2136-9, which is hereby incorporated by reference in its entirety). The associations between tHcy levels and fracture risk were independent of BMD and other potential risk factors for fracture (see van Meurs et al. N Engl J Med 2004; 350: 2033-2041; McLean et al. N Engl J Med 2004, 350:2042-2049; Sawka et al. Arch Intern Med. 2007 Oct. 22; 167(19): 2136-9; each of which is hereby incorporated by reference in its entirety).

Consistent with these results, a study in 433 stroke patients, aged greater than 65 years, found that the age-adjusted incidence rates per 1000 person-years for hip fractures increased almost linearly from 2.89 in the lowest quartiles of Hcy levels to 27.87 in the highest quartiles (see Sato et al. Bone 2005; 36:721-726, which is hereby incorporated by reference in its entirety). Together, these results suggest that increased Hcy levels are a strong and independent risk factor for osteoporotic fractures in older men and women.

Skeletal abnormalities are not present at birth and are unusual in infants and very young children (see Mudd et al. Am J Hum Genet 1985; 37:1-31, which is hereby incorporated by reference in its entirety). The first signs of skeletal involvement are usually genu valgum and pes cavus, with elongation of the long bones—a typical characteristic of Marfan syndrome—often developing close to puberty (see Morris et al. J Inherit Metab Dis 2017; 40:49-74; which is hereby incorporated by reference in its entirety). Osteoporosis, especially of the vertebrae and long bones, is common in CBSDH patients and may lead to scoliosis/kyphosis and/or vertebral collapse (see Mudd et al. Am J Hum Genet 1985; 37:1-31; Weber et al. Mol Genet Metab 2016; 117: 351-354; each of which is hereby incorporated by reference in its entirety). Other skeletal manifestations may include Marfanoid facial features caused by prominent upper teeth and a high palate and anterior chest wall deformities, such as pectus excavatum or carinatum (see Morris et al. J Inherit Metab Dis 2017; 40:49-74; Sweetser et al. N Engl J Med 2016; 375:1879-1890; Brenton et al. J Bone Joint Surg Br 1972; 54:277-298; each of which is hereby incorporated by reference in its entirety). Because of these shared skeletal characteristics between Marfan syndrome and CBSDH, CBSDH patients are sometimes mischaracterized as Marfan patients.

A study in 25 Irish patients with CBSDH followed over 25 years found that the risk of osteoporosis was considerably lower in patients identified through newborn screening with good Hcy-lowering treatment compliance (diet, vitamins, and/or betaine), compared with non-compliant patients or in those with a late diagnosis (see Yap et al. J Inherit Metab Dis 1998; 21:738-747). Supportive evidence for these results came from a small Korean study in five CBSDH patients with good, long-term metabolic control. In this study, patients receiving early Hcy-lowering therapy had fewer skeletal abnormalities than those with a later diagnosis (see Lim et al. Osteoporos Int 2013, 24:2535-2538, which is hereby incorporated by reference in its entirety). Finally, in a study using a murine model for CBSDH, normalization of tHcy levels by treatment with a CBS ET was associated with osteoporosis prevention (see Majtan et al. Enzyme replacement prevents neonatal death, liver damage, and osteoporosis in murine homocystinuria, FASEB J 2017, which is hereby incorporated by reference in its entirety).

The precise mechanisms leading to low BMD and skeletal fragility in patients with CBSDH are not fully understood (see Weber et al. Mol Genet Metab 2016; 117:351-354; Lim J S, Lee D H. Changes in bone mineral density and body composition of children with well-controlled homocystinuria caused by CBS deficiency. Osteoporos Int 2013; 24:2535-2538, both of which are hereby incorporated by reference in its entirety). However, many of the connective tissue disorders in patients with CBSDH resemble those seen in Marfan Syndrome, a connective tissue disorder caused by mutations in the fibrillin-1 gene and characterized by features including elongation of the long bones and osteoporosis-type fractures (see Hubmacher et al. Biochemistry 2011; 50:5322-5332; Hubmacher et al. J Biol Chem 2010; 285:1188-1198, both of which are hereby incorporated by reference in its entirety). Elevated Hcy levels are believed to lead to bone fragility and fractures via two distinct pathways (see Behera et al. J Cell Physiol 2016, which is hereby incorporated by reference in its entirety). The first results in reduced accrual of bone mass during childhood and adolescence via impaired fibrillin assemblies. The second pathway leads to impaired bone remodeling, resulting in brittle bones via decreased collagen crosslink formation (see Behera et al. J Cell Physiol 2016; Kang et al. J Clin Invest 1973; 52:2571-2578, both of which are hereby incorporated by reference in its entirety). Together, these data suggest that accrual of bone mass during childhood and adolescence, a critical period for skeletal growth, is deficient in patients with CBSDH and that this negatively affects attainment of peak bone mass.

Moreover, a strong relationship exists between Hcy levels and risk of fracture, in elderly populations (see Sato et al. Bone 2005; 36:721-726; van Meurs et al. N Engl J Med 2004; 350:2033-2041; McLean et al. N Engl J Med 2004; 350:2042-2049; each of which is hereby incorporated by reference in its entirety). Results from two international, prospective, population-based studies, including 2,406 subjects aged greater than or equal to 55 years, showed that a homocysteine level in the highest age-specific quartile was associated with an increase by a factor of 1.9 in the risk of fracture (see van Meurs et al. N Engl J Med 2004; 350: 2033-2041, which is hereby incorporated by reference in its entirety). An increased homocysteine level was a strong and independent risk factor for osteoporotic fractures in older men and women in the general population, similar in magnitude to that of established risk factors for fractures (low bone mineral density, cognitive impairment, recent falls) and for cardiovascular disease (see van Meurs et al. N Engl J Med 2004; 350:2033-2041, which is hereby incorporated by reference in its entirety). Furthermore, a US prospective study of 1,999 subjects (HOPE-2 trial sub-study) found that a serum tHcy level in the highest quartile was associated with a 1.9-fold increased risk of hip fractures among women and a four-fold increased risk among men, compared with serum tHcy levels in the lowest quartile (see Sawka et al. Arch Intern Med. 2007 Oct. 22; 167(19):2136-9, which is hereby incorporated by reference in its entirety). The associations between tHcy levels and fracture risk were independent of BMD and other potential risk factors for fracture (see van Meurs et al. N Engl J Med 2004; 350:2033-2041; McLean et al. N Engl J Med 2004; 350:2042-2049; Sawka et al. Arch Intern Med. 2007 Oct. 22; 167(19):2136-9, each of which is hereby incorporated by reference in its entirety). Consistent with these results, a study in 433 stroke patients, aged >65 years, found that the age-adjusted incidence rates per 1000 person-years for hip fractures increased almost linearly from 2.89 in the lowest quartiles of Hcy levels to 27.87 in the highest quartiles (see Sato et al. Bone 2005; 36:721-726, which is hereby incorporated by reference in its entirety). Together, these results suggest that increased Hcy levels are a strong and independent risk factor for osteoporotic fractures in older men and women.

The precise mechanisms leading to low BMD and skeletal fragility in patients with CBSDH are not fully understood (see Weber et al. Mol Genet Metab 2016; 117:351-354; Lim J S, Lee D H. Changes in bone mineral density and body composition of children with well-controlled homocystinuria caused by CBS deficiency. Osteoporos Int 2013; 24:2535-2538, both of which are hereby incorporated by reference in its entirety). However, many of the connective tissue disorders in patients with CBSDH resemble those seen in Marfan Syndrome, a connective tissue disorder caused by mutations in the fibrillin-1 gene and characterized by features including elongation of the long bones and osteoporosis-type fractures (see Brenton et al. J Bone Joint Surg Br 1972; 54:277-298; Hubmacher et al. Biochemistry 2011; 50:5322-5332; Hubmacher et al. J Biol Chem 2010; 285:1188-1198, each of which is hereby incorporated by reference in its entirety).

In healthy individuals, fibrillin-1, together with collagen and elastin polymers, assembles to form the ECM, the architectural scaffolds for bone formation, homeostasis and repair (see Olivieri et al. Fibrogenesis Tissue Repair 2010; 3:24, which is hereby incorporated by reference in its entirety). Studies show that elevated tHcy levels can lead to structural modifications of fibrillin-1 fragments, which prevent multimerization and lead to fibrillin-1 degradation (see Hubmacher et al. J Biol Chem 2005; 280:34946-34955; Hubmacher et al. J Biol Chem 2010; 285:1188-1198, both of which are hereby incorporated by reference in its entirety). This process is further impaired by the homocysteinylation of fibronectin, which prevents the formation of fibronectin-fibrillin complexes necessary for fibrillin-1 multimerization (see Hubmacher et al. Biochemistry 2011; 50:5322-5332, which is hereby incorporated by reference in its entirety). Such findings suggest that elevated Hcy levels have a detrimental effect on ECM formation.

In healthy individuals, fibrillin assemblies (i.e. microfibrils) play an important role in bone mineralization, through storage and activation of transforming growth factor-beta (TGF-beta) and bone morphogenetic proteins (BMP) (see Nistala et al. Ann N Y Acad Sci 2010; 1192:253-256; Nistala et al. J Biol Chem 2010; 285:34126-34133, both of which are hereby incorporated by reference in its entirety). Impaired activation of TGF-beta and BMPs could potentially contribute to the skeletal phenotype observed in both Marfan syndrome and CBSDH and might also decrease bone mineral content, as observed in mild forms of CBSDH (see Herrmann et al. Clin Chem 2005; 51:2348-2353, which is hereby incorporated by reference in its entirety). Moreover, there is in vivo and in vitro evidence that Hcy may weaken bone strength through decreased collagen crosslink formation (see Kang et al. J Clin Invest 1973; 52:2571-2578, which is hereby incorporated by reference in its entirety). Together, these data suggest that accrual of bone mass during childhood and adolescence, a critical period for skeletal growth, is deficient in patients with CBSDH and that this may negatively impact attainment of peak bone mass.

In addition to its effects on bone deposition, elevated Hcy levels increase the rate of bone remodeling by increasing osteoclast (OC) activity and decreasing osteoblast (OB) activity (see Behera et al. J Cell Physiol 2016; Herrmann et al. Clin Chem 2005; 51:2348-2353; Vacek et al. Clin Chem Lab Med 2013; 51:579-590; Vijayan et al. J Endocrinol 2017; 233:243-255, each of which is hereby incorporated by reference in its entirety). An imbalance between OB and OC activities can lead to brittle bones and an increased incidence of fractures. Mechanisms leading to Hcy-mediated decreases in OB activity are believed to include decreased bone blood flow (a consequence of decreased NO availability) (see Tyagi et al. Vasc Health Risk Manag 2011; 7:31-35, which is hereby incorporated by reference in its entirety) and increased rates of OB apoptosis (FIG. 2 and Tables 14) (see Behera et al. J Cell Physiol 2016; Kim et al. Bone 2006; 39:582-590, both of which are hereby incorporated by reference in its entirety). Mechanisms leading to enhanced OC activity are believed to include increased levels of intracellular ROS, which enhance both OC differentiation and OC activity via increased matrix metalloproteinase (MMP) activity (see Vacek et al. Clin Chem Lab Med 2013; 51:579-590, which is hereby incorporated by reference in its entirety) and suppression of OC apoptosis (see Behera et al. J Cell Physiol 2016; Herrmann et al. Clin Chem 2005; 51:2348-2353; Koh et al. J Bone Miner Res 2006; 21:1003-1011, each of which is hereby incorporated by reference in its entirety). Indeed, a recent study in CD1 mice fed a high Hcy diet showed that short-term (7 day) Hcy administration was associated with a loss of tissue mineral density (TMD) and increased OC numbers, whereas long-term Hcy administration (30 days) led to OC reprogramming, apoptosis and mineralization, which reinstated TMD but compromised tissue biomechanical properties (see Vijayan et al. J Endocrinol 2017; 233:243-255, which is hereby incorporated by reference in its entirety).

Thus, elevated Hcy levels can lead to bone fragility and fractures via two distinct pathways (see Behera et al. J Cell Physiol 2016, which is hereby incorporated by reference in its entirety). The first results in reduced accrual of bone mass during childhood and adolescence, via impaired ECM formation and suppressed activation of fibrillin-1-associated TGF-beta and BMP. The second pathway leads to impaired bone remodeling, resulting in brittle bones, via increased OC and decreased OB activities.

Elevated Hcy levels are associated with increased oxidative stress in the bone microenvironment. Increased ROS induces osteoblast apoptosis, thereby decreasing osteoblast genesis. This increase in oxidative stress further decreases NO availability through production of superoxide anions, which might also decrease bone blood flow and angiogenesis. The ROS generated by this process activates osteoclast genesis by monocyte fusion, further contributing to loss of BMD, leading to osteoporosis.

A recent study in newborn CBS knockout (KO) mice, maintained on standard rodent chow without Met restriction, found that subcutaneous administration of a CBS ET, using recombinant PEGylated human truncated CBS (PEG-CBS) for 5 months, prevented the reduction in bone mineral density in these animals, and could also normalize these values in animals that were treated later in life (see Majtan et al. Enzyme replacement prevents neonatal death, liver damage, and osteoporosis in murine homocystinuria. FASEB J 2017, which is hereby incorporated by reference in its entirety). In this study, changes in body composition that characterize both the KO model and CBSDH patients were prevented. In both plasma and tissues, tHcy and Cys levels were normalized, Cth levels increased and SAM/SAH ratios improved.

Supportive evidence for the effects of Hcy-lowering on skeletal outcomes derives from a 25-year survey of 25 Irish patients with CBSDH (see Yap et al. J Inherit Metab Dis 1998; 21:738-747, which is hereby incorporated by reference in its entirety). In this study, osteoporosis (diagnosed by radiological examination, rather than DXA) was present in one of the three treatment non-compliant patients identified by NBS and in one of the four patients with a late diagnosis (at two years of age). None of the 18 patients who had been compliant with early treatment (from 6 weeks of age) showed signs of osteoporosis.

A small study was conducted in Korea in five CBSDH patients (3 boys and 3 girls), all diagnosed at young age (3 during NBS and 2 at age 7 years), with good metabolic control for 3.4 years (see Lim et al. Osteoporos Int 2013; 24:2535-2538, which is hereby incorporated by reference in its entirety). Mean plasma tHcy level at diagnosis was 34.3±52.6 (13 to 78.6) µmol/L. plasma Met was 716±1347.6 (24.3 to 1566) µmol/L and treatment comprised a low-Met diet with pyridoxine, betaine and folic acid supplementation. Body composition measurements and BMDs for all patients were within normal ranges for the Korean population, and no significant changes were observed in skeletal morphology over time. Three patients (60%) had mild scoliosis of the T-L spine (Cobb angles 7.3°, 7.6° and 10.3°), and fractures were reported four times in three patients. Of these, two were caused by a sports injury and one by a traffic accident. Two cases of mild compression fracture of the lumbar spine were detected by radiography and a history of severe back pain was documented. Patients receiving an early diagnosis showed fewer skeletal abnormalities than those with a later diagnosis. This study showed however, that even patients receiving an early diagnosis by NBS, who were compliant with dietary treatment and had only slight to moderately elevated levels of tHcy, already displayed skeletal abnormalities and multiple fractures as children.

Together, these findings suggest a beneficial effect of early Hcy-lowering treatment on skeletal outcomes in patients with CBSDH. It should be noted that in treatment-compliant patients tHcy levels were lowered but not normalized, and though fewer skeletal abnormalities were present in these patients, significant negative clinical outcomes (osteoporosis and fractures) were noted in this largely young patient group.

C. Vascular Complications

The relationship between CBSDH and vascular disease was first demonstrated in 1985 in an epidemiological study in patients with moderate to severely elevated Hcy levels due to homozygous CBSDH (see Mudd et al. Am J Hum Genet 1985; 37:1-31, which is hereby incorporated by reference in its entirety).

Thromboembolism is the major cause of morbidity and premature death in CBSDH patients (see Mudd et al. Am J Hum Genet 1985; 37:1-31; Karaca et al. Gene 2014; 534: 197-203; Yap S. J Inherit Metab Dis 2003; 26:259-265, each of which is hereby incorporated by reference in its entirety). The overall rate of thromboembolic events in patients with untreated CBSDH is approximately 10% per year (see Cattaneo M. Semin Thromb Hemost 2006; 32:716-723, which is hereby incorporated by reference in its entirety), with risk increasing after surgery and during or immediately after pregnancy (see Mudd et al. Am J Hum Genet 1985; 37:1-31; Novy et al. Thromb Haemost 2010; 103:871-873, both of which are hereby incorporated by reference in its entirety). Thromboembolism can affect any blood vessel, but venous thrombosis (in particular CSVT) is more common than arterial thrombosis in patients with CBSDH (see Mudd et al. Am J Hum Genet 1985; 37:1-31; Karaca et al. Gene 2014; 534:197-203; Eslamiyeh et al. Iran J Child Neurol 2015; 9:53-57; Saboul et al. J Child Neurol 2015; 30:107-112, each of which is hereby incorporated by reference in its entirety). Cerebrovascular accidents, especially CSVT, have been described in infants (see Mahale et al. J Pediatr Neurosci. 2017 April-June; 12(2):206-207, which is hereby incorporated by reference in its entirety), although more typically appear in young adults (see Yap et al. Arterioscler Thromb Vasc Biol 2001; 21:2080-2085, which is hereby incorporated by reference in its entirety).

The risk of thromboembolic events was approximately 25% by age 16 years and 50% by age 29 years. In 1999, Hankey et al. reported that all three genetic causes of HCU (CBSDH, MTHFR deficiency and vitamin B12 deficiency) were associated with a high risk of premature cardiovascular (CV) disease, affecting half of all homozygotes by the age of 30 years (see Hankey et al. Lancet 1999; 354:407-413, which is hereby incorporated by reference in its entirety). The only biochemical change common to all three disorders are elevated serum Hcy levels (often greater than 100 µmol/L) (see Faeh et al. Swiss Med Wkly 2006; 136:745-756, which is hereby incorporated by reference in its entirety). Several reports described how treatments decreasing tHcy levels significantly reduced the incidence of vascular events, the main cause of morbidity, in CBSDH patients (see Yap et al. J Inherit Metab Dis 2001; 24:437-447; Wilcken D E, Wilcken B. The natural history of vascular disease in homocystinuria and the effects of treatment. J Inherit Metab Dis 1997; 20:295-300, both of which are hereby incorporated by reference in its entirety). Since then, a number of other studies demonstrated an increased risk of vascular events, in particular venous thrombosis, in CBSDH patients (see Karaca et al. Gene 2014; 534:197-203; Kelly et al. Neurology 2003; 60:275-279; Lussana et al. Thromb Res 2013; 132:681-684; Magner et al. J Inherit Metab Dis 2011; 34:33-37, each of which is hereby incorporated by reference in its entirety).

An elevated plasma tHcy level is a risk factor for vascular disease and a strong predictor of mortality in patients with coronary artery disease, both with and without CBSDH (see Mudd et al. Am J Hum Genet 1985; 37:1-31; Karaca et al. Gene 2014; 534:197-203; Kelly et al. Neurology 2003; 60:275-279; Faeh et al. Swiss Med Wkly 2006; 136:745-756; Boushey et al. JAMA 1995; 274:1049-1057; Clarke R et al. JAMA 2002; 288:2015-2022; Hankey et al. Lancet 1999; 354:407-413; Khan et al. Stroke 2008; 39:2943-2949; Graham et al. The European Concerted Action Project. JAMA 1997; 277:1775-1781; Clarke et al. N Engl J Med 1991; 324:1149-1155; Clarke et al. Ir J Med Sci 1992; 161:61-65; Woodward et al. Blood Coagul Fibrinolysis 2006; 17:1-5; Refsum et al. Annu Rev Med 1998; 49:31-62; Yoo et al. Stroke 1998; 29:2478-2483; Selhub et al. N Engl J Med 1995; 332:286-291; Wald et al. BMJ 2002; 325:1202; Bautista et al. J Clin Epidemiol 2002; 55:882-887; Brattstrom et al. Atherosclerosis 1990; 81:51-60; Lussana et al. Thromb Res 2013; 132:681-684; Casas et al. Lancet 2005; 365:224-232; McCully K S. Am J Pathol 1969; 56:111-128; Magner et al. J Inherit Metab Dis 2011; 34:33-37; Wilcken et al. J Clin Invest 1976; 57:1079-1082; Nygard et al. N Engl J Med 1997; 337:230-236; each of which is hereby incorporated by reference in its entirety). Although there is evidence for a relationship between tHcy levels and CV risk (see Boushey et al. JAMA 1995; 274:1049-1057, which is hereby incorporated by reference in its entirety), the relationships between tHcy and stroke/peripheral arterial disease are considerably stronger (see Clarke et al. JAMA 2002; 288:2015-2022; Khan et al. Stroke 2008; 39:2943-2949; Wald et al. BMJ 2002; 325:1202; Casas et al. Lancet 2005; 365:224-232; Brattstrom et al. Haemostasis 1989; 19 Suppl 1:35-44; each of which is hereby incorporated by reference in its entirety). Although large studies (NORVIT, HOPE-2, VITATOPS) in the general population initially concluded that lowering Hcy levels had a minor effect on major vascular events and recurrent cardiovascular disease, a further, more specific analysis of the data has clearly shown the clinical benefits of tHcy reduction on stroke.

There is considerable evidence that Hcy-lowering decreases stroke risk in the general population with mildly elevated tHcy levels (see Saposnik et al. Stroke 2009; 40:1365-1372; Huo et al. JAMA 2015; 313:1325-1335; Lonn et al. N Engl J Med 2006; 354:1567-1577; Hankey et al. Lancet Neurol 2012; 11:512-520; Spence J D, Lancet Neurol. 2007 September; 6(9):830-8, each of which is hereby incorporated by reference in its entirety). In the HOPE-2 study (see Saposnik et al. Stroke 2009; 40:1365-1372, which is hereby incorporated by reference in its entirety) of 5,552 patients, minor reductions in tHcy levels (3 mmol/L vs placebo) led to a significant reduction in stroke incidence (27% relative risk reduction, 1.3% absolute risk reduction), suggesting that even small decreases in tHcy levels can be beneficial. This effect was most pronounced in patients with baseline Hcy in the upper quartile who had a 4.3% absolute risk reduction. Although it is unclear whether Hcy-lowering affects overall CV outcomes in patients with mildly elevated tHcy and without CBSDH (see Marti-Carvajal et al. Cochrane Database Syst Rev 2015; 1:CD006612, which is hereby incorporated by reference in its entirety), its vascular benefits have been consistently demonstrated in patients with CBSDH (see Yap et al. J Inherit Metab Dis 1998; 21:738-747; Eslamiyeh et al. Iran J Child Neurol 2015; 9:53-57; Saboul et al. J Child Neurol 2015; 30:107-112; Yap et al. Arterioscler Thromb Vasc Biol 2001; 21:2080-2085; Woods et al. BMJ Case Rep 2017; Wilcken et al. J Inherit Metab Dis 1997; 20:295-300; Yap et al. Semin Thromb Hemost 2000; 26:335-340; Ruhoy et al. Pediatr Neurol 2014; 50:108-111, each of which is hereby incorporated by reference in its entirety).

1. Mechanism

A number of studies have shown that elevated Hcy levels contribute to development of atherosclerosis or thrombosis through oxidative stress associated mechanisms (see Faverzani et al. Cell Mol Neurobiol 2017; Nowak et al. Arterioscler Thromb Vasc Biol 2017; 37:e41-e52; Vanzin et al. Mol Genet Metab 2011; 104:112-117; Vanzin et al. Gene 2014; 539:270-274; Vanzin et al. Cell Mol Neurobiol 2015; 35:899-911; each of which is hereby incorporated by reference in its entirety), including inflammatory and immune activation via NF-κB (see Rodriguez-Ayala et al. Atherosclerosis 2005; 180:333-340; van Guldener et al. Curr Hypertens Rep 2003; 5:26-31, both of which are hereby incorporated by reference in its entirety). Medial damage leading to thrombosis is believed to be caused by Hcy-mediated endothelial dysfunction (see Jiang et al. Arterioscler Thromb Vasc Biol 2005; 25:2515-2521; Hossain et al. J Biol Chem 2003; 278:30317-30327; Cai et al. Blood 2000; 96:2140-2148; Zhang et al. J Biol Chem 2001; 276:35867-35874; Papapetropoulos et al. Proc Natl Acad Sci USA 2009; 106:21972-21977; Szabo et al. Br J Pharmacol 2011; 164:853-865; Chiku et al. J Biol Chem 2009; 284:11601-11612; Wang et al. Antioxid Redox Signal 2010; 12:1065-1077; Saha et al. FASEB J 2016; 30:441-456; Ebbing et al. JAMA 2008; 300:795-804; Bonaa et al. N Engl J Med 2006; 354:1578-1588; Marti-Carvajal et al. Cochrane Database Syst Rev 2015; 1:CD006612; Celermajer et al. J Am Coll Cardiol 1993; 22:854-858; Rubba et al. Metabolism 1990; 39:1191-1195; each of which is hereby incorporated by reference in its entirety), enhanced coagulation pathways (see Spence J D. Int J Stroke. 2016 October; 11(7):744-7; Fryer et al. Arterioscler Thromb 1993; 13:1327-1333; Lentz et al. J Clin Invest 1991; 88:1906-1914; each of which is hereby incorporated by reference in its entirety) and increased vascular dilatation. Such pro-thrombotic mechanisms are similar to those observed in Marfan patients (see Kelly et al. Neurology 2003; 60:275-279; Tripathi P. International Cardiovascular Forum J 2016; 6:13; van Guldener et al. Curr Hypertens Rep 2003; 5:26-31; Hackam et al. JAMA 2003; 290:932-940; Baumbach et al. Circ Res 2002; 91:931-937; Evangelisti et al. Int J Cardiol 2009; 134:251-254; de Valk et al. Stroke 1996; 27:1134-1136, each of which is hereby incorporated by reference in its entirety).

A causal relationship between tHcy levels and CV risk derived from a meta-analysis of data from 27 studies (more than 4,000 patients) showed a graded risk for atherosclerosis of CV, cerebrovascular and peripheral vessels, such that a 5 µM increase in Hcy conferred a 80% increased risk to women and a 60% increased risk to men (see Boushey et al. JAMA 1995; 274:1049-1057, which is hereby incorporated by reference in its entirety). A meta-analysis of data from 30 prospective or retrospective studies involving 5073 ischemic heart disease (IHD) events and 1113 strokes found that a 25% lower than usual (corrected for regression dilution bias) Hcy level (approximately 3 µmol/L) was associated with an 11% (odds ratio (OR), 0.89; 95% CI, 0.83 to 0.96) lower IHD risk and a 19% (OR, 0.81; 95% CI, 0.69 to 0.95) lower stroke risk (see Clarke R, et al. JAMA 2002; 288:2015-2022, which is hereby incorporated by reference in its entirety).

A study in patients with and without pre-existing vascular disease demonstrated an increase, after Met loading, of plasma Hcy (exceeding the highest values in comparable healthy control subjects) in 1/21 subjects with MI (5%), 14/37 subjects with aorto-iliac disease (38%) and 17/53 subjects with cerebrovascular disease (32%). This suggests that the links between Hcy levels and peripheral arterial disease (PAD) and stroke are considerably greater than the link between Hcy levels and MI (see Brattstrom et al. Haemostasis 1989; 19 Suppl 1:35-44, which is hereby incorporated by reference in its entirety). An independent, graded association between Hcy levels and stroke was described in a prospective study conducted among a UK cohort of 457 stroke patients and 179 control subjects from the same community (see Khan et al. Stroke 2008; 39:2943-2949). The highest Hcy levels were seen in patients with small vessel disease (SVD) (16.2 versus 11.8 µmol/L in control subjects without stroke, p<0.001 after adjusting for age, gender, vascular risk factors, vitamin levels and renal function). Within SVD cases, the highest Hcy levels were observed in individuals with lacunar infarction with confluent leukoaraiosis. Moreover, there was a correlation between Hcy levels and leukoaraiosis severity (r=-0.225; p<0.001).

These findings were further supported by a Mendelian randomization study, demonstrating a genetic association between MTHFR polymorphisms regulating Hcy metabolism and stroke risk (see Casas et al. Lancet 2005; 365:224-232, which is hereby incorporated by reference in its entirety). A literature search for all relevant studies on associations between Hcy levels and the MTHFR TT and CC polymorphisms on stroke risk identified 111 studies, including 15,635 individuals without cardiovascular disease (CVD). The weighted mean difference in Hcy levels between TT and CC homozygotes was 1.93 µmol/L (95% CI 1.38 to 2.47). Based on results from a previous meta-analysis of prospective studies, in which a 5 µmol/L increase in plasma Hcy levels corresponded to an OR for stroke of 1.59 (1.29 to 1.96), a 1.93 µmol/L increase in Hcy levels in healthy individuals with the TT genotype would result in an expected OR for stroke of 1.20 (1.10 to 1.31) (see Wald et al. BMJ 2002; 325:1202, which is hereby incorporated by reference in its entirety). Consistent with this result, Khan et al. reported a 1.26 (1.14 to 1.40) OR for stroke for TT versus CC homozygotes (p=0.29), irrespective of age group, ethnicity or geographical location. Together, these results suggested a causative role for elevated Hcy levels in stroke pathogenesis in the general population.

Whether moderate increases in serum Hcy typical in patients with heterozygous CBSDH because vascular disease has been examined in studies much smaller than those conducted in the general population. According to Mudd et al., the risk of vascular events in patients with mildly elevated tHcy levels due to heterozygous CBSDH (<5% by age 50 years) is similar to that in the general population (see Mudd et al. Am J Hum Genet 1981; 33:883-893, which is hereby incorporated by reference in its entirety). Consistent with this, an ultrasound study in individuals with homozygous and heterozygous CBSDH found impaired endothelial function in the systemic arteries of homozygous children as young as four years of age, whereas endothelial function was largely unaffected in heterozygous adults (see Celermajer et al. J Am Coll Cardiol 1993; 22:854-858, which is hereby incorporated by reference in its entirety).

Although a similar study demonstrated signs of premature arterial disease in both homozygotes and heterozygotes, individuals with the homozygous disorder developed signs at a much younger age (19 years versus 45 years) and disease severity was considerably greater (see Rubba et al. Metabolism 1990; 39:1191-1195, which is hereby incorporated by reference in its entirety).

Overall, observations in CBSDH patients were consistent with those from previous studies, with vascular risk increasing with Hcy levels (see Boushey et al. JAMA 1995; 274:1049-1057; Clarke et al. JAMA 2002; 288:2015-2022; Khan et al. Stroke 2008; 39:2943-2949; each of which is hereby incorporated by reference in its entirety).

These results suggest that an elevated Hcy level is a risk factor for CV disease. In addition, lowering Hcy levels has been shown to significantly reduce the risk of stroke in the general population and in patients with CBSDH.

Studies have shown that elevated Hcy levels caused by CBSDH can potentially contribute to development of atherosclerosis and/or thrombosis via various mechanisms. These include molecular events such as induction of oxidative stress and its downstream effects such as activation of NF-κB (nuclear factor kappa-light-chain-enhancer of activated B cells), a transcriptional factor regulating proinflammatory and other damage-associated genes. Various Hcy-mediated effects modulating the physio-chemical properties of the vascular wall, such as those leading to endothelial dysfunction or arterial stiffness, could contribute to development of hypertension, thrombosis or other vascular abnormalities. Finally, there is evidence for direct induction of coagulation pathways by Hcy, a more direct route leading to thrombosis (see Faverzani et al. Cell Mol Neurobiol 2017; Hainsworth et al. Biochim Biophys Acta 2016; 1862:1008-1017; Ganguly et al. Nutr J 2015; 14:6; Tripathi P. Molecular and biochemical aspects of homocysteine in cardiovascular diseases. International Cardiovascular Forum J 2016; 6:13; Fryer et al. Arterioscler Thromb 1993; 13:1327-1333; each of which is hereby incorporated by reference in its entirety). Following a brief description of the molecular and biochemical mechanisms of atherosclerosis, the subsections below will review potential mechanisms leading to vascular disease in individuals with elevated tHcy levels, including those with CBSDH.

2. Atherosclerosis

Among the most well studied conditions leading to thrombosis and, consequently, vascular blockage, is atherosclerosis, a progressive inflammatory disease affecting coronary, cerebral and peripheral circulations (see Libby et al. Circulation 2005; 111:3481-3488, which is hereby incorporated by reference in its entirety). In its early stages, vascular injury leads to endothelial cell (EC) activation, monocyte recruitment into the intima and macrophage activation. An inflammatory atherosclerotic lesion (the fatty streak), comprising monocyte-derived, lipid-laden macrophages (foam cells) and T-lymphocytes, is formed. Progressive lipid accumulation forms a lipid core surrounded by a fibrous cap. During the later stages, activated macrophages secrete enzymes that weaken the fibrous cap, leading to plaque rupture, hemorrhage or thrombosis and ischemic attacks/acute coronary syndrome. Plaque rupture exposes tissue factor to the blood within the arterial lumen, allowing it to form complexes with coagulation factors VII/VIIa. This process initiates the coagulation cascade, leading to thrombogenesis. Disrupted plaques can lead either to mural or occlusive thrombosis, causing partial or full blockage, respectively. Mural thrombosis causes ischemic symptoms, such as unstable angina, whereas occlusive thrombosis leads to acute coronary events, such as MI and stroke. Cytokines are involved in all stages of atherosclerosis and have a profound influence on its pathogenesis (see Ramji et al. Cytokine Growth Factor Rev 2015; 26:673-685, which is hereby incorporated by reference in its entirety). In addition to being secondary to atherosclerosis, thrombosis can also be activated in the absence of plaque formation, for example, as a consequence of atrial fibrillation or by direct activation of the clotting cascade.

3. Oxidative Stress

Studies in patients with elevated Hcy levels showed that treated and, especially, untreated patients were susceptible to oxidative stress, as evidenced by altered biomarkers reflecting lipid, protein and DNA oxidative damage in various tissues (see Vanzin et al. Mol Genet Metab 2011; 104:112-117; Vanzin et al. Gene 2014; 539:270-274; Vanzin et al. Cell Mol Neurobiol 2015; 35:899-911, each of which is hereby incorporated by reference in its entirety). Oxidative stress, defined as an imbalance in redox homeostasis, plays a key role in such vascular pathologies as atherosclerosis and its associated thrombosis, where oxidative modification of low-density lipoproteins, endothelial activation and initiation of vascular inflammatory responses are implicated (see Nowak et al. Arterioscler Thromb Vasc Biol 2017; 37: e41-e52, which is hereby incorporated by reference in its entirety). Oxidative stress can be caused by increased levels of ROS (e.g. superoxide ($O^{2-}$) and hydroxyl ($HO^-$) radicals and hydrogen peroxide ($H_2O_2$)) and/or by decreased levels of tissue antioxidants (e.g. superoxide dismutase, catalase and glutathione peroxidase) (see Faverzani et al. Cell Mol Neurobiol 2017; Nowak et al. Arterioscler Thromb Vasc Biol 2017; 37: e41-e52, both of which are hereby incorporated by reference in their entireties). In healthy individuals, ROS are produced as byproducts of normal oxidative metabolism. However, in addition, ROS generation is triggered by such CV risk factors as cigarette smoke, alcohol consumption, hypercholesterolemia, hypertension, diabetes and elevated Hcy levels.

At a molecular level, there are numerous ways that Hcy could cause increased oxidative stress, some discussed previously. For example, accumulation of immunogenic homocysteinylated proteins in the vascular wall could promote inflammation and, consequently, ROS ($O^{2-}$) generation by activated phagocytes). Another potential mechanism is Hcy-induced activation of NMDA receptors, triggering signaling pathways leading to ROS generation. In cardiac microvascular ECs, Hcy induced increased levels of NADPH oxidase, cell surface enzymes that, especially in activated cells, produce high levels of $O^{2-}$. A recent study (see Chen et al. Sci Rep. 2017 Jul. 31; 7(1):6932, which is hereby incorporated by reference in its entirety) suggested that, in the ischemic rat brain, Hcy induced mitochondrial dysfunction, with the expected result of increased ROS production. Hcy is also believed to decrease bioavailability of the beneficial vasodilator NO. $O^{2-}$ reacts with NO to yield the reactive nitrogen species peroxynitrite and, indeed, an Hcy induced increase in tyrosine nitration, an indicator of peroxynitrite-induced protein damage, has also been reported (see Tyagi et al. Vasc Health Risk Manag 2011; 7:31-35, which is hereby incorporated by reference in its entirety). More broadly, thiol-thiol interactions involving Hcy would be expected to perturb cellular redox status, for example, potentially decreasing availability of reduced glutathione and even impairing protein assembly and folding.

In a study of CBSDH patients before and after treatment, treatment with pyridoxine, folate, betaine and vitamin B12 supplements attenuated lipid oxidative damage in patients but did not change sulfhydryl content or total antioxidant status, both indicators of tissue antioxidant capacity. Nonetheless, there was a significant negative correlation between sulfhydryl group content and Hcy levels, and a positive correlation between levels of the lipid peroxidation product malondialdehyde and those of Hcy. This suggested a potential mechanistic role for Hcy in the oxidative damage observed in CBSDH (see Vanzin et al. Mol Genet Metab 2011; 104:112-117, which is hereby incorporated by reference in its entirety). Altered lipid profiles, in particular decreased levels of high-density lipoprotein and enrichment of proinflammatory lipid species, were observed in the plasma of untreated and treated CBSDH patients (see Vanzin et al. Cell Mol Neurobiol 2015; 35:899-911, which is hereby incorporated by reference in its entirety). In another study, significantly more DNA damage was reported in CBSDH patients than in healthy individuals (see Vanzin et al. Gene 2014; 539:270-274, which is hereby incorporated by reference in its entirety). Together, these findings implicate oxidative stress in the pathogenesis of vascular damage associated with elevated Hcy levels. No correlation was found between Met levels and any oxidative stress-associated parameters, suggesting that Met and its derivatives contribute little to the oxidative damage in CBSDH (see Vanzin et al. Mol Genet Metab 2011; 104:112-117, which is hereby incorporated by reference in its entirety).

Among a plethora of other molecular effects, oxidative stress is associated with activation of NF-κB, a group of transcription factors regulating expression of proinflammatory genes, such as cytokines, known to be involved in initiation and progression of atherosclerosis and thrombosis (see Rodriguez-Ayala et al. Atherosclerosis 2005; 180:333-340, which is hereby incorporated by reference in its entirety). In vitro studies showed that treatment of ECs with Hcy activated NF-kβ via ROS production (see van Guldener et al. Curr Hypertens Rep 2003; 5:26-31, which is hereby incorporated by reference in its entirety). Besides modulating gene expression, chemical modification of cellular macromolecules by oxidative stress can directly impact the structure and function of the vasculature and have other localized or systemic effects, as discussed in the rest of the section.

4. Changes in the Vascular Wall

Endothelial dysfunction is generally defined as an imbalance between endothelial-associated factors modulating vascular contractility and relaxation. Among these factors, NO or "endothelial derived relaxation factor" is the most well-known, while hydrogen sulfide ($H_2S$) is another described more recently (see Jiang et al. Arterioscler Thromb Vasc Biol 2005; 25:2515-2521, which is hereby incorporated by reference in its entirety). Several in vitro studies examined effects of Hcy on endothelial function, albeit using very high levels of Hcy (see Jiang et al. Arterioscler Thromb Vasc Biol 2005; 25:2515-2521; Hossain et al. J Biol Chem 2003; 278:30317-30327; Cai et al. Blood 2000; 96:2140-2148; Zhang et al. J Biol Chem 2001; 276:35867-35874; each of which is hereby incorporated by reference in its entirety). One such study reported an unfolded protein response and programmed cell death in human umbilical vein endothelial cells (HUVEC) treated with Hcy, though Hcy concentrations were several-fold higher than those observed in patients with severely elevated Hcy levels (see Zhang et al. J Biol Chem 2001; 276:35867-35874, which is hereby incorporated by reference in its entirety). In other reports, Cth gamma-lyase (CGL), an enzyme involved in Cth metabolism, generated excess E125 in patients with elevated Hcy levels (see Papapetropoulos et al. Proc Natl Acad Sci USA 2009; 106:21972-21977; Szabo C et al. Br J Pharmacol 2011; 164:853-865; Chiku et al. J Biol Chem 2009; 284:11601-11612, each of which is hereby incorporated by reference in its entirety). This observation was important because increased $H_2S$ levels were reported to significantly increase collateral vessel growth, capillary density and regional tissue blood flow (see Wang et al. Antioxid Redox Signal 2010; 12:1065-1077, which is hereby incorporated by reference in its entirety). However, high Hcy levels (0.002 to 2 mM) did not significantly affect EC proliferation or phospho-eNOS levels in vitro (see Saha et al. Cystathionine beta-synthase regulates endothelial function via protein S-sulfhydration. FASEB J 2016; 30:441-456, which is hereby incorporated by reference in its entirety). Overall, these results suggest a possible role for Hcy in endothelial dysfunction, though it is not yet clear whether Hcy directly affects ECs in vivo due to the high Hcy levels tested in vitro.

In a recent pharmacological and genetic study, loss of CBS function in ECs was associated with a 50% decrease in cellular $H_2S$ and a 400% decrease in glutathione, with a concomitant increase in cellular ROS levels (see Saha et al. FASEB J 2016; 30:441-456, which is hereby incorporated by reference in its entirety). Silencing CBS in ECs compromised phenotypic and signaling responses to vascular endothelial growth factor (VEGF) and this effect was exacerbated by decreased transcription of vascular endothelial growth factor receptor-2 (VEGFR-2) and neuropilin-1 (NRP-1), primary receptors regulating endothelial functions such as angiogenesis. Transcriptional downregulation of VEGFR-2 and NRP-1 was mediated by decreased stability of transcription factor specificity protein 1 (Sp1), a sulfhydration target of $H_2S$. Replenishing $H_2S$, but not glutathione, in CBS-silenced ECs restored Sp1 levels and Sp1 binding to the VEGFR-2 promoter, as well as increasing VEGFR-2 and NRP-1 expression and VEGF-dependent cell proliferation and migration. This suggests that CBS-mediated protein 5-sulfhydration is important for maintaining vascular health and function, supporting previous observations that patients with CBSDH exhibited endothelial dysfunction (see Celermajer et al. J Am Coll Cardiol 1993; 22:854-858; Rubba et al. Metabolism 1990; 39:1191-1195, both of which are hereby incorporated by reference in their entireties) and raises the possibility that CBSDH patients suffer from an additional and distinct type of vascular damage, in addition to the type of vascular damage observed in individuals with Hcy levels elevated by other causes.

Dysregulated endothelial function, or other effects on vascular contractility, can lead to blood pressure (BP) abnormalities. Plasma Hcy level was directly linked to BP and Hcy lowering, using folic acid, was associated with decreased BP (see Tripathi P. Molecular and biochemical aspects of homocysteine in cardiovascular diseases. International Cardiovascular Forum J 2016; 6:13; Hackam et al. JAMA 2003; 290:932-940, both of which are hereby incorporated by reference in its entirety). While mechanisms leading to these effects were unclear, Hcy levels are more strongly associated with systolic than diastolic BP. This suggests that elevated Hcy levels increase arterial stiffness. The degree of arterial stiffness is largely determined by the number and function of smooth muscle cells (SMC), the collagen:elastin ratio in the ECM, the quality of collagen and endothelial function (see Tripathi P. Molecular and biochemical aspects of homocysteine in cardiovascular diseases. International Cardiovascular Forum J 2016; 6:13, which is hereby incorporated by reference in its entirety).

Potentially, high levels of Hcy are associated with increased arterial stiffness because of increased SMC proliferation, collagen production and elastin fiber formation (see van Guldener et al. Curr Hypertens Rep 2003; 5:26-31, which is hereby incorporated by reference in its entirety). However, it is also possible that Hcy decreases arterial stiffness by impairing collagen crosslinking. In a study conducted in minipigs, diet-induced Hcy elevation led to "mega artery syndrome" with hyperpulsatile arteries, systolic (but not diastolic) hypertension and extended reactive hyperemia of conduit arteries with dilation of the aorta (see van Guldener et al. Homocysteine and blood pressure. Curr Hypertens Rep 2003; 5:26-31, which is hereby incorporated by reference in its entirety). There was also fragmentation of the arterial wall elastic lamina, correlated with aortic stiffness.

Consistent with these findings, a study conducted in mice, with and without CBSDH, found that the cross-sectional area of the vessel wall was significantly greater in CBS+/− mice fed a control diet (437±22 $\mu M^2$) and CBS+/+ (442±36 $\mu m^2$) and CBS+/− (471±46 $\mu m^2$) mice fed a high-Met diet, compared with in CBS+/+ (324±18 $\mu m^2$) mice fed a control diet (p<0.05) (see Baumbach et al. Structure of cerebral arterioles in cystathionine beta-synthase-deficient mice. Circ Res 2002; 91:931-937, which is hereby incorporated by reference in its entirety).

During maximal vasodilation, the stress-strain curves in cerebral arterioles of CBS+/− mice on the control diet and CBS+/+ and CBS+/− mice on the high-Met diet were shifted to the right of the curve for CBS+/+ mice on the control diet. This indicated that cerebral arteriole distensibility was greater in mice with elevated plasma tHcy levels. These results suggest that elevated Hcy levels induced cerebral vascular hypertrophy and altered cerebral vascular mechanics, both effects potentially contributing to an increased incidence of thrombosis, for example, stroke, even in the absence of atherosclerosis (see Baumbach et al. Circ Res 2002; 91:931-937, which is hereby incorporated by reference in its entirety).

Further support for effects of elevated Hcy on vasodilation derives from a study in 5 Italian patients with CBSDH and tHcy levels ranging from 193.6 to 342 $\mu mol/L$ (see Evangelisti et al. Int J Cardiol 2009; 134:251-254, which is hereby incorporated by reference in its entirety). Patients showed signs of mild heart valve prolapse and/or regurgitation and connective tissue manifestation.

5. Thrombosis

Elevated Hcy levels are associated with higher risk of deep vein thrombosis, cerebral sinus thrombosis and retinal vein thrombosis (see Spence J D. Lancet Neurol. 2007 September; 6(9):830-8, which is hereby incorporated by reference in its entirety) though multiple studies failed to find an association with risk of MI. Consistent with these results, additional though small studies suggest that CBSDH is associated with thrombosis, but not necessarily atherosclerosis. Vascular imaging of patients with familial hypercholesterolemia (FH) and CBSDH showed that, while FH patients exhibited diffuse and focal thickening of carotid arteries and endothelial dysfunction leading to reduced blood flow, CBSDH patients rarely had plaques in their carotid arteries and were similar to healthy control subjects with regard to both intima-media thickness (IMT) and blood flow velocity in the middle cerebral artery (see Rubba et al. Stroke 1994; 25:943-950, which is hereby incorporated by reference in its entirety). This study suggests that typical atherosclerotic lesions may not be required to precede thrombotic events in CBSDH and that medial damage leading to thrombosis may also be caused by arterial dilatations.

Support for this observation derives from a study comparing the prevalence of carotid and femoral atherosclerosis (determined by IMT and ankle-brachial index) in 13 patients with enzymatically-proven heterozygous CBSDH, compared with in 12 healthy subjects with normal Met-loading test results (see de Valk et al. Stroke 1996; 27:1134-1136, which is hereby incorporated by reference in its entirety). No significant differences were observed between groups in mean IMT values, IMT frequency distribution or IMT in each of five arterial segments. These results might be explained by the fact that heterozygous individuals were too young (all <50 years old) to develop structural vascular changes. However, these data also suggest that elevated Hcy levels may primarily affect the coagulation cascade, at least in younger patients. Indeed, a case report of three unrelated CBSDH patients found that one patient experienced stroke due to intraluminal thrombosis and another patient experienced cardiac or arterial thromboembolism, also without evidence of craniocervical atherosclerosis (see Kelly et al. Neurology 2003; 60:275-279, which is hereby incorporated by reference in its entirety).

Consistent with these observations, Hcy addition to HUVEC and CV1 ECs irreversibly inactivated anticoagulants, protein C and thrombomodulin (see Lentz et al. J Clin Invest 1991; 88:1906-1914, which is hereby incorporated by reference in its entirety). Moreover, Hcy addition to cultured human ECs increased procoagulant tissue factor activity in time- and concentration-dependent manners (see Fryer et al. Arterioscler Thromb 1993; 13:1327-1333, which is hereby incorporated by reference in its entirety).

In both studies, Hcy enhanced the coagulation pathways via a mechanism involving its free thiol group. Together, these data support the hypothesis that perturbations in vascular coagulant mechanisms contribute to increased vascular risk in patients with CBSDH and that this may play an earlier role in CBSDH patients, before effects of Hcy on atherosclerosis become apparent.

Lowering Plasma Hcy Levels Reduces Risk of Vascular Complications, Particularly Stroke, in CBSDH Patients and in the General Population Recent analyses have found a strong link in the general population between elevated tHcy and stroke risk (see Saposnik et al. Stroke 2009; 40:1365-1372; Spence J D. Homocysteine lowering for stroke prevention: Unravelling the complexity of the evidence. Int J Stroke. 2016 October; 11(7):744-7; Hankey et al. Lancet Neurol 2012; 11:512-520, each of which is hereby incorporated by reference in its entirety).

In the past, the benefits of Hcy-lowering interventions in patients with elevated Hcy levels appeared mixed, with some studies showing a reduction in vascular risk (see Yap et al. J Inherit Metab Dis 1998; 21:738-747; Yap et al. Arterioscler Thromb Vasc Biol 2001; 21:2080-2085; Wilcken et al. J Inherit Metab Dis 1997; 20:295-300; Yap et al. Semin Thromb Hemost 2000; 26:335-340; Saposnik et al. Stroke 2009; 40:1365-1372; Huo et al. JAMA 2015; 313: 1325-1335; Hankey et al. Lancet Neurol 2012; 11:512-520, each of which is hereby incorporated by reference in its entirety) and others showing no benefit (see Marti-Carvajal et al. Cochrane Database Syst Rev 2015; 1:CD006612; Ebbing et al. JAMA 2008; 300:795-804; Bonaa et al. N Engl J Med 2006; 354:1578-1588; Liem et al. Heart 2005; 91:1213-1214; Toole et al. JAMA 2004; 291:565-575; B vitamins in patients with recent transient ischemic attack or stroke in the VITAmins TO Prevent Stroke (VITATOPS) trial: a randomized, double-blind, parallel, placebo-controlled trial (see Lancet Neurol 2010; 9:855-865; Albert et al. JAMA 2008; 299:2027-2036, each of which is hereby incorporated by reference in its entirety). Many of these trials tested vitamin interventions, primarily B vitamin (B6 and B12) and folate supplementation, for Hcy lowering. Consequently, study outcomes were subject to confounding factors, such as whether subjects lived in regions where folate fortification is practiced, had renal dysfunction making them more vulnerable to cobalamin toxicity, had vitamin B12 deficiencies related to poor absorption, which is relatively common in the elderly, or were on antiplatelet medication. These recent analyses considered these confounding factors, and concluded that, when such key variables are accounted for, elevated tHcy increases the risk of stroke in the general population (see Mudd et al. Arterioscler Thromb Vasc Biol 2000; 20:1704-1706; Spence J D. Int J Stroke. 2016 October; 11(7):744-7; Spence J D, Clin Chem Lab Med. 2013 Mar. 1; 51(3):633-7, each of which is hereby incorporated by reference in its entirety).

Hcy-lowering therapy reduces risk of stroke, even in individuals without CBSDH. In the HOPE-2 (Heart Outcomes Prevention Evaluation 2) trial, 5,522 adults aged ≥55 years, with a history of vascular disease or diabetes mellitus and at least one additional CV risk factor, were randomized to either vitamin supplementation (folic acid, vitamin B6 and vitamin B12) or placebo for 5 years (see Saposnik et al. Stroke 2009; 40:1365-1372, which is hereby incorporated by reference in its entirety). Mean baseline Hcy concentrations were 11.5 µmol/L in both groups and patients taking a daily vitamin supplement containing >0.2 mg folic acid at baseline were excluded from the study. Overall, Hcy-lowering (mean 3.0 µmol/L vs placebo) was associated with a significant 27% relative risk reduction (1.3% absolute reduction) in stroke (HR, 0.75; 95% CI, 0.59 to 0.97) and nonsignificant reductions in ischemic stroke (HR, 0.81; 95% CI, 0.60 to 1.09) and hemorrhagic stroke (HR, 0.80; 95% CI, 0.32 to 2.02). In subgroup analyses, the relative risk of stroke was most reduced among patients with baseline Hcy levels in the highest quartile (4.3% absolute risk reduction). Treatment benefit was greatest in patients aged <69 years, those from regions without folic acid food fortification and those not receiving antiplatelet or lipid-lowering drugs at enrollment. Thus, the HOPE-2 trial reported a reduced incidence rate of stroke in individuals receiving B vitamins versus placebo (hazard ratio (HR) 0.75; 95% CI, 0.59 to 0.97), whereas the risk of MI was similar in both treatment groups (RR 0.98; 95% CI, 0.85 to 1.14) (see Saposnik et al. Stroke 2009; 40:1365-1372; Lonn E, Yusuf S, Arnold M J et al. Homocysteine lowering with folic acid and B vitamins in vascular disease. N Engl J Med 2006; 354:1567-1577, both of which are hereby incorporated by reference in its entirety).

Consistent with results from the HOPE-2 trial, a sub-analysis of the VITATOPS trial, in which 8,164 patients with recent stroke or transient ischemic attack were randomized to double-blind treatment with B vitamins or placebo for a median 3.4 years, found that B vitamins significantly reduced the primary composite outcome (stroke, MI or death from vascular causes) among patients not taking antiplatelet therapy at baseline (17 versus 21% with placebo; HR 0.76, 0.60 to 0.96). No significant effect of B vitamins was observed in individuals receiving antiplatelet therapy (see Hankey et al. Antiplatelet therapy and the effects of B vitamins in patients with previous stroke or transient ischemic attack: a post-hoc sub-analysis of VITATOPS, a randomized, placebo-controlled trial. Lancet Neurol 2012; 11:512-520, which is hereby incorporated by reference in its entirety). In this study, tHcy levels were significantly decreased from 12.4 to 13.7 µmol/L at baseline to 9.9 to 10.5 µmol/L after vitamin therapy, irrespective of whether patients received antiplatelet therapy (p<0.0001 for both treatment groups) (see Hankey et al. Lancet Neurol 2012; 11:512-520, which is hereby incorporated by reference in its entirety).

Inflammatory cascades are believed to contribute to ischemic stroke pathogenesis. A report from the Framingham Offspring Study in 3,224 participants (see Shoamanesh et al. Neurology. 2016 September; 87(12):1206-11, which is hereby incorporated by reference in its entirety) found that elevated levels of tHcy and three other inflammatory markers were strongly associated with the risk of ischemic stroke and improved the predictive ability of the Framingham Stroke Risk Profile score.

A meta-analysis of data from the VISP and VITATOPS studies found that patients with normal renal function not previously exposed to high dose cyanocobalamin benefited significantly from vitamin therapy including high dose cyanocobalamin (0.78, 0.67 to 0.90; interaction p=0.03) whereas vitamin therapy including high dose cyanocobalamin (a form of vitamin B) had no effect on stroke risk in individuals with impaired renal function (RR 1.04, 95% CI 0.84 to 1.27) (see Spence J D. Lancet Neurol. 2007 September; 6(9):830-8, which is hereby incorporated by reference in its entirety). These results suggested potentially confounding effects of cyanocobalamin, known to be nephrotoxic, associated with cyanide accumulation, in patients with significantly impaired renal function (see Spence J D, Clin Chem Lab Med. 2013 Mar. 1; 51(3):633-7, which is hereby incorporated by reference in its entirety). Consistent with this, in the DIVINe trial (Diabetic Intervention with Vitamins in Nephropathy), high doses B vitamins, including cyanocobalamin at 1000 µg, were harmful, exacerbating eGFR decline (see Spence J D. Int J Stroke. 2016 October; 11(7):744-7; House et al. JAMA 2010; 303: 1603-1609, both of which are hereby incorporated by reference in their entireties). Together, such findings support the use of non-cyanide containing B vitamins, such as methylcobalamin, instead of cyanocobalamin, to lower Hcy levels in individuals at high risk of stroke, especially those with renal insufficiency.

Cyanocobalamin and cyanide toxicity were further implicated in previous trials as confounding factors in the presence of renal impairment by results from the CSPPT (China Stroke Primary Prevention Trial (see Huo et al. JAMA. 2015 Apr. 7; 313(13):1325-35, which is hereby incorporated by reference in its entirety). The treatment benefit demonstrated with renal impairment in the CSPPT was counter to the lack of benefit observed in the DIVINe, VISP and VITOPS trials, likely due to cyanocobalamin treatment in the latter trials.

Because in China folate fortification has not yet been implemented, the effect of folic acid supplementation on lowering tHcy levels could be studied there in a large population. The CSPPT was a randomized double-blind trial conducted in 20,702 adults with hypertension but no history of stroke or MI, which demonstrated that folic acid significantly decreased the risk of first stroke (2.7 vs 3.4% without folic acid, HR 0.79; 95% CI 0.68 to 0.93), first ischemic stroke (2.2 vs 2.8% without folic acid, HR 0.76; 95% CI 0.64 to 0.91) and composite CV events (CV death, MI and stroke; 3.1% vs 3.9% without folic acid, HR 0.80; 95% CI 0.69 to 0.92). There were, in contrast, no significant differences between the two groups in risks of hemorrhagic stroke, all-cause deaths or frequencies of AEs. In a sub-study of the CSPPT (see Xu et al. JAMA Intern Med. 2016 Oct. 1; 176(10):1443-1450, which is hereby incorporated by reference in its entirety), both subjects with or without renal impairment (eGFR below 60 mL/min/1.73 m$^2$) benefited from folic acid, and the sub-study furthermore confirmed that the group treated with folic acid had a much greater drop in serum Hcy than did the group not receiving folic acid (1.9 vs 0.2 µmol/L, respectively, p<0.001).

A 2017 Cochrane review (see Marti-Carvajal et al. Cochrane Database Syst Rev. 2017 Aug. 17; 8:CD006612, which is hereby incorporated by reference in its entirety), analyzing 15 randomized controlled trials involving 74,422 participants, reported a small difference in effect of Hcy-lowering with B vitamins on stroke but no effects on MI, death from any cause or AEs. Compared with placebo/standard care, Hcy lowering interventions were associated with a decreased incidence of nonfatal or fatal stroke (4.33% vs 5.1% for control; RR 0.90, 95% CI 0.82 to 0.99), but had no effect on the incidence of nonfatal or fatal MI (7.1% vs 6.0% for placebo; relative risk (RR) 1.02, 95% CI 0.95 to 1.10) or death from any cause (11.7% vs 12.3% for placebo; RR 1.01, 95% CI 0.96 to 1.06) in the general population. This review was an update of three earlier versions (2009, 2013 and 2015), which had previously concluded that there was no evidence supporting effects of Hcy-lowering interventions on CV events, though the 2015 review had indicated a non-significant trend in reduced incidence of stroke (see Marti-Carvajal Cochrane Database Syst Rev 2015; 1:CD006612, which is hereby incorporated by reference in its entirety). The strength of the evidence on Hcy lowering interventions on stroke has become stronger as additional trials have become available.

The studies included in the review used various regimens of vitamin supplementation as Hcy-lowering therapy (see Marti-Carvajal et al. Cochrane Database Syst Rev. 2017 Aug. 17; 8:CD006612, which is hereby incorporated by reference in its entirety). The 2017 review added three new trials to those in the 2015 review. Of the total, 10 trials used pyridoxine plus vitamins B9 (folate) and B12, five used only vitamin B9 and one of the 10 used 5-methyltetrahydrofolate instead of folic acid. Some trials included concomitant drugs (in both control and vitamin treated groups), 7 trials with lipid-lowering and one with anti-hypertensive agents. Overall, the Hcy-lowering treatments resulted in a relatively small decrease in mean tHcy levels. Moreover, three studies were performed in a folic acid-fortified population and two in a mixed population (some subjects receiving a fortified diet and others not), which may have masked Hcy-lowering effects. Considering the confounding factors that might influence such studies, it is not a surprise that the earlier reviews did not identify any significant CV effects of the vitamin treatment regimens and that only modest effects on stroke were reported in the newest review. It is also notable that the many potential causes of elevated Hcy levels were not examined in the studies included in the Cochrane review (see Marti-Carvajal et al. Cochrane Database Syst Rev 2015; 1:CD006612, which is hereby incorporated by reference in its entirety). There may be additional factors affecting the pathophysiology of vascular risk in patients with CBSDH and at younger ages than in the general population. It is noteworthy that even modest decreases in Hcy levels are significantly associated with reductions in stroke risk.

An interesting question arising from several of these analyses is why some studies indicated an effect of Hcy levels on stroke but not on MI. Relevant to this question, Spence (see Spence J D. Lancet Neurol. 2007 September; 6(9):830-8, which is hereby incorporated by reference in its entirety) pointed out key differences between MI and cerebral infarction, with cerebral infarction being closely associated to thrombosis/embolic events but in situ thrombosis being secondary to plaque rupture in a coronary artery in nearly all MI events. Thus, Spence concluded that a substantial proportion of strokes are related to thrombotic processes, which can be associated with raised tHcy.

Elevated tHcy levels may be important not only in cardioembolic stroke but also atheroembolic and lacunar infarction. A study in elderly patients with atrial fibrillation treated with anticoagulant therapy found that high levels of tHcy ($>90^{th}$ percentile) were associated with a 4.7-fold increase in ischemic complications (see Poli et al. J Am Coll Cardiol 2009; 54:999-1002, which is hereby incorporated by reference in its entirety). Another study in patients with cryptogenic ischemic stroke found that those with patent foramen ovale (a risk factor for cerebral infarction) had significantly higher plasma tHcy levels than those without (8.9±3 versus 7.9±2.6 µmol/L respectively; p=0.021) (see Ozdemir et al. J Neurol Sci 2008; 275:121-127, which is hereby incorporated by reference in its entirety). In reviewing such findings, Spence (see Spence J D. Homocysteine lowering for stroke prevention: Unravelling the complexity of the evidence. Int J Stroke. 2016 October; 11(7):744-7, which is hereby incorporated by reference in its entirety) suggested that Hcy affects primarily the formation of red thrombus (a fibrin polymer mesh with entrapped red blood cells, that forms in the setting of stasis) but that lacunar infarction and carotid plaques are also significantly related to tHcy as levels of tHcy were also significantly higher in patients with microemboli on transcranial Doppler (16.2 vs. 10.1 mmol/L) and most such microemboli are thought to be platelet aggregates, reduced by dual antiplatelet therapy (see Spence J D. Homocysteine lowering for stroke prevention: Unravelling the complexity of the evidence. Int J Stroke. 2016 October; 11(7):744-7, which is hereby incorporated by reference in its entirety).

A study conducted in 32 CBSDH patients (aged between 9 and 66 years) treated with pyridoxine, folic acid and hydroxocobalamin for a total of 539 patient-years, reported two vascular events (one fatal pulmonary embolus and one MI) during treatment (see Wilcken et al. J Inherit Metab Dis 1997; 20:295-300, which is hereby incorporated by reference in its entirety). According to the epidemiological study by Mudd et al., 21 events would have been expected over the same period of time without treatment (RR 0.09 (95% CI 0.02 to 0.38); p=0.0001). A second study, conducted in 84 patients, from three countries, aged between 2.5 and 70 years reported five cases of venous embolism (VE) during 1314 patient-years of treatment, one pulmonary embolism, two MIs, and two abdominal aneurysms (see Yap et al. Semin Thromb Hemost 2000; 26:335-340, which is hereby incorporated by reference in its entirety). According to Mudd et al., (see Mudd et al. Am J Hum Genet 1985; 37:1-31, which is hereby incorporated by reference in its entirety) 53 cases of VE would have been expected in untreated patients (RR 0.091 (95% CI 0.043 to 0.190); p<0.001).

Supportive evidence for these results derives from a large international multicenter observational study of 158 patients with CBSDH (see Yap et al. Arterioscler Thromb Vasc Biol 2001; 21:2080-2085, which is hereby incorporated by reference in its entirety), the majority ranging from 10 to 30 years of age. In this study 17 vascular events were observed among 12 treated individuals, three cases of pulmonary embolism, two MIs, five cases of deep venous thrombosis, three cerebrovascular accidents, one transient ischemic attack, one sagittal sinus thrombosis and two abdominal aortic aneurysms. Without treatment, 112 vascular events would have been expected in a similar population (RR 0.09 (95% CI 0.036 to 0.228); p<0.0001). This study also highlights how even treated and extensively followed young adult CBSDH patients suffer from poor clinical outcomes compared with the general population.

An elevated plasma tHcy level is a risk factor for vascular disease and a strong predictor of mortality in patients with CAD, both with and without CBSD (see Mudd et al. Am J Hum Genet 1985; 37:1-31; Karaca et al. Gene 2014; 534: 197-203; Kelly et al. Neurology 2003; 60:275-279; Faeh et al. Swiss Med Wkly 2006; 136:745-756; Boushey et al. JAMA 1995; 274:1049-1057; Clarke et al. JAMA 2002; 288:2015-2022; Hankey et al. Lancet 1999; 354:407-413; Khan et al. Stroke 2008; 39:2943-2949; Graham et al. JAMA 1997; 277:1775-1781; Clarke et al. N Engl J Med 1991; 324:1149-1155; Clarke et al. Ir J Med Sci 1992; 161:61-65; Woodward et al. Blood Coagul Fibrinolysis 2006; 17:1-5; Refsum et al. Annu Rev Med 1998; 49:31-62; Yoo et al. Stroke 1998; 29:2478-2483; Selsun et al. N Engl J Med 1995; 332:286-291; Wald et al. BMJ 2002; 325:1202; Bautista et al. J Clin Epidemiol 2002; 55:882-887; Brattstrom et al. Atherosclerosis 1990; 81:51-60; Lussana et al. Thromb Res 2013; 132:681-684; Casas et al. Lancet 2005; 365:224-232; McCully K S. Am J Pathol 1969; 56:111-128; Magner et al. J Inherit Metab Dis 2011; 34:33-37; Wilcken et al. J Clin Invest 1976; 57:1079-1082; Nygard et al. N Engl J Med 1997; 337:230-236, each of which is hereby incorporated by reference in its entirety).

Of the evidence for a causal relationship between tHcy levels and CV risk (see Boushey et al. JAMA 1995; 274: 1049-1057, which is hereby incorporated by reference in its entirety), the strongest relationships were demonstrated between tHcy and stroke or PAD, (see Clarke et al. JAMA 2002; 288:2015-2022; Khan et al. Stroke 2008; 39:2943-2949; Wald et al. BMJ 2002; 325:1202; Casas et al. Lancet 2005; 365:224-232; Brattstrom et al. Haemostasis 1989; 19 Suppl 1:35-44, each of which is hereby incorporated by reference in its entirety) including in patients with both homozygous and heterozygous CBS mutations (see Rubba et al. Metabolism 1990; 39:1191-1195, which is hereby incorporated by reference in its entirety).

Mechanisms potentially linking elevated Hcy to vascular damage are varied and complex. Several studies implicated oxidative stress (see Faverzani et al. Cell Mol Neurobiol 2017; Nowak et al. Arterioscler Thromb Vasc Biol 2017; 37: e41-e52; Vanzin et al. Mol Genet Metab 2011; 104:112-117; Vanzin et al. Gene 2014; 539:270-274; Vanzin et al. Lipid, Cell Mol Neurobiol 2015; 35:899-911, each of which is hereby incorporated by reference in its entirety), including by inflammatory/immune activation via NF-κB (see Rodriguez-Ayala et al. Atherosclerosis 2005; 180:333-340; van Guldener et al. Curr Hypertens Rep 2003; 5:26-31, both of which are hereby incorporated by reference in its entirety). While such inflammatory processes are characteristic of atherosclerosis, typical atherosclerotic lesions do not need to precede thrombotic events in patients with CBSDH (see Rubba et al. Stroke 1994; 25:943-950; de Valk et al. Stroke 1996; 27:1134-1136, both of which are hereby incorporated by reference in its entirety). Instead, medial damage leading to thrombosis is believed to be caused by Hcy-mediated endothelial dysfunction (see Marti-Carvajal et al. Cochrane Database Syst Rev 2015; 1:CD006612; Celermajer et al. J Am Coll Cardiol 1993; 22:854-858; Rubba et al. Metabolism 1990; 39:1191-1195; Jiang et al. Arterioscler Thromb Vasc Biol 2005; 25:2515-2521; Hossain et al. J Biol Chem 2003; 278:30317-30327; Cai et al. Blood 2000; 96:2140-2148; Zhang et al. J Biol Chem 2001; 276:35867-35874; Papapetropoulos et al. Proc Natl Acad Sci USA 2009; 106:21972-21977; Szabo et al. Br J Pharmacol 2011; 164: 853-865; Chiku et al. J Biol Chem 2009; 284:11601-11612; Wang et al. Antioxid Redox Signal 2010; 12:1065-1077; Saha S, et al. FASEB J 2016; 30:441-456; Ebbing et al. JAMA 2008; 300:795-804; Bonaa et al. N Engl J Med 2006; 354:1578-1588, each of which is hereby incorporated by reference in its entirety) enhanced coagulation pathways (see Spence J D. Int J Stroke. 2016 October; 11(7):744-7; Fryer et al. Arterioscler Thromb 1993; 13:1327-1333; Lentz et al. J Clin Invest 1991; 88:1906-1914, each of which is hereby incorporated by reference in its entirety) and increased vascular dilatation, similar to thrombotic processes implicated in Marfan patients (see Kelly et al. Neurology 2003; 60:275-279; Tripathi P. Molecular and biochemical aspects of homocysteine in cardiovascular diseases. International Cardiovascular Forum J 2016; 6:13; van Guldener et al. Curr Hypertens Rep 2003; 5:26-31; Hackam et al. JAMA 2003; 290:932-940; Baumbach et al. Circ Res 2002; 91:931-937; Evangelisti et al. Int J Cardiol 2009; 134:251-254; de Valk et al. Stroke 1996; 27:1134-1136, each of which is hereby incorporated by reference in its entirety). Consistent with observations of endothelial dysfunction in patients with CBSDH, pharmacological and genetic research implicated CBS-mediated protein S-sulfhydration in the maintenance of vascular health and function (see Celermajer et al. J Am Coll Cardiol 1993; 22:854-858; Rubba et al. Metabolism 1990; 39:1191-1195, both of which are hereby incorporated by reference in its entirety). Thus, it is likely that the mechanisms of vascular damage in CBSDH patients are more varied than in the general population with CV disease.

There is considerable evidence that Hcy-lowering is beneficial against stroke risk in individuals with and without CBSDH (see Saposnik et al. Stroke 2009; 40:1365-1372; Huo et al. JAMA 2015; 313:1325-1335; Lonn et al. N Engl J Med 2006; 354:1567-1577; Hankey et al. Lancet Neurol 2012; 11:512-520; Spence J D. Lancet Neurol. 2007 September; 6(9):830-8; each of which is hereby incorporated by reference in its entirety). Although mean baseline Hcy levels were relatively low in the studies conducted in the general population, reductions in stroke incidence were significantly correlated with Hcy-lowering interventions, pointing to the benefits of even small decreases in tHcy levels.

Updated reviews of relevant trials support beneficial effects of Hcy-lowering treatments in stroke (see Marti-Carvajal et al. Cochrane Database Syst Rev. 2017 Aug. 17; 8:CD006612, which is hereby incorporated by reference in its entirety). Confounding factors, such as whether there was folate fortification, vitamin B12 deficiency or renal dysfunction leaving patients vulnerable to high dose cyanocobalamin, or whether subjects were on antiplatelet medications, have blurred trial outcomes. Recent analyses demonstrated that, when such factors were accounted for, the link between tHcy and stroke risk was strong in the general population (see Spence J D, Clin Chem Lab Med. 2013 Mar. 1; 51(3):633-7, which is hereby incorporated by reference in its entirety). Importantly, however, in patients with CBSDH with much higher tHcy levels than the general population, vascular benefits of Hcy lowering have been consistently demonstrated (see Yap et al. J Inherit Metab Dis 1998; 21:738-747; Eslamiyeh et al. Iran J Child Neurol 2015; 9:53-57; Saboul et al. J Child Neurol 2015; 30:107-112; Yap et al. Arterioscler Thromb Vasc Biol 2001; 21:2080-2085; Woods et al. BMJ Case Rep 2017; 2017; Wilcken et al. J Inherit Metab Dis 1997; 20:295-300; Yap et al. Semin Thromb Hemost 2000; 26:335-340; Ruhoy et al. Pediatr Neurol 2014; 50:108-111, each of which is hereby incorporated by reference in its entirety).

These findings suggest that an elevated Hcy level is a risk factor for CV disease, especially stroke, in patients with and without CBSDH and that CV or cerebrovascular risk can be reduced through long-term Hcy-lowering therapy.

Thromboembolism is the major cause of morbidity and premature death in CBSDH patients (see Mudd et al. Am J Hum Genet 1985; 37:1-31; Karaca et al. Gene 2014; 534: 197-203; Yap S. J Inherit Metab Dis 2003; 26:259-265, each of which is hereby incorporated by reference in its entirety). The overall rate of thromboembolic events in patients with untreated CBSDH is approximately 10% per year (see Cattaneo M. Semin Thromb Hemost 2006; 32:716-723, which is hereby incorporated by reference in its entirety), with the risk increasing after surgery and during or immediately after pregnancy (see Mudd et al. Am J Hum Genet 1985; 37:1-31; Novy et al. Thromb Haemost 2010; 103:871-873, both of which are hereby incorporated by reference in its entirety). Thromboembolism can affect any blood vessel, but venous thrombosis (in particular cerebral sinovenous thrombosis (CSVT)) is more common than arterial thrombosis in patients with CBSDH (see Mudd et al. Am J Hum Genet 1985; 37:1-31; Karaca et al. Gene 2014; 534:197-203; Eslamiyeh et al. Iran J Child Neurol 2015; 9:53-57; Saboul et al. J Child Neurol 2015; 30:107-112, each of which is hereby incorporated by reference in its entirety).

A study in 629 untreated CBSDH patients showed that, of the observed 253 vascular events (occurring in 158 patients), 81 (32%) were cerebrovascular accidents, 130 (51%) affected peripheral veins (with 32 resulting in pulmonary embolism), 10 (4%) led to myocardial infarctions (MI), 28 (11%) affected peripheral arteries and four (2%) fell into none of these categories (see Mudd et al. Am J Hum Genet 1985; 37:1-31, which is hereby incorporated by reference in its entirety). Cerebrovascular accidents, especially CSVT, have been described in infants (see Mahale et al. J Pediatr Neurosci. 2017 April-June; 12(2):206-207, which is hereby incorporated by reference in its entirety), although more typically appear in young adults (see Yap et al. Arterioscler Thromb Vasc Biol 2001; 21:2080-2085, which is hereby incorporated by reference in its entirety). Cerebrovascular events were reported to be only marginally related to the pyridoxine-response category of the patients.

The risk of vascular events was approximately 30% in patients aged <20 years, rising to 50% by the age of 30 years. However, symptoms can occur at any age and fatal thrombosis has been described in infants as young as 6 months (see Cardo et al. Dev Med Child Neurol 1999; 41:132-135, which is hereby incorporated by reference in its entirety). After the age of 10 years, one vascular event is expected per 25 years. In general, the first signs of CBSDH in children are mental retardation, presenting as developmental delay during the first or second year of life and/or lens dislocation/high myopia. In contrast, adults are more likely to present with vascular events.

D. Effects of Diet on Phenotypic Outcomes

In some embodiments, I278T mice, a mouse model of HCU, were used to evaluate long-term impact of enzyme therapy for HCU with 20NHS PEG-CBS on clinical endpoints relevant to human patients. The efficacy of 20NHS PEG-CBS on a background of normal methionine intake (REG) and a Met-restricted diet (MRD) as well as with MRD alone. Treatment with 20NHS PEG-CBS can result in 90% decrease in plasma homocysteine concentrations and correction of learning/cognition, endothelial dysfunction, hemostasis, bone mineralization, and body composition phenotypes associated with HCU. In certain embodiments, treatment with 20NHS PEG-CBS with a background of the MRD normalized plasma Hcy. The MRD alone has been observed to decrease plasma Hcy by 67% and correct the HCU phenotype in I278T mice. However, the MRD increased anxiety and reduced bone mineral content in both I278T mice and wild-type controls. Therefore, 20NHS PEG-CBS is highly efficacious for the treatment for HCU in subjects with a background of a REG or a Met-restricted diet. In fact, ET with 20NHS PEG-CBS on background of normal Met intake performs equally or yields better results compared with a Met-restricted diet.

E. Neurological Complications

Studies have shown that early decreases in Hcy levels, induced by a low Met diet, folic acid/B vitamin supplementation and/or pyridoxine and betaine therapy can prevent and sometimes reverse progression of various neurological disorders and allow normal IQ development in patients with CBSDH (see El Bashir et al. JIMD Rep 2015; 21:89-95; Yap et al. J Inherit Metab Dis 2001; 24:437-447; Mech A W, Farah A. Correlation of clinical response with homocysteine reduction during therapy with reduced B vitamins in patients with MDD who are positive for MTHFR C677T or A1298C polymorphism: a randomized, double-blind, placebo-controlled study. J Clin Psychiatry 2016; 77:668-671; Grobe H. Eur J Pediatr 1980; 135:199-203; each of which is hereby incorporated by reference in its entirety). Further evidence is provided in case studies in patients with CBSDH, in which significant decreases, even normalization, of Hcy levels resulted in complete or partial correction of CNS outcomes (see Yap et al. J Inherit Metab Dis 2001; 24:437-447; Brenton et al. J Child Neurol 2014; 29:88-92; Rezazadeh et al. Child Neurol Open 2014; 1:2329048X14545870; Kaeser et al. J Neurol Neurosurg Psychiatry 1969; 32:88-93; Colafrancesco et al. Eur J Pediatr 2015; 174:1263-1266; Yokoi et al. Pediatr Int 2008; 50:694-695; Li et al. Pathology 1999; 31:221-224, each of which is hereby incorporated by reference in its entirety).

Associations between elevated levels of Hcy and CNS symptoms, including mental retardation, neurodegenerative diseases, seizures, dystonia, psychosis, cognitive impairment, dementia, and depression, are well documented in CBSDH patients and in the general population (see Morris et al. J Inherit Metab Dis 2017; 40:49-74; Abbott et al. Am J Med Genet 1987; 26:959-969; Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327; Hidalgo et al. Eur Child Adolesc Psychiatry 2014; 23:235-238; Smith et al. PLoS One 2010; 5: e12244; Seshadri et al. N Engl J Med 2002; 346:476-483; Bottiglieri et al. J Neurol Neurosurg Psychiatry 2000; 69:228-232; Bjelland et al. Arch Gen Psychiatry 2003; 60:618-626; Tolmunen et al. Am J Clin Nutr 2004; 80:1574-1578; Kaeser et al. J Neurol Neurosurg Psychiatry 1969; 32:88-93; Golimbet et al. Psychiatry Res 2009; 170:168-171; Clarke et al. Arch Neurol 1998; 55:1449-1455; Permoda-Osip et al. Neuropsychobiology 2014; 69:107-111; Oliveira et al. BMJ Case Rep 2016; 2016; Troen et al. Proc Natl Acad Sci USA 2008; 105:12474-12479; Sudduth et al. J Cereb Blood Flow Metab 2013; 33:708-715; Hainsworth et al. Biochim Biophys Acta 2016; 1862:1008-1017; Herrmann et al. Clin Chem Lab Med 2011; 49:435-441; Kim et al. J Nutr 2007; 137:2093-2097; Selhub et al. Am J Clin Nutr 2000; 71:614S-620S; McCaddon et al. Dement Geriatr Cogn Disord 2001; 12:309-313; Smallwood et al. Neuropathol Appl Neurobiol 2012; 38:337-343; Beydoun et al. BMC Public Health 2014; 14:643; Gortz et al. J Neurol Sci 2004; 218:109-114; Health Quality O. Vitamin B12 and cognitive function: an evidence-based analysis. Ont. Health Technol. Assess. Ser.13 (23), 1e45. 2013. Ref Type: Online Source; Salagre et al. Eur Psychiatry 2017; 43:81-91, each of which is hereby incorporated by reference in its entirety). The mechanisms leading to CNS disorders in individuals with elevated Hcy levels are believed to involve tHcy-mediated neuronal damage (see Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327; Hainsworth et al. Biochim Biophys Acta 2016; 1862:1008-1017; Stefanello et al. Metab Brain Dis 2007; 22:172-182; Toborek et al. Atherosclerosis 1995; 115:217-224, each of which is hereby incorporated by reference in its entirety), damage to the vascular endothelium caused by Hcy-mediated oxidative stress (see Vivitsky et al. Am J Physiol Regul IntegrComp Physiol 2004; 287: R39-R46, which is hereby incorporated by reference in its entirety), neuron loss (see Yeganeh et al. J Mol Neurosci 2013; 50:551-557; Heider et al. J Neural Transm Suppl 2004; 1-13, both of which are hereby incorporated by reference in its entirety) and attenuated neural network activity (see Gortz et al. J Neurol Sci 2004; 218: 109-114, which is hereby incorporated by reference in its entirety). Depression and convulsions are thought to be caused, at least in part, by Hcy-mediated decreases in cerebral adenosine levels, with subsequent decreases in levels of norepinephrine and dopamine (see Mech et al. J Clin Psychiatry 2016; 77:668-671; Domagala et al. Thromb Res 1997; 87:411-416; Vivitsky et al. Am J Physiol Regul IntegrComp Physiol 2004; 287: R39-R46; Folstein et al. Am J Psychiatry 2007; 164:861-867, each of which is hereby incorporated by reference in its entirety).

These findings demonstrated a strong correlation between Hcy levels and an increased risk of CNS disorders in patients with CBSDH. Early Hcy-lowering therapy is essential for the normal development of children with early-onset CBSDH and for the correction or improvement of CNS disorders in patients diagnosed with CBSDH later in life.

A study in 63 CBSDH patients found that 51% had psychiatric disorders, including anxiety and episodic depression (10%), chronic behavioral disorders (e.g. aggression and drug or alcohol abuse) (17%), chronic obsessive-compulsive disorder (5%) and personality disorders (19%) (see Abbott et al. Am J Med Genet 1987; 26:959-969, which is hereby incorporated by reference in its entirety). Psychosis may be a presenting sign in adolescence (see Hidalgo et al. Eur Child Adolesc Psychiatry 2014; 23:235-238, which is hereby incorporated by reference in its entirety).

If untreated, approximately 90% of pyridoxine non-responsive patients have learning difficulties (see Mudd et al. Am J Hum Genet 1985; 37:1-31, which is hereby incorporated by reference in its entirety), with IQs typically ranging from 10 to 138, with a mean of 57 in pyridoxine non-responsiveness individuals, compared with 79 in untreated pyridoxine-responsive patients and 105 in treated pyridoxine-responsive patients with good compliance (see Yap et al. J Inherit Metab Dis 2001; 24:437-447, which is hereby incorporated by reference in its entirety). Seizures affect 20% of non-responsive patients by the age of 12 years and several cases were reported of movement disorders unrelated to basal ganglia infarction, including polymyoclonus, dystonia and Parkinson disease (see Morris et al. J Inherit Metab Dis 2017; 40:49-74; Rezazadeh et al. Child Neurol Open 2014; 1:2329048X14545870, both of which are hereby incorporated by reference in its entirety).

An association between CBSDH and neuropsychiatric symptoms was first described by Schimke et al. in 1965 (see Schimke et al. JAMA 1965; 193:711-719, which is hereby incorporated by reference in its entirety). The association was later supported by a study reporting psychopathology in more than 50% of CBS-deficient patients (see Abbott et al. Am J Med Genet 1987; 26:959-969, which is hereby incorporated by reference in its entirety). Since then, numerous epidemiological studies showed positive, dose-dependent relationships between even mild increases in plasma tHcy and the risk of CNS disorders, including mental retardation and neurodegenerative diseases (see Morris et al. J Inherit Metab Dis 2017; 40:49-74; Seshadri et al. N Engl J Med 2002; 346:476-483; Clarke et al. Arch Neurol 1998; 55:1449-1455; Hainsworth et al. Biochim Biophys Acta 2016; 1862:1008-1017; Herrmann et al. Clin Chem Lab Med 2011; 49:435-441; Kim J et al. J Nutr 2007; 137:2093-2097; Selhub et al. Am J Clin Nutr 2000; 71:614S-620S; McCaddon et al. Dement Geriatr Cogn Disord 2001; 12:309-313; Smallwood et al. Neuropathol Appl Neurobiol 2012; 38:337-343; Beydoun et al. BMC Public Health 2014; 14:643; each of which is hereby incorporated by reference in its entirety). In general, patients with severely elevated Hcy levels (50 to 200 μM/L) tend to present with acute neuronal dysfunction, including seizures and psychosis, whereas more moderate Hcy levels (15 to 50 μM/L) are associated with cognitive impairment and dementia (see Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327; Gortz et al. J Neurol Sci 2004; 218:109-114, both of which are hereby incorporated by reference in its entirety).

An elevated Hcy level is widely accepted as a robust and independent risk factor for cognitive impairment (see Smith et al. PLoS One 2010; 5: e12244; Seshadri et al. N Engl J Med 2002; 346:476-483, both of which are hereby incorporated by reference in their entireties) onset of dementia (see Health Quality O. Vitamin B12 and cognitive function: an evidence-based analysis. Ont. Health Technol. Assess. Ser. 13 (23), 1e45. 2013. Ref Type: Online Source, which is hereby incorporated by reference in its entirety) and Alzheimer's disease (see Seshadri et al. N Engl J Med 2002; 346:476-483, which is hereby incorporated by reference in its entirety). In addition, increased Hcy levels (>15 μmol/L) were shown to be present in up to 90% of patients with depression (see Bottiglieri et al. J Neurol Neurosurg Psychiatry 2000; 69:228-232; Bjelland et al. Arch Gen Psychiatry 2003; 60:618-626, both of which are hereby incorporated by reference in their entireties), with men in the upper tercile for tHcy levels being more than twice as likely to suffer depression as those in the lowest tercile (see Tolmunen et al. Am J Clin Nutr 2004; 80:1574-1578, which is hereby incorporated by reference in its entirety). An elevated Hcy level is commonly reported in cases of schizophrenia, multiple sclerosis, Parkinson's disease, fibromyalgia/chronic fatigue syndrome (see Kaeser et al. J Neurol Neurosurg Psychiatry 1969; 32:88-93; Golimbet et al. Psychiatry Res 2009; 170:168-171; Clarke et al. Arch Neurol 1998; 55:1449-1455; each of which is hereby incorporated by reference in its entirety) and recurrent dystonia without cerebrovascular disease (see Sinclair et al. Mov Disord 2006; 21:1780-1782, which is hereby incorporated by reference in its entirety). A possible association between T833C polymorphism of the CBS gene and bipolar disorder was described (see Permoda-Osip et al. Neuropsychobiology 2014; 69:107-111, which is hereby incorporated by reference in its entirety) and a recent meta-analysis indicated a relationship between elevated Hcy levels and mania/euthymia in individuals with bipolar disease (see Salagre et al. Eur Psychiatry 2017; 43:81-91, which is hereby incorporated by reference in its entirety). The first known case of peripheral neuropathy associated with CBSDH was recently described in an 18-year old man with CBSDH (see Oliveira et al. BMJ Case Rep 2016; 2016, which is hereby incorporated by reference in its entirety), and a lethal case of psychosis was described in a 17-year old with previously undiagnosed CBSDH (see Hidalgo et al. Eur Child Adolesc Psychiatry 2014; 23:235-238, which is hereby incorporated by reference in its entirety).

Direct evidence for a relationship between Hcy levels and dementia derive from animal studies in which Hcy administration was associated with development of brain lesions (see Troen et al. Proc Natl Acad Sci USA 2008; 105:12474-12479; Sudduth et al. J Cereb Blood Flow Metab 2013; 33:708-715, each of which is hereby incorporated by reference in its entirety). In the first such study, male C57BL6/J mice with elevated Hcy levels (induced by a vitamin B deficient diet) had significantly impaired spatial learning and memory, with significant rarefaction of the hippocampal microvasculature without concomitant gliosis or neurodegeneration (see Troen et al. Proc Natl Acad Sci USA 2008; 105:12474-12479, which is hereby incorporated by reference in its entirety). Total hippocampal capillary length was inversely correlated with Morris water maze escape latencies ($r=-0.757$, $p<0.001$) and with plasma tHcy ($r=-0.631$, $p<0.007$). Mice fed a Met rich diet showed similar, but less pronounced, effects. These findings suggested that elevated Hcy levels are associated with cerebral microvascular rarefaction leading to cognitive dysfunction in the absence of or preceding neurodegeneration. This may explain the link between elevated Hcy levels and cognitive decline in humans.

In the second study, healthy mice were fed a diet deficient in folate, vitamins B6 and $B_{12}$ and supplemented with Met to induce moderately elevated l-Icy levels (plasma tHcy 82.93±3.56 μmol/L). These mice had spatial memory deficits, as assessed with the two-day radial-arm water maze (see Sudduth et al. J Cereb Blood Flow Metab 2013; 33:708-715, which is hereby incorporated by reference in its entirety). MRI and histology revealed significant microhemorrhage rates. Neuroinflammation and increased expression and activity of MIMP2 and MMP9, both enzymes implicated in pathogenesis of cerebral hemorrhage, were also observed. This suggested a link between elevated Hcy levels and vascular dementia, such as in Alzheimer's disease.

In humans, changes in white matter (a sign of vascular damage) are frequently associated with elevated Hcy levels, both in individuals with (see El Bashir et al. JIMD Rep 2015; 21:89-95; Vatanavicharn et al. J Inherit Metab Dis 2008; 31 Suppl 3:477-481; Brenton et al. J Child Neurol 2014; 29:88-92; Ruhoy et al. Pediatr Neurol 2014; 50:108-111; each of which is hereby incorporated by reference in its entirety) and without (see Hogervorst et al. Arch Neurol 2002; 59:787-793; Kloppenborg et al. Neurology 2014; 82:777-783; each of which is hereby incorporated by reference in its entirety) CBSDH. However, these changes are not always associated with evidence of stroke. In addition, brain imaging studies in CBSDH patients often show signs of atrophy or venous occlusion (see Vatanavicharn et al. J Inherit Metab Dis 2008; 31 Suppl 3:477-481, which is hereby incorporated by reference in its entirety).

The scan reveals diffuse symmetrical abnormal increased signal of the subcortical white matter and, to a lesser extent, of the deeper white matter, in the cerebral hemispheres, primarily the parieto-occipital regions 1. Mechanism The precise mechanisms by which elevated Hcy levels affect neurological health are unknown. Several animal studies showed associations between elevated tHcy levels and neurotoxicity and accompanying nerve and mental impairment.

An early study showed that very high intraperitoneal doses of Hcy induced generalized convulsive status epilepticus in rats with cobalt-induced lesions in the motor cortex (see Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327, which is hereby incorporated by reference in its entirety). Seizures were enhanced by the addition of Met and vitamin B and there was some evidence for synergistic effects of pyridoxal 5'-phosphate and Hcy in blocking the postsynaptic g-aminobutyric acid receptor. Moreover, Hcy-treatment of rodent neocortical tissues led to adenosine trapping in the form of AdoHcy (see Heinecke et al. J Biol Chem 1987; 262:10098-10103, which is hereby incorporated by reference in its entirety). The authors stated that adenosine is predominantly a depressant in cerebral actions and that the convulsive conditions and that the mental changes associated with high levels of Hcy may be mediated by decreased levels of cerebral adenosine.

Hcy is associated with both neurotoxicity and morphological changes in the brain (see Hainsworth et al. Biochim Biophys Acta 2016; 1862:1008-1017, which is hereby incorporated by reference in its entirety). For example, studies in rats and rabbits showed that neuronal damage was caused by Hcy-mediated increases in thiobutyric acid reactive substances (TBARS), indicators of oxidative stress (see Stefanello et al. Metab Brain Dis 2007; 22:172-182; Toborek et al. Atherosclerosis 1995; 115:217-224, both of which are hereby incorporated by reference in its entirety). Similar increases in plasma TBARS were also observed in humans following an orally administered Met load (see Domagala et al. Thromb Res 1997; 87:411-416, which is hereby incorporated by reference in its entirety). Moreover, a study in a murine model for elevated Hcy levels suggested that cellular damage caused by oxidative stress may be enhanced in patients with CBSDH because decreased Cys levels result in low levels of neuronal glutathione, an important antioxidant synthesized from glutamate, Cys and glycine (see Vivitsky et al. Am J Physiol Regul IntegrComp Physiol 2004; 287: R39-R46, which is hereby incorporated by reference in its entirety).

In vivo Hcy injection into the left ventricle of rat brains produced dose-dependent neuronal loss (see Yeganeh et al. J Mol Neurosci 2013; 50:551-557, which is hereby incorporated by reference in its entirety) and incubation of mesencephalic tegmental neurons from rats with Hcy led to fewer and shorter dopaminergic neurites (see Heider et al. J Neural Transm Suppl 2004; 1-13, which is hereby incorporated by reference in its entirety). In both studies, the effects of Hcy were blunted by co-administration of Hcy with antagonists of NMDA and metabotropic glutamate receptors, suggesting a glutamate-receptor mediated pathway for Hcy-induced neuronal damage. Further evidence for this pathway derives from a study in which Hcy administration led to dose-dependent lipid peroxidation in rat brain synaptosomes (see Jara-Prado et al. Neurotox Res 2003; 5:237-243, which is hereby incorporated by reference in its entirety). Once again, effects were inhibited by administration of an NMDA receptor antagonist.

A study in spontaneously active embryonic rat cortical neurons showed that Hcy levels above the range for severely elevated Hcy caused a dose-dependent suppression of neural network activity (see Gortz et al. J Neurol Sci 2004; 218: 109-114, which is hereby incorporated by reference in its entirety). The effects observed in this study were not clinically relevant because such exaggerated Hcy levels are never reached in patients with CBSDH. However, modest elevations in homocysteinesulfinic acid and homocysteic acid (oxidized forms of Hcy often found in patients with elevated Hcy levels) had a similar effect. In each case, damage to the neural network was inhibited by 2-amino-5-phosphonovaleric acid, again implicating the NMDA receptor as a mediator of this Hcy induced neuronal dysfunction. These results suggested that the neuronal dysfunction associated with elevated Hcy levels is likely caused by oxidized forms of Hcy, rather than by Hcy itself.

The absence of mental retardation, convulsions, and other CNS disorders in patients with Marfan syndrome and other connective tissue disorders suggest that the neurological disorders in CBSDH patients are not caused by defects in either fibrillin or collagen (see Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327, which is hereby incorporated by reference in its entirety). In patients with untreated CBSDH, elevated levels of SAM and decreased levels of SAH inhibit the transmethylation reactions required for myelin synthesis, leading to further nerve damage (see Mudd et al. Disorders of transsulfuration. In: Scriver C L, Beaudet A L, Sly W S, Valle D, eds. The Metabolic and Molecular Basis of inherited Diseases. 7 ed. New York: McGraw Hill; 2001; 1279-1327; which is hereby incorporated by reference in its entirety). Decreased myelin synthesis may be also be caused by low levels of serine in patients with CBSDH, due to increased remethylation rates (see Orendac et al. J Inherit Metab Dis 2003; 26:761-773; which is hereby incorporated by reference in its entirety). Finally, Hcy metabolism plays a key role in synthesis of monoamines by providing methyl groups for production of norepinephrine and dopamine (see Mech et al. J Clin Psychiatry 2016; 77:668-671; Folstein et al. Am J Psychiatry 2007; 164:861-867, both of which are hereby incorporated by reference in its entirety). Indeed, the "homocysteine hypothesis of depression" (see Folstein et al. Am J Psychiatry 2007; 164:861-867, which is hereby incorporated by reference in its entirety) states that low levels of norepinephrine and dopamine, resulting from elevated Hcy levels, are a major cause of depression.

Electron microscopy of rat brain biopsies showed cerebrovascular structural alterations in animals fed a high Hcy diet for 8 weeks. These alterations were associated with high plasma tHcy levels (see Lee et al. J Nutr 2005; 135:544-548, which is hereby incorporated by reference in its entirety). Consumption of dietary folic acid for a further 8 weeks decreased plasma tHcy to normal levels and significantly decreased the incidence of damaged vessels. This suggested that Hcy lowering, using folic acid supplementation, might reduce the detrimental effects on the vascular endothelium of experimentally-induced elevated Hcy levels.

A study designed to evaluate the efficacy and safety of reduced B vitamins as a monotherapy in adults with major depressive disorder (MDD) and CBSDH, due to at least one MTHFR polymorphism (N=330), found that treatment with a combination of reduced B vitamins significantly decreased tHcy levels in 131 treated patients (82.4%) (mean reduction in this subgroup was 25%; p<0.001), whereas placebo-treated patients demonstrated a small elevation in tHcy levels (see Mech et al. J Clin Psychiatry 2016; 77:668-671, which is hereby incorporated by reference in its entirety). Treated patients, on average, had a 12-point reduction on the Montgomery Asberg-Depression Rating Scale (MADRS) by Week 8, and 42% achieved full remission (p<0.001). Further clinical improvement was correlated with a significant decrease in tHcy levels in the majority of responders. Although this study was not conducted in patients with CBSDH, it demonstrated a clear benefit for Hcy lowering in individuals with depression, supporting the 'Hcy hypothesis of depression' (see Folstein et al. Am J Psychiatry 2007; 164:861-867, which is hereby incorporated by reference in its entirety).

The benefits of Hcy-lowering therapy in individuals with psychiatric symptoms associated with CBSDH were first demonstrated in a study of 12 late-diagnosed patients (see Grobe H. Eur J Pediatr 1980; 135:199-203, which is hereby incorporated by reference in its entirety). Three of these patients were never treated effectively and had serious psychological disorders, with premature death. The remaining 8 patients ranged from 1 to 26 years of age (mean 13 years) and all had psychiatric symptoms, including irritability, ADHD, apathy and psychosis. Treatment with pyridoxine or with a low Met diet with supplemental L-cystine for 2 to 9 years was associated with a striking improvement in behavior and intellectual development, correlated with biochemical normalization. The authors emphasized the need to treat all patients, regardless of age at diagnosis and prior treatment, because of the reversibility and improvement of the CBSDH associated sequelae observed in their study.

More recent data from the Irish screening program was used to compare the mental capabilities of 23 pyridoxine non-responsive individuals with CBSDH (339 patient-years of treatment) with those of 10 unaffected sibling controls (see Yap et al. J Inherit Metab Dis 2001; 24:437-447, which is hereby incorporated by reference in its entirety). Of the 23 patients identified, 19 were diagnosed with CBSDH through NBS and treated early in life (within 6 weeks of birth), two were late-detected (age 2.2 and 2.9 years) and two had been untreated at the time of assessment. All patients were treated with a Met-free, cysteine-supplemented synthetic amino acid mixture, with vitamin B12 and folate supplements, as required. Betaine was used in the last 5 years as an adjunct to treatment in early-treated patients who became poorly compliant with diet and in all patients with late-detected CBSDH.

Overall, 13 of the 19 patients in the early-treated group (mean age 14.4 years; range 4.4 to 24.9) were compliant with treatment (defined by a lifetime plasma fHcy median <11 µmol/L) and had no complications, whereas the remaining 6 (mean age 19.9 years; range 13.8 to 25.5), who had poor compliance, developed complications. Mean full-scale IQ (FIQ) was 105.8 (range 84 to 120) in the compliant group compared with 80.8 (range 40 to 103) in the poorly compliant group. The control group (n=10) with a mean age of 19.4 years (range 9.7 to 32.9) years had a mean FIQ of 102 (range 76 to 116). The two late-detected patients, aged 18.9 and 18.8 years, had FIQ of 80 and 102, respectively, while the two untreated patients, aged 22.4 and 11.7 years, had FIQ of 52 and 53, respectively. There were no significant differences between compliant, early-treated individuals and their unaffected siblings (controls) except in FIQ, which was significantly higher in the affected siblings (p=0.0397). Despite the relatively small numbers, these results suggest that early treatment with good biochemical control prevents mental retardation.

Similar results were obtained in a case-control study reporting on neurodevelopmental, educational and cognitive outcomes in 32 cases of CBSDH and 25 sibling controls in Qatar (see El Bashir et al. JIMD Rep 2015; 21:89-95, which is hereby incorporated by reference in its entirety). The mean age of subjects in this study was 11.2 years (range 0.6 to 29) and 56% were male. Compared with unaffected siblings, affected individuals had lower total IQ (particularly in terms of short-term memory, quantitative reasoning and visual-spatial domains) and a significant number of adolescents and adult cases had medical co-morbidities as well as behavioral and emotional problems. Of these, 9 cases (28%) of CBSDH were diagnosed by NBS and treated in the first month of life. The rest were diagnosed between 14 and 240 months of age. On-treatment tHcy and Met levels were significantly better in those diagnosed through NBS than in those diagnosed clinically, possibly because of better compliance with diets and medications early in life. A significant difference in IQ was observed between early- and clinically-diagnosed patients. Although the differences in language domains, attendance at special schools and access to extra support in class were not statistically significant between groups, the 'clinically detected' group clearly had more reported difficulties.

Although the numbers of patients studied here are small, a notable difference is seen between the children diagnosed at birth and those diagnosed as toddlers. An average tHcy level of 115 µmol/L in the clinically diagnosed group was associated with poor clinical outcomes and very low IQs.

Further evidence for the benefits of Hcy-lowering treatment on psychopathology in CBSDH patients derives from a retrospective chart review of data from all patients with HCU presenting at Boston Children's Hospital since 1963 (unpublished data courtesy of M. Almuqbil, et al.). Overall, 19 patients with HCU were identified, three of which were excluded from the analysis because of the possibly confounding presence of methylmalonic acidemia (also associated with psychological defects) in addition to CBSDH. Of the remaining 16 patients, 7 (6 with CBSDH and one with cobalamin (Cbl) deficiency) had good compliance with early treatment (four on diet alone, two with diet plus betaine and one with Cbl). Six of these patients had no obvious psychiatric symptoms other than mild cognitive deficits. In contrast, 9 patients (7 with pyridoxine non-responsive CBSDH and two with CblG deficiency) had poor or variable compliance with treatment (two on betaine and diet, one on diet alone, three on B vitamins and two with folic acid and betaine). All 7 patients with CBSDH and poor compliance had psychiatric problems, including depression (n=4), paranoid experiences (n=2), paranoia and delusional psychosis (n=1), anxiety and mood dysregulation (n=1) and ADHD that improved with good metabolic control (n=1). The two CblG cases were markedly anxious or agitated. Age, gender and cognitive levels did not appear to significantly differentiate between the psychiatrically affected and non-affected individuals. These results suggest that good metabolic control (Hcy and/or Met lowering) has the potential to delay, and possibly prevent, the onset of psychiatric and behavioral conditions in CBSDH patients. However, the study did not ascertain whether poorly controlled CBSDH leads to psychopathology, or whether comorbidity with psychopathology itself hinders good compliance with treatment outcome.

Associations between elevated levels of Hcy and CNS symptoms, including mental retardation, neurodegenerative diseases, seizures, dystonia, psychosis, cognitive impairment, dementia and depression, are well documented in individuals with and without CBSDH (see Morris et al. J Inherit Metab Dis 2017; 40:49-74; Abbott et al. Am J Med Genet 1987; 26:959-969; Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327; Hidalgo et al. Eur Child Adolesc Psychiatry 2014; 23:235-238; Schimke et al. JAMA 1965; 193:711-719; Smith et al. PLoS One 2010; 5: e12244; Seshadri et al. N Engl J Med 2002; 346:476-483; Bottiglieri et al. J Neurol Neurosurg Psychiatry 2000; 69:228-232; Bjelland et al. Arch Gen Psychiatry 2003; 60:618-626; Tolmunen et al. Am J Clin Nutr 2004; 80:1574-1578; Kaeser et al. J Neurol Neurosurg Psychiatry 1969; 32:88-93; Golimbet et al. Psychiatry Res 2009; 170: 168-171; Clarke et al. Arch Neurol 1998; 55:1449-1455; Sinclair et al. Mov Disord 2006; 21:1780-1782; Permoda-Osip et al. Neuropsychobiology 2014; 69:107-111; Oliveira et al. BMJ Case Rep 2016; 2016; Troen et al. Proc Natl Acad Sci USA 2008; 105:12474-12479; Sudduth et al. J Cereb Blood Flow Metab 2013; 33:708-715; Hainsworth et al. Biochim Biophys Acta 2016; 1862:1008-1017; Herrmann et al. Clin Chem Lab Med 2011; 49:435-441; Kim et al. J Nutr 2007; 137:2093-2097; Selhub et al. Am J Clin Nutr 2000; 71:614S-620S; McCaddon et al. Dement Geriatr Cogn Disord 2001; 12:309-313; Smallwood et al. Neuropathol Appl Neurobiol 2012; 38:337-343; Beydoun et al. BMC Public Health 2014; 14:643; Gortz et al. J Neurol Sci 2004; 218:109-114; Health Quality O. Vitamin B12 and cognitive function: an evidence-based analysis. Ont. Health Technol. Assess. Ser. 13 (23), 1e45. 2013. Ref Type: Online Source; Salagre et al. Eur Psychiatry 2017; 43:81-91, each of which is hereby incorporated by reference in its entirety). The mechanisms leading to CNS disorders in individuals with elevated levels of Hcy are believed to involve tHcy-mediated neuronal damage (see Mudd et al. Disorders of transsulfuration. In: Scriver C L, Beaudet A L, Sly W S, Valle D, eds. The Metabolic and Molecular Basis of Inherited Diseases. 7 ed. New York: McGraw Hill; 2001; 1279-1327; Hainsworth et al. Biochim Biophys Acta 2016; 1862:1008-1017; Stefanello et al. Metab Brain Dis 2007; 22:172-182; Toborek et al. Atherosclerosis 1995; 115:217-224, each of which is hereby incorporated by reference in its entirety), damage to the vascular endothelium caused by Hcy-mediated oxidative stress (see Vivitsky et al. Am J Physiol Regul IntegrComp Physiol 2004; 287: R39-R46, which is hereby incorporated by reference in its entirety), neuron loss (see Yeganeh et al. J Mol Neurosci 2013; 50:551-557; Heider et al. J Neural Transm Suppl 2004; 1-13, both of which are hereby incorporated by reference in its entirety) and attenuated neural network activity (see Gortz et al. J Neurol Sci 2004; 218:109-114, which is hereby incorporated by reference in its entirety). Depression and convulsions are thought to be caused, at least in part, by Hcy-mediated decreases in cerebral adenosine levels, with subsequent decreases in levels of norepinephrine and dopamine (see Mech et al. J Clin Psychiatry 2016; 77:668-671; Domagala et al. Thromb Res 1997; 87:411-416; Vivitsky et al. Am J Physiol Regul IntegrComp Physiol 2004; 287: R39-R46; Folstein et al. Am J Psychiatry 2007; 164:861-867; each of which is hereby incorporated by reference in its entirety).

Numerous studies, both in animal models for CBSDH (see Lee et al. J Nutr 2005; 135:544-548, which is hereby incorporated by reference in its entirety) and in patients with CBSDH (see El Bashir et al. JIMD Rep 2015; 21:89-95; Yap et al. J Inherit Metab Dis 2001; 24:437-447; Mech et al. J Clin Psychiatry 2016; 77:668-671; Grobe H. Eur J Pediatr 1980; 135:199-203, each of which is hereby incorporated by reference in its entirety), have shown that early decreases in Hcy levels, induced by a low Met diet, folic acid/B vitamin supplementation and/or pyridoxine/betaine therapy can prevent, and sometimes reverse, progression of various neurological disorders. Further evidence is provided by a series of 6 case studies in patients with CBSDH, in which significant decreases, even normalization, of Hcy levels resulted in complete or partial correction of CNS outcomes (see Yap et al. J Inherit Metab Dis 2001; 24:437-447; Brenton et al. J Child Neurol 2014; 29:88-92; Rezazadeh et al. Child Neurol Open 2014; 1:2329048X14545870; Kaeser et al. J Neurol Neurosurg Psychiatry 1969; 32:88-93; Colafrancesco et al. Eur J Pediatr 2015; 174:1263-1266; Yokoi et al. Pediatr Int 2008; 50:694-695; Li et al. Pathology 1999; 31:221-224, each of which is hereby incorporated by reference in its entirety).

These findings demonstrate a strong correlation between Hcy levels and an increased risk of CNS disorders in CBSDH patients and in the general population. Early Hcy-lowering therapy is essential for the normal development of children with early-onset CBSDH and for the correction or improvement of CNS disorders in patients diagnosed with CBSDH later in life.

IX. Definitions

As used in this specification, the singular forms "a," "an," and "the" include plural references unless the context clearly dictates otherwise.

Where a range of values is provided, it is intended that each intervening value between the upper and lower limit of that range and any other stated or intervening value in that stated range is encompassed within the disclosure and specifically disclosed. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used herein, "co-administered" or "co-administration" means the administration of two or more therapeutic components, including pharmaceutical composition.

As used herein, a "drug product" refers to a dosage form of a pharmaceutical composition including the drug substance of a PEGylated human truncated CBS protein with an amino acid sequence of SEQ ID NO: 1 (e.g., 20NHS PEG-CBS).

As used herein, a "drug substance" refers to a PEGylated CBS protein with an amino acid sequence of SEQ ID NO: 1 (e.g., 20NHS PEG-CBS).

As used herein, a "negative clinical outcome" refers to an undesirable phenotypic outcome resulting from a disease, disorder, or condition.

As used herein, "recombinant," when used with reference to, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all.

Recombinant techniques can include, e.g., use of a recombinant nucleic acid such as a cDNA encoding a protein or an antisense sequence, for insertion into an expression system, such as an expression vector; the resultant construct is introduced into a cell, and the cell expresses the nucleic acid, and the protein, if appropriate. Recombinant techniques also encompass the ligation of nucleic acids to coding or promoter sequences from different sources into one expression cassette or vector for expression of a fusion protein, constitutive expression of a protein, or inducible expression of a protein.

As used herein, the terms "subject", "individual" or "patient" are used interchangeably herein and refer to a vertebrate, preferably a mammal. Mammals include, but are not limited to, humans.

As used herein, "associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

As used herein, "pharmaceutically acceptable excipient" or "pharmaceutically acceptable carrier" refers to an excipient that may optionally be included in the compositions of the disclosure and that causes no significant adverse toxicological effects to the patient. In particular, in the present instance, such refers to an excipient that can be taken into the mammalian subject's body in association with an active compound (here PEGylated htCBS or "20NHS PEG-CBS") with no significant adverse toxicological effects to the subject.

As used herein, the terms "adjuvant," "diluent," or "carrier" mean any substance, not itself a therapeutic agent, used as a carrier for delivery of a therapeutic agent and suitable for administration to a subject, e.g. a mammal or added to a pharmaceutical composition to improve its handling or storage properties or to permit or facilitate formation of a dose unit of the composition into a discrete article such as a capsule or tablet suitable for oral administration. The terms "adjuvant," "diluent," or "carrier" encompass "excipients," including "pharmaceutically acceptable excipients," "vehicles," "solvents," and the like, as those terms are used herein. Excipients and vehicles include any such materials known in the art, e.g., any liquid, gel, solvent, liquid diluent, solubilizer, or the like, which is non-toxic, and which does not interact with other components of the composition in a deleterious manner. Administration can mean oral administration, inhalation, enteral administration, feeding or inoculation by intravenous injection. The excipients may include standard pharmaceutical excipients and may also include any components that may be used to prepare foods and beverages for human and/or animal consumption, feed or bait formulations or other foodstuffs.

As used herein, "drug" or "pharmacologically active agent" or any other similar term means any chemical or biological material or compound, inclusive of peptides, suitable for administration by the methods previously known in the art and/or by the methods taught in the present disclosure, that induces a desired biological or pharmacological effect, which may include, but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anesthetic effect, or it may be systemic. This disclosure is not drawn to novel permeants or to new classes of active agents. Rather it is limited to the mode of delivery of agents or permeants which exist in the state of the art or which may later be established as active agents and which are suitable for delivery by the present disclosure.

As used herein, the term "about," particularly in reference to a given quantity, is meant to encompass deviations of plus or minus five percent.

As used herein, the terms "pharmacologically effective amount" or "therapeutically effective amount" as related to the present composition refer to a non-toxic, but sufficient amount of the active agent (or composition containing the active agent) to provide the desired level in the bloodstream or at the site of action (e.g. intracellularly) in the subject to be treated, and/or to provide a desired physiological, biophysical, biochemical, pharmacological or therapeutic response, such as amelioration of the manifestations of homocystinuria. The exact amount required will vary from subject to subject, and will depend on numerous factors, such as the active agent, the activity of the composition, the delivery device employed, the physical characteristics of the composition, intended patient use (i.e., the number of doses administered per day), as well as patient considerations, such as species, age, and general condition of the subject, the severity of the condition being treated, additional drugs being taken by the subject, mode of administration, and the like. These factors and considerations can readily be determined by one skilled in the art, based upon the information provided herein. An appropriate "effective" amount in any individual case may be determined by one of ordinary skill in the art using routine experimentation, based upon the information provided herein.

As used herein, the term "nucleic acid" may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

As used herein, a "mutant" is a mutated protein designed or engineered to alter properties or functions relating to glycosylation, protein stabilization and/or ligand binding.

As used herein, the terms "native" or "wild-type" relative to a given cell, polypeptide, nucleic acid, trait or phenotype, refers to the form in which that is typically found in nature.

As used herein, the terms "protein," "polypeptide," "oligopeptide" and "peptide" have their conventional meaning and are used interchangeably to denote a polymer of at least two amino acids covalently linked by an amide bond, regardless of length or post-translational modification (e.g., glycosylation, phosphorylation, lipidation, myristylation, ubiquitination, etc.). Furthermore, the polypeptides described herein are not limited to a specific length. Included within this definition are D- and L-amino acids, and mixtures of D- and L-amino acids. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Polypeptides can also refer to amino acid subsequences comprising epitopes, i.e., antigenic determinants substantially responsible for the immunogenic properties of a polypeptide and being capable of evoking an immune response.

As used herein, "position corresponding to" and the like refers to a position of interest (i.e., base number or residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 90%, greater than 95%, greater than 96%, greater than 97%, greater than 98% or greater than 99%. The position of interest is then given the number assigned in the reference nucleic acid molecule. For example, if a particular polymorphism in Gene-X occurs at nucleotide 2073 of SEQ ID NO: X, to identify the corresponding nucleotide in another allele or isolate, the sequences are aligned and then the position that lines up with 2073 is identified. Since various alleles may be of different length, the position designating 2073 may not be nucleotide 2073, but instead is at a position that "corresponds" to the position in the reference sequence.

As used herein, the term "long-term administration" refers to administration of the CBS enzyme, htCBS, or htCBS mutant (e.g., with a C15S mutation) conjugated to a PEG moiety over a time-period of 6 weeks or longer.

As used herein, the term "continuous administration" refers to repeated administration of the CBS enzyme, htCBS, or htCBS mutant (e.g., with a C15S mutation) conjugated to a PEG moiety throughout the course of a study via subcutaneous injection or implanted osmotic pump.

Described herein are methods of treating homocystinuria through enzyme therapy (ET) with the drug product described herein including a PEGylated human truncated CBS protein with a mutation at amino acid position 15 of a cysteine to a serine.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

The present disclosure is further illustrated by the following non-limiting examples.

EXAMPLES

Example 1. Experimental Protocols

A. Fermentation

An expression vector, harboring the sequence coding for the truncated human CBS was transformed into B1-21 (DE3) *E. coli* bacteria, and bacteria from kanamycin-resistant clones were grown in 5 ml of Luria-Bertani (LB) medium, with 30 µg/mL kanamycin, overnight at 37° C. on a rotational shaker at 275 rpm. One mL of the overnight culture was added to a 100 mL Terrific Broth (TB) medium with 30 µg/mL kanamycin and grown overnight. Ten ml of the pre-culture was then added to a 1 liter of TB medium containing 0.001% of thiamine-HCl pH 8.0, 0.0025% of pyridoxine-HCl pH 8.0, 0.3 mM δ-ALA pH 8.0, 150 µM ferric chloride, 30 µg/mL of kanamycin. The culture was then grown at 30° C. on a rotational shaker at 275 rpm until OD600 reached the value of about 0.6-0.7 and protein expression was induced by addition of 1 mM IPTG. Fermentation was continued for additional 16 hours. Cells were harvested by 10 minutes of 6000 relative centrifugal force (rcf) centrifugation at 4° C., washed with ice-cold 0.9% NaCl, re-centrifuged as above, and frozen at −80° C. Lysis buffer (20 mM NaH2PO4, pH 7.2, 40 mM NaCl, 0.1 mM PLP) was then added to the cell pellet and the latter was homogenized in a Dounce homogenizer and treated with lysozyme (2 mg/mL final), incubated for 1 hour at 4° C. on a rocking platform, sonicated to reduce viscosity, and centrifuged at 53,000 rcf. The supernatant, comprising the soluble fraction was then stored at −80° C.

Optimization and scale-up plans were designed to establish a fermentation process for high level expression of CBS, amounts and addition profiles of media supplements such as 5-aminolevulinic acid (ALA), thiamine (vitamin B1), pyridoxine HCl and/or ferric chloride, C-source and their starting and feeding conditions, temperature, pH as well as induction conditions (inducer concentration and length of induction period).

The highest cell density and best expression levels were achieved with minimal salt medium (C-source: glycerol), supplemented by a total of 0.05 g/L B6 and 0.5 g/L ALA during an induction period of 24 hours at 30° C.

At the end of fermentation (EOF), a cell density at 600 nm (OD600) of approximately 110±10 was achieved, which corresponded to a wet weight of approximately 90±10 g/L. The CBS titer of the fermentation process was approximately 2.5-3.0 g CBS/L as determined by radioactive and colorimetric activity assays.

B. Purification

The overall enzymatic activity recovery target for the purified enzyme from cell lysate was 30% assuming at least three chromatography steps would be required. The developed process was evaluated at the scale of a 60 mL capture column.

1. Capturing Step

Anion exchange chromatography (AEX) was used as first capturing step in the production of recombinant CBS. The eluate was then polished for further purification by capture on DEAE-Sepharose resin at near neutral pH, followed by a linear gradient of $KH_2PO_4$. DEAE-Sepharose is a weak exchanger, which means that the charge of the system was dependent on the surrounding pH. Thereby, the pH has a close relation to the dynamic binding capacity (DBC) of the resin. Lowering the binding pH to 6.4 did not decrease the performance of the capturing step. The loading time was about 30 minutes if the dilution for the cell paste used 5 volumes of disruption buffer for the solubilization.

Washing was performed for 10 column volume with the loading capacity close to the determined maxima of 7 g/L CBS (which is equivalent to a DBC of approximately 35 g total protein per L resin). Elution was performed under elution conductivity conditions of 16 mS/cm in the presence of 120 mM NaCl.

Recovery was observed to be about 90% as long the cell extract was loaded within a narrow time frame. Depending on the CBS titer inside the cell extract, a purification factor of approximately 3.5 was reached by this capturing step.

2. Immobilized Metal Affinity Chromatography (IMAC)

IMAC, also referred to as Co' immobilized metal affinity chromatography, with zinc (Zn) ions, uses binding-selectivity for orthogonal separation between CBS from the host cell protein (HCP). A purification factor of about 2.5 was observed.

The elution step included 11 mM Imidazole in combination with desalting the CBS fraction. The sodium chloride concentration was lowered from 400 mM (load/wash) to 50 mM inside the elution buffer. It could be shown in small scale screenings that the conductivity has a big influence on the elution behavior itself. For example, it was possible to elute the CBS only by pure water, without imidazole. The stability of CBS was increased by increasing the amount of sodium chloride inside the elution buffer. At 150 mM sodium chloride the elution behavior was only slightly changed.

Using HEPES as the buffer system, a DBC of 12-15 g/L could be measured. Additionally, the stability of the sample was increased not only for precipitation but rather the degradation was decreased. By addition of EDTA, the degradation was stopped by using HEPES buffer, in contrast to the currently used phosphate buffer system. In the scale-up, EDTA and ammonium sulfate were immediately added after the elution is finished which should inhibit the degradation. Additionally, the following polishing was performed as quickly as possible in order to keep the incubation time in this state short. The IMAC elution pool was loaded onto hydrophobic interaction chromatography (HIC) column within 3 hours for polishing.

3. Polishing Step

The separation at the final chromatography step of the CBS purification train was based on hydrophobic interaction. The major column separated the protein of interest, CBS, from most of the HCP by differences in elution conditions. Most of the HCP binds stronger onto the HIC than the CBS, indicating that CBS is less hydrophobic than most of the remaining HCPs.

In comparison to IMAC, HIC has a low binding separation (less than 10%). Over 90% of the remaining HCP impurities were separated from the HIC by the elution step. The CBS recovery of the HIC was about 95%. The DBC was between about 16 g/L to about 18 g/L. The performance of this polishing step was quite robust. pH for the elution step was between 6 and 8. Buffer system (phosphate or 20 mM HEPES) had no measurable influence.

The purification factor of this polishing step was about 1.1 due to the low remaining HCP content inside the load, which was typical for a final chromatography step. The purity of the final CBS between all performed downstream production processes was similarly high, which indicates that this polishing step compensated different degrees of impurities inside the load.

Adaptations may be performed in order to adapt the process steps to the existing equipment and to allow later scale-up to 100 L fermentation volume for production. To ensure a reliable product quality EDTA (e.g., 10 mM) can be added into several process steps, to prevent product degradation caused by metalloproteases.

C. PEGylation

The PEGylation reaction behaved like a second order reaction with product-induced inhibition. Since the hydrolysis at the NETS-PEG cannot be the reason for the inhibition of the reaction and the final PEGylation pattern was reached after 4 hours of PEGylation, the remaining (about 50%) NETS-PEG was observed to still be active. Interestingly, the addition of further NETS-PEG into the reaction mix increased the PEGylation pattern. CBS concentration was 8 g/L inside the reaction mixture to obtain the desired PEGylation pattern without increasing the NETS-PEG to CBS ratio in absence of DMSO.

D. Data and Statistical Analysis

Table 4 provides details on software, analytical tools, and algorithms used for data analysis in the Examples herein.

TABLE 4

| Programs and Statistical Analysis | |
|---|---|
| Chromatogram acquisition and chromatographic peak integration | AB Sciex ANALYST ™ 1.6 Software |
| Standard regression, concentration calculations, data management | Thermo Scientific Watson LIMS ™ |
| Interface between Watson LIMS and data system | Text file |
| Calculations for SS and WS control | Microsoft Excel |
| Regression model | Linear |
| Weighting factor | 1/x2 |
| Concentration presentation | 3 significant figures |
| Concentration unit | µmol/L or µM of equivalent matrix |
| Summary statistics reported | Mean, SD, % DEV, % CV |
| Number of decimal places for % DEV and % CV | 2 |

All chromatograms were reviewed by the analyst to ensure that chromatographic peak shape and peak integrations were satisfactory. Data transferred manually were cross-checked against the source data which are part of the study raw data. Run acceptance criteria were set prior to analysis based on results from calibration standards, QC and blank QCs. Data are presented as mean±standard error of the mean (SEM).

Statistical analysis was conducted using ANOVA followed by Tukey's multiple comparison test to determine significance.

E. CBS Activity Assay Based on Conversion of Radiolabeled Ser

CBS catalyzes a β-replacement reaction in which serine (Ser) condenses with Hcy in a pyridoxal 5'-phosphate (PLP)-dependent manner to form Cth. The activity of the CBS enzyme was determined by a radioisotope assay using 14C-labeled Ser as a substrate:

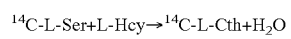
$^{14}$C-L-Ser+L-Hcy→$^{14}$C-L-Cth+$H_2O$

An aliquot of 7 µl (total 420 ng) pure 20NHS PEG-CBS in dilution buffer (0.1 M Tris-HCl at pH 8.6 containing 1 mM DTT, 10 µM PLP and 0.5 mg/ml bovine serum albumin (BSA)) or 7 µl plasma (no dilution necessary for D25 and D27 samples) was added to 88 µl reaction mixture (0.1 M Tris-HCl at pH 8.6 containing 10 mM L-Ser, 0.5 mM PLP, 0.5 mg/ml BSA and 0.3 µCi L-[14C(U)]-Ser). Samples were equilibrated to 37° C. by incubating in a water bath for 5 min. The reaction was initiated with 5 µl 0.2 M Hcy (final concentration 10 mM) and incubated for an additional 30 min at 37° C.

Assay initiation and sampling of the resulting mixture were staggered so that each reaction time was exactly 30 min. Descending paper chromatography was used to separate the radioactive product (Cth) from the labeled substrate (Ser). To stop the reaction, the assay mixture was cooled in an ice bath and a 20 µl aliquot was pipetted onto grade 3 CHR chromatography paper (Whatman, GE Healthcare, Pittsburgh, PA, USA) for separation. The 14C-Cth formed in the reaction was separated from 14C-Ser by overnight elution with 2-propanol:formic acid:H2O (75:5.7:18.9 v/v). A standard containing a mixture of Cth and Ser was run along with samples on each side of the chromatography paper. The chromatography paper was dried, and standard lanes were stained with an acidic ninhydrin solution. The areas of each sample lane containing labeled Cth were excised, submerged in 5 ml Opti-flour scintillation cocktail (PerkinElmer, North Billerica, MA, USA) and counted in a Beckman LS-3801 scintillation counter. An enzyme-free sample was used as a blank to monitor the background radioactivity and this was subtracted from counts in each sample. For the pure enzyme control, CBS specific activity values were expressed as enzyme units (the amount of enzyme that produces 1 µmol of Cth/h) per mg CBS (i.e. U/mg protein). For plasma samples, activity values were expressed as milli-units (the amount of enzyme that produces 1 nmol Cth/h) per µl plasma (i.e. mU/µl plasma).

These stock solutions having a nominal value of 25 mg/ml (24.8-26.7 mg/ml in phosphate buffered saline, pH 7.4 (PBS)) were stored in aliquots at −80° C. On each treatment day, single use, fresh solutions of enzyme were prepared by dilution of the stock solutions into PBS to final concentrations of 1 mg/ml and these were delivered to mice at a dose of 7.5 mg/kg. Volumes injected to administer the target dose were calculated based on weights on the days indicated. Any solution remaining upon completion of injections for that day was discarded.

F. Western Blotting

The drug product was injected into four I278T−/− mice and blood collected at 24 hours after the first injection and 72 hours after the last injection to serve as a control. D25 and D27 plasma samples from all groups in Example 5 were analyzed by western blotting to detect potential in vivo de-PEGylation. Plasma samples (4 µl per lane) were loaded on gradient (4%-20%) MiniProtean TGX gels (Bio-Rad, Hercules, CA, USA) and proteins separated by electrophoresis under denaturing, reducing conditions. Molecular weight markers (Precision Plus Protein Dual Color Standard, Bio-Rad) and aliquots from each preparation (150-500 ng per lane) were processed similarly and electrophoresed along with the plasma samples. After electrophoretic separation, protein bands were transferred to PVDF membranes (BioRad). Individual membranes were blocked overnight at 4° C. in blocking solution (5% nonfat milk in PBS with 0.02% Tween 20). The membranes were then washed and incubated with rabbit polyclonal anti-hCBS antibody (Orphan Technologies UCD Kraus lab batch #R2B2, antiserum diluted 5000-fold in blocking solution) for 1 h. Membranes were then washed and incubated with horseradish peroxidase (HRP) conjugated anti-rabbit IgG (Jackson Laboratories, Bar Harbor, Maine, USA, 5,000-fold diluted in blocking solution) for 30 minutes. After washing the membranes, bands were visualized by incubating with a chemiluminescent substrate (SuperSignal West Pico, ThermoFisher Scientific, Waltham, MA, USA) for 5 minutes, followed by signal capture on clear-blue X-ray film (CL-Xposure Film, ThermoFisher Scientific). The developed films were scanned using a flatbed scanner (Perfection V550 Photo Color Scanner, Epson, Long Beach, CA, USA).

G. Chemicals

Unless stated otherwise, all materials were purchased from Sigma or Fisher Scientific. L-[U-14C]-serine was obtained from Perkin Elmer Life Sciences.

H. Plasma Collection and Analysis

A single-use lancet for submandibular bleeding was used for blood collection into BD Microtainer PST tubes with lithium heparin (Becton, Dickinson and Company, NJ, USA). Tubes were then centrifuged at 10,000×g for 5 min, followed by transfer of plasma to 1.5 ml tubes and storage at −80° C. Plasma sulfur amino acid metabolites were determined by stable-isotope-dilution liquid chromatography tandem mass spectrometry (LC-MS/MS) as described elsewhere.

I. Animal Studies

Studies were conducted using a CBS knockout strain of mice expressing the human I278T mutant CBS transgene (I278T CBS −/− (I278T −/−) mice). A breeding pair of heterozygous transgenic I278T mice on the C57BL6 background was provided by Dr. Warren Kruger (Fox Chase Cancer Center, Philadelphia, PA, USA). The mice have the mouse CBS gene knocked down and also express the I278T human CBS, under control of the metallothionein promoter (see Wang, et al. (2005) Hum Mol Genet 14, 2201-2208, which is hereby incorporated by reference in its entirety). The mutant enzyme has about 2%-3% of the CBS WT activity, such that transgene expression rescues the neonatal lethality normally observed in CBS knockout homozygous mice (see Watanabe et al. (1995) Proceedings of the National Academy of Sciences USA 92, 1585-1589; Maclean et al. (2010) Molecular Genetics and Metabolism 101, 163-171; each of which is hereby incorporated by reference in its entirety). Unless otherwise indicated, animals were maintained on a standard irradiated extruded rodent chow (Teklad 2920X, Envigo, Indianapolis, IN, USA).

To produce CBS homozygous transgenic study animals, homozygous or heterozygous males were bred with heterozygous females, to produce litters containing CBS homozygous (−/−) pups, among other genotypes, all expressing the I278T transgene. Breeding pairs and neonatal mice were provided with zinc (25 mM zinc sulfate in the drinking water) to induce transgene expression. The homozygous strain (I278T−/−), which have a homocystinuria (HCU) phenotype, serve as a model for CBSDH, while the other genotypes obtained were not used in this study (see Wang, et al. (2005) Hum Mol Genet 14, 2201-2208, which is hereby incorporated by reference in its entirety).

All animal procedures used in this study were reviewed and approved by the University of Colorado-Denver IACUC, which adheres to all federal, state and local laws, regulations and policies. The University of Colorado-Denver is an AAALAC Accredited (#00235), Public Health Service Assured (#A 3269-01) and USDA Licensed (#84-R-0059) Institution. Procedures involving mice were performed under IACUC-approved protocol #B-49414(03)1E.

Mice were propagated and genotyped at our facility as described previously in Wang, et al. (2005) Hum Mol Genet 14, 2201-2208, which is hereby incorporated by reference in its entirety. Breeding pairs were maintained on extruded standard diet 2920X (Envigo, CA, USA) and water containing 25 mM ZnCl2 to induce transgene expression and thus rescue the homozygous I278T pups from neonatal death. After weaning at 21 days of age, homozygous I278T mice and their WT siblings were assigned into one of eight groups. At age of 24 days, mice were switched to amino acid-defined diets with either normal (Envigo TD.170063, 4% Met; Groups A, B, C and D) or restricted methionine content (Envigo TD.110591, 0.5% Met; Groups E, F, G and H). In addition to a new diet at day 24, mice also received subcutaneously injected PBS vehicle (Groups A, C, E and G) or 10 mg/kg 20NHS PEG-CBS (Groups B, D, F and H) 3 times a week (Monday, Wednesday, Friday) through week 22 of age. Mice were weighed weekly with weights used to calculate 20NHS PEG-CBS injection volumes for the week.

J. Enzyme Storage and Preparations

20NHS PEG-CBS in a liquid formulation was used for a stability study performed under cGMP as described herein and, from this study, the following samples were obtained: Control enzyme or "control preparation" (T0-80 C) stored below −65° C. and enzyme samples incubated under accelerated stability conditions, at 25° C., for 2 days (T2D-25C), 1 month (T1M-25C), and 6 months (T6M-25C).

Example 2. Measuring Reductions of the Level of PEGylation in Drug Product Preparations Drug product preparations with varying degrees of de-PEGylation were generated for an accelerated stability study, performed under "good manufacturing practices" (GMP) conditions for the drug product, by incubating the drug product at 25° C. for two days, one month, or six months. The control sample was stored within the recommended temperature range, i.e., below −65° C.

PEGylation differences among preparations were confirmed by reversed-phase high-performance liquid chromatography (RP-HPLC). Ten highly PEGylated and less PEGylated species were distinguished, as well as CBS without PEGylation and heme cofactor (P10) released upon enzyme denaturation. The extent of de-PEGylation in each sample was determined by comparing relative areas of peaks corresponding to variably PEGylated or fully de-PEGylated species. RP-HPLC results are shown in Table 5. "CBS" is native (unmodified) enzyme, and the remaining peaks are the preparations with different levels of PEGylation.

TABLE 5

| PEAK | CONTROL (%) | 2 DAYS (%) | 1 MONTH (%) | 6 MONTHS (%) |
|---|---|---|---|---|
| P10/Heme | 1.41 | 1.52 | 1.66 | 1.66 |
| CBS | 0.06 | 0.05 | 0.42 | 3.07 |
| P1 | 0.52 | 0.64 | 2.25 | 9.03 |
| P2 | 0.15 | 0.26 | 1.37 | 6.29 |
| P3 | 5.92 | 6.67 | 14.59 | 27.17 |
| P4 | 14.89 | 16.19 | 24.11 | 25.34 |
| P5 | 24.35 | 24.51 | 25.80 | 16.34 |
| P6 | 25.02 | 24.40 | 17.53 | 7.21 |
| P7 | 16.94 | 15.94 | 8.53 | 2.15 |
| P8 | 7.79 | 7.12 | 2.92 | 0.55 |
| P9 | 2.45 | 2.27 | 0.69 | 0.00 |
| P11 | 0.48 | 0.37 | 0.10 | 0.00 |

RP-HPLC analysis indicated that, compared with the control sample, significant de-PEGylation was present in preparations incubated for 1 month and, even more, for 6 months at 25° C. As shown in Table 5, those samples showed higher proportion of peaks corresponding to less PEGylated forms (e.g. P3) and concomitantly lower abundance of peaks for more PEGylated forms (e.g. P6 and P7). In addition, a peak corresponding to unmodified (or fully de-PEGylated) CBS was most prominent in the preparation incubated for six months, In the preparation incubated at 25° C. for 2 days, however, the distribution of variably PEGylated species was more similar to that in the control enzyme that was always stored at less than or equal to −65° C.

Example 3. Efficacy of Preparations with Reduced Levels of PEGylation in Mice

To assess biological equivalence among the drug product and de-PEGylated preparations thereof, efficacy was analyzed in I278T CBS−/− (I278T−/−) mice, a model recapitulating biochemical sequelae of CBSDH, that is, abnormalities in plasma levels of methionine (Met) metabolites, including elevated homocysteine (Hcy) and suppressed cysteine (Cys). Plasma aminothiols (total Cys and Hcy) and the remaining amino acids, as well as SAM and SAH, were measured by LC-MS/MS carried out as described in Arning et al. (2016) Methods Mol Biol 1378, 255-262, which is hereby incorporated by reference in its entirety.

I278T CBS−/− (I278T−/−) mice are deficient in the mouse CBS gene and express the I278T mutant human CBS gene, carrying the most widely found pathogenic mutation in CBSDH patients. These mice express approximately 2%-3% of wildtype CBS activity and have a homocystinuria (HCU) phenotype (see Wang, et al. (2005) Hum Mol Genet 14, 2201-2208, which is hereby incorporated by reference in its entirety). This includes elevations in both plasma and tissue levels of Hcy, Met and S-adenosylhomocysteine (SAH), and a concomitant decrease in plasma Cth and Cys levels. This mouse strain was originally obtained from Professor Warren D. Kruger at the Fox Chase Cancer Center (Philadelphia, PA, USA).

Both male and female adult I278T−/− mice, maintained on a standard (REG) diet, were used to test efficacy. At study initiation, mice were divided into four groups, corresponding to the four preparations. Blood was collected for baseline measurements at least one week prior to dosing. Blood was collected from the submandibular vein of conscious study animals using a disposable lancet designed for submandibular sampling into plasma preparation tubes with lithium heparin and gel (Greiner Bio-One, Monroe, NC, USA or the equivalent from other vendors). Plasma was collected from blood samples after centrifugation at 1,200×g for 10 min and was stored at −80° C. in 1.5 ml tubes until analysis.

Beginning on day 1 (D1), mice received three subcutaneous (SC) injections, each at 7.5 mg/kg, per week (on Monday, Wednesday, and Friday) of the respective preparation corresponding to its experimental group.

Treatment continued for 24 days. Preparation injection days were D1, D3, D5, D8, D10, D12, D15, D17, D19, D22, and D24. Blood was collected at least once per week, at 24 hours after an injection as well as at 72 hours after the last injection. In addition to the baseline (D0) collection, blood sampling was performed on D2, D11, D18, D25, and D27. Plasma was prepared from all blood samples immediately after collection and stored as frozen aliquots until analysis. An aliquot of each sample was analyzed for Met metabolites, while aliquots of some (D25 and D27) were also assayed for CBS activity as described in Example 4. The Met metabolites assayed were: Hcy, Cth, Cys, Met, Bet, dimethylglycine (DMG), glycine (Gly), serine (Ser), S-adenosylmethionine (SAM), and S-adenosylhomocysteine (SAH). Unless otherwise indicated, results for both sexes were pooled.

The preparations were compared based on their ability to improve, when given by subcutaneous injection, plasma levels of the Met metabolites analyzed. In addition, in vivo de-PEGylation of the preparations was examined in the same mice.

In addition to the baseline (D0), blood sampling was performed on D2, D11, D18, D25, and D27. Plasma was prepared from all blood samples immediately after collection and stored frozen in aliquots until analysis. An aliquot of each sample was analyzed for Met metabolites, while aliquots of some (D25 and D27) were also assayed for CBS activity. Selected aliquots (D2 and D27) were also analyzed by western blotting to assess in vivo 20NHS PEG-CBS de-PEGylation.

In CBSDH patients, plasma and tissue levels of Hcy, and often Met, are high, while those of Cth and Cys are low. I278T−/− mice on a standard diet have elevated Hcy and decreased Cys levels in the plasma, thus recapitulating key aspects of the metabolic dysregulation observed in CBSDH patients (see Wang, et al. (2005) Hum Mol Genet 14, 2201-2208, which is hereby incorporated by reference in its entirety). Among the metabolites analyzed in this study, plasma Hcy is the marker that is most commonly monitored clinically (see Morris et al. (2017) J Inherit Metab Dis 40, 49-74, which is hereby incorporated by reference in its entirety).

Plasma Hcy, Cys, Cth, and Met levels (means±SEM) is shown in Table 6.

exhibited equivalent efficacy as the control preparation stored below −65° C. (T0-80C) and the preparation incubated for 2 days at 25° C. (T2D-25C). Statistical analysis of global effects indicated that the preparation incubated for 6 months (T6M-25C) was significantly less effective, based on Hcy levels, than the other preparations ($p<0.00501$). On D27, Hcy levels remained lower than on D0 for the other two preparations ($p<0.01$). The preparation incubated for 6 months (T6M-25C), in contrast, was still efficacious but significantly less so than the others ($p<0.01$), resulting in plasma Hcy levels of about 200 µM, compared with 88-145 µM in the other three groups. At 72 hours after the last injection, Hcy levels were partially increased, but had not yet returned to the levels in untreated mice ($p<0.01$ on D27 vs D0 for the control preparation (T0-80C) and the preparation incubated for 2 days (T2D-25C), but non-significant differences for the preparations incubated for 1 month (T1M-25C) and 6 months (T6M-25C)). These results were consistent with the previous pharmacodynamic studies in Majtan et al. Life Sci 200, 15-25 (2018), which is hereby incorporated by reference in its entirety.

Statistical analysis of global effects indicated that the preparation incubated for 6 months had a significantly lower effect on Cys levels than did the other preparations ($p<0.001$). Plasma Cys levels, suppressed in CBSDH model mice, were normalized (about 200-250 µM) by all preparations, except the preparation incubated for six months (T6M-25C). The elevated Cys levels returned to baseline within 72 hours after the injection schedule had ended.

Though highly variable, plasma Cth levels were elevated by treatment with all preparations, consistent with the observations that all preparations had CBS catalytic activity. Therefore, the preparation incubated for six months (T6M-

TABLE 6

Average plasma metabolite levels

| Preparation | Day | Hcy µM | SEM µM | Cth µM | SEM µM | Cys µM | SEM µM | Met µM | SEM µM |
|---|---|---|---|---|---|---|---|---|---|
| T0-80C | 0 | 484.3 | 41.1 | 0.7 | 0 | 145.3 | 6.9 | 50 | 1.5 |
| T2D-25C |  | 490.6 | 62.7 | 0.7 | 0 | 136.6 | 3.4 | 61 | 3.5 |
| T1M-25C |  | 451.5 | 51.8 | 0.7 | 0 | 126.1 | 20 | 58 | 2.2 |
| T6M-25C |  | 483.5 | 35 | 0.7 | 0 | 150.4 | 6.5 | 82 | 21.6 |
| T0-80C | 2 | 193.5 | 14.6 | 73.9 | 1.7 | 191.3 | 15 | 54 | 5.3 |
| T2D-25C |  | 151.3 | 10.6 | 69.9 | 2.2 | 192 | 25.3 | 71 | 7.2 |
| T1M-25C |  | 174.8 | 10.7 | 101.1 | 10.3 | 175.5 | 12 | 88 | 5.2 |
| T6M-25C |  | 203 | 18.1 | 99.1 | 14.8 | 134.5 | 7.9 | 86 | 7.6 |
| T0-80C | 11 | 121.3 | 11 | 43.3 | 3.4 | 223.8 | 12.6 | 54 | 3.9 |
| T2D-25C |  | 111.8 | 8.8 | 53.5 | 2.1 | 224.5 | 5.8 | 76 | 8.3 |
| T1M-25C |  | 130 | 4.3 | 51.8 | 8.3 | 233 | 8.1 | 61 | 5.8 |
| T6M-25C |  | 194.8 | 23.1 | 81.8 | 18.7 | 156 | 12.2 | 85 | 17.4 |
| T0-80C | 18 | 109.9 | 19.8 | 64.8 | 8.2 | 194.3 | 5.7 | 55 | 1 |
| T2D-25C |  | 103.2 | 18.1 | 78.1 | 9.8 | 201.3 | 9.9 | 77 | 2.9 |
| T1M-25C |  | 124.7 | 19.5 | 100.5 | 5.6 | 198.3 | 16.3 | 75 | 3.5 |
| T6M-25C |  | 197.8 | 41.1 | 62.5 | 11.7 | 191.7 | 4.1 | 51 | 4 |
| T0-80C | 25 | 134 | 26.9 | 61.2 | 9.2 | 205.8 | 22 | 55 | 1.6 |
| T2D-25C |  | 88.3 | 5.8 | 53.4 | 4.3 | 237.3 | 18.1 | 61 | 1.9 |
| T1M-25C |  | 144.9 | 34.6 | 67.4 | 10.4 | 222.5 | 23.2 | 61 | 6.6 |
| T6M-25C |  | 226 | 39.1 | 65.9 | 4.6 | 155.3 | 18.8 | 54 | 4.6 |
| T0-80C | 27 | 245.3 | 10.8 | 67.1 | 8.5 | 159 | 5.6 | 52 | 3 |
| T2D-25C |  | 260 | 21.7 | 93.9 | 9.8 | 119.3 | 1.2 | 81 | 8.4 |
| T1M-25C |  | 301 | 51.6 | 59.2 | 11.6 | 145.1 | 20.4 | 54 | 10 |
| T6M-25C |  | 343 | 40.5 | 29.1 | 1.9 | 120.8 | 11.4 | 52 | 4.4 |

As shown in Table 6, plasma Hcy levels in I278T−/− mice were very high (≥450 µM on D0) and dropped substantially within 24 hours of the first injection, regardless of preparation. The preparation incubated at 25° C. for one month (T1M-25C), having undergone substantial de-PEGylation, 25C) is more likely to have differences in pharmacokinetics instead of pharmacodynamics compared to the other three preparations.

Plasma Met levels showed no prominent patterns in response to the treatments, consistent with previous observations that plasma Met levels reflected primarily dietary Met intake in CBSDH model mice, with or without 20NHS PEG-CBS treatment Majtan et al. J Inherit Metab Dis 41 (Suppl 1), S56 (2018). Statistical analysis indicated no significant differences in Cth levels among the four preparations.

In addition to Hcy, Cys, Cth, and Met, several other analytes were included in the metabolite panel, and levels of these metabolites showed no significant differences among groups. The additional analytes are shown in Table 7.

TABLE 7

Average levels of additional analytes

| Preparation | Day | Ser μM | SEM μM | Gly μM | SEM μM | Bet μM | SEM μM | DMG μM | SEM μM | SAM/SAH ratio | SEM ratio |
|---|---|---|---|---|---|---|---|---|---|---|---|
| T0-80C | 0 | 117 | 11.8 | 136 | 6.4 | 25.6 | 5.1 | 3 | 0.5 | 0.1 | 0 |
| T2D-25C |  | 110.8 | 2 | 146.5 | 9.7 | 22.6 | 2 | 3 | 0.3 | 0.1 | 0 |
| T1M-25C |  | 119.3 | 15.6 | 133.3 | 12.3 | 28.1 | 4.2 | 3.3 | 0.9 | 0.2 | 0.1 |
| T6M-25C |  | 127.3 | 10 | 147.8 | 14.1 | 31 | 6.2 | 4.3 | 1.3 | 0.1 | 0 |
| T0-80C | 2 | 59.2 | 8.1 | 148.8 | 6.4 | 24.6 | 2.3 | 2.9 | 0.3 | 1.2 | 0.3 |
| T2D-25C |  | 88.2 | 12.8 | 192 | 15.3 | 27.1 | 2.1 | 3.4 | 0.2 | 1.1 | 0.2 |
| T1M-25C |  | 88.8 | 10.1 | 170.8 | 11 | 35.2 | 3.1 | 4 | 1 | 0.8 | 0.2 |
| T6M-25C |  | 86.7 | 8.5 | 205.5 | 9.5 | 37.4 | 5.5 | 4.7 | 0.8 | 0.4 | 0.1 |
| T0-80C | 11 | 92.1 | 7.3 | 168.5 | 8.1 | 24.7 | 1.2 | 2.4 | 0.3 | 2.1 | 0.1 |
| T2D-25C |  | 124.6 | 21.2 | 211.5 | 21.5 | 35.9 | 8.3 | 3.2 | 0.7 | 1.7 | 0.2 |
| T1M-25C |  | 106 | 9 | 172.8 | 21.5 | 31 | 5.7 | 3 | 0.9 | 2 | 0.3 |
| T6M-25C |  | 103.8 | 7.1 | 198 | 10.4 | 37.8 | 7.7 | 4.6 | 1.2 | 0.9 | 0.3 |
| T0-80C | 18 | 88 | 9.3 | 190.3 | 11.8 | 24.6 | 1.7 | 2.4 | 0.4 | 1.3 | 0.2 |
| T2D-25C |  | 91.9 | 11 | 193 | 8.3 | 31 | 6.5 | 3 | 0.6 | 1.1 | 0 |
| T1M-25C |  | 77.5 | 10.1 | 158 | 22 | 29 | 5.4 | 3.1 | 0.9 | 1 | 0.2 |
| T6M-25C |  | 69.3 | 4.9 | 172 | 6.7 | 26.9 | 4.2 | 3.3 | 0.8 | 0.8 | 0.3 |
| T0-80C | 25 | 79.3 | 7.7 | 173.5 | 5.1 | 21.4 | 1.5 | 2.1 | 0.3 | 1.6 | 0.4 |
| T2D-25C |  | 89.3 | 6.3 | 176.3 | 10.4 | 25.1 | 2.7 | 2.7 | 0.5 | 1.7 | 0.2 |
| T1M-25C |  | 82.1 | 12.5 | 155.5 | 13.4 | 25.6 | 2.3 | 2.6 | 0.5 | 1.4 | 0.3 |
| T6M-25C |  | 63.3 | 6 | 168.5 | 12.9 | 23 | 2.2 | 2.9 | 0.7 | 1 | 0.3 |
| T0-80C | 27 | 67 | 10.1 | 190.3 | 29.6 | 24.6 | 2.4 | 2.3 | 0.5 | 0.5 | 0.1 |
| T2D-25C |  | 83.3 | 4.2 | 206 | 9.1 | 33.6 | 5.5 | 3.1 | 0.4 | 0.2 | 0.1 |
| T1M-25C |  | 52.8 | 10.2 | 137 | 20.5 | 24.3 | 3.4 | 2.3 | 0.4 | 0.4 | 0.2 |
| T6M-25C |  | 69.7 | 4.8 | 156.8 | 16.6 | 27.6 | 3.3 | 3 | 0.7 | 0.2 | 0 |

As shown in Table 7 (and as provided in Table 6), T0-80C refers to the control preparation, T2D-25C refers to the preparation incubated for 2 days at −25° C., T1M-25C refers to the preparations incubated for 1 month at 25° C., and T6M-25C refers to the preparations incubated for 6 months at 25° C. The RP-HPLC results indicated that significant de-PEGylation had occurred in 20NHS PEG-CBS incubated in vitro at 25° C. for 1 month and, even more at 6 months. Nevertheless, treatment of I278T−/− mice with all four preparations resulted in dramatic lowering of plasma Hcy levels though in the most significantly de-PEGylated sample (preparation incubated for 6 months at 25° C.) this lowering was significantly less pronounced (p<0.01). Similarly, plasma Cys levels were elevated by all preparations, though, again, the preparation incubated for 6 months at 25° C. was significantly less effective (p<0.001) than the others. All samples collected during the treatment period showed elevated, though variable, plasma levels of Cth, the product formed by each preparation from its substrate Hcy, compared with baseline levels (D0). This indicated that the preparations were all catalytically active, a finding consistent with specific activity measurements performed on the preparations prior to injection. Plasma Met levels were not significantly impacted by the treatments, in agreement with our previous findings that Met levels appear to be mostly affected by dietary intake, not drug product treatment, and the fact that all mice were on a standard diet throughout the study. All treatments led to elevated plasma CBS activity, but there was significantly lower activity (p<0.01) in mice receiving the preparation incubated for 6 months at 25° C. compared with in the other groups. Thus, treatment with the most de-PEGylated preparation resulted in lower enzymatic activity in the plasma, which translated into lower efficacy in vivo, while the other two 25° C.-incubated preparations were as effective as the control samples. Notably, the preparation incubated for one month, that was significantly de-PEGylated as compared with the control, showed similar efficacy to the control. The levels of de-PEGylation observed after incubation for 2 days, 1 months, or 6 months, likely would be achieved only under accelerated stability testing conditions and are highly unlikely to occur in the clinical setting.

Example 4. Enzyme Activity of Preparations with Reduced Levels of PEGylation

At, 24 and 72 hours following the last injection, plasma CBS activity, that is, the catalytic activity of the preparations in plasma samples collected on D25 and D27, was measured.

Using a colorimetric assay described in Kayastha et al Anal Biochem 193(2), 200-203 (1991), which is hereby incorporated by reference in its entirety, the stability study results indicated no loss in CBS specific activity (200±100 U/mg protein for the batch) during the 6 months incubation period, with activity measurements of 145, 204, 170, and 205 U/mg protein for the control, 2 days, 1 months, and 6 months preparations, respectively.

Another CBS activity assay based on conversion of radiolabeled Ser as described in Example 1 was also performed. Measurements of CBS activities are shown in Table 8.

TABLE 8

CBS activities

| Sample | Day | Cth counts in aliquot [cpm] | Total counts in assay [cpm] | L-Cth produced in assay [nmol] | CBS specific activity [nmol/h/ul] | Average activity [nmol/h/ul] | SEM [nmol/h/ul] |
|---|---|---|---|---|---|---|---|
| Blank | NA | 65 | 0 | 0 | 0.00 | NA | NA |
| T0-80C (control) | | 11767 | 58510 | 341.64 | 97.61 | | |
| T2D-25C (control) | | 8696 | 43155 | 251.99 | 72.00 | | |
| T1M-25C (control) | | 9058 | 44965 | 262.55 | 75.02 | | |
| T6M-25C (control) | | 6705 | 33200 | 193.86 | 55.39 | | |
| T0-80C | 25 | 12166 | 60505 | 353.29 | 100.94 | | |
| T0-80C | | 9707 | 48210 | 281.50 | 80.43 | | |
| T0-80C | | 8665 | 43000 | 251.08 | 71.74 | | |
| T0-80C | | 16448 | 81915 | 478.31 | 136.66 | 97.4 | 14.4 |
| T2D-25C | | 12422 | 61785 | 360.77 | 103.08 | | |
| T2D-25C | | 12178 | 60565 | 353.64 | 101.04 | | |
| T2D-25C | | 10432 | 51835 | 302.67 | 86.48 | | |
| T2D-25C | | 10884 | 54095 | 315.86 | 90.25 | 95.2 | 4.0 |
| T1M-25C | | 13751 | 68430 | 399.57 | 114.16 | | |
| T1M-25C | | 15838 | 78865 | 460.50 | 131.57 | | |
| T1M-25C | | 11961 | 59480 | 347.31 | 99.23 | | |
| T1M-25C | | 8253 | 40940 | 239.05 | 68.30 | 103.3 | 13.4 |
| T6M-25C | | 5806 | 28705 | 167.61 | 47.89 | | |
| T6M-25C | | 6084 | 30095 | 175.73 | 50.21 | | |
| T6M-25C | | 5933 | 29340 | 171.32 | 48.95 | | |
| T6M-25C | | 3312 | 16235 | 94.80 | outlier | 49.0 | 0.7 |
| T0-80C | 27 | 4707 | 23210 | 135.52 | 38.72 | | |
| T0-80C | | 3717 | 18260 | 106.62 | 30.46 | | |
| T0-80C | | 40 | −125 | −0.73 | outlier | | |
| T0-80C | | 5804 | 28695 | 167.55 | 47.87 | 39.0 | 5.0 |
| T2D-25C | | 5410 | 26725 | 156.05 | 44.59 | | |
| T2D-25C | | 3852 | 18935 | 110.56 | 31.59 | | |
| T2D-25C | | 2989 | 14620 | 85.37 | 24.39 | | |
| T2D-25C | | 2450 | 11925 | 69.63 | 19.89 | 30.1 | 5.4 |
| T1M-25C | | 5357 | 26460 | 154.50 | 44.14 | | |
| T1M-25C | | 7348 | 36415 | 212.63 | 60.75 | | |
| T1M-25C | | 3253 | 15940 | 93.07 | 26.59 | | |
| T1M-25C | | 1665 | 8000 | 46.71 | 13.35 | 36.2 | 10.3 |
| T6M-25C | | 1463 | 6990 | 40.82 | 11.66 | | |
| T6M-25C | | 1668 | 8015 | 46.80 | 13.37 | | |
| T6M-25C | | 1048 | 4915 | 28.70 | 8.20 | | |
| T6M-25C | | 696 | 3155 | 18.42 | 5.26 | 9.6 | 1.8 |

Based on the findings, de-PEGylation in vivo was not significant. Furthermore, when accelerated in vitro up to and including levels in the preparation incubated, dePEGylation was not observed to affect CBS activity or in vivo efficacy.

Consistent with the improvements in Met metabolites, all preparations led to elevated plasma CBS activity in all groups, though the preparation incubated for 6 months was observed to have significantly lower than in the others on D25 ($p<0.04$), but not on D27. Again, the significant de-PEGylation in the preparation incubated for 1 month did not affect plasma CBS activity levels achieved in vivo, with results comparable to those with the control.

Specific activities of the control, preparation incubated for 2 days, preparation incubated for 1 month, and preparation incubated for 6 months were 2324.11, 1714.19, 1786.08, and 1318.76 U/mg protein, respectively, when assayed using the same method, monitoring radioactive Ser conversion. The preparation incubated for one month (T1M-25C), that was significantly de-PEGylated as compared with the control, showed similar activity to the control.

Example 5. Western Blot Analysis of De-PEGylation In Vivo

To assess whether the drug product was subject to de-PEGylation in vivo, plasma aliquots from CBSDH model mice treated with the control were analyzed by western blotting. On D2, the PEGylation pattern in the plasma samples was observed to be similar to that in the control prior to injection, with no un-PEGylated enzyme detected and no evident trend toward a higher abundance of less PEGylated bands. On D27, collected at 72 hours after the final injection, there were small increases in un-PEGylated enzyme detected in all mice. However, the change in PEGylation pattern was minor when compared with the pre-injection material and the ratios among the different bands were approximately the same on D27 as on D2. Similarly, de-PEGylation in vivo was minimal with the other preparations, even though, prior to injection, preparations incubated for 1 month and 6 months showed, by RP-HPLC, substantial levels of de-PEGylated enzyme, including unmodified CBS, especially in the preparation incubated for 6 months. It is possible that these most de-PEGylated forms degraded or were cleared more rapidly after injection, so therefore were not present in the plasma samples analyzed by western blotting. Similar analyses of the other three preparations also showed minimal de-PEGylation once they were injected in vivo.

Example 6. Comparison of the Efficacy of Long-Term Treatment with 20NHS PEG-CBS to a Met-Restricted Diet Dysregulation of sulfur amino acid metabolism is the key feature of HCU phenotype in both human patients and mouse models of the disease. Sustained improvement or regaining of the metabolic control are the key aspects of successful treatment (see Morris et al. (2017) J Inherit Metab Dis 40, 49-74; Majtan et al. (2017) FASEB J 31, 5495-5506; Majtan et al. (2018) Enzyme Replacement Therapy Ameliorates Multiple Symptoms of Murine Homocystinuria. Molecular therapy: the journal of the American Society of Gene Therapy 26, 834-844; each of which is hereby incorporated by reference in its entirety). Beginning from week 4 of age, mice were maintained on diets with normal (REG) or restricted (MRD) methionine content and received subcutaneous injections of either PBS vehicle or 10 mg/kg 20NHS PEG-CBS three times a week until the study end at week 22 of age. Table 9 show levels of plasma sulfur metabolites in mice at 18 weeks of age. Representative snapshots at plasma concentrations of total homocysteine, total cysteine, cystathionine, methionine and SAM/SAH ratio are provided. Study groups described and analyzed in this and subsequent Examples herein are summarized as follows:

WT (REG+PBS) refers to wild type mice on normal diet receiving subcutaneous injection of PBS;

WT (REG+20 NHS PEG-CBS) refers to wild type mice on normal diet receiving subcutaneous injection of 20NHS PEG-CBS;

I278T (REG+PBS) refers to I278T mice on normal diet receiving subcutaneous injection of PBS;

I278T (REG+20NHS PEG-CBS) refers to I278T mice on normal diet receiving subcutaneous injection of 20NHS PEG-CBS;

WT (MRD+PBS) refers to wild type mice on Met-restricted diet receiving subcutaneous injection of PBS;

WT (MRD+20NHS PEG-CBS) refers to wild type mice on Met-restricted diet receiving subcutaneous injection of 20NHS PEG-CBS;

I278T (MRD+PBS) refers to I278T mice on Met-restricted diet receiving subcutaneous injection of PBS; and I278T (MRD+20NHS PEG-CBS) refers to I278T mice on Met-restricted diet receiving subcutaneous injection of 20NHS PEG-CBS.

and entirely normalized at 14 μM in mice on the MRD diet ($p<0.001$) compared to vehicle-injected I278T mice. Plasma Cys levels were, almost 3-fold lower in I278T mice on the REG diet receiving vehicle compared to the controls (105 versus 295 μM, $p<0.001$) and within a normal range in all the remaining groups. Consistent with its role as the product of the reaction catalyzed by 20NHS PEG-CBS, plasma Cth levels were elevated in all mice receiving 20NHS PEG-CBS treatment compared to their vehicle-injected counterparts. The elevation of plasma Cth depended on the concentration of Hcy, the limiting substrate, reaching 76 and 18 μM in I278T mice on the REG and MRD diets, respectively ($p<0.001$). The 20NHS PEG-CBS retained its efficacy even when substrate concentrations were very low as indicated by about 8-fold higher plasma Cth levels in 20NHS PEG-CBS-treated controls compared to those receiving vehicle. Plasma Met levels were higher in all groups on the REG than on the MRD diet. However, plasma Met levels in I278T on the MRD were similar to the controls on the REG diet (51 versus 52 μM, p=ns) and were normalized by 20NHS PEG-CBS treatment (30 μM, $p<0.001$). The ratio of SAM to SAH, reflecting methylation capacity, was substantially reduced in I278T mice on the REG diet (0.12) and partially elevated on the MRD diet (1.77) compared to the respective controls (3.29 and 3.84 in WT on the REG and MRD diets, respectively; $p<0.001$). With 20NHS PEG-CBS treatment, the SAM/SAH ratios were significantly improved and fully normalized in I278T mice on the REG (2.26, $p<0.001$) and MRD (4.01, $p<0.001$), respectively. In general, differences among groups described herein for W18 time point were consistent with those observed during the entire course of the study.

Guidelines for management of CBS-deficient HCU recommend keeping plasma total Hcy concentration below 50 and 100 μM in patients who are fully responsive and non-responsive to pyridoxine, respectively (see Morris et al. (2017) J Inherit Metab Dis 40, 49-74, which is hereby incorporated by reference in its entirety). In our study, I278T mice were unable to achieve this target level even when maintained on severe Met restriction receiving 8-times less

TABLE 9

Plasma metabolite levels

| Mouse Model | Plasma metabolite [uM] | | | | | | | | | |
|---|---|---|---|---|---|---|---|---|---|---|
| | tHcy | SEM | tCys | SEM | Cth | SEM | Met | SEM | SAM/SAH ratio | SEM |
| WT (REG + PBS) | 13.4 | 1.0 | 294.7 | 7.2 | 1.4 | 0.1 | 52.0 | 2.1 | 3.3 | 0.2 |
| WT (REG + 20NHS PEG-CBS) | 5.5 | 0.3 | 281.1 | 7.3 | 10.9 | 0.6 | 65.5 | 5.8 | 4.9 | 0.3 |
| I278T (REG + PBS) | 423.0 | 22.1 | 104.5 | 3.6 | 1.0 | 0.1 | 59.6 | 3.0 | 0.1 | 0.0 |
| I278T (REG + 20NHS PEG-CBS) | 40.7 | 2.8 | 268.5 | 8.9 | 76.0 | 7.2 | 71.5 | 4.3 | 2.3 | 0.2 |
| WT (MRD + PBS) | 15.7 | 1.8 | 304.1 | 9.7 | 1.0 | 0.1 | 31.9 | 1.6 | 3.8 | 0.2 |
| WT (MRD + 20NHS PEG-CBS) | 6.1 | 0.4 | 278.8 | 9.4 | 8.3 | 0.8 | 21.0 | 1.4 | 4.9 | 0.3 |
| I278T (MRD + PBS) | 139.8 | 16.1 | 257.6 | 4.7 | 0.6 | 0.0 | 50.9 | 1.9 | 1.8 | 0.3 |
| I278T (MRD + 20NHS PEG-CBS) | 13.7 | 1.5 | 327.3 | 13.2 | 17.7 | 1.3 | 29.9 | 1.7 | 4.0 | 0.4 |

As shown in Table 9, plasma Hcy levels were in the normal healthy range (about 16 μM) in WT mice regardless of diet or treatment. However, in I278T mice on REG diet receiving vehicle, plasma Hcy levels were greatly elevated compared to the controls (423 μM, $p<0.001$). On the MRD diet, plasma Hcy levels were substantially lower (140 μM i.e. 67% decrease), but still remained markedly elevated compared to the controls ($p<0.001$). The 20NHS PEG-CBS treatment significantly decreased plasma Hcy levels in I278T mice on the REG diet to 41 (90% decrease, $p<0.001$)

Met than the standard recommended intake for mouse (0.5 g/kg and 4 g/kg Met in the MRD and REG diets, respectively). Except the initial sample taken at week 6 of age, plasma Hcy levels fluctuated between 121-195 μM in I278T mice on the MRD during the study. Using the same mouse model as shown in Gupta et al. (2014) Cystathionine beta-synthase-deficient mice thrive on a low-methionine diet. FASEB J 28, 781-790, which is hereby incorporated by reference in its entirety, similar MRD diet containing 0.5 g/kg Met was found to decrease serum Hcy to 81 μM in 34-weeks-old I278T mice. The difference could be attributed to age of mice and length of their maintenance on the diet. In contrast, plasma Hcy levels of I278T mice on the REG diet and treated with 20NHS PEG-CBS varied in 26-41 µM range, except the last sample taken at week 22 of age. Moreover, administration of 20NHS PEG-CBS to I278T mice on the MRD diet completely normalized plasma Hcy below 15 µM. This data suggests that, unlike ET, even severe Met restriction cannot bring plasma Hcy levels to therapeutic target in HCU mice. If the full metabolic normalization is desired, a combination of ET with some level of Met restriction would be needed to achieve this goal.

These results are evidence that full metabolic normalization is not required to achieve correction of HCU phenotype and thus there seems to exist a threshold effect when it comes to manifestation of HCU phenotype in mice. In fact, less severe mouse models of HCU with plasma Hcy levels between 170 and 300 µM had much less severe phenotype (see, Gupta et al. (2009)). Mouse models of cystathionine beta-synthase deficiency reveal significant threshold effects of hyperhomocysteinemia. FASEB J 23, 883-893, which is hereby incorporated by reference in its entirety) or showed no clinical symptoms of HCU (see Majtan et al. (2018) Human mutation 39, 210-218, which is hereby incorporated by reference in its entirety). It seems this threshold applies to human patients as well as treated HCU patients showed reduced risk and incidence of vascular events despite failing to achieve metabolic normalization (see Wilcken et al. (1997) Journal of Inherited Metabolic Disease 20, 295-300; Yap et al. (2000) Vascular complications of severe hyperhomocysteinemia in patients with homocystinuria due to cystathionine beta-synthase deficiency: effects of homocysteine-lowering therapy. Seminars in thrombosis and hemostasis 26, 335-340; Yap et al. (2001) Vascular outcome in patients with homocystinuria due to cystathionine beta-synthase deficiency treated chronically: a multicenter observational study. Arteriosclerosis, thrombosis, and vascular biology 21, 2080-2085; each of which is hereby incorporated by reference in its entirety).

Example 7. Flow-Mediated Vasodilation (FMD)

I278T mice suffer from endothelial dysfunction, and thromboembolism is the major cause of morbidity and early death of HCU patients (see Majtan et al. (2018) Human mutation 39, 210-218, which is hereby incorporated by reference in its entirety). As the presence of endothelial dysfunction is closely associated with cardiovascular risk, endothelium-dependent flow-mediated vasodilation (FMD) was evaluated in femoral artery of the studied mice (data not shown). Endothelium-dependent flow-mediated vasodilation was performed as described in (see Schuler et al. (2014) Measurement of endothelium-dependent vasodilation in mice—brief report. Arteriosclerosis, thrombosis, and vascular biology 34, 2651-2657, which is hereby incorporated by reference in its entirety). mice were anesthetized with isoflurane (3% induction and 1.5% maintenance). Body temperature was kept at 37±1° C. by using a heated examination table that was also equipped with EKG electrodes and monitored using rectal thermometer probe. Hindlimbs were shaved and covered with warm ultrasound gel. The ultrasound probe was attached to a stereotactic holder and was manually aligned with the femoral vein visible at the upper inner thigh. the high-frequency, high-resolution Vevo 2100 imaging platform equipped with 30-70 MHz linear array microscan transducer (Fujifilm VisualSonics, Toronto, ON, Canada) was used to image the femoral arteries in mice. A vascular occluder (Docx, Ukiah, CA, USA) was placed around the lower limb to induce occlusion of the distal hindlimb as an ischemic trigger. Once a clear image of the vessel wall was obtained and baseline readings recorded, the experiment started by inflation of the vascular occluder for 5 minutes. Following hindlimb ischemia, the cuff was deflated, and FA diameter measurements were continuously recorded for 5 minutes at 30 second intervals. Femoral artery diameter in acquired images was determined offline manually.

To determine the effects of long-term administration of the drug product on clinical symptoms of murine HCU, I278T mice (+/+ and -/-) on a Met-restricted diet (MRD) were administered either a vehicle (PBS) or 20NHS PEG-CBS at 10 mg/kg (drug product) three times a week through the age of Week 22. Mice were on one of two diets: 1) a regular diet (REG) with 4.0 g/kg Met, or 2) a Met-restricted diet (MRD) with 0.5 g/kg Met. Mice were divided into the following groups: A (+/+, REG, PBS); B (+/+, REG, drug product); C (-/-, REG, PBS); D (-/-, REG, drug product); E (+/+, MRD, PBS); F (+/+, MRD, drug product); G (-/-, MRD, drug product); H (-/-, MRD, drug product).

I278T mice were observed to show significant loss of femoral artery flexibility (i.e. arterial rigidity) compared to the control group (+/+) with drug treatment normalizing the phenotype. Femoral artery diameter at baseline T0 was observed to be smaller in mice on MRD than observed in mice on a REG diet. After recording the baseline values, 5 minutes of occlusion with no blood flow induced reactive hyperemia characterized by temporal increase of artery diameter before returning to baseline. Table 10 shows the femoral artery diameter of mice on the REG or MRD diet as evaluated in 19-week-old mice.

TABLE 10

Femoral artery diameters

| Mouse model | Timepoint [minutes] | | | | | | | | | | | |
|---|---|---|---|---|---|---|---|---|---|---|---|---|
| | -120 | 0 | 30 | 60 | 90 | 120 | 150 | 180 | 210 | 240 | 270 | 300 |
| WT (REG + PBS) | 197.0 | 204.4 | 222.8 | 232.7 | 238.4 | 234.6 | 225.8 | 218.6 | 210.9 | 201.7 | 199.2 | 197.1 |
| SEM | 1.0 | 1.6 | 2.1 | 2.2 | 1.8 | 2.9 | 3.0 | 3.5 | 2.5 | 1.0 | 1.4 | 1.4 |
| WT (REG + 20NHS PEG-CBS) | 196.6 | 209.4 | 225.9 | 232.0 | 231.4 | 232.7 | 227.7 | 222.2 | 218.4 | 211.8 | 207.6 | 202.7 |
| SEM | 1.4 | 3.0 | 4.9 | 4.5 | 3.8 | 3.8 | 3.6 | 3.6 | 3.9 | 3.3 | 2.7 | 2.8 |
| I278T (REG + PBS) | 196.3 | 205.6 | 205.7 | 209.4 | 215.6 | 215.7 | 211.5 | 210.8 | 205.8 | 202.5 | 198.1 | 198.0 |
| SEM | 1.5 | 0.6 | 2.8 | 2.2 | 2.7 | 3.4 | 2.8 | 2.6 | 2.4 | 2.0 | 1.6 | 1.2 |
| I278T (REG + 20NHS PEG-CBS) | 194.8 | 203.6 | 215.9 | 226.5 | 231.7 | 232.3 | 229.1 | 222.5 | 216.9 | 208.6 | 203.1 | 199.9 |
| SEM | 2.0 | 2.8 | 3.3 | 3.4 | 4.5 | 4.5 | 4.4 | 4.5 | 4.2 | 4.1 | 3.1 | 2.3 |
| WT (MRD + PBS) | 194.0 | 202.8 | 214.5 | 219.1 | 227.9 | 223.6 | 219.2 | 211.8 | 204.2 | 198.6 | 195.7 | 194.2 |
| SEM | 2.3 | 1.8 | 2.9 | 2.5 | 3.3 | 3.3 | 3.2 | 2.9 | 2.8 | 2.4 | 2.5 | 2.4 |

TABLE 10-continued

Femoral artery diameters

| Mouse model | Timepoint [minutes] | | | | | | | | | | | |
|---|---|---|---|---|---|---|---|---|---|---|---|---|
| | −120 | 0 | 30 | 60 | 90 | 120 | 150 | 180 | 210 | 240 | 270 | 300 |
| WT (MRD + 20NHS PEG-CBS) | 195.6 | 203.3 | 218.9 | 226.5 | 229.7 | 227.4 | 219.7 | 215.9 | 209.7 | 202.7 | 199.4 | 196.8 |
| SEM | 1.4 | 1.6 | 2.4 | 3.1 | 2.5 | 2.9 | 2.4 | 3.0 | 2.4 | 1.7 | 1.4 | 1.3 |
| I278T (MRD + PBS) | 196.0 | 204.1 | 216.5 | 225.8 | 230.4 | 232.5 | 226.2 | 220.0 | 213.7 | 208.3 | 203.1 | 199.5 |
| SEM | 2.0 | 2.3 | 2.0 | 2.9 | 2.8 | 1.7 | 2.8 | 3.0 | 3.1 | 3.2 | 3.0 | 2.7 |
| I278T (MRD + 20NHS PEG-CBS) | 195.6 | 208.9 | 222.7 | 229.5 | 236.2 | 234.8 | 225.3 | 219.4 | 212.2 | 205.9 | 201.5 | 198.7 |
| SEM | 2.5 | 2.0 | 3.5 | 3.3 | 3.1 | 2.8 | 2.1 | 3.5 | 3.3 | 3.3 | 3.5 | 2.9 |

As shown in Table 10, I278T mice on the REG diet receiving vehicle clearly showed endothelial dysfunction as indicated by significantly lower maximal dilation of the femoral artery at 60 and 90 second time points (both 216 µm) following 5 minutes ischemia compared to the controls (238 and 235 µm, p<0.001) as well as I278T mice on the same diet, but receiving 20NHS PEG-CBS treatment (both 232 µm, p<0.01). I278T mice receiving vehicle on the REG diet showed significantly decreased response compared to all other groups. In contrast, none of the mice on the MRD diet showed any signs of impaired endothelial function and exhibited a normal vascular response to ischemia with and without 20NHS PEG-CBS treatment.

Treatment of I278T mice on MRD was observed to normalize the femoral artery diameter to the same level as mice on a REG diet.

Example 8. Carotid Artery Chemical Injury Thrombosis Model (CITM)

Measurements carotid artery chemical injury thrombosis model (CITM) were performed as described in Marchi et al. (2012) Thrombosis and hemostasis 108, 516-526, which is hereby incorporated by reference in its entirety. Mice were anesthetized with intraperitoneal injection of combination of ketamine (induction dose of 80-100 mg/kg, then 10-20 mg/kg/hr for maintenance) and xylazine (induction dose of 8-16 mg/kg, then 1-2 mg/kg/hr for maintenance) and body temperature maintained at 36-38° C. using heating pad and monitored with a rectal thermometer probe. The trachea was exposed and cannulated and the animals were ventilated mechanically with air and supplemental oxygen. The common carotid arteries were exposed, and baseline flow was monitored with a 0.5 PBS Doppler flow probe (Transonic Systems, Ithaca, NY, USA). For the artery injury, a 1×1 mm Whatman filter paper soaked in 10% ferric chloride solution was placed on the carotid artery for 1 minute. Blood flow in the vessel was monitored and recorded for up to 20 minutes, using the ultrasound probe. The time to occlusion (TTO) was defined as the time between FeCl3 administration and lack of flow for 1 minute. Blood was drawn from the inferior vena cava into a syringe flushed with 3.2% sodium citrate and processed to platelet-poor plasma by centrifugation at 5,000×g for 10 min. At the end of the procedure, the mice were euthanized by cervical dislocation followed by bilateral thoracotomy. Table 11 shows results from the Carotid artery chemical injury thrombosis model (CITM). Time to stable occlusion in the carotid artery after chemical injury induced by 10% $FeCl_3$ was determined in 22-week-old mice. Only I278T mice on the REG diet and receiving vehicle showed significantly increased time to occlusion, while the MRD diet and/or the treatment with 20NHS PEG-CBS normalized this parameter to control levels. "CBS" in Table 11 represents 20NHS PEG-CBS.

TABLE 11

| | Time to occlusion | | | | | | | |
|---|---|---|---|---|---|---|---|---|
| | Wild-type (WT) | | | | I278T | | | |
| | REG + PBS | REG + CBS | MRD + PBS | MRD + CBS | REG + PBS | REG + CBS | MRD + PBS | MRD + CBS |
| Time to Occlusion [min:sec:ms] | 8:41:40 | 8:48:30 | 9:17:51 | 8:26:14 | 10:58:42 | 8:48:39 | 7:33:55 | 7:53:26 |
| SEM | 12:19:29 | 12:30:24 | 12:40:56 | 12:17:19 | 12:47:22 | 12:34:05 | 12:24:22 | 12:25:21 |

I278T mice showed delay in experimental thrombosis, which was normalized by either treatment. To assess whether I278T mice display pro-thrombotic phenotype and, if so, how diet and enzyme therapy would affect it, experimental thrombosis of the common carotid artery was induced using 10% $FeCl_3$. The vehicle-injected I278T mice on the REG diet displayed substantially longer times to stable occlusion that did the other groups (10 minutes 59 seconds), indicating that, unlike HCU patients, I278T mice do not show a pro-thrombotic phenotype, and moreover, showed significant delays in thrombosis compared with controls (8 minutes 42 seconds, p<0.05). Interestingly, treatment of I278T mice with 20NHS PEG-CBS (8 minutes 49 seconds) or with the MRD diet (7 minutes 34 seconds) normalized the times for occlusion to values seen in controls.

Thromboembolism is the major cause of morbidity and mortality in HCU (see, Mudd, et al. (2001) Disorders of transsulfuration. In The Metabolic and Molecular Bases of Inherited Disease (Scriver, C. R., Beaudet, A. L., Sly, W. S., Valle, D., Childs, B., Kinzler, K., and Vogelstein, B., eds) pp. 2007-2056, McGraw-Hill, New York; Morris et al. (2017) *J Inherit Metab Dis* 40, 49-74; each of which is hereby incorporated by reference in its entirety), yet I278T mice on the REG diet receiving placebo failed to exhibit the propensity for thrombosis despite significant endothelial dysfunction. Similar finding was reported earlier using the same I278T mouse model (see, Dayal et al. (2012) Blood 119, 3176-3183, which is hereby incorporated by reference in its entirety) as well as for total CBS knock-out mouse (see Maclean et al. (2010) Molecular Genetics and Metabolism 101, 163-171; which is hereby incorporated by reference in its entirety).

Both the endothelial dysfunction and paradoxically prolonged time to occlusion have been normalized in I278T mice on the MRD diet or those on the REG diet, but treated with 20NHS PEG-CBS. These results indicate that, despite lack of hypercoagulative state in I278T mice, Met restriction or administration of 20NHS PEG-CBS may be effective in correcting pathological hemostasis observed in other mouse models of HCU and, more importantly, in human patients.

Example 9. Behavioral Testing

In all behavioral studies, the experimenter was blinded with regard to the genotype, diet and treatment of the mice. The open-field task examines aspects of anxiety-like behavior (see Prut et al. (2003) European journal of pharmacology 463, 3-33, which is hereby incorporated by reference in its entirety). Mice freely explored an open box (44×44×24 cm) while being tracked from above for a 10 min trial. Prior to starting the trial, the center and perimeter were delineated using the animal tracking software (Ethovision XT, Noldus, Wageningen, Netherland). The software was used to determine the amount of time spent in the center versus periphery, as well as the distance travelled.

The puzzle box task was performed as previously described in Ben Abdallah et al. (2011) Experimental neurology 227, 42-52, which is hereby incorporated by reference in its entirety. mice were given 3 min to enter a goal box (15×28×28 cm). If the mouse did not enter the goal box, it was encouraged and directed by the experimenter. The covered goal box was adjacent to a well-lit uncovered arena (58×28×28 cm). The entry of the goal box began as a doorway (trial 1), then was changed to an underpass (trials 2, 3, 4), the underpass was then filled with sawdust (trials 5, 6, 7), and then the filled underpass was covered with a small rectangular piece of cardboard (trials 8, 9). Each mouse underwent nine trials over a period of 3 days. The first day consisted of trials 1-3, the second day consisted of trials 4-6, and trials 7-9 occurred on the third day.

To test higher-order cognitive functioning, a problem-solving test was administered, in which mice are required to complete escape tasks of increasing difficulty within a limited amount of time. A puzzle box arena was designed with a PLEXIGLAS' white box divided with a black barrier into two compartments, start and goal zones. Mice were introduced into a brightly-lit start zone and were observed to prefer the smaller covered/dark goal zone, which is accessible through a narrow underpass. The tests consisted of nine trials distributed over three consecutive days during which mice are trained to overcome obstructions at the underpass in order to access the goal zone. Obstructions were three kinds and ranged from easy to intermediate and difficult. Table 12 is a summary of trials 1-9 (T1-T9).

TABLE 12

Summary of trials

| | T1 | T2 | T3 | T4 | T5 | T6 | T7 | T8 | T9 |
|---|---|---|---|---|---|---|---|---|---|
| Underpass | None | Open | Open | Open | Sawdust | Sawdust | Sawdust | Sawdust + Cover | Sawdust + Cover |

Either treatment of I278T mice improves their learning capability and cognition, but Met restriction increases anxiety. Developmental delay and various psychiatric symptoms are common among HCU patients. First, the open field test was performed to assess anxiety level and locomotor activity in studied mice. Table 13 and Table 14 show results of an open field test. Table 13 shows the distance traveled for each group of mice.

TABLE 13

Distance traveled [centimeters (cm)]

| WT-REG | WT-MRD | I278T-REG | I278T-MRD |
|---|---|---|---|
| 3873 | 5839 | 3326 | 3506 |
| 4665 | 4420 | 3569 | 4854 |
| 4202 | 5906 | 3397 | 4927 |
| 3990 | 6367 | 3684 | 6484 |
| 6161 | 3443 | 2968 | 4511 |
| 3754 | 3243 | 3713 | 6169 |
| 4541 | 4920 | 2860 | 4400 |
| 3668 | 3348 | 2732 | 4210 |
| 4123 | 5442 | 2184 | 4293 |
| 4319 | 5534 | 7454 | 5148 |
| 3960 | 5839 | 5650 | 4896 |
| 3484 | 5747 | 2256 | 4585 |
| 4581 | 6029 | 3033 | 5398 |
| 3954 | 4699 | 3083 | 3100 |
| 3988 | 3676 | 3289 | 5876 |
| 2985 | 4584 | 9967 | 5630 |
| 3606 | 4229 | 3798 | 5362 |
| 3463 | 5140 | 5028 | 5791 |
| | 4912 | 3951 | 7466 |
| | 4667 | 5851 | 4750 |
| | | 4703 | 4405 |
| | | 4522 | |
| | | 3816 | |
| | | 3970 | |
| | | 3155 | |
| | | 5986 | |
| | | 4390 | |

Table 14 shows the time spent in the center for each group of mice.

TABLE 14

Time spent in center [seconds]

| WT-REG | WT-MRD | I278T-REG | I278T-MRD |
|---|---|---|---|
| 82 | 102 | 211 | 275 |
| 157 | 94 | 159 | 150 |
| 175 | 110 | 169 | 159 |
| 110 | 84 | 155 | 170 |
| 188 | 75 | 224 | 199 |
| 381 | 155 | 412 | 110 |
| 170 | 183 | 358 | 139 |
| 204 | 60 | 332 | 142 |
| 180 | 130 | 159 | 113 |
| 290 | 89 | 194 | 167 |

TABLE 14-continued

Time spent in center [seconds]

| WT-REG | WT-MRD | I278T-REG | I278T-MRD |
|---|---|---|---|
| 199 | 147 | 212 | 165 |
| 249 | 72 | 106 | 151 |

TABLE 14-continued

Time spent in center [seconds]

| WT-REG | WT-MRD | I278T-REG | I278T-MRD |
|---|---|---|---|
| 248 | 124 | 399 | 199 |
| 221 | 120 | 172 | 220 |
| 162 | 135 | 131 | 103 |
| 244 | 180 | 219 | 130 |
| 170 | 289 | 372 | 179 |
| 208 | 117 | 232 | 64 |
| 128 | 40 | 337 | 141 |
| 254 | 97 | 164 | 233 |
| 268 | | 221 | 164 |
| 182 | | 131 | |
| 348 | | 252 | |
| 85 | | 171 | |
| 187 | | 142 | |
| | | 206 | |
| | | 198 | |
| | | 101 | |
| | | 274 | |
| | | 102 | |
| | | 234 | |

No significant impact of 20NHS PEG-CBS treatment on anxiety level or locomotion of both the control and I278T mice was observed. However, the mice on the MRD, regardless of genotype, showed significantly increased distance traveled in the testing arena (p<0.01) and were more anxious as they spent less time in center of the arena (p<0.001) compared with the mice on the REG diet. While mouse gender and PBS vehicle or 20NHS PEG-CBS injections did not show any significant impact on mice behavior, the REG (filled symbols) and MRD (open symbols) diets resulted in changes in locomotion and anxiety level in both WT and I278T mice.

Second, cognition/executive function of the studied mice was evaluated in the puzzle box test (FIG. 2), where mice must reach a dark goal box to escape brightly lit arena. Table 15 shows the time to reach the goal box in WT and I278T mice on either diet receiving vehicle or 20NHS PEG-CBS. This sequence enabled assessment of problem-solving abilities (Trials number 2, 5 and 8) and learning/short-term memory (Trials number 3, 6 and 9). In addition, repetition on the next day provided a measure of long-term memory (Trials number 4 and 7).

TABLE 15

Time to goal box

| Mouse Model | Trial 1 | 2 | 3 | 4 | 5 | 6 | 7 | 8 | 9 |
|---|---|---|---|---|---|---|---|---|---|
| WT (REG + PBS) | 90.3 | 50.0 | 34.8 | 27.5 | 136.7 | 98.7 | 70.4 | 101.9 | 134.5 |
| SEM | 20.4 | 17.8 | 16.4 | 10.3 | 26.4 | 20.9 | 20.6 | 22.0 | 25.0 |
| WT (REG + 20NHS PEG-CBS) | 113.6 | 45.5 | 39.3 | 15.8 | 157.6 | 49.9 | 40.3 | 84.3 | 79.4 |
| SEM | 21.2 | 18.5 | 17.1 | 10.7 | 27.5 | 21.7 | 21.5 | 22.8 | 26.0 |
| I278T (REG + PBS) | 107.1 | 77.5 | 63.4 | 42.6 | 237.5 | 174.7 | 166.6 | 195.8 | 201.6 |
| SEM | 16.4 | 14.3 | 13.3 | 8.3 | 21.3 | 16.8 | 16.6 | 17.7 | 20.1 |
| I278T (REG + 20NHS PEG-CBS) | 97.5 | 28.3 | 32.3 | 15.8 | 146.4 | 71.2 | 72.7 | 95.1 | 93.5 |
| SEM | 23.2 | 20.3 | 18.8 | 11.7 | 30.1 | 23.8 | 23.5 | 25.0 | 28.5 |
| WT (MRD + PBS) | 80.9 | 25.3 | 24.8 | 10.9 | 100.8 | 18.0 | 40.8 | 52.9 | 47.0 |
| SEM | 24.5 | 21.4 | 19.8 | 12.4 | 31.7 | 25.1 | 24.8 | 26.4 | 30.0 |
| WT (MRD + 20NHS PEG-CBS) | 71.2 | 22.6 | 15.2 | 17.2 | 103.8 | 51.2 | 49.5 | 82.0 | 50.3 |
| SEM | 22.2 | 19.3 | 17.9 | 11.2 | 28.7 | 22.7 | 22.4 | 23.9 | 27.2 |
| I278T (MRD + PBS) | 55.2 | 30.9 | 18.5 | 6.5 | 100.6 | 19.7 | 22.2 | 41.9 | 59.6 |
| SEM | 20.4 | 17.8 | 16.4 | 10.3 | 26.4 | 20.9 | 20.6 | 22.0 | 25.0 |
| I278T (MRD + 20NHS PEG-CBS) | 44.4 | 29.3 | 15.0 | 9.6 | 123.9 | 55.5 | 55.3 | 98.5 | 98.5 |
| SEM | 26.0 | 22.7 | 21.0 | 13.1 | 33.6 | 26.6 | 26.3 | 28.0 | 31.8 |

Access to the goal box was made more difficult by each trial as indicated in Table 15, which shows the time in seconds required in each of 9 trials for mice in the study groups to get to the goal box. Mean and standard error of the mean (SEM) were calculated for the results provided in Table 15 (data not shown). Control mice on either diet receiving vehicle or 20NHS PEG-CBS performed similarly with no signs of cognitive impairment. On other hand, I278T mice on the REG diet showed significantly poorer performance, indicating cognitive impairment, compared with those on the MRD diet or controls (p<0.001). With 20NHS PEG-CBS treatment, the I278T mice performed as well as control mice on both diets.

I278T mice on a REG diet and PBS injections were observed to be cognitively impaired compared to I278T mice on a MRD diet and PBS injections and the mice on both REG and MRD diets injected with the drug product. The conclusion was supported by the inability of the mice on a REG diet with PBS injections to reach the goal box in time, when the difficulty of the task is increased (i.e., trials 5-10). No significant differences in the time to reach the goal box was observed between the mice on a REG diet or on a MRD diet, in which both groups were administered the drug product.

Figure 2:
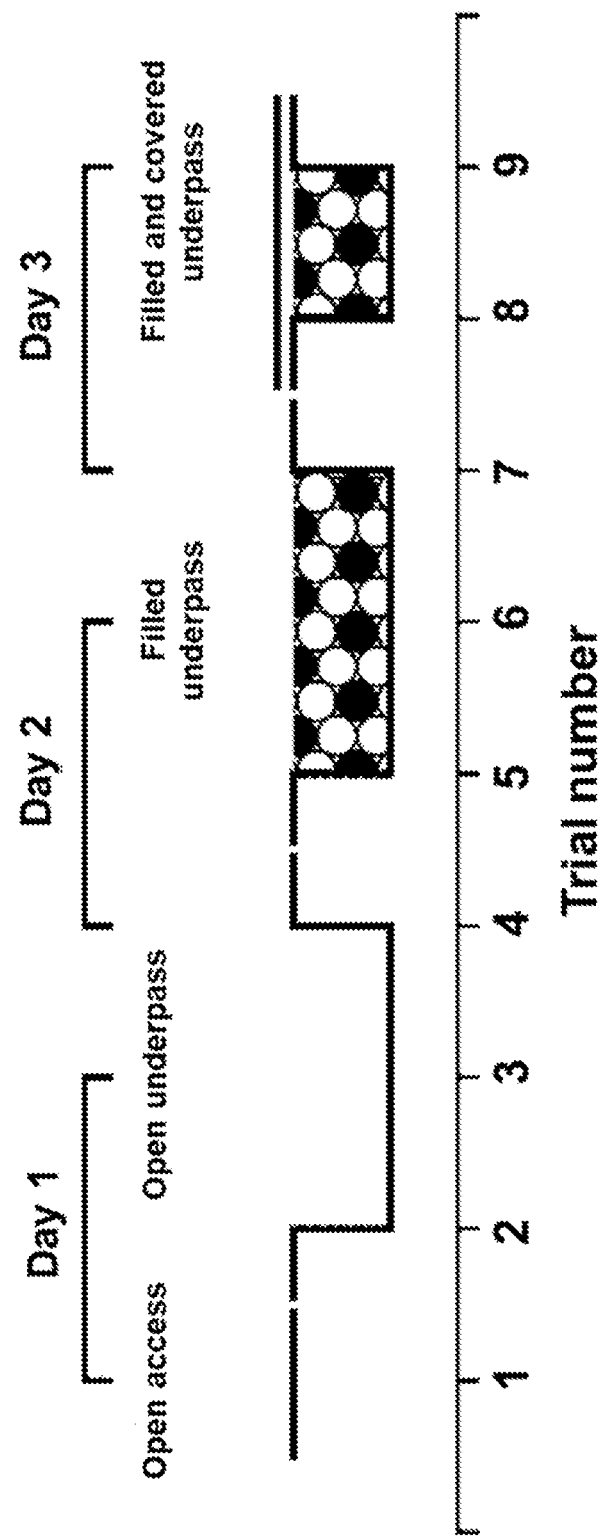
FIG. 2 is a diagram of entry conditions in the puzzle box test for each trial during the three-day testing period.

Many psychological and psychiatric conditions are common in HCU patients, such as psychosis, obsessive-compulsive disorder, depression and behavior/personality disorders (see Abbott et al. (1987) American Journal of Medical Genetics 26, 959-969, which is hereby incorporated by reference in its entirety). In addition, individuals with HCU have many developmental and cognitive difficulties with significant number of cases having learning disability and lower IQs (see El Bashir et al. JIMD reports 21, 89-95, which is hereby incorporated by reference in its entirety). Behavioral testing of our mice showed that this phenotype is indeed replicated in I278T mice showing cognitive impairment when maintained on the REG diet and receiving vehicle compared with controls and I278T mice maintained on the MRD or treated with 20NHS PEG-CBS (FIG. 2 and Table 15). To our knowledge this is the first report of such phenotype and its successful correction in any mouse model of CBS-deficient HCU. In addition, mice showed significantly increased activity and anxiety level when maintained on the MRD compared with those on the REG diet.

I278T mice receiving vehicle on the REG diet were significantly cognitively impaired compared to the ones on the MRD diet as indicated by the longer time to reach goal box (Table 15). However, I278T injected with 20NHS PEG-CBS on the REG diet performed similarly as controls or I278T mice on the MRD diet (Table 15). Solid lines with filled symbols and dashed lines with open symbols designate mice on the REG and MRD diets, respectively. Data points in all plots represent average values and error bars show standard deviations (SDs).

These behavioral traits are likely unrelated to HCU as it affected mice regardless of genotype and 20NHS PEG-CBS treatment. It has been shown that essential amino acid deprivation, including Met restriction, is sensed in the anterior piriform cortex and subsequent glutamatergic signaling influences mice behavior (see Anthony et al. (2013) Detection of amino acid deprivation in the central nervous system. Current opinion in clinical nutrition and metabolic care 16, 96-101, which is hereby incorporated by reference in its entirety). Glutamate is the main excitatory neurotransmitter in the central nervous system, which could explain increased locomotion, restlessness and anxiety level.

Example 10. Dual-Energy X-Ray Absorptiometry (DEXA)

Bone density and body composition were assessed in anesthetized mice (combination of 60 mg/kg ketamine and 15 mg/kg xylazine in PBS injected intraperitoneally) using a GE Lunar PIXImus scanner (Lunar Corp., Madison, WI, USA). Mice were placed on a tray with their abdomen down and scanned from the neck down excluding the tail. After the scan, the mice were placed back into their cage to recover.

Met restriction impairs bone mineralization and body composition, while 20NHS PEG-CBS treatment normalizes phenotype of I278T on the REG diet. Among the clinical symptoms observed in HCU patients are thinness, low body mass index and osteoporosis (see Mudd et al. (2001) Disorders of transsulfuration. In The Metabolic and Molecular Bases of Inherited Disease (Scriver, C. R., Beaudet, A. L., Sly, W. S., Valle, D., Childs, B., Kinzler, K., and Vogelstein, B., eds) pp. 2007-2056, McGraw-Hill, New York, which is hereby incorporated by reference in its entirety). Thus, mice were studied using DEXA to evaluate their bone mineral content and body composition. Table 16 shows results of a bone mineralization and body composition assessment by DEXA. The DEXA scans were performed when the mice reached age of 22 weeks. Table 16 includes bone mineral content, fat mass, and lean mass.

TABLE 16

DEXA results

| Parameters | BMC [g] | SEM | Fat mass [g] | SEM | Lean mass [g] | SEM |
|---|---|---|---|---|---|---|
| WT (REG + PBS) | 0.39 | 0.01 | 4.24 | 0.33 | 16.97 | 0.51 |
| WT (REG + 20NHS PEG-CBS) | 0.40 | 0.01 | 6.24 | 0.46 | 17.69 | 0.63 |
| I278T (REG + PBS) | 0.33 | 0.01 | 2.63 | 0.15 | 13.81 | 0.39 |
| I278T (REG + 20NHS PEG-CBS) | 0.40 | 0.01 | 5.08 | 0.36 | 17.11 | 0.47 |
| WT (MRD + PBS) | 0.34 | 0.01 | 5.51 | 0.49 | 14.71 | 0.43 |
| WT (MRD + 20NHS PEG-CBS) | 0.36 | 0.01 | 4.05 | 0.25 | 14.91 | 0.35 |
| I278T (MRD + PBS) | 0.35 | 0.01 | 6.07 | 0.23 | 16.02 | 0.38 |
| I278T (MRD + 20NHS PEG-CBS) | 0.36 | 0.01 | 4.89 | 0.20 | 15.18 | 0.39 |

On the REG diet, bone mineral content (BMC) was significantly lower in vehicle-receiving I278T mice compared to the controls (0.33 vs 0.39 g, $p<0.001$), while treatment with 20NHS PEG-CBS fully normalized it (0.4 vs 0.4 g, p=ns). On the MRD diet, all groups showed equivalent BMC (0.34-0.36 g), which was significantly reduced compared to the controls on the REG diet ($p<0.05$) and similar to vehicle-injected I278T mice on the REG diet. On the REG diet, I278T mice receiving vehicle were significantly leaner than those in other groups, specifically contained less fat tissue (2.63 vs 4.24 g, $p<0.01$) and lean mass (13.81 vs 16.97 g, $p<0.001$) that controls. Treatment with 20NHS PEG-CBS normalized body composition of I278T mice on the REG diet. On the MRD diet, amount of fat mass was comparable in all groups and similar to that of controls or 20NHS PEG-CBS-treated I278T mice on the REG diet. Likewise, amount of lean mass was similar in all groups on the MRD diet (14.71-16.02 g), but significantly reduced compared with controls and 20NHS PEG-CBS-treated I278T mice on the REG diet ($p<0.05$).

Skeletal abnormalities and connective tissue defects are the most prominent clinical symptoms in HCU patients (see Mudd et al. (2001) Disorders of transsulfuration. In The Metabolic and Molecular Bases of Inherited Disease (Scriver, C. R., Beaudet, A. L., Sly, W. S., Valle, D., Childs, B., Kinzler, K., and Vogelstein, B., eds) pp. 2007-2056, McGraw-Hill, New York, which is hereby incorporated by reference in its entirety). Osteoporosis, often associated with scoliosis, and low body mass index are typical findings in untreated or late diagnosed patients regardless of a severity of the disease (see Mudd et al. (2001) Disorders of transsulfuration. In The Metabolic and Molecular Bases of Inherited Disease (Scriver, C. R., Beaudet, A. L., Sly, W. S., Valle, D., Childs, B., Kinzler, K., and Vogelstein, B., eds) pp. 2007-2056, McGraw-Hill, New York; Parrot et al. (2000) J Inherit Metab Dis 23, 338-340; each of which is hereby incorporated by reference in its entirety). Decreased bone mineralization, low fat content and low overall weight was found in the KO and I278T (see Majtan et al. (2017) FASEB J 31, 5495-5506; Gupta et al. (2009) FASEB J 23, 883-893; Majtan et al. (2018) Enzyme Replacement Therapy Ameliorates Multiple Symptoms of Murine Homocystinuria. Molecular therapy: the journal of the American Society of Gene Therapy 26, 834-844; each of which is hereby incorporated by reference in its entirety), but not the HO mouse model of HCU (see Majtan et al. (2018) Human mutation 39, 210-218; which is hereby incorporated by reference in its entirety). As shown in Table 16, these findings were supported in I278T mice on the REG diet receiving vehicle as well as the efficacy of 20NHS PEG-CBS in normalizing this phenotype. On other hand, severe Met restriction resulted in a decreased bone mineralization, lower amount of lean mass and normal to increased amount of fat mass in all mice on the MRD regardless of genotype and treatment compared to WT mice on the REG diet. With exception of fat mass, MRD essentially yielded overall picture very similar to untreated I278T mice on the REG diet receiving vehicle. Previously, MRD diet was found very effective at correcting HCU phenotype in I278T mice including bone mineralization (see Gupta et al. (2014) FASEB J 28, 781-790; Kruger et al. (2016) Annals of the New York Academy of Sciences 1363, 80-90; each of which is hereby incorporated by reference in its entirety).

Example 11. Cause of Death of HCU Mice on High Met Diet

Data on mice indicated that severe Met restriction in HCU patients could lead to unwanted outcome. Female HO mice, but not male HO mice, were observed to die suddenly after switch to a high methionine diet (HMD), which included 8.2 g of MET per kg of diet. To analyze the cause of death, adult female HO mice were put on a HMD, adolescent I278T mice were put on a HMD diet, REG diet (Met 4.0 g of Met per kg of diet), or REG+0.1/0.2/0.4% Met in water. Mice were monitored daily, regularly weighed, and bled. Freshly found carcasses were subjected to necropsy and histological analysis.

Mice were sorted into 6 groups (A-F). Group A consisted of 7 female HO mice on a HMD. Group B consisted of one male I278T mouse and one female I278T mouse on HMD. Group C consisted of one male I278T mouse and one female I278T mouse on REG diet and supplemented with 0.4% Met. Group D consisted of one male I278T mouse and two female I278T mice on REG diet supplemented with 0.2% Met. Group E consisted of one male I278T mouse and one female I278T mouse on REG diet and supplemented with 0.1% Met. Group F consisted of one female I278T mouse and two male I278T mice on REG diet. Controls for gross necropsy included four female HO mice; two male and two females adult I278T and WT, 2 females adolescent I278T mice, and three male and three females adolescent I278T and WT mice. All necropsy controls were on the standard (STD) diet.

Three out of the seven female HO mice on the HMD died between day 11 and day 18. These mice were not thriving and losing weight or weight gain was completely halted. While on the HMD, both Hcy and Met were observed to increase substantially, while Cys was maintained low at all times. Preliminary histological findings showed degenerate ovarian follicles, exocrine pancreas with saponification of fat, vacuoles, and multifocal mineralization in cardiac muscle, medulla with dead neurons, thymic dysplasia with prominent apoptosis of T lymphocytes, liver steatosis, inflammation, and fibrosis.

For the I278T mice, plasma Hcy was observed to increase in the mice receiving supplemented Met in water and not from their diet. Plasma Met was observed to increase similarly to Hcy but depended on Met intake except for the control mice on the REG diet. Preliminary histological findings for the I278T mice showed exocrine pancreas with fibrosis and inflammation, liver inflammation, steatosi, degenerated hair follicles and intestinal epithelium, thymic dysplasia with prominent apoptosis of T lymphocytes, and blood in the duodenum.

Weight and metabolite levels over the time course were measured. Gross necropsy and optical histology are also performed.

Example 12. Toxicity Study in Non-Human Primates (NHP)

Toxicity of the drug product described herein was determined following subcutaneous (SC) administration once every 3 days and once every day to the NHP for 26 weeks.

Groups of 8 male and female cynomolgus monkeys received SC injections of vehicle control (PBS) or the drug product (dose volume about 0.4 mL/kg) according to the following study design. The top dose in this study represents a maximum feasible dose based on the maximum achievable concentration of 20NHS PEG-CBS in the formulation and the maximum dose volume that can be safely administered to monkeys by SC injection on a chronic basis (see Gad et al. Int J Toxicol. 2016 March-April; 35(2):95-178, which is hereby incorporated by reference in its entirety). The dose range spans the anticipated therapeutic dose range (0.5 to 7 mg/kg). The top dose was based on considerations of viscosity of the formulation for subcutaneous injection, recommended volumes for chronic injections in monkeys and the projected exposure time in monkeys compared to humans. Table 17 shows the details for treatment groups 1-6.

TABLE 17

Study Design for 26-Week Toxicology Study in NHP

| | | | | Number of Animals (per sex) | | |
| Group | Treatment | Frequency | Dose (mg/kg) | 13 Week | 17 Week (Recovery) | 26 Week |
| --- | --- | --- | --- | --- | --- | --- |
| 1 | Control | Every 3 days | 0 | 3 | 2 | 3 |
| 2 | Low | Every 3 days | 2 | 3 | 2 | 3 |
| 3 | Intermediate | Every 3 days | 7 | 3 | 2 | 3 |
| 4 | High | Every 3 days | 10 | 3 | 2 | 3 |
| 5 | Control 2 | Daily | 0 | 3 | 2 | 3 |
| 6 | Repeat dose | Daily | 0.5 | 3 | 2 | 3 |

Assessment of toxicity was based on mortality; clinical observations; body weights and temperature; blood pressure; qualitative food consumption; ophthalmic observations; physical, neurological, and respiratory examinations; ECG; and clinical and anatomic pathology. Blood samples were collected for metabolites and activity, complement (CH50), ADA and anti-PEG antibody, and TK analyses.

No drug product-related changes in PR interval, QRS duration, QT interval, corrected QT (QTc) interval, or heart rate were observed during the dosing phase for any of the groups. No rhythm abnormalities or qualitative ECG changes were attributed to the drug product during qualitative assessment of the ECGs.

No drug product-related effects on clinical pathology, organ weights, macroscopic findings were observed at any scheduled sacrifice. All animals survived to their scheduled sacrifice. Additionally, no drug product-related clinical observations; alteration in body weight, body weight gain, or blood pressure; or change in neurobehavioral observations, body temperature, or respiration were noted for any of the dosages.

Therefore, given the totality of the safety database for 20NHS PEG-CBS, PEG-related vacuolation is not expected to be a risk in human studies. The repeat dose toxicology data in cynomolgus monkeys, combined with the safety data in various mouse models of CBSDH following repeat dosing for up to 6 months, are considered appropriate and sufficient to support the human starting dose and dose escalation in a clinical trial.

SC injection sites were observed during the study described above. Minimal to slight perivascular mononuclear infiltrates at one or more subcutaneous injection sites was observed in NHP injected with the drug product in the repeat-dose.

Example 13. Treatment of Homocystinuria in Humans

To analyze the treatment of homocystinuria in humans, a two-part, double-blind, randomized, placebo-controlled study will be performed in patients with genetically confirmed CBSDH. Eligible patients will be enrolled and randomized in a 3:1 ratio of patients receiving the drug product to placebo. Cohorts will include patients aged between 16 and 65 years old, inclusive, with genetic confirmation of CBSDH and elevated plasma tHcy levels of greater than or equal to 80 µM. According to the 2016 Guidelines for the Diagnosis and Management of CBSDH, tHcy levels should be maintained as close to normal as possible (at or below 10 to 15 µM), and certainly below 100 µM (see Morris et al. J Inherit Metab Dis. 2017 January; 40(1):49-74, which is hereby incorporated by reference in its entirety). An inclusion criterion of greater than or equal to 80 µM allows inclusion of patients with typical levels of 100 µM while acknowledging day-to-day and assay variability. Alternatively, a tHcy level of greater than or equal to 30 may be used to define a patient with CBSDH.

The drug product will be supplied as a 1 mL sterile solution of the drug substance at 25±3 mg/mL filled into a 2 mL single use vial. Treatment will last 12 weeks with sentinel dosing and is divided into a dosing period and a study drug (drug product or placebo) washout period.

The study drug (drug product or placebo) will be administered via SC injection. Injection will occur in the arms, abdomen, thighs, or buttocks as determined by the administrator of the injection. The maximum volume per injection site was 2 mL or per the institution's standard procedures.

Three dose levels are planned to be evaluated sequentially via three consecutive cohorts. Each dose level cohort will include four subjects: three subjects will be randomized to receive the active drug (20NHS PEG-CBS) and one subject will be randomized to receive placebo (3:1 randomization ratio active/placebo). The study drug will be administered SC on a weekly basis. Each cohort will be administered the following dosages:
Cohort 1: 0.33 mg/kg;
Cohort 2: 0.66 mg/kg; and
Cohort 3: 1.0 mg/kg.

The dosing period will consist of 6 weekly doses of the study drug followed by a 6-week period during which no study drug is administered. A study with an extended dosing period using the protocol below will be performed for longer than 12 weeks.

During Week 1 on Day 1, each subject is admitted to the clinical site as an inpatient for a minimum 24-hour stay during which he/she undergoes pre-dose and post-dose safety monitoring (vital signs, 12-lead ECG), blood sampling for safety laboratory parameters, blood sampling for pharmacokinetic (PK)/pharmacodynamic (PD) assessments, and antibody levels (pre-dose only), followed by the first study drug administration.

Blood sampling for PK/PD assessments, and follow-up safety monitoring of vital signs, 12-lead ECG, and assessment of adverse effects (AEs) or severe adverse effects (SAEs), as well as blood sampling for safety laboratory parameters will also be performed beginning on Day 2. Blood samples and fingerstick blood spot samples will be drawn pre-dose (0 hour) and 2, 4, 8, 12 hours (Day 1) and 24 hours (Day 2, before discharge) following study drug administration at the site. Exploratory fingerstick tHcy assessments from DBS and blood spots on PSD will be conducted on site. Clinical assessments and other safety assessments will be performed also.

On Day 3, the subject will return to the site for blood sampling or PK/PD assessments (48-hour sampling), exploratory fingerstick tHcy assessments on DBS and PSD, and follow-up on safety monitoring of AEs or SAEs, vital signs, 12 lead ECG and blood sampling for safety laboratory parameter.

On Days 4, 5, 6, and 7, the subject undergoes home visit assessments conducted by a visiting qualified health care professional for follow-up on safety monitoring of any AEs or SAEs, vital signs, and blood sampling for safety laboratory parameters and PK/PD assessments (72 [Day 4], 96 [Day 5], 120 [Day 6], and 144 [Day 7] hours after administration of study drug. If indicated by any safety signal/concern, the subject will be instructed to attend an unscheduled site visit for full assessment.

During Weeks 2 to 5, each subject will have a weekly site visit for study drug administration, safety assessments, immunogenicity (Week 3 only), PK/PD blood samplings, and exploratory fingerstick tHcy assessments on deep brain stimulation (DBS) and power spectral density (PSD) on Visits 4, 5, 6, and 7.

The washout period will begin on Day 36 upon completion of study drug dosing period. Safety monitoring as well as serial PK/PD assessments will be conducted during this period. Each subject will experience weekly home visits by a visiting health care professional, followed by one site visit at the conclusion of 6 weeks of washout. Assessments during this period include monitoring of safety, vital signs, and blood sampling for routine laboratory testing, PK, PD, and immunogenicity. Exploratory fingerstick tHcy assessments from DBS and blood spots on PSD were conducted at the clinical site on the last visit of the washout period.

With respect to safety, the starting dose of 0.33 mg/kg once weekly is about 30-fold lower than the NOAEL in NHP (i.e. 10 mg/kg every 3 days). The planned top dose of 1.0 mg/kg is about 10-fold lower than the NOAEL in the NHP. Thus, the planned dose range in the protocol provides a large margin of safety.

In addition to safety considerations, extrapolation of PK/PD data from mice, rats and NHP indicate that the planned doses and interval will achieve therapeutically relevant plasma concentrations in CBSDH patients. The pharmacology studies in mice indicate that an exposure of about 50 mU/μL, after a single injection, was efficacious. PK/PD extrapolations in humans indicate that a dose of 0.33 mg/kg twice weekly or 0.66 mg/kg weekly will reach this efficacious level after 6 weeks of dosing. The extrapolated/predicted half-life in humans is 175 hours or 7.3 days.

Example 14. Preliminary Phase 1/2 Clinical Study Results

Preliminary results from ongoing Phase 1/2 study—examining patients aged between 12 and 65 years old, inclusive, with documented history of HCU secondary to genetic deficiency in CBS with total homocysteine (tHcy) levels greater than/equal to 80 μM—(as described in detail in Example 13) confirm efficacy of 1 mg/kg doses of 20NHS PEG-CBS administered once or twice per week with exposure for a period of up to 1 year, up to 6 months, up to 45 days, or up to 1 month in both pediatric and adult patients. Studies demonstrate good safety profile with low safety risk and low immunogenicity. For example, most TEAEs (treatment emergent adverse events) were mild, a few were moderate. Only 1 SAE (significant adverse events) was recorded in a patient; the patient missed 1 dose of 20NHS PEG-CBS and resumed dosing with no issues.

Mild immunogenicity was observed. Anti-drug antibody (ADA) titers observed were similar to pre-dose titers except for 1 patient, with a maximum titer of 4,100. Moreover, detected antibodies are non-neutralizing based on PK results. Anti-PEG titers observed were similar to pre-dose titers and likewise are non-neutralizing based on PK results. These results are superior to comparison enzyme therapies, e.g., Palynziq, which showed ADA titers of 1,000,000 by 3 months and anti-PEG titers of ~10,000 by 1 month. Other enzyme therapies routinely observe titers of ≥1,000.

Preliminary results demonstrate an average decrease of up to about 50% from baseline tHcy levels in Week 1 and Week 6 (at 1 mg/kg once or twice per week) in 3 out of 4 unblinded cohorts (with 1 out of 4 cohorts receiving placebo control and no active drug product). Daily sampling during Week 1 and Week 6 showed an approximately 40-60% decrease from baseline tHcy levels in 3 out of 4 unblinded cohorts (with 1 out of 4 cohorts receiving placebo control and no active drug product). Peak efficacy observed (in 1 out of 4 unblinded cohorts) resulted in tHcy levels in ⅔ patients drop to approximately 50 μM from baseline levels of about 100 μM to about 200 μM. 20NHS PEG-CBS levels correlated closely with tHcy decreases on a per patient basis. Updated models predict that a twice weekly dose (1 or 1.5 mg/kg) will more than double peak efficacy observed and achieve steady state levels of tHcy.

The results demonstrate that 20NHS PEG-CBS administered to subjects according to the methods above is active and stable in plasma (unlike native enzyme) and dramatically reduces elevated tHcy levels (intracellular and plasma), independent of the underlying pathology.

Figure 3:
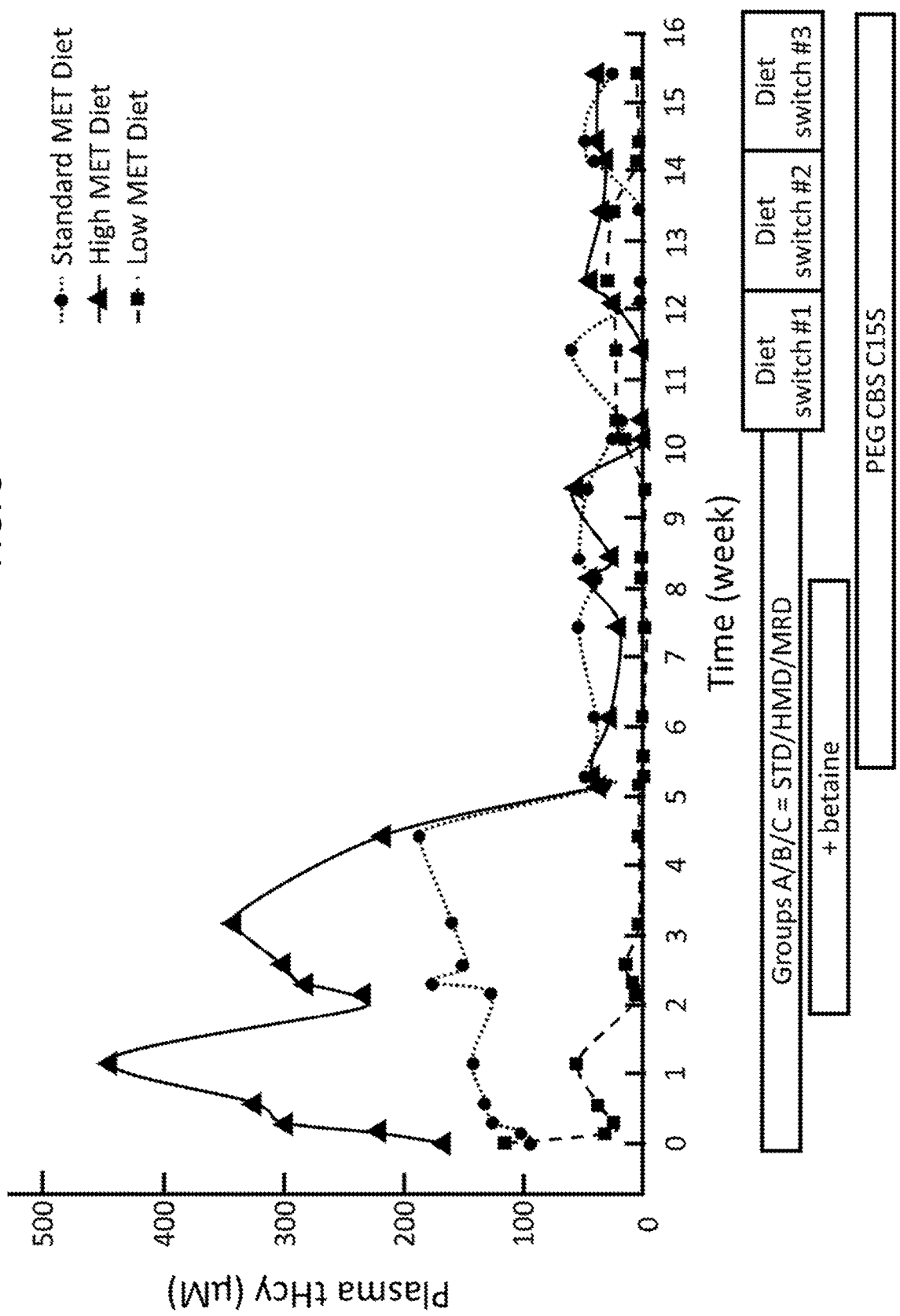
FIG. 3 shows preclinical study results in a mouse model of homocystinuria employing long-term continuous treatment with 20NHS PEG-CBS (referred to as "PEG CBS C15S" in the figure) on backgrounds of varying diet (standard methionine diet ("STD"), high methionine diet ("HMD"), and/or low or restricted methionine diet ("MRD")).

Example 15. 20NHS PEG-CBS Allows Diet Relaxation and Cessation of Betaine in Mouse Models of Homocystinuria Preclinical studies in a mouse model of homocystinuria demonstrate long-term continuous treatment (e.g., up to 16 weeks) with 20NHS PEG-CBS significantly reduces and/or normalizes tHcy levels regardless of diet. As shown in FIG. 3, HO mice on standard methionine diet ("STD") had elevated tHcy levels (e.g., greater than 100 μM) even with administration of betaine. Administration of 20NHS PEG-CBS dramatically reduced or normalized tHcy levels, even after withdrawal of betaine.

HO mice were used to recapitulate key biochemical indicators of homocystinuria in human subjects. Both male and female HO mice were used and maintained, unless otherwise indicated, on a standard complete diet (STD, Teklad complete diet 2920X, with 5.0 g/kg Met and 3.0 g/kg cystine). Mice were divided into three groups, A, B and C. Group A remained on the STD through week 10. Groups B and C were placed on a high Met diet (HMD, Met-enriched amino acid defined diet TD.01084, 8.2 g/kg Met and 3.5 g/kg cystine) and Met restricted diet (MRD, Met-deficient amino acid defined diet TD.110591, 0.5 g/kg Met and 3.5 g/kg cystine), respectively, through week 10. The three groups were maintained on these diets for the first 2 weeks without additional treatments. (Deaths in Group B during this period necessitated enrollment of additional mice to complete the study.) Mice continued on the diets and were also given betaine (2% w/v in the drinking water) from week 3-week 5. Mice continuing on the diets and betaine were also treated with 20NHS PEG-CBS (7.5 mg/kg SC, 3 times per week), beginning on week 6. Betaine was then discontinued, beginning on week 9, while 20NHS PEG-CBS treatments continued until the end of the study (week 16). Diet switching was performed as follows: Switch #1 (week 11-week 12), Groups A, B and C switched to HMD, MRD and STD, respectively; switch #2 (week 13-week 14), Groups A, B and C switched to MRD, STD and HMD, respectively; switch #3 (week 15-week 16), Groups A, B and C switched back to their original diets, STD, HMD and MRD, respectively. Blood was collected 1-3 times per week throughout the study and plasma levels of metabolites, including Hcy, Met and Cys, were assayed. Blood samples were collected from the submandibular vein of conscious study animals using a disposable lancet designed for submandibular sampling into Capiject T-MLHG lithium heparin tubes (Terumo Medical Corporation, Somerset, NJ, USA). Plasma was collected from blood samples after centrifugation at 1,200×g for 10 min and was stored at −80° C. in 1.5 ml tubes. Plasma aminothiols (total Cys and Hcy) and the remaining amino acids, as well as SAM and SAH, were measured by LC-MS/MS as described in Arning and Bottiglieri, Clinical Applications of Mass Spectrometry in Biomolecular Analysis, U. Garg, Editor. 2016, Springer: Seacaucus, NJ p. 255-262, the contents of which are incorporated by reference herein in their entirety. Factorial ANOVA followed by Tukey's HSD post-hoc test was applied. Values of p<0.05 were considered statistically significant.

As shown in FIG. 3, plasma Hcy levels were changed dramatically from baseline levels (~95-166 μM) in mice on STD, in accordance with Met levels in the respective diets. Thus, after switching to a MRD alone, Hcy levels decreased to ~26-56 μM while the HMD increased Hcy levels to over 400 μM. Betaine normalized Hcy levels (≤16 μM) in mice on the MRD, but was only partially effective and ineffective in those on the HMD and STD, respectively. This observation supported the practice of treating HCU with a combination of betaine and Met restriction. In mice on HMD or STD, still receiving betaine, introduction of 20NHS PEG-CBS dramatically decreased Hcy levels, to ~22-55 μM. Importantly, when betaine was discontinued but 20NHS PEG-CBS treatment continued, these low Hcy levels remained stable and those in mice on MRD remained normalized. Furthermore, plasma Hcy also remained at these low, stable levels upon dietary switching, even when those on MRD were switched to the STD or HMD.

Plasma Met levels were increased about 2-fold in HO mice on the HMD and even more severely, up to 7-fold, with the addition of betaine (data not shown). This, along with the Hcy elevation, likely contributed to the high mortality in Group B, exacerbated in females. The greatly elevated Met observed with betaine in mice on the HMD was consistent with the fact that Met, along with dimethylglycine (DMG), is a product of the reaction between betaine and Hcy, catalyzed by betaine-homocysteine methyltransferase (BHMT). Thus, DMG levels were also highest in Group B, consistent with the increased availability of the BHMT substrate Hcy in this group.

When added to betaine, 20NHS PEG-CBS treatment was highly effective at decreasing plasma Met levels in Group B, to values comparable to those in Groups A and C. Again, these low Met levels were maintained by 20NHS PEG-CBS treatment, even after betaine withdrawal and subsequent dietary switching. Another interesting observation was that DMG levels in Group B dropped to about half when 20NHS PEG-CBS treatment was administered together with betaine (data not shown). This suggested that 20NHS PEG-CBS competed effectively with betaine for Hcy.

Though plasma Cys levels in HO mice are approximately half of those in WT controls (~200 µM), they were fully normalized (~226-236 µM) in HO mice on the MRD (data not shown). Betaine alone did not improve Cys levels in any of the groups but addition of 20NHS PEG-CBS partially to fully normalized Cys levels in mice on the HMD (~152-219 µM) and STD (~156-195 µM). Though there was considerable fluctuation throughout the study, the Cys levels normalized by 20NHS PEG-CBS appeared to be unaffected by betaine removal or subsequent dietary switching. Consistent with its catalytic activity, 20NHS PEG-CBS elevated Cth levels in all groups, particularly those beginning on the STD or HMD suggesting a correlation between levels of Hcy and Cth, though with much fluctuation (data not shown).

Also monitored was the ratio of S-adenosylmethionine (SAM) to S-adenosylhomocysteine (SAH) (data not shown). Compared with the other groups, the SAM/SAH ratio was substantially higher in mice in Group C, decreasing somewhat with 20NHS PEG-CBS treatment. In Groups A and B, 20NHS PEG-CBS treatment caused a moderate increase in SAM/SAH ratio. During 20NHS PEG-CBS treatment, SAM/SAH ratios in all groups were similar, though, prior to diet switching, were slightly higher in Group C.

Overall, in the presence of betaine, 20NHS PEG-CBS treatment substantially decreased plasma Met levels in HO mice fed the HMD and Hcy levels in those fed HMD or STD. In HO mice on the MRD, betaine alone was sufficient to normalize plasma Hcy. 20NHS PEG-CBS, but not betaine, normalized Cys levels in mice on STD or HMD. Upon removal of betaine, 20NHS PEG-CBS alone was sufficient to maintain these metabolic improvements, even when Met intake was varied by diet switching. This observation, along with the changes in DMG levels, indicated that betaine supplementation did not provide an added advantage when co-administered with 20NHS PEG-CBS.

Example 16. Preparation and Analysis of Lyophilized 20NHS PEG-CBS Formulations

Different formulations of 20NHS PEG-CBS were tested in order to identify formulations that resulted in (i) reduction of lyophilization time, (ii) reduction of reconstitution time, (iii) reduction of viscosity, and/or (iv) reduction of de-PEGylation of 20NHS PEG-CBS. 20NHS PEG-CBS, at a concentration of 25.4 mg/ml in 25 mM potassium phosphate, 5% sucrose at pH 7.5 as described below was used to prepare the formulations described in Table 18.

TABLE 18

Lyophilized Formulations

| Formulation No. | Buffer | Excipient 1 | Excipient 2 | pH | Features |
|---|---|---|---|---|---|
| F1 | 15 mM K-phosphate | 8% trehalose | — | 7.5 | Alternative sugar—different cake structure and drying kinetics—effect on reconstitution time and chance of process time reduction |
| F2 | 15 mM K-phosphate | 4% mannitol | — | 7.5 | Crystalline cake former—different cake structure and drying kinetics—effect on reconstitution time and chance of process time reduction |
| F3 | 15 mM K-phosphate | 8% trehalose | 0.01% (w/v) PS80 | 7.5 | Effect on reconstitution time, effect on freezing behavior |
| F4 | 15 mM K-phosphate | 260 mM arginine | — | 7.5 | Alternative cake former/stabilizer and viscosity reducer |
| F5 | 15 mM K-phosphate | 208 mM arginine | 52 mM phenylalanine | 7.5 | Alternative cake former/stabilizer and viscosity reducer, chance of process time reduction |
| F6 | 15 mM K-phosphate | 1% trehalose | 4% mannitol | 7.5 | Semi-crystalline cake, effect on reconstitution time and chance of process time reduction |
| F7 | 15 mM K-phosphate | 6% trehalose | 100 mM arginine | 7.5 | Alternative cake former/stabilizer and viscosity reducer, semi-crystalline cake |

The active formulations were analyzed prior to lyophilization (herein referred to as "T-Liquid") as well as after lyophilization (herein referred to as "T-Lyo" and "T0" of the stability study). Subsequently, the lyophilized material was placed on a stability study for up to 3 months (T3M) at 5° C., 25° C./60% r.h. and 40° C./75% r.h. Stability of the lyophilized formulations was also tested at one month (T1M).

A. Sample Preparation

Three days before the formulation preparation, 20NHS PEG-CBS, (25.4 mg/ml in 25 mM potassium phosphate, 5% sucrose, pH 7.5) was taken out of the freezer (−80° C.) and thawed for 72 hours in a refrigerator at 5° C. After thawing, 20NHS PEG-CBS, in 25.4 mg/ml in 25 mM potassium phosphate, 5% sucrose, pH 7.5, was homogenized by gentle swirling. The formulations were produced by dialysis, under controlled conditions at 5° C. for 24 hours, using 20-kDa cut-off dialysis cassettes and three buffer exchanges at a volume ratio of ≥1:45 each time (3,300 ml buffer per exchange). The buffer was exchanged after 3 and 6 hours of total dialysis time, the last dialysis step was performed overnight. After dialysis, the formulations were removed from the dialysis cassettes, followed by the analysis of pH, osmolality and protein concentration. For all formulations, the protein concentration was found to be within the specifications of 20-30 mg/ml. For Formulation F3 described in Table 18, a stock solution of 10% (w/v) polysorbate 80 (PS80) was spiked into the dialyzed material to achieve its final concentration of 0.01% (w/v).

B. Lyophilization

Freeze drying of the formulations was performed by using an Epsilon 2-12D pilot scale freeze dryer (RND-FD02, Martin Christ, Germany). Prior to the start of primary drying, all formulations were combined in one freeze dryer. The vacuum during the freeze drying process was controlled by a capacitance gauge. The optimized lyophilization process is summarized in Table 19. After equilibration of the vials to 5° C., the vials were frozen to −45° C. and equilibrated for further 5 hours at −45° C. Shelf temperature was set to −15° C. for 31 hours in primary drying. Secondary drying was performed at a shelf temperature of 40° C. for 2.5 hours. At the end of the lyophilization process, the chamber was aerated with nitrogen to 800 mbar and the vials were stoppered by lifting the shelves. After stoppering, the chamber was aerated to atmospheric pressure with nitrogen.

C. Reconstitution of the Lyophilized Formulations

The lyophilized products were reconstituted using highly purified water. The reconstitution volume was gravimetrically determined as the weight loss during lyophilization. The reconstitution time was measured as the time to achieve a full reconstitution of the lyophilized product after the liquid has been added. The reconstitution behavior was judged, mainly with respect to foaming. The reconstitution times for all formulations throughout the stability study were determined. Overall, the reconstitution times ranged between 54 seconds and 4.75 minutes. Between the formulations, no substantial differences between the reconstitution times were observed, except for formulation F5, where more time was needed to reach full reconstitution. Furthermore, all formulations showed comparable foam formation of a moderate to strong level.

D. Analysis of the Lyophilized Formulations

The optical appearance of the lyophilized formulations at T0 of the stability study was evaluated. Parameters taken into consideration included compactness of the cake, contact to walls of vial, shape of the cake, color and overall appearance. All formulations with cake structure showed a good appearance, being dense and brownish in nature. Furthermore, slight vertical shrinkage of the crystalline cake was observed. F1, F3 and F6 showed some minor cracks within the cake, whereas the cakes of all other formulation appeared undamaged. Overall, no major differences between the formulations were observed. The optical appearance of the cake did not change after one month of stability study for any of the tested storage conditions. Evaluation of the optical appearance of a subset of formulations (F1, F3, and F7) at three months also did not reveal any changes in the optical appearance.

The vials were inspected for the presence or absence of visible particles under gentle, manual, radial agitation for 5 seconds in front of a white background and for 5 seconds in front of a black background according to the European Pharmacopoeia (9th edition; monograph 2.9.20) at 2,000-3,750 lux. All formulations were found to be free of visible proteinaceous particles and were characterized by an intense coloration. Moreover, some sample were classified as viscous solutions or showed a tendency to trap air bubbles.

The pH value of the formulations was measured with a calibrated pH meter (SevenCompact™ SC S210-B, Mettler Toledo AG, Schwerzenbach, Switzerland) using a normal ionic strength electrode (InLab™ Micro Pro ISM) for small sample volumes. pH analyses were performed for all formulations prior to lyophilization as well as throughout the course of the stability study. For all samples, pH values within the specification range of pH 7.5±0.3 were measured.

Osmolality of the samples was measured by the method of freezing-point depression using a Gonotec OSMOMAT 3000 osmometer (Gonotec GmbH, Germany). Osmolality of the lyophilized formulations was compared to the osmolality values of 20NHS PEG-CBS (25.4 mg/ml in 25 mM potassium phosphate, 5% sucrose, pH 7.5). Comparable osmolality values were obtained prior to and after lyophilization.

The protein concentration in all formulations was analyzed by UV spectroscopy prior to lyophilization as well as throughout the stability study. All obtained protein concentrations were within the specification range of 20-30 mg/ml. When comparing the protein concentrations prior and after lyophilization, a difference of ≤5% was observed for all formulations. Hence, the analysis of both the protein concentration and the osmolality indicates an accurate determination of the water loss during freeze drying.

Viscosity measurements were made using a Kinexus ultraplus rheometer (Malvern Instruments, UK). The determined viscosities of the formulations were in a range of ~18 to 27 mPa*s Table 25. No influence of the storage time or temperature on the viscosity was observed. When comparing the formulations, however, substantially different viscosities were measured. When comparing the viscosity values to the results of the UV spectroscopy, the correlation of the solution viscosity to the protein concentration was apparent.

Turbidity of the formulations was measured using a NEPHLA turbidimeter (Dr. Lange, Germany). Overall, low turbidities were obtained for all formulations after preparation as well as within the course of the stability study. No substantial difference between formulations was observed. Two samples stored at 2-8° C. (F2 and F4) showed a higher turbidity than the respective samples stored at 25° C. or 40° C. These increased values are likely to be a measurement artifact.

The color of the formulations in liquid was also assessed by using a spectral colorimeter (LICO 690 Professional, UK). All samples irrespective of time point and formulation composition were classified as being closest to R1 within the red scale.

Quantification and visualization of sub-visible particles (~1-100 μm), as well as differentiation of silicone oil droplets and protein particles, were performed by using Micro-Flow Imaging (MFI). The concentrations of the particles ≥2 μm determined by MFI were determined. Overall, very low particle concentrations were determined for all formulations, storage conditions and time points. No clear trends with respect to changes in the particle content within the course of the stability study were identified.

High performance size-exclusion chromatography (HP-SEC) was performed after formulation preparation as well as at all stability time points after reconstitution of the lyophilized samples. Overall, all samples showed a high PEG-CBS content and no increase of the content of the non-PEGylated molecule throughout the stability study.

Reverse phase high performance liquid chromatography was also performed for all the samples. Ten discernable peaks were identified in the chromatogram and were named Peak 1 through Peak 10 with increasing retention time. Here, a decrease of the relative areas of Peaks 6-9 and an increase of relative areas of Peaks 1-4 was observable.

The behavior of the frozen formulations under vacuum was analyzed by freeze drying microscopy (FDSC 196, Resultec, Germany). Freeze drying microscopy (FDM) measurements were performed at T-liquid (formulation prior to lyophilization) in order to adjust the lyophilization process parameters according to the collapse onset temperatures (Tc,on). The determined Tc,on values were in the range of −22° C. to −14° C. Thus, none of the formulations showed collapse at temperatures above −25° C., corresponding to the set temperature of the shelves during primary drying of the lyophilization run.

In summary, seven formulations were screened with respect to their reconstitution time, viscosity as well as stability after storage at 2-8° C., 25° C. and 40° C. for up to three months. With respect to the cake reconstitution time and sample viscosity no considerable differences, neither between formulations, nor between the analytical time points, were seen. For the product cakes of F5 a substantially longer reconstitution time in comparison to the other candidates was measured. All samples stored at 2-8° C. or 25° C. showed overall good stability. However, at storage conditions of 40° C., some differences between the formulations were revealed. For example, HP-SEC analysis showed a decreased relative content of PEG-CBS for formulations F2, F4 and F6 in combination with an increased relative content of Peak 1 after storage for one month. RP-HPLC analysis showed a decrease of the relative areas of Peaks 6-9 accompanied by an increase of relative areas of Peaks 1-4 of formulations F2 and F5. Thus, samples undergoing an annealing step during freezing overall appeared less stable than samples without an annealing step during freezing.

Among the formulations tested, F1, F3 and F7 formulations showed very high stability at all storage conditions (with a few exceptions). Taken together, formulations F1, F3 and F7 showed comparably good results among them and at all analytical time points.

Example 17. Analysis and Optimization of Lyophilization Process Parameters

The F1 formulation described in Example 16 consisting of 15 mM K-phosphate, 8% trehalose, pH 7.5 was used to optimize the lyophilization process. Expected outcomes of an optimized lyophilization include (i) reduction of the lyophilization cycle time without a cake melt, (ii) reduction of reconstitution time and (iii) reduction of de-PEGylation of 20NHS PEG-CBS.

The lyophilization process optimization was performed in the course of three consecutive lyophilization cycles at different process parameters. In particular, (i) primary drying (PD) time, (ii) PD temperature and (iii) secondary drying (SD) time were varied between the cycles. The aim of cycle 1 was to optimize the primary drying parameters, whereas the focus of cycle 2 was the secondary drying characterization and cycle 3 was aimed at reducing the process time to less than 48 hours.

Three consecutive lyophilization cycles were performed in an Epsilon 2-12D pilot scale freeze-dryer. The chamber pressure was controlled by a capacitance gauge and regulated by a vacuum pump and a controlled nitrogen dosage.

TABLE 19

Optimized lyophilization process parameters

| Step No. | Step | Time (hh:mm:ss) | Temperature (° C.) | Pressure (mbar) | Total time (h) | Ramp (° C./min) |
|---|---|---|---|---|---|---|
| 1 | Loading | 0:00:00 | 5 | 1000 | 0.0 | |
| 2 | Equilibration at 5° C. | 1:00:00 | 5 | 1000 | 1.0 h | |
| 3 | Freezing | 1:40:00 | −45 | 1000 | 2.7 | 0.50 |
| 4 | Freezing | 5:00:00 | −45 | 1000 | 6.7 | |
| 5 | Primary drying | 0:30:00 | −45 | 0.1 | 7.2 | |
| 6 | Primary drying | 1:00:00 | −15 | 0.1 | 8.2 | 0.50 |
| 7 | Primary drying | 31:00:00 | −15 | 0.1 | 39.2 | |
| 8 | Secondary drying | 3:00:00 | 40 | 0.1 | 42.2 | 0.31 |
| 9 | Secondary drying | 2:30:00 | 40 | 0.1 | 44.7 | |
| 10 | Aeration | 00:30:00 | 40 | 800 | 45.2 | |
| 11 | Stoppering | 0:01:00 | 40 | 800 | 45.2 | |
| 12 | Storage | 0:30:00 | 5 | 1000 | 45.7 | |

The lyophilized formulations obtained from the optimized lyophilization process were assessed by the analytical methods described herein.

The freeze-dried cakes were optically evaluated after drying. Parameters taken into consideration included compactness of the cake, contact to walls of vial, shape of the cake, color and overall appearance. Analysis of the lyophilized samples revealed a good appearance with a dense structure and brownish coloration.

The water content of the lyophilized cakes was determined by using a coulometric Karl Fischer titrator Aqua 40.00 (Analytik Jena GmbH). Low residual moisture content of all samples was observed.

Differential scanning calorimetry (DSC) in a Mettler Toledo DSC1_943 (Mettler Toledo, Germany) was performed for the measurement of the glass transition temperature (Tg), crystallization and endothermal melting of the lyophilized products. Overall, results ranged between 111° C. and 117° C., indicating stable product cakes. Prior to analysis by visual inspection, turbidity, UV spectroscopy, HP-SEC and RP-HPLC, the lyophilized vials were reconstituted. Water was used to reconstitute the vials. The observed reconstitution times were short and comparable, ranging from ~1 to ~1.5 minutes. Upon reconstitution, the lyophilized product showed moderate to strong foaming.

Visual inspection was performed for the presence or absence of visible particles under gentle, manual, radial agitation for 5 seconds in front of a white background and for 5 seconds in front of a black background according to the European Pharmacopoeia (9th edition; monograph 2.9.20) between 2,000-3,750 lux. The inspection was performed independently by two trained examiners. No visible particles were detected in any of the analyzed samples, irrespective of the process conditions. All solutions appeared colored and viscous. Additionally, air bubbles were detected in some cases after reconstitution.

The NEPHLA turbidimeter (Dr. Lange, Dusseldorf, Germany), operating at 860 nm and detecting at a 90° angle, was used for turbidity measurements. Very low turbidities were obtained for all samples throughout the study. Modifying the different process parameters of the optimization cycles did not affect the turbidity of the formulation.

UV spectroscopy was performed by using a C Technologies SoloVPE instrument. All protein concentrations were within the specifications of 20-30 mg/ml. For most measurements, a slight trend towards higher protein concentration was observed after lyophilization and reconstitution (T-Lyo) compared to T-Liquid. The higher absorbance in the case of the T-Lyo samples of all three cycles might have resulted from light scattering, e.g., caused by air bubbles that were also observed in the visual inspection.

Comparable HP-SEC profiles with high PEG-CBS contents between 93 and 95% were determined throughout the study. No de-PEGylated CBS was detected in any of the samples. Therefore, the altered lyophilization process parameters did not affect the PEGylation of the samples nor did they lead to the generation of new species detectable by HP-SEC. Consistent with the HP-SEC profiles, the modified lyophilization process conditions also revealed no impact on the PEGylation profile.

Protein concentration was determined using A280 nm GPBT1198. Free-PEG content was determined via RP-HPLC GPBT3078. No distinct changes in the protein concentration of the samples before and after lyophilization, nor between center and edge vial samples were observed. Comparing the samples before and after lyophilization, no substantial changes in free-PEG content and activity were determined. Thus, optimized lyophilization cycle parameters did not negatively affect the analyzed product quality attributes.

In summary, the lyophilization process was successfully optimized by adjusting the freezing, PD and SD parameters. The optimized process is characterized by a substantially reduced run time of ≤48 hours. None of the applied solid or liquid state analytical methods indicated an impairment of the process optimization on the product quality. Moreover, the comparison of edge and center vial positions within cycle 3 showed the product to be robust against batch product temperature inhomogeneity during PD.

Example 18. Evaluation of Downstream Purification Process Parameters

Alternate downstream processes for purification of the enzyme cystathionine-β-synthase (CBS) were performed at a large scale, with the goal of improving yield and recovery of the existing process. Biomass was produced by a fed-batch fermentation (high cell density fermentation) in minimal medium at 10 L scale. At harvest, the biomass was separated from the medium via centrifugation, resuspended in lysis buffer and disrupted via high pressure homogenization. After separation of cell extract from cell debris via centrifugation, the CBS containing supernatant was clarified by depth filtration sequence and then used as starting material for subsequent chromatography train comprising (i) anion exchange chromatography (AEX) as capturing step using HiTrap DEAE Sepharose FF (GE) (ii) immobilized metal affinity chromatography (IMAC) (with Zn2+ charged medium) intermediate step using Chelating Sepharose FF (GE) and (iii) hydrophobic interaction chromatography (HIC) as polishing step using Butyl-S Sepharose 6 FF (GE). After diafiltration by tangential flow filtration (TFF) of the purified CBS, the PEGylation was performed. For formulation, the PEGylated CBS was diafiltered and concentrated by TFF again. PEI precipitation (0.35%) of the cell lysate, change of buffer system from phosphate to HEPES, and Triton X-100 replacement by Tween™20 were used in alternative processes.

A. Fermentation

For biomass generation needed for purification process optimization and scale-up, two consistent 10 L fed-batch fermentations were performed in minimal medium. For all scale-up runs, the biomass produced in fermenter 2 (harvest volume 9.2 L; biomass: 1791 g) was used.

B. Scale-Up of Downstream Purification Process

Purification process 1 included one or more of the following steps (i) cell harvest (ii) cell resuspension (iii) cell disruption (iv) polyethylenimine (PEI) precipitation (v) centrifugation (vi) sterile filtration (vii) capture using DEAE Sepharose FF with a third wash step for rebuffering from phosphate to HEPES (viii) intermediate step using chelating Sepharose FF charged with zinc ions (ix) polishing step using butyl-s-Sepharose 6 FF (x) TFF (xi) PEGylation.

Purification process 2 included one or more of the following steps (i) cell harvest (ii) cell resuspension (iii) cell disruption (iv) centrifugation (v) depth filtration (vi) sterile filtration (vii) capture using DEAE Sepharose FF (viii) intermediate step using Chelating Sepharose FF charged with zinc ions (ix) polishing step using butyl-s-Sepharose 6 FF with a second wash step included for rebuffering from HEPES to phosphate and a dilution step included to avoid precipitation of CBS (x) TFF (xi) PEGylation.

C. Capture Step

After cell disruption via high pressure homogenization, a PEI precipitation followed by sterile filtration was conducted. The total CBS recovery of the capture step was 58.1% (5.4 g CBS; 2.5 g/L CBS). The total protein content of the capture elution pool was 7.5 g. The CBS recovery and yield of the purification process 2a was confirmed (85.1% recovery; 5.4 g CBS; 2.6 g/L CBS) and higher than in the purification process 1 (47.7% recovery; 5.3 g CBS; 1.03 g/L CBS). Overall, the PEI precipitation and the rebuffering on the column had no obvious negative effects on yield.

D. Intermediate Step

The capture elution pool was stored overnight at 4° C. to 8° C. and processed further on process day 2 in an intermediate step using Chelating Sepharose FF charged with zinc ions.

E. Polishing Step

The intermediate elution pool was diluted with 20 mM HEPES buffer to obtain a CBS concentration of around 1.6 g/L. Subsequently, 10 mM EDTA was added for overnight storage at 4° C. to 8° C. On process day 3, ammonium sulfate (1.4 M final concentration) was added prior to loading the polishing column.

In the flow-through, there was no absorbance signal measured, i.e. there was no protein and no CBS wash out. The elution profile in purification process was determined.

The purification process yielded a CBS recovery of 92.9% or greater. Due to the pre-dilution of the intermediate elution pool, there was no concentration effect and precipitation of CBS on the polishing column observed, which resulted in an increase of recovery of around 8%. The overall CBS recovery was 38.7% or greater for all purification processes tested. The elution pool was diafiltered against PEGylation buffer and concentrated to 40 g/L CBS via TFF (Vivaflow 200, 50 kDa, PES). With the TFF-retentate, comprehensive analysis was conducted in order to determine CBS quality.

F. PEGylation

A small volume (1 mL) of the TFF-retentate was PEGylated in small-scale and, analyzed by SDS-PAGE, HPLC (SE-, RP- and AEX-) and IEF and compared to the PEG-CBS reference standard. PEGylation kinetics were monitored with SE-HPLC (one measurement after four to five hours) and the relative retention=tR(PEG-CBS)/tR(CBS)× 100% with tR being the retention time of the respective species was determined. If the relative retention (given as integer) was larger than 85%, this indicated that additional PEG may need to be added. The relative retention time after 4.3 h was 82.4%, i.e. it was below the threshold of 85%. Therefore, no additional PEG was added. After 24 h PEGylation, the relative retention time was 82.8%.

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

The invention claimed is:

1. A lyophilized formulation of a drug substance, wherein:
   (i) the drug substance comprises:
   (a) an isolated cystathionine B-synthase (CBS) protein comprising SEQ ID NO: 1; and
   (b) a polyethylene glycol (PEG) molecule covalently bound to the CBS protein; and
   (ii) wherein, upon reconstitution of the lyophilized formulation to a reconstituted liquid formulation, the reconstituted liquid formulation comprises:
   (a) the drug substance in a concentration of about 20-30 mg/ml;
   (b) about 15 mM of potassium phosphate; and
   (c) about 8% (w/v) trehalose.

2. The lyophilized formulation of claim 1, wherein the drug substance is obtained or obtainable by using methoxy-PEG-CO(CH2)3COO-NHS to PEGylate the CBS protein.

3. The lyophilized formulation of claim 2, wherein the drug substance is obtained or obtainable by using ME-200GS to PEGylate the CBS protein.

4. A reconstituted liquid formulation comprising:
   (i) a drug substance in an amount of about 25 mg, wherein the drug substance comprises:
   (a) an isolated cystathionine β-synthase (CBS) protein comprising SEQ ID NO: 1; and
   (b) a PEG molecule covalently bound to the CBS protein; and
   (ii) about 15 mM of potassium phosphate;
   (iii) about 8% (w/v) trehalose; and
   (iv) 1 mL of water.

5. The reconstituted liquid formulation of claim 4, wherein the drug substance is obtained or obtainable by using methoxy-PEG-CO(CH2) 3COO-NHS to PEGylate the CBS protein.

6. The reconstituted liquid formulation of claim 4, wherein the drug substance is obtained or obtainable by using ME-200GS to PEGylate the CBS protein.

7. A method of treating homocystinuria in a subject, the method comprising: administering to the subject the reconstituted liquid formulation of claim 5.

8. The method of claim 7, wherein the reconstituted liquid formulation is administered at a dosage of the drug substance selected from the range of about 0.25 mg/kg to about 10 mg/kg.

9. The method of claim 8, wherein the dosage is about 0.33 mg/kg.

10. The method of claim 8, wherein the dosage is about 0.66 mg/kg.

11. The method of claim 8, wherein the dosage is about 1.0 mg/kg.

12. The method of claim 8, wherein the dosage is about 1.5 mg/kg.

13. The method of claim 7, further comprising administering to the subject at least one selected from the group consisting of: pyridoxine, vitamin B6, and betaine.

14. The method of claim 7, wherein the subject is on a methionine (Met)-restricted diet.

15. The method of claim 7, further comprising administering an anti-platelet agent.

16. The method of claim 7, wherein the administering step (i) occurs about once every 3 days, about once per day, or about once per week; or (ii) is repeated for about 6 weeks, for about 3 months, for about 6 months, for longer than 6 months, or for the remaining lifespan of the subject.

17. A method of decreasing the level of homocysteine (Hcy) in a subject, the method comprising: administering to the subject the reconstituted liquid formulation of claim 5.

18. The method of claim 17, wherein the reconstituted liquid formulation is administered at a dosage of the drug substance selected from: the range of about 0.25 mg/kg to about 10 mg/kg; about 0.33 mg/kg; about 0.66 mg/kg; about 1.0 mg/kg; about 1.5 mg/kg; about 7.0 mg/kg; about 10 mg/kg; and less than 10 mg/kg.

19. The method of claim 17, (i) further comprising administering to the subject at least one selected from the group consisting of: pyridoxine, vitamin B6, and betaine; (ii) wherein the subject is on a methionine (Met)-restricted diet; or (iii) further comprising administering an anti-platelet agent.

20. The method of claim 17, wherein the administering step (i) occurs about once every 3 days, about once per day, or about once per week; or (ii) is repeated for about 6 weeks, for about 3 months, for about 6 months, for longer than 6 months, or for the remaining lifespan of the subject.

21. A method of increasing the level of cysteine (Cys) or cystathionine (Cth) in a subject, the method comprising: administering to the subject the reconstituted liquid formulation of claim 5.

22. A method of treating, alleviating, or preventing negative clinical outcomes associated with the ocular system, skeletal system, vascular system, and/or central nervous system of a subject, the method comprising: administering to the subject the reconstituted liquid formulation of claim 5.

* * * * *

UNITED STATES PATENT AND TRADEMARK OFFICE
CERTIFICATE OF CORRECTION

PATENT NO. : 12,364,765 B2
APPLICATION NO. : 17/622112
DATED : July 22, 2025
INVENTOR(S) : Erez Bublil et al.

Page 1 of 1

It is certified that error appears in the above-identified patent and that said Letters Patent is hereby corrected as shown below:

In the Claims

Column 129, Claim 1, Line 28:
"B-synthase" should read: -- β-synthase --.

Signed and Sealed this
Fourteenth Day of October, 2025

John A. Squires
*Director of the United States Patent and Trademark Office*

SEQUENCE LISTING

<160> NUMBER OF SEQ ID NOS: 5

<210> SEQ ID NO 1
<211> LENGTH: 412
<212> TYPE: PRT
<213> ORGANISM: Homo sapiens

<400> SEQUENCE: 1

```
Pro Ser Glu Thr Pro Gln Ala Glu Val Gly Pro Thr Gly Ser Pro His
1               5                   10                  15

Arg Ser Gly Pro His Ser Ala Lys Gly Ser Leu Glu Lys Gly Ser Pro
            20                  25                  30

Glu Asp Lys Glu Ala Lys Glu Pro Leu Trp Ile Arg Pro Asp Ala Pro
        35                  40                  45

Ser Arg Cys Thr Trp Gln Leu Gly Arg Pro Ala Ser Glu Ser Pro His
    50                  55                  60

His His Thr Ala Pro Ala Lys Ser Pro Lys Ile Leu Pro Asp Ile Leu
```

```
                65                  70                  75                  80
Lys Lys Ile Gly Asp Thr Pro Met Val Arg Ile Asn Lys Ile Gly Lys
                85                  90                  95

Lys Phe Gly Leu Lys Cys Glu Leu Leu Ala Lys Cys Glu Phe Phe Asn
            100                 105                 110

Ala Gly Gly Ser Val Lys Asp Arg Ile Ser Leu Arg Met Ile Glu Asp
        115                 120                 125

Ala Glu Arg Asp Gly Thr Leu Lys Pro Gly Asp Thr Ile Ile Glu Pro
    130                 135                 140

Thr Ser Gly Asn Thr Gly Ile Gly Leu Ala Leu Ala Ala Ala Val Arg
145                 150                 155                 160

Gly Tyr Arg Cys Ile Ile Val Met Pro Glu Lys Met Ser Ser Glu Lys
                165                 170                 175

Val Asp Val Leu Arg Ala Leu Gly Ala Glu Ile Val Arg Thr Pro Thr
            180                 185                 190

Asn Ala Arg Phe Asp Ser Pro Glu Ser His Val Gly Val Ala Trp Arg
        195                 200                 205

Leu Lys Asn Glu Ile Pro Asn Ser His Ile Leu Asp Gln Tyr Arg Asn
    210                 215                 220

Ala Ser Asn Pro Leu Ala His Tyr Asp Thr Thr Ala Asp Glu Ile Leu
225                 230                 235                 240

Gln Gln Cys Asp Gly Lys Leu Asp Met Leu Val Ala Ser Val Gly Thr
                245                 250                 255

Gly Gly Thr Ile Thr Gly Ile Ala Arg Lys Leu Lys Glu Lys Cys Pro
            260                 265                 270

Gly Cys Arg Ile Ile Gly Val Asp Pro Glu Gly Ser Ile Leu Ala Glu
        275                 280                 285

Pro Glu Glu Leu Asn Gln Thr Glu Gln Thr Thr Tyr Glu Val Glu Gly
    290                 295                 300

Ile Gly Tyr Asp Phe Ile Pro Thr Val Leu Asp Arg Thr Val Val Asp
305                 310                 315                 320

Lys Trp Phe Lys Ser Asn Asp Glu Glu Ala Phe Thr Phe Ala Arg Met
                325                 330                 335

Leu Ile Ala Gln Glu Gly Leu Leu Cys Gly Gly Ser Ala Gly Ser Thr
            340                 345                 350

Val Ala Val Ala Val Lys Ala Ala Gln Glu Leu Gln Glu Gly Gln Arg
        355                 360                 365

Cys Val Val Ile Leu Pro Asp Ser Val Arg Asn Tyr Met Thr Lys Phe
    370                 375                 380

Leu Ser Asp Arg Trp Met Leu Gln Lys Gly Phe Leu Lys Glu Glu Asp
385                 390                 395                 400

Leu Thr Glu Lys Lys Pro Trp Trp Trp His Leu Arg
                405                 410

<210> SEQ ID NO 2
<211> LENGTH: 551
<212> TYPE: PRT
<213> ORGANISM: Homo sapiens

<400> SEQUENCE: 2

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30
```

-continued

```
Pro Glu Asp Lys Glu Ala Lys Glu Pro Leu Trp Ile Arg Pro Asp Ala
         35                  40                  45
Pro Ser Arg Cys Thr Trp Gln Leu Gly Arg Pro Ala Ser Glu Ser Pro
 50                  55                  60
His His His Thr Ala Pro Ala Lys Ser Pro Lys Ile Leu Pro Asp Ile
65                  70                  75                  80
Leu Lys Lys Ile Gly Asp Thr Pro Met Val Arg Ile Asn Lys Ile Gly
                 85                  90                  95
Lys Lys Phe Gly Leu Lys Cys Glu Leu Leu Ala Lys Cys Glu Phe Phe
            100                 105                 110
Asn Ala Gly Gly Ser Val Lys Asp Arg Ile Ser Leu Arg Met Ile Glu
        115                 120                 125
Asp Ala Glu Arg Asp Gly Thr Leu Lys Pro Gly Asp Thr Ile Ile Glu
130                 135                 140
Pro Thr Ser Gly Asn Thr Gly Ile Gly Leu Ala Leu Ala Ala Ala Val
145                 150                 155                 160
Arg Gly Tyr Arg Cys Ile Ile Val Met Pro Glu Lys Met Ser Ser Glu
                165                 170                 175
Lys Val Asp Val Leu Arg Ala Leu Gly Ala Glu Ile Val Arg Thr Pro
            180                 185                 190
Thr Asn Ala Arg Phe Asp Ser Pro Glu Ser His Val Gly Val Ala Trp
        195                 200                 205
Arg Leu Lys Asn Glu Ile Pro Asn Ser His Ile Leu Asp Gln Tyr Arg
    210                 215                 220
Asn Ala Ser Asn Pro Leu Ala His Tyr Asp Thr Thr Ala Asp Glu Ile
225                 230                 235                 240
Leu Gln Gln Cys Asp Gly Lys Leu Asp Met Leu Val Ala Ser Val Gly
                245                 250                 255
Thr Gly Gly Thr Ile Thr Gly Ile Ala Arg Lys Leu Lys Glu Lys Cys
            260                 265                 270
Pro Gly Cys Arg Ile Ile Gly Val Asp Pro Glu Gly Ser Ile Leu Ala
        275                 280                 285
Glu Pro Glu Glu Leu Asn Gln Thr Glu Gln Thr Thr Tyr Glu Val Glu
290                 295                 300
Gly Ile Gly Tyr Asp Phe Ile Pro Thr Val Leu Asp Arg Thr Val Val
305                 310                 315                 320
Asp Lys Trp Phe Lys Ser Asn Asp Glu Glu Ala Phe Thr Phe Ala Arg
                325                 330                 335
Met Leu Ile Ala Gln Glu Gly Leu Leu Cys Gly Gly Ser Ala Gly Ser
            340                 345                 350
Thr Val Ala Val Ala Val Lys Ala Ala Gln Glu Leu Gln Glu Gly Gln
        355                 360                 365
Arg Cys Val Val Ile Leu Pro Asp Ser Val Arg Asn Tyr Met Thr Lys
    370                 375                 380
Phe Leu Ser Asp Arg Trp Met Leu Gln Lys Gly Phe Leu Lys Glu Glu
385                 390                 395                 400
Asp Leu Thr Glu Lys Lys Pro Trp Trp Trp His Leu Arg Val Gln Glu
                405                 410                 415
Leu Gly Leu Ser Ala Pro Leu Thr Val Leu Pro Thr Ile Thr Cys Gly
            420                 425                 430
His Thr Ile Glu Ile Leu Arg Glu Lys Gly Phe Asp Gln Ala Pro Val
        435                 440                 445
Val Asp Glu Ala Gly Val Ile Leu Gly Met Val Thr Leu Gly Asn Met
```

```
                450                 455                 460
Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
                500                 505                 510

His Glu Gln Ile Gln Tyr His Ser Thr Gly Lys Ser Ser Gln Arg Gln
        515                 520                 525

Met Val Phe Gly Val Val Thr Ala Ile Asp Leu Leu Asn Phe Val Ala
        530                 535                 540

Ala Gln Glu Arg Asp Gln Lys
545                 550

<210> SEQ ID NO 3
<211> LENGTH: 1656
<212> TYPE: DNA
<213> ORGANISM: Homo sapiens

<400> SEQUENCE: 3
atgccgtcag aaaccccgca ggcagaagtg ggtccgacgg gttgcccgca ccgtagcggt      60
ccgcattctg caaaaggcag tctggaaaaa ggttccccgg aagataaaga agccaaagaa     120
ccgctgtgga ttcgtccgga cgcaccgtca cgctgtacct ggcagctggg tcgtccggca     180
agcgaatctc cgcatcacca tacggctccg gcgaaaagtc cgaaaattct gccggatatc     240
ctgaagaaaa ttggtgacac cccgatggtt cgtatcaaca aaatcggcaa aaaattcggt     300
ctgaaatgcg aactgctggc taaatgtgaa ttttcaatg cgggcggttc cgtgaaagat     360
cgtatctcac tgcgcatgat tgaagatgct gaacgcgacg gcaccctgaa accgggtgat     420
acgattatcg aaccgacctc tggcaacacg ggtatcggtc tggcactggc ggcggcagtc     480
cgtggttatc gctgcattat cgtgatgccg aaaaaatga ctctgaaaa agttgatgtc      540 ctgcgtgctc tgggcgcgga aattgttcgt accccgacga atgcccgctt cgacagtccg     600
gaatcccatg tgggtgttgc atggcgcctg aaaaacgaaa tcccgaattc gcacattctg     660
gatcagtatc gtaacgctag caatccgctg gcgcattacg ataccacggc cgacgaaatc     720
ctgcagcaat gtgatggcaa actggacatg ctggtcgctt ctgtgggtac cggcggtacc     780
attacgggca tcgcgcgtaa actgaaagaa aaatgcccgg gctgtcgcat atcggtgtg      840 gatccggaag gcagtattct ggcggaaccg gaagaactga accagaccga acaaaccacg     900
tatgaagttg aaggcatcgg ttacgatttt attccgaccg tcctggatcg cacggtggtt     960
gacaaatggt tcaaaagcaa tgacgaagaa gcctttacct tcgcacgtat gctgatcgct    1020
caggaaggtc tgctgtgcgg tggttcagca ggttcgacgg tcgcagtggc agttaaagct    1080
gcgcaggaac tgcaagaagg tcaacgttgt gtcgtgattc tgccggattc tgttcgcaac    1140
tacatgacca aatttctgag tgaccgttgg atgctgcaaa aaggcttcct gaaagaagaa    1200
gatctgaccg agaaaaaacc gtggtggtgg cacctgcgcg tgcaggaact gggtctgtcc    1260
gcaccgctga ccgttctgcc gaccatcacg tgcggccata cgattgaaat cctgcgtgaa    1320
aaaggttttg atcaggcccc ggttgtcgac gaagcaggcg tgattctggg tatggttacc    1380
ctgggtaaca tgctgagttc cctgctggcg ggcaaagtgc aaccgagcga tcaggttggt    1440
aaagtcatct acaaacaatt caaacagatt cgtctgaccg atacgctggg ccgcctgtcg    1500
cacatcctgg aaatggacca tttcgcgctg gttgtgcacg aacagattca ataccatagc    1560
```

```
accggcaaat catcgcagcg ccaaatggtc tttggtgtcg tgacggccat tgatctgctg    1620
aatttcgtgg ccgcacaaga acgtgaccag aaataa                              1656
```

<210> SEQ ID NO 4
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335
```

```
Met Leu Ile Ala Gln Glu Gly Leu Leu Cys Gly Gly Ser Ala Gly Ser
                340                 345                 350

Thr Val Ala Val Ala Val Lys Ala Ala Gln Glu Leu Gln Glu Gly Gln
                355                 360                 365

Arg Cys Val Val Ile Leu Pro Asp Ser Val Arg Asn Tyr Met Thr Lys
            370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg
                405                 410

<210> SEQ ID NO 5
<211> LENGTH: 413
<212> TYPE: PRT
<213> ORGANISM: Artificial Sequence
<220> FEATURE:
<223> OTHER INFORMATION: Description of Artificial Sequence: Synthetic
      Truncated human C15S mutant CBS polypeptide

<400> SEQUENCE: 5

Met Pro Ser Glu Thr Pro Gln Ala Glu Val Gly Pro Thr Gly Ser Pro
1               5                   10                  15

His Arg Ser Gly Pro His Ser Ala Lys Gly Ser Leu Glu Lys Gly Ser
                20                  25                  30

Pro Glu Asp Lys Glu Ala Lys Glu Pro Leu Trp Ile Arg Pro Asp Ala
            35                  40                  45

Pro Ser Arg Cys Thr Trp Gln Leu Gly Arg Pro Ala Ser Glu Ser Pro
        50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
                100                 105                 110

Asn Ala Gly Gly Ser Val Lys Asp Arg Ile Ser Leu Arg Met Ile Glu
            115                 120                 125

Asp Ala Glu Arg Asp Gly Thr Leu Lys Pro Gly Asp Thr Ile Ile Glu
        130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285
```

```
Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
                340                 345                 350

Thr Val Ala Val Ala Val Lys Ala Ala Gln Glu Leu Gln Glu Gly Gln
            355                 360                 365

Arg Cys Val Val Ile Leu Pro Asp Ser Val Arg Asn Tyr Met Thr Lys
    370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg
                405                 410
```